(12) United States Patent
Matsukawa et al.

(10) Patent No.: US 8,999,989 B2
(45) Date of Patent: Apr. 7, 2015

(54) BENZENE OR THIOPHENE DERIVATIVE AND USE THEREOF AS VAP-1 INHIBITOR

(75) Inventors: Tatsuya Matsukawa, Tokyo (JP); Kazuhiro Masuzaki, Toyko (JP); Akiko Kawasaki, Tokyo (JP); Akiko Akasaka, Tokyo (JP); Yosuke Kawai, Tokyo (JP)

(73) Assignee: R-Tech Ueno, Ltd., Tokyo (JP)

( * ) Notice: Subject to any disclaimer, the term of this patent is extended or adjusted under 35 U.S.C. 154(b) by 626 days.

(21) Appl. No.: 12/991,035

(22) PCT Filed: May 29, 2009

(86) PCT No.: PCT/JP2009/060302
§ 371 (c)(1),
(2), (4) Date: Nov. 4, 2010

(87) PCT Pub. No.: WO2009/145360
PCT Pub. Date: Dec. 3, 2009

(65) Prior Publication Data
US 2011/0059957 A1    Mar. 10, 2011

(30) Foreign Application Priority Data
May 30, 2008   (JP) ................................ 2008-143197

(51) Int. Cl.
| | |
|---|---|
| A61K 31/496 | (2006.01) |
| C07D 241/04 | (2006.01) |
| C07D 213/74 | (2006.01) |
| C07C 243/32 | (2006.01) |
| C07C 243/34 | (2006.01) |
| C07C 281/02 | (2006.01) |
| C07C 281/06 | (2006.01) |
| C07D 233/88 | (2006.01) |
| C07D 237/20 | (2006.01) |
| C07D 239/42 | (2006.01) |
| C07D 241/20 | (2006.01) |
| C07D 241/24 | (2006.01) |
| C07D 265/36 | (2006.01) |
| C07D 333/36 | (2006.01) |
| C07D 401/04 | (2006.01) |
| C07D 409/06 | (2006.01) |
| C07D 417/04 | (2006.01) |
| C07D 487/08 | (2006.01) |

(52) U.S. Cl.
CPC ............ *C07D 213/74* (2013.01); *C07C 243/32* (2013.01); *C07C 243/34* (2013.01); *C07C 281/02* (2013.01); *C07C 281/06* (2013.01); *C07D 233/88* (2013.01); *C07D 237/20* (2013.01); *C07D 239/42* (2013.01); *C07D 241/20* (2013.01); *C07D 241/24* (2013.01); *C07D 265/36* (2013.01); *C07D 333/36* (2013.01); *C07D 401/04* (2013.01); *C07D 409/06* (2013.01); *C07D 417/04* (2013.01); *C07D 487/08* (2013.01)

(58) Field of Classification Search
USPC ............ 514/343.5, 253.01; 548/399; 544/360
See application file for complete search history.

(56) References Cited

U.S. PATENT DOCUMENTS

| | | | |
|---|---|---|---|
| 3,658,746 A | 4/1972 | Rosendahl et al. | |
| 4,888,283 A | 12/1989 | Bertini et al. | |
| 4,985,461 A * | 1/1991 | Hsu et al. ........................ | 514/615 |
| 2002/0173521 A1 | 11/2002 | Smith et al. | |
| 2006/0068339 A1 | 3/2006 | Fukuzawa et al. | |
| 2007/0078128 A1 | 4/2007 | Saito et al. | |
| 2010/0016354 A1 | 1/2010 | Honda et al. | |
| 2010/0099718 A1 | 4/2010 | Matsukura et al. | |
| 2010/0190834 A1 | 7/2010 | Mashima et al. | |
| 2010/0210697 A1 | 8/2010 | Mashima et al. | |

FOREIGN PATENT DOCUMENTS

| | | | | |
|---|---|---|---|---|
| CA | 2 425 192 A1 | 4/2003 | | |
| DE | 1 902 932 A1 | 8/1970 | | |
| DE | 1902932 A1 * | 8/1970 | ............ | C08G 22/04 |
| EP | 0 303 283 A2 | 2/1989 | | |
| EP | 1 314 723 A1 | 5/2003 | | |
| EP | 2 119 719 A1 | 11/2009 | | |
| JP | 61-239891 A | 10/1986 | | |
| JP | 1 834 953 A1 | 9/2007 | | |
| WO | WO 93/23023 A1 | 11/1993 | | |
| WO | WO 02/02090 A2 | 1/2002 | | |

(Continued)

OTHER PUBLICATIONS

Artico et al, Eur. J. Med. Chem. (1992), pp. 219-228.*
Boomsma et al., *Diabetologia*, 42:233-237 (1999).
Dura, Eszter, *Lege Artis Medicinae*, 16(7):637-642 (2006).
Garpenstrand et al., *Medical Oncology*, 21(3): 241-250 (2004).
Garpenstrand et al., *Diabetic Medicine*, 16: 514-521 (1999).
Park et al., *Bioorganic & Medicinal Chemistry*, 14:395-408 (2006).
Stolen et al., *The FASEB Journal*, 18(6): 702-704 (Feb. 20, 2004).
Tiedeman et al., *Journal of Applied Polymer Science*, 17: 1813-1818 (1973).
Vasiliu et al., *Analele Univ. Bucuresti, Ser. Stiinte Naturale*, 13(1): 85-93 (1964).

(Continued)

*Primary Examiner* — Brandon Fetterolf
*Assistant Examiner* — Janet L Coppins
(74) *Attorney, Agent, or Firm* — Leydig, Voit & Mayer, Ltd.

(57) ABSTRACT

The present invention provides a novel benzene derivative or thiophene derivative useful as a VAP-1 inhibitor, or a medicament for the prophylaxis or treatment of a VAP-1 associated disease and the like, namely, a compound represented by the formula (I): wherein each symbol is as defined in the present specification, or a pharmaceutically acceptable salt thereof.

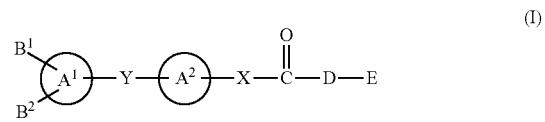

(I)

21 Claims, No Drawings

(56) References Cited

FOREIGN PATENT DOCUMENTS

| | | |
|---|---|---|
| WO | WO 02/02541 A2 | 1/2002 |
| WO | WO 02/38152 A1 | 5/2002 |
| WO | WO 02/38153 A1 | 5/2002 |
| WO | WO 02/064550 A1 | 8/2002 |
| WO | WO 02/070464 A2 | 9/2002 |
| WO | WO 03/037328 A1 | 5/2003 |
| WO | WO 03/084959 A1 | 10/2003 |
| WO | WO 03/093248 A1 | 11/2003 |
| WO | WO 03/103567 A2 | 12/2003 |
| WO | WO 2004/067521 A1 | 8/2004 |
| WO | WO 2004/087138 A1 | 10/2004 |
| WO | WO 2005/080319 A1 | 9/2005 |
| WO | WO 2006/011631 A2 | 2/2006 |
| WO | WO 2006/028269 A2 | 3/2006 |
| WO | 2006/110516 A1 | 10/2006 |
| WO | 2006/120125 A1 | 11/2006 |
| WO | WO 2007/071840 A2 | 6/2007 |
| WO | 2008/046216 A1 | 4/2008 |
| WO | WO 2008/066145 A1 | 6/2008 |
| WO | WO 2008/067219 A2 | 6/2008 |
| WO | WO 2008/094575 A2 | 8/2008 |
| WO | WO 2008/113711 A1 | 9/2008 |
| WO | WO 2008/119662 A1 | 10/2008 |
| WO | WO 2008/137605 A1 | 11/2008 |
| WO | WO 2009/001857 A1 | 12/2008 |
| WO | WO 2009/051233 A1 | 4/2009 |
| WO | WO 2009/073620 A2 | 6/2009 |
| WO | 2009/100536 A1 | 8/2009 |

OTHER PUBLICATIONS

Artico et al., *Eur. J. Med. Chem.*, 27(3): 219-228 (1992).
Smith et al., *J. Exp. Med.*, 188(1): 17-27 (1998).
Rineh et al., "Synthesis, Analgesic and Anti-Inflammatory Activity of 4-(2-Phenoxyphenyl) semicarbazones," *Arch. Pharm. Chem. Life Sci.*, 340: 409-415 (2007).

* cited by examiner

BENZENE OR THIOPHENE DERIVATIVE AND USE THEREOF AS VAP-1 INHIBITOR

TECHNICAL FIELD OF THE INVENTION

The present invention relates to a novel benzene or thiophene derivative (compound represented by the below-mentioned formula (I) (hereinafter to be also referred to as compound (I)) and a pharmaceutically acceptable salt thereof, hereinafter to be sometimes collectively referred to as the compound of the present invention). In addition, the present invention relates to a vascular adhesion protein-1 inhibitor, a pharmaceutical agent for the prophylaxis or treatment of vascular adhesion protein-1 associated disease and the like, which comprise the compound of the present invention as an active ingredient.

BACKGROUND OF THE INVENTION

The vascular adhesion protein-1 (hereinafter to be abbreviated as VAP-1) is amine oxidase (semicarbazide sensitive amine oxidase, SSAO) abundantly existing in human plasma, which shows a remarkably increased expression in vascular endothelium and vascular smooth muscle in the inflammatory lesion. Although the physiological role of VAP-1 has not been elucidated until recently, VAP-1 gene was cloned in 1998, and VAP-1 was reported to be a membrane protein which, as an adhesion molecule, controls rolling and migration of lymphocytes and NK cells under the expression control of inflammatory cytokine. Although amine to be the substrate is unknown, it is considered to be methylamine produced in any part in the living body. It is also known that hydrogen peroxide and aldehyde produced due to the intramolecular amine oxidase activity are important factors for adhesion activity.

Recent reports have demonstrated that VAP-1 enzyme activity in plasma increases both in type I and type II diabetic patients, and the increase is particularly noticeable in diabetic patients affected with retinopathy complications (see non-patent document 1 and non-patent document 2).

Furthermore, VAP-1 has also been reported to relate to the following diseases (1)-(6): (1) cirrhosis, essential stabilized hypertension, diabetes, arteriosclerosis (see patent document 1 and patent document 2); (2) endothelial injury (in diabetes, arteriosclerosis and hypertension), cardiovascular disease relating to diabetes or uremia, pain relating to gout and arthritis, retinopathy (in diabetic patients) (see patent document 3); (3) inflammatory disease or symptom (of binding tissue) (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis); inflammatory disease or symptom of gastrointestinal tract [Crohn's disease, ulcerative colitis, irritable bowel syndrome (spastic colon), fibrosis of liver, inflammation (stomatitis) of oral mucous membrane and recurrent aphthous stomatitis]; inflammatory disease or symptom of central nervous system (multiple sclerosis, Alzheimer's disease, and ischemia-reperfusion injury relating to ischemic stroke); pulmonary inflammatory disease or symptom (asthma, adult respiratory distress syndrome, chronic obliterative pulmonary diseases); (chronic) inflammatory disease or symptom of the skin (psoriasis, allergic lesion, lichen planus, pityriasis rosea, contact dermatitis, atopic dermatitis, pityriasis rubra pilaris); disease relating to carbohydrate metabolism (diabetes and complications derived from diabetes) including disease of microvessel and large vessel (arteriosclerosis, vascular retinopathy, retinopathy, nephropathy, nephrotic syndrome and neuropathy (multiple neuropathy, mononeuropathy and autonomic neuropathy), foot ulcer, articular problem and increase in infection risk); disease relating to abnormality in the differentiation or function of adipocyte or function of smooth muscle cell (arteriosclerosis and obesity); vascular disease [atherosclerosis, nonatherosclerotic disease, ischemic cardiac diseases including myocardial infarction and peripheral arterial obstruction, Raynaud's disease and Raynaud's phenomenon, thromboangiitis obliterans (Buerger's disease)]; chronic arthritis; inflammatory bowel disease; skin disease (see patent document 4, patent document 5 and patent document 6); (4) diabetes (see patent document 7); (5) SSAO-mediated complications [diabetes (insulin-dependent diabetes (IDDM) and noninsulin-dependent diabetes (NIDDM)) and vascular complications (heart attack, angina pectoris, apoplexy, adamputation, blindness and renal failure)] (see patent document 8); (6) vascular hyperpermeable disease [aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer; chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by, ocular inflammatory disease including itching, flare, edema and ulcer, erythema, erythema exsudativum multiforme, erythema nodosum, erythema annulare, scleredema, dermatitis, angioneurotic edema, laryngeal edema, glottic edema, subglottic laryngitis, bronchitis, rhinitis, pharyngitis, sinusitis and laryngitis or otitis media] (see patent document 9); and the like.

Patent document 9, patent document 10, patent document 11 and patent document 12 describe thiazole derivatives having specific structures and that they can be used for the prophylaxis or treatment of VAP-1 associated disease such as macular edema, vascular hyperpermeable disease and the like.

Patent document 9, patent document 10 and patent document 12 describe a thiazole derivative conceptually containing a hydrazino group or a hydrazinocarbonyl group at the molecular terminal. However, they do not disclose the novel compound specified by the present invention.

CITATION LIST

Patent Documents patent document 1: JP-A-61-239891
patent document 2: U.S. Pat. No. 4,888,283
patent document 3: WO 1993/23023
patent document 4: WO 2002/02090
patent document 5: WO 2002/02541
patent document 6: US 2002/0173521 A
patent document 7: WO 2002/38152
patent document 8: WO 2002/38153
patent document 9: WO 2004/087138
patent document 10: WO 2004/067521 patent document 11 : WO 2006/011631
patent document 12 : WO 2006/028269

Non-Patent Documents non-patent document 1 : Diabetologia, 42 (1999) 233-237
non-patent document 2 : Diabetes Medicine, 16 (1999) 514-521

SUMMARY OF THE INVENTION

Problems to be Solved by the Invention

The present invention aims to provide a novel benzene or thiophene derivative useful as a VAP-1 inhibitor, a pharmaceutical agent for the prophylaxis or treatment of VAP-1 associated diseases and the like.

As a result of intensive studies, the present inventors have found that a benzene or thiophene derivative having a specific functional group (hydrazinocarbonyl group) at the molecular terminal has superior VAP-1 inhibitory effect, is superior in enzyme selectivity and can eliminate concerned side effects, and conducted further studies, which resulted in the completion of the present invention.

Accordingly, the present invention is as follows.
(1) A compound represented by the formula (I):

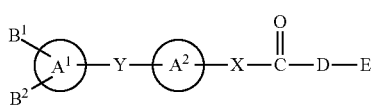

wherein
$A^1$ is a residue derived from benzene or a heterocycle containing at least one nitrogen atom or sulfur atom;
$A^2$ is a divalent residue derived from optionally substituted benzene or optionally substituted thiophene;
$B^1$ is hydrogen, hydroxy, halogen, lower alkyl, cyclo lower alkyl, halogenated lower alkyl, lower alkoxy, acyl, acylamino, optionally substituted carbamoyl, lower alkylsulfonylamino or lower alkylcarbonyloxy (provided when $A^1$ is a residue derived from thiazole, $B^1$ is not acylamino);
$B^2$ is hydrogen or a functional group containing at least one nitrogen atom (provided when $A^1$ is a residue derived from thiazole, $B^2$ is not acylamino);
or $B^1$ and $B^2$ are optionally bonded to each other to form a cyclic structure;
Y is a group represented by the formula (II):

wherein J is a bond, lower alkylene, lower alkenylene, lower alkynylene, $-(CH_2)_n-O-$, $-(CH_2)_n-NH-$, $-(CH_2)_n-CO-$ or $-(CH_2)_n-SO_2-$ (wherein n is an integer of 0 to 6);
L is a bond, $-O-$, $-NH-$, $-CO-$ or $-SO_2-$;
M is a bond, lower alkylene, lower alkenylene or lower alkynylene, provided that when J is $-(CH_2)_n-O-$, L is not $-O-$, $-NH-$ and $-SO_2-$, when J is $-(CH_2)_n-NH-$, L is not $-O-$ and $-NH-$, when J is $-(CH_2)_n-CO-$, L is not $-CO-$, when J is $-(CH_2)_n-SO_2-$, L is not $-O-$ and $-SO_2-$ (wherein n is as defied above);
X is $-(CH_2)_m-$, $-(CH_2)_m-O-$, $-(CH_2)_m-S-$ or $-(CH_2)_m-NR^2-$ (wherein m is an integer of 0 to 6 and $R^2$ is hydrogen, lower alkyl or acyl);

D is $-NR^3-$ wherein $R^3$ is hydrogen, lower alkyl, acyl, or lower alkoxycarbonyl; and
E is optionally substituted amino, or a pharmaceutically acceptable salt thereof.
(2) The compound of the above-mentioned (1), which is selected from
N-{4-[2-(4-hydrazinocarbonylmethylphenyl)ethyl]phenyl}acetamide,
N-{3-[2-(4-hydrazinocarbonylmethylphenyl)ethyl]phenyl}acetamide,
N-{2-acetylamino-5-[2-(4-hydrazinocarbonylmethylphenyl)ethyl]bpyridin-3-yl}acetamide,
N-{6-[2-(4-hydrazinocarbonylmethylphenyl)ethyl]pyridin-2-yl}acetamide,
N-{4-[2-(4-hydrazinocarbonylmethylphenyl)ethyl]-3-trifluoromethylphenyl}acetamide,
2-{4-[2-(4-hydrazinocarbonylmethylphenyl)ethyl]phenoxy}acetamide,
N-{5-[2-(hydrazinocarbonylmethylphenyl)ethyl]pyrazin-2-yl}acetamide,
N-{2-acetylamino-5-[2-(4-hydrazinocarbonylmethylphenyl)ethyl]phenyl}acetamide,
{4-[2-(1H-imidazol-2-yl)ethyl]phenyl}acetohydrazide,
{4-[2-(3H-imidazol-4-yl)ethyl]phenyl}acetohydrazide,
N-{5-[2-(4-hydrazinocarbonylmethylphenyl)ethyl]pyridin-2-yl}acetamide,
{4-[2-(6-morpholin-4-ylpyridin-3-yl)ethyl]phenyl}acetohydrazide,
2-{4-[2-(4-hydrazinocarbonylmethylphenyl)ethynyl]phenoxy}acetamide,
[4-(1H-imidazol-2-ylethynyl)phenyl]acetohydrazide,
[4-(6-morpholin-4-ylpyridin-3-ylethynyl)phenyl]acetohydrazide,
N-[5-(4-hydrazinocarbonylmethylphenylethynyl)pyrazin-2-yl]acetamide,
N-[2-acetylamino-4-(4-hydrazinocarbonylmethylphenylethynyl)phenyl]acetamide,
N-[3-acetylamino-5-(4-hydrazinocarbonylmethylphenylethynyl)pyridin-2-yl]acetamide,
5-[2-(4-hydrazinocarbonylmethylphenyl)ethyl]pyrazine-2-carboxamide,
2-{4-[2-(2-piperidin-4-yl-1,3-thiazol-4-yl)ethyl]phenyl}acetohydrazide,
2-acetylamino-4-[2-(4-hydrazinocarbonylmethylphenyl)ethyl]phenyl acetate,
{4-[2-(1-methyl-1H-imidazol-2-yl)ethyl]phenyl}acetohydrazide,
N-[4-(4-hydrazinocarbonylmethylphenylethynyl)phenyl]acetamide,
N-[3-(4-hydrazinocarbonylmethylphenylethynyl)phenyl]acetamide,
[4-(1-methyl-1H-imidazol-2-ylethynyl)phenyl]acetohydrazide,
2-{4-[(2-piperidin-4-yl-1,3-thiazol-4-yl)ethynyl]phenyl}acetohydrazide,
N-[5-(4-hydrazinocarbonylmethylphenylethynyl)pyridin-2-yl]acetamide,
N-[6-(4-hydrazinocarbonylmethylphenylethynyl)pyridin-2-yl]acetamide,
2-(4-{2-[4-(dimethylamino)phenyl]ethyl}phenyl)acetohydrazide,
2-(4-{2-[4-(diethylamino)phenyl]ethyl}phenyl)acetohydrazide,
2-{4-[2-(4-pyrrolidin-1-ylphenyl)ethyl]phenyl}acetohydrazide,
2-{4-[2-(4-piperidin-1-ylphenyl)ethyl]phenyl}acetohydrazide, 2-{4-[2-(4-piperazin-1-ylphenyl)ethyl]
phenyl}acetohydrazide,
2-(4-{2-[4-(4-acetylpiperazin-1-yl)phenyl]ethyl}phenyl)ac-
etohydrazide,
2-{2-[4-(4-methylpiperazin-1-yl)phenyl]ethyl}phenyl)
acetohydrazide,
2-{4-[2-(4-morpholin-4-ylphenyl)ethyl]
phenyl}acetohydrazide,
2-(4-{2-[3-(dimethylamino)phenyl]ethyl}phenyl)acetohy-
drazide,
2-{4-[2-(3-pyrrolidin-1-ylphenyl)ethyl]
phenyl}acetohydrazide,
2-{4-[2-(4-piperidin-1-ylphenyl)ethyl]
phenyl}acetohydrazide,
2-{4-[2-(3-piperazin-1-ylphenyl)ethyl]
phenyl}acetohydrazide,
2-(4-{2-[3-(4-acetylpiperazin-1-yl)phenyl]ethyl}phenyl)ac-
etohydrazide,
2-{4-[2-(3-morpholin-4-ylphenyl)ethyl]
phenyl}acetohydrazide,
2-(4-{2-[6-(dimethylamino)pyridin-3-yl]ethyl}phenyl)ac-
etohydrazide,
2-{4-[2-(6-pyrrolidin-1-ylpyridin-3-yl)ethyl]
phenyl}acetohydrazide,
2-{4-[2-(6-piperidin-1-ylpyridin-3-yl)ethyl]
phenyl}acetohydrazide,
2-{4-[2-(6-piperazin-1-ylpyridin-3-yl)ethyl]
phenyl}acetohydrazide,
2-(4-{2-[6-(4-acetylpiperazin-1-yl)pyridin-3-yl]
ethyl}phenyl)acetohydrazide,
2-(4-{2-[6-(4-methylpiperazin-1-yl)pyridin-3-yl]
ethyl}phenyl)acetohydrazide,
2-{4-[2-(6-pyrrolidin-1-ylpyridin-2-yl)ethyl]
phenyl}acetohydrazide,
2-{4-[2-(6-piperidin-1-ylpyridin-2-yl)ethyl]
phenyl}acetohydrazide,
2-{4-[2-(6-piperazin-1-ylpyridin-2-yl)ethyl]
phenyl}acetohydrazide,
2-(4-{2-[6-(4-acetylpiperazin-1-yl)pyridin-2-yl]
ethyl}phenyl)acetohydrazide,
2-{4-[2-(6-morpholin-4-ylpyridin-2-yl)ethyl]
phenyl}acetohydrazide,
2-{4-[2-(2-pyrrolidin-1-ylpyrimidin-5-yl)ethyl]
phenyl}acetohydrazide,
2-{4-[2-(2-piperidin-1-ylpyrimidin-5-yl)ethyl]
phenyl}acetohydrazide,
2-{4-[2-(2-piperazin-1-ylpyrimidin-5-yl)ethyl]
phenyl}acetohydrazide,
2-(4-{2-[2-(4-acetylpiperazin-1-yl)pyrimidin-5-yl]
ethyl}phenyl)acetohydrazide,
2-{4-[2-(2-morpholin-4-ylpyrimidin-5-yl)ethyl]
phenyl}acetohydrazide,
2-(4-{2-[4-piperazin-1-yl-2-(trifluoromethyl)phenyl]
ethyl}phenyl)acetohydrazide,
2-(4-{2-[4-(4-acetylpiperazin-1-yl)-2-(trifluoromethyl)phe-
nyl]ethyl}phenyl)acetohydrazide,
N-[4-{2-[4-(hydrazinocarbonylmethyl)phenyl]ethyl}-2-(tri-
fluoromethyl)phenyl]acetamide,
N-[3-{2-[4-(hydrazinocarbonylmethyl)phenyl]ethyl}-2-(tri-
fluoromethyl)phenyl]acetamide,
2-{4-[2-(3-oxo-3,4-dihydro-2H-1,4-benzooxazin-6-yl)
ethyl]phenyl}acetohydrazide,
2-{4-[2-(4-methyl-3,4-dihydro-2H-1,4-benzooxazin-7-yl)
ethyl]phenyl}acetohydrazide,
2-(4-{2-[4-(2,5-diazabicyclo[2.2.1]hept-2-yl)phenyl]
ethyl}phenyl)acetohydrazide,
2-(4-{2-[4-(5-acetyl-2,5-diazabicyclo[2.2.1]hept-2-yl)phe-
nyl]ethyl}phenyl)acetohydrazide,
2-(4-{2-[6-(1H-pyrazol-1-yl)pyridin-2-yl]ethyl}phenyl)ac-
etohydrazide,
2-(4-{2-[4-(piperazin-1-ylmethyl)phenyl]ethyl}phenyl)
acetohydrazide,
2-(4-{2-[3-(piperazin-1-ylmethyl)phenyl]ethyl}phenyl)ac-
etohydrazide,
2-(4-{2-[4-(morpholin-4-ylmethyl)phenyl]ethyl}phenyl)ac-
etohydrazide,
2-(4-{2-[3-(morpholin-4-ylmethyl)phenyl]ethyl}phenyl)ac-
etohydrazide,
2-(4-{2-[2-(1-acetylpiperidin-4-yl)-1,3-thiazol-4-yl]
ethyl}phenyl)acetohydrazide,
N-{5-[2-(4-hydrazinocarbonylmethylphenyl)ethyl]-2-
thienyl}acetamide,
2-{4-[2-(5-piperazin-1-ylthiophen-2-yl)ethyl]
phenyl}acetohydrazide,
2-(4-{2-[5-(4-acetylpiperazin-1-yl)thiophen-2-yl]
ethyl}phenyl)acetohydrazide,
2-{4-[2-(5-morpholin-4-ylthiophen-2-yl)ethyl]
phenyl}acetohydrazide,
N-{4-[2-(4-hydrazinocarbonylmethylphenyl)ethyl]-1,3-
thiazol-2-yl}ethanesulfonylamide,
N-{4-[2-(4-hydrazinocarbonylmethylphenyl)ethyl]-1,3-
thiazol-2-yl}methanesulfonylamide,
2-[4-(2-{4-[ethyl(methyl)amino]phenyl}ethyl)phenyl]ac-
etohydrazide,
2-[4-(2-{4-[methyl(propyl)amino]phenyl}ethyl)phenyl]ac-
etohydrazide,
2-[4-(2-{4-[ethyl(propyl)amino]phenyl}ethyl)phenyl]aceto-
hydrazide,
2-(4-{2-[4-(dipropylamino)phenyl]ethyl}phenyl)acetohy-
drazide,
2-[4-(2-{4-[(2-aminoethyl)(ethyl)amino]phenyl}ethyl)phe-
nyl]acetohydrazide,
N-[2-(ethyl{4-[2-(4-hydrazinocarbonylmethylphenyl)ethyl]
phenyl}amino)ethyl]acetamide,
2-(4-{2-[6-(diethylamino)pyridin-3-yl]ethyl}phenyl)aceto-
hydrazide,
2-{4-[2-(5-piperazin-1-ylpyridin-2-yl)ethyl]
phenyl}acetohydrazide,
2-(4-{2-[5-(4-acetylpiperazin-1-yl)pyridin-2-yl]
ethyl}phenyl)acetohydrazide,
2-(4-{2-[5-(diethylamino)pyridin-2-yl]ethyl}phenyl)aceto-
hydrazide,
2-[4-(2-{6-[ethyl(methyl)amino]pyridin-3-yl}ethyl)phenyl]
acetohydrazide,
2-[4-(2-{6-[methyl(propyl)amino]pyridin-3-yl}ethyl)phe-
nyl]acetohydrazide,
2-[4-(2-{6-[ethyl(propyl)amino]pyridin-3-yl}ethyl)phenyl]
acetohydrazide,
2-(4-{2-[6-(dipropylamino)pyridin-3-yl]ethyl}phenyl)ac-
etohydrazide,
2-(4-{2-[6-(diethylamino)pyridin-2-yl]ethyl}phenyl)aceto-
hydrazide,
2-(4-{2-[2-(4-acetylpiperazin-1-yl)-1,3-thiazol-4-yl]
ethyl}phenyl)acetohydrazide,
2-{4-[2-(2-piperazin-1-yl-1,3-thiazol-4-yl)ethyl]
phenyl}acetohydrazide,
2-(4-{2-[6-(4-acetylpiperazin-1-yl)-3-(trifluoromethyl)pyri-
din-2-yl]ethyl}phenyl)acetohydrazide,
2-(4-{2-[6-piperazin-1-yl-3-(trifluoromethyl)pyridin-2-yl]
ethyl}phenyl)acetohydrazide,
2-{4-[2-(6-piperazin-1-ylpyridazin-3-yl)ethyl]
phenyl}acetohydrazide, 2-(4-{2-[6-(4-acetylpiperazin-1-yl)pyridazin-3-yl]
  ethyl}phenyl)acetohydrazide,
2-{4-[2-(5-piperazin-1-ylpyrazin-2-yl)ethyl]
  phenyl}acetohydrazide,
2-(4-{2-[5-(4-acetylpiperazin-1-yl)pyrazin-2-yl]
  ethyl}phenyl)acetohydrazide,
2-{4-[2-(5-piperazin-1-ylpyridin-3-yl)ethyl]
  phenyl}acetohydrazide,
2-{4-[2-(6-piperazin-1-ylpyrazin-2-yl)ethyl]
  phenyl}acetohydrazide,
2-{4-[2-(4-piperazin-1-ylpyridin-2-yl)ethyl]
  phenyl}acetohydrazide,
2-{4-[2-(2-piperazin-1-ylpyridin-4-yl)ethyl]
  phenyl}acetohydrazide,
2-{4-[2-(6-piperazin-1-ylpyrimidin-4-yl)ethyl]
  phenyl}acetohydrazide,
2-{4-[2-(4-piperazin-1-ylpyrimidin-2-yl)ethyl]
  phenyl}acetohydrazide,
4-{2-[5-(4-acetylpiperazin-1-yl)pyridin-2-yl]ethyl}benzyl
  hydrazinecarboxylate,
N-(4-{2-[5-(4-acetylpiperazin-1-yl)pyridin-2-yl]
  ethyl}benzyl)hydrazinecarboxamide,
4-{2-[5-(4-acetylpiperazin-1-yl)pyridin-2-yl]ethyl}phenyl
  hydrazinecarboxylate,
3-{2-[5-(4-acetylpiperazin-1-yl)pyridin-2-yl]ethyl}benzyl
  hydrazinecarboxylate,
N-(3-{2-[5-(4-acetylpiperazin-1-yl)pyridin-2-yl]
  ethyl}benzyl)hydrazinecarboxamide,
4-{2-[5-(4-acetylpiperazin-1-yl)pyridin-2-yl]ethyl}-3-fluo-
  robenzyl hydrazinecarboxylate,
N-(4-{2-[5-(4-acetylpiperazin-1-yl)pyridin-2-yl]ethyl}-3-
  fluorobenzyl)hydrazinecarboxamide
2-(5-{2-[5-(4-acetylpiperazin-1-yl)pyridin-2-yl]
  ethyl}thiophen-2-yl)ethyl hydrazinecarboxylate,
5-{2-[5-(4-acetylpiperazin-1-yl)pyridin-2-yl]
  ethyl}thiophene -2-carbohydrazide,
N-[2-(5-{2-[5-(4-acetylpiperazin-1-yl)pyridin-2-yl]
  ethyl}thiophen-2-yl)ethyl]hydrazinecarboxamide,
2-(3-{2-[5-(4-acetylpiperazin-1-yl)pyridin-2-yl]
  ethyl}phenyl)acetohydrazide,
3-(4-{2-[5-(4-acetylpiperazin-1-yl)pyridin-2-yl]
  ethyl}phenyl)propanehydrazide,
2-(5-{2-[5-(4-acetylpiperazin-1-yl)pyridin-2-yl]
  ethyl}thiophen-2-yl)acetohydrazide,
3-(4-{2-[5-(4-acetylpiperazin-1-yl)pyridin-2-yl]
  ethyl}thiophen-2-yl)propanehydrazide,
2-(4-{2-[5-(4-acetylpiperazin-1-yl)pyridin-2-yl]
  ethyl}phenyl)ethyl hydrazinecarboxylate,
N-[2-(4-{2-[5-(4-acetylpiperazin-1-yl)pyridin-2-yl]
  ethyl}phenyl)ethyl]hydrazinecarboxamide,
3-(4-{2-[5-(4-acetylpiperazin-1-yl)pyridin-2-yl]
  ethyl}thiophen-2-yl)propylhydrazinecarboxylate, and
N-[3-(4-{2-[5-(4-acetylpiperazin-1-yl)pyridin-2-yl]
  ethyl}thiophen-2-yl)propyl]hydrazinecarboxamide, or a
  pharmaceutically acceptable salt thereof.
(3) The compound of the above-mentioned (1) or (2), which is
  used as a pharmaceutical agent, or a pharmaceutically
  acceptable salt thereof.
(4) A pharmaceutical composition comprising the compound
  of the above-mentioned (1) or (2) or a pharmaceutically
  acceptable salt thereof as an active ingredient.
(5) A VAP-1 inhibitor comprising the compound of the above-
  mentioned (1) or (2) or a pharmaceutically acceptable salt
  thereof as an active ingredient.
(6) A pharmaceutical agent for the prophylaxis or treatment of
  VAP-1 associated disease, which comprises the compound
  of the above-mentioned (1) or (2) or a pharmaceutically
  acceptable salt thereof as an active ingredient.
(7) The pharmaceutical agent of the above-mentioned (6),
  wherein the aforementioned VAP-1 associated disease is
  macular edema (diabetic and nondiabetic macular edema),
  aged macular degeneration, aged disciform macular
  degeneration, cystoid macular edema, palpebral edema,
  retina edema, diabetic retinopathy, chorioretinopathy,
  neovascular maculopathy, neovascular glaucoma, uveitis,
  iritis, retinal vasculitis, endophthalmitis, panophthalmitis,
  metastatic ophthalmia, choroiditis, retinal pigment epithe-
  litis, conjunctivitis, cyclitis, scleritis, episcleritis, optic
  neuritis, retrobulbar optic neuritis, keratitis, blepharitis,
  exudative retinal detachment, corneal ulcer, conjunctival
  ulcer, chronic nummular keratitis, Thygeson keratitis, pro-
  gressive Mooren's ulcer, ocular inflammatory disease
  caused by bacterial or viral infection, and by ophthalmic
  operation, ocular inflammatory disease caused by physical
  injury to the eye, symptom caused by ocular inflammatory
  disease including itching, flare, edema and ulcer, erythema,
  erythema exsudativum multiforme, erythema nodosum,
  erythema annulare, scleredema, dermatitis (psoriasis,
  allergic lesion, lichen planus, pityriasis rosea, contact der-
  matitis, atopic dermatitis, pityriasis rubra pilaris), angion-
  eurotic edema, laryngeal edema, glottic edema, subglottic
  laryngitis, bronchitis, rhinitis, pharyngitis, sinusitis and
  laryngitis or otitis media, cirrhosis, essential stabilized
  hypertension, diabetes, arteriosclerosis, endothelial injury
  (in diabetes, arteriosclerosis and hypertension), cardiovas-
  cular disease relating to diabetes or uremia, pain relating to
  gout and arthritis, inflammatory disease or symptom of
  binding tissue (rheumatoid arthritis, ankylosing spondyli-
  tis, psoriatic arthritis and osteoarthritis or degenerative
  joint disease, Reiter's syndrome, Sjogren's syndrome,
  Behcet's syndrome, relapsing polychondritis, systemic
  lupus erythematosus, discoid lupus erythematodes, sys-
  temic sclerosis, eosinophilic fasciitis, polymyositis, der-
  matomyositis, polymyalgia rheumatica, vasculitis, tempo-
  ral arthritis, polyarteritis nodosa, Wegener's
  granulomatosis, mixed connective tissue diseases and
  juvenile rheumatoid arthritis), inflammatory disease or
  symptom of gastrointestinal tract [Crohn's disease, ulcer-
  ative colitis, irritable bowel syndrome (spastic colon),
  fibrosis of the liver, inflammation of the oral mucous mem-
  brane (stomatitis and recurrent aphthous stomatitis)],
  inflammatory disease or symptom of central nervous sys-
  tem (multiple sclerosis, Alzheimer's disease, and
  ischemia-reperfusion injury relating to ischemic stroke),
  pulmonary inflammatory disease or symptom (asthma,
  adult respiratory distress syndrome, chronic obliterative
  pulmonary diseases), disease relating to carbohydrate
  metabolism (diabetes and complications derived from dia-
  betes) including disease of microvessel and large vessel
  (arteriosclerosis, retinopathy, nephropathy, nephrotic syn-
  drome and neuropathy (multiple neuropathy, mononeur-
  opathy and autonomic neuropathy), foot ulcer, articular
  problem and increase in infection risk), disease relating to
  abnormality in the differentiation or function of adipocyte
  or function of smooth muscle cell (arteriosclerosis and
  obesity), vascular disease [atheromatous atherosclerosis,
  nonatheromatous atherosclerotic disease, ischemic cardiac
  diseases including myocardial infarction and peripheral
  arterial obstruction, Raynaud's disease and Raynaud's
  phenomenon, thromboangiitis obliterans (Buerger's dis-
  ease)], chronic arthritis, inflammatory bowel disease, or
  SSAO-mediated complications [diabetes (insulin-depen-
  dent diabetes (IDDM) and noninsulin-dependent diabetes (NIDDM)) and vascular complications (heart attack, angina pectoris, apoplexy, amputation, blindness and renal failure)], ophthalmic disease associated with hypoxia or ischemia [retinopathy of prematurity, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency], angiogenesis or cataract.

(8) Use of the compound of the above-mentioned (1) or (2), or a pharmaceutically acceptable salt thereof, for the production of a pharmaceutical agent as a VAP-1 inhibitor.

(9) Use of the compound of the above-mentioned (1) or (2), or a pharmaceutically acceptable salt thereof, for the production of a pharmaceutical agent for the prophylaxis or treatment of a VAP-1 associated disease.

(10) Use of the above-mentioned (9), wherein the aforementioned VAP-1 associated disease is macular edema (diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media, cirrhosis, essential stabilized hypertension, diabetes, arteriosclerosis, endothelial injury (in diabetes, arteriosclerosis and hypertension), cardiovascular disease relating to diabetes or uremia, pain relating to gout and arthritis, inflammatory disease or symptom of binding tissue (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [Crohn's disease, ulcerative colitis, irritable bowel syndrome (spastic colon), fibrosis of the liver, inflammation of the oral mucous membrane (stomatitis and recurrent aphthous stomatitis)], inflammatory disease or symptom of central nervous system (multiple sclerosis, Alzheimer's disease, and ischemia-reperfusion injury relating to ischemic stroke), pulmonary inflammatory disease or symptom (asthma, adult respiratory distress syndrome, chronic obliterative pulmonary diseases), disease relating to carbohydrate metabolism (diabetes and complications derived from diabetes) including disease of microvessel and large vessel (arteriosclerosis, retinopathy, nephropathy, nephrotic syndrome and neuropathy (multiple neuropathy, mononeuropathy and autonomic neuropathy), foot ulcer, articular problem and increase in infection risk), disease relating to abnormality in the differentiation or function of adipocyte or function of smooth muscle cell (arteriosclerosis and obesity), vascular disease [atheromatous atherosclerosis, nonatheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, or SSAO-mediated complications [diabetes (insulin-dependent diabetes (IDDM) and noninsulin-dependent diabetes (NIDDM)) and vascular complications (heart attack, angina pectoris, apoplexy, amputation, blindness and renal failure)], ophthalmic disease associated with hypoxia or ischemia [retinopathy of prematurity, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency], angiogenesis, or cataract.

(11) A method of inhibiting VAP-1 in a subject, which comprises administering an effective amount of the compound of the above-mentioned (1) or (2) or a pharmaceutically acceptable salt thereof to the subject.

(12) A method for the prophylaxis or treatment of VAP-1 associated disease in a subject, which comprises administering an effective amount of the compound of the above-mentioned (1) or (2) or a pharmaceutically acceptable salt thereof to the subject.

(13) The method of the above-mentioned (12), wherein the aforementioned VAP-1 associated disease is macular edema (diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media, cirrhosis, essential stabilized hypertension, diabetes, arteriosclerosis, endothelial injury (in diabetes, arteriosclerosis and hypertension), cardiovascular disease relating to diabetes or uremia, pain relating to gout and arthritis, inflammatory disease or symptom of binding tissue (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [Crohn's disease, ulcerative colitis, irritable bowel syndrome (spastic colon), fibrosis of the liver, inflammation of the oral mucous membrane (stomatitis and recurrent aphthous stomatitis)], inflammatory disease or symptom of central nervous system (multiple sclerosis, Alzheimer's disease, and ischemia-reperfusion injury relating to ischemic stroke), pulmonary inflammatory disease or symptom (asthma, adult respiratory distress syndrome, chronic obliterative pulmonary diseases), disease relating to carbohydrate metabolism (diabetes and complications derived from diabetes) including disease of microvessel and large vessel (arteriosclerosis, retinopathy, nephropathy, nephrotic syndrome and neuropathy (multiple neuropathy, mononeuropathy and autonomic neuropathy), foot ulcer, articular problem and increase in infection risk), disease relating to abnormality in the differentiation or function of adipocyte or function of smooth muscle cell (arteriosclerosis and obesity), vascular disease [atheromatous atherosclerosis, nonatheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, or SSAO-mediated complications [diabetes (insulin-dependent diabetes (IDDM) and noninsulin-dependent diabetes (NIDDM)) and vascular complications (heart attack, angina pectoris, apoplexy, amputation, blindness and renal failure)], ophthalmic disease associated with hypoxia or ischemia [retinopathy of prematurity, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency], angiogenesis or cataract.

Effect of the Invention

The compound of the present invention has superior VAP-1 inhibitory activity and superior enzyme selectivity, and therefore, can remove side effects and the like which are undesirable as a pharmaceutical product. Therefore, the compound is useful as a VAP-1 inhibitor, a pharmaceutical agent for the prophylaxis or treatment of a VAP-1 associated disease and the like.

EMBODIMENT OF THE INVENTION

The terms used for the present invention in the above- and below-mentioned descriptions of the present specification are explained in detail in the following.

The term "halogen" means fluorine, bromine, chlorine or iodine.

The term "lower" is used to mean a group having 1 to 6 carbon atoms, preferably 1 to 4, unless otherwise specified.

Examples of the "lower alkyl" include a straight chain or branched chain alkyl having 1 to 6 carbon atoms (e.g., methyl, ethyl, propyl, isopropyl, butyl, isobutyl, sec-butyl, tert-butyl, pentyl, tert-pentyl and hexyl) and the like. Among these, $C_1$-$C_4$ alkyl is more preferable.

Examples of the "halogenated lower alkyl" include the above-mentioned "lower alkyl" substituted by the above-mentioned "halogen". When it is substituted by a plurality of halogen, the halogen may be the same or different. Specific examples thereof include trifluoromethyl, trichloromethyl, pentafluoroethyl and the like.

Examples of the "lower alkylene" include a straight chain or branched chain alkylene having 1 to 6 carbon atoms (e.g., methylene, ethylene, trimethylene, propylene, ethylidene and propylidene) and the like. Among these, $C_1$-$C_4$ alkylene is more preferable.

Examples of the "lower alkenylene" include a straight chain or branched chain alkenylene having 2 to 6 carbon atoms (e.g., vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene) and the like. Among these, $C_2$-$C_4$ alkenylene is more preferable.

The above-mentioned "lower alkenylene" may be an E-form or Z-form. When the compound of the present invention has a lower alkenylene moiety, the compound of the present invention encompasses any geometric isomer wherein the lower alkenylene moiety is an E-structure or Z-structure.

Examples of the "lower alkynylene" include a straight chain or branched chain alkynylene having a carbon number of 2 to 6, which has 1 to 3 triple bonds (e.g., ethynylene, 1-propynylene, 1-methyl-1-propynylene, 2-methyl-1-propynylene, 2-propynylene, 2-butynylene, 1-butynylene, 3-butynylene, 2-pentynylene, 1-pentynylene, 3-pentynylene, 4-pentynylene, 2-pentyn-4-ynylene, 2-hexynylene, 1-hexynylene, 5-hexynylene, 3-hexynylene, 4-hexynylene, 3,3-diethyl-1-propynylene, 2-ethyl-1-propynylene) and the like. Among these, $C_2$-$C_4$ alkynylene is more preferable.

Examples of the "aryl" include $C_6$-$C_{10}$ aryl (e.g., phenyl and naphthyl) and the like, where the "aryl" may be substituted and the position of substitution is not particularly limited. Examples of the "substituent" include methyl, ethyl, hydroxy, methoxy, amino, acetyl, halogen and the like. When a plurality of substituents are present, they may be the same or different.

Examples of the "aralkyl" include aralkyl wherein the aryl moiety has 6 to 10 carbon atoms [that is, the aryl moiety is $C_6$-$C_{10}$ aryl of the above-mentioned "aryl"], and the alkyl moiety has 1 to 6 carbon atoms [that is, the alkyl moiety is $C_1$-$C_6$ alkyl of the above-mentioned "lower alkyl"] (e.g., benzyl, phenethyl, 1-naphthylmethyl, 2-naphthylmethyl, 3-phenylpropyl, 4-phenylbutyl and 5-phenylpentyl) and the like.

Examples of the "cyclo lower alkyl" include cycloalkyl having 3 to 6 carbon atoms (e.g., cyclopropyl, cyclobutyl, cyclopentyl, cyclohexyl) and the like.

Examples of the "heterocycle" include "aromatic heterocycle" and "non-aromatic heterocycle". Examples of the "aromatic heterocycle" include a 5- to 10-membered aromatic heterocycle containing, besides carbon atoms, 1 to 3 hetero atoms selected from nitrogen, oxygen and sulfur atom and the like, for example, thiophene, furan, pyrrole, imidazole, pyrazole, thiazole, isothiazole, oxazole, isoxazole, pyridine, pyridazine, pyrimidine, pyrazine and the like. Examples of the "non-aromatic heterocycle" include a 5- to 10-membered non-aromatic heterocycle containing, besides carbon atoms, 1 to 3 hetero atom selected from nitrogen, oxygen and sulfur atom and the like, for example, pyrrolidine, imidazoline, pyrazolidine, pyrazoline, piperidine, piperazine, homopiperazine, triethylenediamine, morpholine, thiomorpholine, dioxolane, oxazolidine, thiazolidine, triazolidine, 2,5-diazabicyclo[2.2.1]heptane and the like.

The "acyl" includes lower alkylcarbonyl, cyclo lower alkylcarbonyl, arylcarbonyl and the like.

Examples of the "lower alkylcarbonyl" include alkylcarbonyl wherein the lower alkyl moiety has 1 to 6 carbon atoms [i.e., lower alkyl moiety is $C_1$-$C_6$ alkyl of the above-mentioned "lower alkyl"] (e.g., acetyl, propionyl, butyryl, isobutyryl, valeryl, isovaleryl, pivaloyl and hexanoyl) and the like.

Examples of the "cyclo lower alkylcarbonyl" include cycloalkylcarbonyl wherein the cyclo lower alkyl moiety has 3 to 6 carbon atoms [i.e., cyclo lower alkyl moiety is $C_3$-$C_6$ cycloalkyl of the above-mentioned "cyclo lower alkyl"] (e.g., cyclopropylcarbonyl, cyclobutylcarbonyl, cyclopentylcarbonyl and cyclohexylcarbonyl) and the like.

Examples of the "arylcarbonyl" include arylcarbonyl wherein the aryl moiety has 6 to 10 carbon atoms [that is, the aryl moiety is $C_6$-$C_{10}$ aryl of the above-mentioned "aryl"] (e.g., benzoyl and naphthoyl) and the like.

Examples of the "acylamino" include acylamino wherein the acyl moiety is the above-mentioned "acyl" (e.g., acetylamino, propionylamino, butyrylamino, isobutyrylamino, valerylamino, isovalerylamino, pivaloylamino, hexanoylamino, cyclopropylcarbonylamino, cyclobutylcarbonylamino, cyclopentylcarbonylamino, cyclohexylcarbonylamino, benzoylamino, naphthoylamino and the like) and the like.

Examples of the "lower alkoxy" include straight chain or branched chain alkoxy having 1 to 6 carbon atoms (e.g., methoxy, ethoxy, propoxy, isopropoxy, butoxy, isobutoxy, sec-butoxy, tert-butoxy, pentoxy, tert-pentoxy and hexoxy) and the like, and $C_1$-$C_4$ alkoxy is more preferable. The "lower alkoxy" is optionally substituted, and examples of the "substituent" include halogen, acyl, aminocarbonyl and the like, and the "halogen" and "acyl" are as defined above. When a plurality of substituents are present, they may be the same or different.

The "alkoxy" includes optionally substituted alkyloxy, cyclo lower alkoxy, aralkyloxy and the like.

Examples of "alkyloxy" of the "optionally substituted alkyloxy" include alkyloxy wherein the alkyl moiety has 1 to 10 carbon atoms (e.g., methoxy, ethoxy, propoxy, isopropoxy, butoxy, isobutoxy, sec-butoxy, tert-butoxy, pentyloxy, tert-pentyloxy, hexyloxy, decyloxy and the like) and the like. Examples of the substituent of the "optionally substituted alkyloxy" include halogen, acyl, aminocarbonyl and the like, and the "halogen" and "acyl" are as defined above. The substitutable position of the substituent is not particularly limited. When a plurality of substituents are present, they may be the same or different.

Examples of "cyclo lower alkoxy" include cycloalkoxy wherein the cyclo lower alkyl moiety has 3 to 6 carbon atoms [that is, the cyclo lower alkyl moiety is $C_3$-$C_6$ cycloalkyl of the above-mentioned "cyclo lower alkyl"] (e.g., cyclopropyloxy, cyclobutyloxy, cyclopentyloxy, cyclohexyloxy and the like) and the like.

Examples of "aralkyloxy" include aralkyloxy wherein the aryl moiety has 6 to 10 carbon atoms [that is, the aryl moiety is $C_6$-$C_{10}$ aryl of the above-mentioned "aryl"] and the alkyl moiety has 1 to 6 carbon atoms [that is, the alkyl moiety is $C_1$-$C_6$ alkyl of the above-mentioned "lower alkyl"] (e.g., benzyloxy, phenethyloxy, 1-naphthylmethyloxy, 2-naphthylmethyloxy, 3-phenylpropyloxy, 4-phenylbutyloxy, 5-phenylpentyloxy and the like) and the like.

The "alkoxycarbonyl" includes alkyloxycarbonyl, cyclo lower alkoxycarbonyl, aralkyloxycarbonyl and the like.

Examples of the "alkyloxycarbonyl" include alkyloxycarbonyl wherein the alkyl moiety has 1 to 10 carbon atoms (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, tert-pentyloxycarbonyl, hexyloxycarbonyl and decyloxycarbonyl etc.) and the like.

Examples of the "cyclo lower alkoxycarbonyl" include cycloalkoxycarbonyl wherein the cyclo lower alkyl moiety has 3 to 6 carbon atoms [that is, cyclo lower alkyl moiety is $C_3$-$C_6$ cycloalkyl of the above-mentioned "cyclo lower alkyl"] (e.g., cyclopropyloxycarbonyl, cyclobutyloxycarbonyl, cyclopentyloxycarbonyl, cyclohexyloxycarbonyl) and the like.

Examples of the "aralkyloxycarbonyl" include aralkyloxycarbonyl wherein the aryl moiety has 6 to 10 carbon atoms [that is, the aryl moiety is $C_6$-$C_{10}$ aryl of the above-mentioned "aryl"], and the alkyl moiety has 1 to 6 carbon atoms [that is, the alkyl moiety is $C_1$-$C_6$ alkyl of the above-mentioned "lower alkyl"] (e.g., benzyloxycarbonyl, phenethyloxycarbonyl, 1-naphthylmethyloxycarbonyl, 2-naphthylmethyloxycarbonyl, 3-phenylpropyloxycarbonyl, 4-phenylbutyloxycarbonyl and 5-phenylpentyloxycarbonyl etc.) and the like.

The "optionally substituted carbamoyl" includes unsubstituted carbamoyl, and carbamoyl substituted by 1 or 2 substituents. The "optionally substituted carbamoyl" is represented by the formula —$CONR^4R^5$.

$R^4$ and $R^5$ may be the same or different and each is hydrogen, a group such as lower alkyl, acyl (particularly, lower alkylcarbonyl), alkoxycarbonyl (particularly, lower alkoxycarbonyl), aryl, aralkyl, cyclo lower alkyl, sulfuryl, sulfinyl, phosphoryl, heterocycle and the like, each of which is optionally substituted by hydroxy and the like. The "lower alkyl", "acyl" (particularly, lower alkylcarbonyl), "alkoxycarbonyl" (particularly, lower alkoxycarbonyl), "aryl", "aralkyl", "cyclo lower alkyl" and "heterocycle" are as defined above.

Examples of the "lower alkylsulfonylamino" include alkylsulfonylamino wherein the lower alkyl moiety has 1 to 6 carbon atoms [that is, the lower alkyl moiety is $C_1$-$C_6$ alkyl of the above-mentioned "lower alkyl"] (e.g., methylsulfonylamino, ethylsulfonylamino, propylsulfonylamino, isopropylsulfonylamino, butylsulfonylamino, isobutylsulfonylamino, sec-butylsulfonylamino, tert-butylsulfonylamino, pentylsulfonylamino, tert-pentylsulfonylamino, hexylsulfonylamino and the like) and di(alkylsulfonyl)amino (e.g., di(methylsulfonyl)amino, di(ethylsulfonyl)amino, (methylsulfonyl)(ethylsulfonyl)amino and the like).

Examples of the "lower alkylcarbonyloxy" include alkylcarbonyloxy wherein the lower alkyl moiety has 1 to 6 carbon atoms [that is, the lower alkyl moiety is $C_1$-$C_6$ alkyl of the above-mentioned "lower alkyl"] (e.g., methylcarbonyloxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, pentylcarbonyloxy, tert-pentylcarbonyloxy, hexylcarbonyloxy and the like).

Examples of the "lower alkylamino" include alkylamino wherein the lower alkyl moiety has 1 to 6 carbon atoms [that is, the lower alkyl moiety is $C_1$-$C_6$ alkyl of the above-mentioned "lower alkyl"] (e.g., methylamino; ethylamino, propylamino, isopropylamino, butylamino, isobutylamino, sec-butylamino, tert-butylamino, pentylamino, tert-pentylamino, hexylamino and the like) and dialkylamino (e.g., dimethylamino, diethylamino, dipropylamino, ethylmethylamino, methylpropylamino, ethylpropylamino and the like).

In compound (I), $A^1$ is a residue derived from benzene or a heterocycle containing at least one nitrogen atom or sulfur atom and, for example, a residue derived from benzene, pyridine, pyridazine, pyrimidine, pyrazine, pyrrole, pyrazole, imidazole, oxazole, isoxazole, thiazole, isothiazole, thiophene and the like can be mentioned. The substitutable position of the residue, namely, the position of a bond to Y is not particularly limited.

As $A^1$, a residue derived from benzene, pyridine, pyridazine, pyrimidine, pyrazine, imidazole, thiazole and thiophene is preferable.

In compound (I), $A^2$ is a divalent residue derived from optionally substituted benzene or optionally substituted thiophene.

The "benzene" and "thiophene" optionally have a substituent, and the position of the substitution is not particularly limited. Examples of the "substituent" of the above-mentioned "optionally substituted benzene" and "optionally substituted thiophene" include halogen (e.g., fluorine, chlorine, bromine), lower alkyl (e.g., methyl, ethyl), lower alkoxy (e.g., methoxy), acyl (e.g., acetyl), halogenated alkyl (e.g., trifluoromethyl) and the like. When a plurality of substituents are present, they may be the same or different.

The position of the bond of X and Y to the above-mentioned "benzene" and "thiophene" is not particularly limited. In the case of "benzene", the bond may be at any of the ortho-position, meta-position and para-position, and in the case of "thiophene", the bond may be at any of the 2-position, the 3-position, the 4-position and the 5-position.

In the case of "benzene", compound (I) wherein X and Y are bonded to the above-mentioned "benzene ring" at the meta-position or para-position to each other as shown in the following formula is preferable, and in the case of "thiophene", compound (I) wherein X and Y are bonded to the above-mentioned "thiophene ring" at the 2-position (or the 5-position) and the 5-position (or the 2-position) or at the 2-position (or the 5-position) and the 4-position (or the 3-position), as shown in the following formula, is preferable.

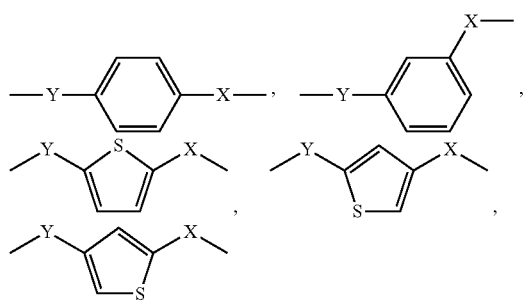

In the formula (I), $B^1$ and $B^2$ are substituents of $A^1$, and the position of substitution is not particularly limited.

In compound (I), $B^1$ is hydrogen, hydroxy, halogen, lower alkyl, cyclo lower alkyl, halogenated lower alkyl, lower alkoxy, acyl, acylamino, optionally substituted carbamoyl, lower alkylsulfonylamino or lower alkylcarbonyloxy (provided when $A^1$ is a residue derived from thiazole, it is not acylamino). The "halogen", "lower alkyl", "cyclo lower alkyl", "halogenated lower alkyl", "lower alkoxy", "acyl", "acylamino", "optionally substituted carbamoyl", "lower alkylsulfonylamino" and "lower alkylcarbonyloxy" are as defined above.

Specific examples of $B^1$ include hydrogen; hydroxy; halogen such as fluorine, chlorine, bromine and the like; lower alkyl such as methyl, ethyl, isopropyl and the like; cyclo lower alkyl such as cyclopropyl and the like; halogenated lower alkyl such as trifluoromethyl and the like; lower alkoxy such as methoxy, ethoxy, trifluoromethoxy, aminocarbonylmethoxy and the like; acyl such as acetyl, ethylcarbonyl and the like; acylamino such as acetylamino, ethylcarbonylamino and the like; optionally substituted aminocarbonyl (carbamoyl) such as aminocarbonyl, N-methylaminocarbonyl, N,N-dimethylaminocarbonyl and the like; lower alkylsulfonylamino such as methylsulfonylamino, ethylsulfonylamino, cyclopropylsulfonylamino, bis(methylsulfonyl)amino and the like; lower alkylcarbonyloxy such as methylcarbonyloxy and the like; and the like.

As $B^1$, hydrogen, methyl, trifluoromethyl, acetylamino, aminocarbonyl (carbamoyl), aminocarbonylmethoxy, methylsulfonylamino, ethylsulfonylamino, methylcarbonyloxy and the like are preferable.

In compound (I), $B^2$ is hydrogen or a functional group containing at least one nitrogen atom (provided when $A^1$ is a residue derived from thiazole, it is not acylamino). Examples of the "functional group containing at least one nitrogen atom" include acylamino; lower alkylamino optionally substituted by amino or acetylamino; optionally substituted heterocyclic group containing at least one nitrogen atom; and methyl substituted by lower alkylamino or optionally substituted heterocyclic group containing at least one nitrogen atom. The "acylamino" and "lower alkylamino" are as defined above. The "heterocyclic group containing at least one nitrogen atom" of the "optionally substituted heterocyclic group containing at least one nitrogen atom" is a heterocyclic group derived from a heterocycle containing at least one nitrogen atom from among the "heterocycle" defined above.

Examples of the substituent of the "optionally substituted heterocyclic group containing at least one nitrogen atom" include methyl, acetyl, hydroxy and the like. When a plurality of substituents are present, they may be the same or different.

Specific examples of $B^2$ include acylamino such as acetylamino, ethylcarbonylamino and the like; lower alkylamino optionally substituted by amino or acetylamino such as methylamino, ethylamino, dimethylamino, diethylamino, dipropylamino, ethylmethylamino, methylpropylamino, ethylpropylamino, ethyl(aminoethyl)amino, ethyl(acetylaminoethyl)amino and the like; heterocyclic group derived from heterocycle containing at least one nitrogen atom optionally substituted by methyl, acetyl and the like, such as pyrrolidine, piperidine, piperazine, homopiperadine, morpholine, triethylenediamine, pyrazole, pyridine, pyridazine, pyrimidine, pyrazine, pyrrole, imidazole, oxazole, isoxazole, thiazole, isothiazole, 2,5-diazabicyclo[2.2.1]heptane and the like; methyl substituted by lower alkylamino or optionally substituted heterocyclic group containing at least one nitrogen atom such as dimethylaminomethyl, pyrrolidylmethyl, piperidylmethyl, piperazinylmethyl, morpholinomethyl and the like; and the like.

As $B^2$, hydrogen, dimethylamino, diethylamino, dipropylamino, ethylmethylamino, methylpropylamino, ethylpropylamino, acetylamino, morpholino, piperidino, piperidinyl, piperazinyl, pyrrolidinyl, pyrazolyl, N-methylpiperazinyl, N-acetylpiperazinyl, N-acetylpiperidinyl, morpholinomethyl, piperazinylmethyl, 2,5-diazabicyclo[2.2.1]hept-2-yl, 5-acetyl-2,5-diazabicyclo[2.2.1]hept-2-yl and the like are preferable.

Alternatively, $B^1$ and $B^2$ are optionally bonded to each other to form a cyclic structure. Examples of the "cyclic structure" include a 5- to 7-membered heterocycle containing, as a ring constituting atom, at least one nitrogen atom (e.g., morpholine, piperazine) and the like. The "cyclic structure" is optionally substituted, and examples of the substituent include oxo, lower alkyl (e.g., methyl), lower halogenated alkyl (e.g., trifluoromethyl), lower acyl (e.g., acetyl) and the like. When a plurality of substituents are present, they may be the same or different.

In compound (I), Y is represented by the formula (II): J-L-M wherein J is a bond, lower alkylene, lower alkenylene, lower alkynylene, $-(CH_2)_n-O-$, $-(CH_2)_n-NH-$, $-(CH_2)_n-CO-$, or $-(CH_2)_n-SO_2-$, L is a bond, $-O-$, $-NH-$, $-CO-$ or $-SO_2-$, M is a bond, lower alkylene, lower alkenylene or lower alkynylene (provided when J is $-(CH_2)_n-O-$, L is not $-O-$, $-NH-$ and $-SO_2-$, when J is $-(CH_2)_n-NH-$, L is not $-O-$ and $-NH-$, when J is $-(CH_2)_n-CO-$, L is not $-CO-$, and when J is $-(CH_2)_n-SO_2-$, L is not $-O-$ and $-SO_2-$ (wherein n is an integer of 0 to 6)). As "lower alkylene", "lower alkenylene" and "lower alkynylene" for J or M, those defined above and the like can be mentioned.

Specific examples of the formula (II): J-L-M include $-(CH_2)_n-$, $-(CH_2)_n-NH-(CH_2)_{n'}-$, $-(CH_2)_n-O-(CH_2)_{n'}-$, $-(CH_2)_n-CO-O-(CH_2)_{n'}-$, $-(CH_2)_n-O-CO-(CH_2)_{n'}-$, $-(CH_2)_n-CO-NH-(CH_2)_{n'}-$, $-(CH_2)_n-NH-CO-(CH_2)_{n'}-$, $-(CH_2)_n-SO_2-NH-(CH_2)_{n'}-$ and $-(CH_2)_n-NH-SO_2-(CH_2)_{n'}-$ (wherein n and n' are each an integer of 0 to 6, n is preferably an integer of 0 to 3, and n' is preferably an integer of 0 to 3), vinyl, ethynylene and the like. Of these, $-(CH_2)_n-$, $-(CH_2)_n-NH-(CH_2)_{n'}-$, $-(CH_2)_n-O-(CH_2)_{n'}-$, $-(CH_2)_n-CO-O-(CH_2)_{n'}-$, $-(CH_2)_n-CO-NH-(CH_2)_{n'}-$ and ethynylene is preferable, $-(CH_2)_n-$ and ethynylene are particularly preferable. More specifically, $-(CH_2)_2-$, $-CH_2-O-$, $-CH_2-NH-$, $-CO-O-$, $-CO-NH-$, ethynylene and the like can be mentioned.

As Y, $-(CH_2)_2-$ and ethynylene are preferable.

In compound (I), X is $-(CH_2)_m-$, $-(CH_2)_m-O-$, $-(CH_2)_m-S-$ or $-(CH_2)_m-NR^2-$ (wherein m is an integer of 0 to 6 and $R^2$ is hydrogen, lower alkyl or acyl). As "lower alkyl" and "acyl" for $R^2$, those defined above and the like can be mentioned. m is preferably an integer of 0 to 3.

As X, a bond ($-(CH_2)_m-$ wherein m is 0), $-CH_2-$, $-(CH_2)_2-$, $-O-$, $-CH_2-O-$, $-(CH_2)_2-O-$, $-CH_2-NH-$, $-(CH_2)_2-NH-$ and the like can be specifically mentioned.

In compound (I), D is $-NR^3-$ wherein $R^3$ is hydrogen, lower alkyl, acyl, or lower alkoxycarbonyl, and as "lower alkyl", "acyl" and "lower alkoxycarbonyl" for $R^3$, those defined above and the like can be mentioned. As D, $-NH-$, $-N(CH_3)-$ and the like can be specifically mentioned, with preference given to $-NH-$.

In compound (I), E is optionally substituted amino, and the "optionally substituted amino" includes unsubstituted amino, and amino substituted by 1 or 2 substituents. The "optionally substituted amino" is represented by the formula: $-NR^6R^7$.

$R^6$ and $R^7$ are the same or different and each is hydrogen, a group such as optionally substituted lower alkyl, acyl (particularly, lower alkylcarbonyl), alkoxycarbonyl, aryl, aralkyl, cyclo lower alkyl, sulfuryl, sulfinyl, phosphoryl, heterocycle, and the like. The "lower alkyl", "acyl" (particularly, lower alkylcarbonyl), "alkoxycarbonyl" (particularly, lower alkoxycarbonyl), "aryl", "aralkyl", "cyclo lower alkyl" and "heterocycle" are as defined above.

Specific examples of $R^6$ and $R^7$ include hydrogen, lower alkyl (e.g., methyl, ethyl and the like), acetyl, butanoyl, decanoyl, 3-hydroxypropanoyl, 6-hydroxyhexanoyl, ethoxycarbonyl, butoxycarbonyl, decyloxycarbonyl, 2-hydroxyethoxycarbonyl and the like.

As E, $-NH_2$ is preferable.

The amino moiety of the "optionally substituted amino" for E may be protected (i.e., substituted) according to the method described in "Protective Groups in Organic Synthesis 3rd Edition" (John Wiley and Sons, 1999), and the like (that is, $R^6$ and $R^7$ may be amino protecting groups).

In compound (I), $-X-CO-D-E$ (molecular terminal) wherein X is a bond, $-O-$, $-CH_2-$, $-(CH_2)_2-$, $-CH_2-O-$, $-(CH_2)_2-O-$, $-CH_2-NH-$, $-(CH_2)_2-NH-$ or $-(CH_2)_3-NH-$; D is $-NH-$; and E is $-NH_2$ and the like are preferable. Specifically, as $-X-CO-D-E$, $-CO-NH-NH_2$, $-O-CO-NH-NH_2$, $-CH_2-CO-NH-NH_2$, $-(CH_2)_2-CO-NH-NH_2$, $-CH_2-O-CO-NH-NH_2$, $-(CH_2)_2-O-CO-NH-NH_2$, $-(CH_2)_3-O-CO-NH-NH_2$, $-CH_2-NH-CO-NH-NH_2$, $-(CH_2)_2-NH-CO-NH-NH_2$, $-(CH_2)_3-NH-CO-NH-NH_2$ and the like are mentioned and preferable.

Specific examples of compound (I) include
N-{4-[2-(4-hydrazinocarbonylmethylphenyl)ethyl]phenyl}acetamide,
N-{3-[2-(4-hydrazinocarbonylmethylphenyl)ethyl]phenyl}acetamide,
N-{2-acetylamino-5-[2-(4-hydrazinocarbonylmethylphenyl)ethyl]pyridin-3-yl}acetamide,
N-{6-[2-(4-hydrazinocarbonylmethylphenyl)ethyl]pyridin-2-yl}acetamide,
N-{4-[2-(4-hydrazinocarbonylmethylphenyl)ethyl]-3-trifluoromethylphenyl}acetamide,
2-{4-[2-(4-hydrazinocarbonylmethylphenyl)ethyl]phenoxy}acetamide,
N-{5-[2-(hydrazinocarbonylmethylphenyl)ethyl]pyrazin-2-yl}acetamide,
N-{2-acetylamino-5-[2-(4-hydrazinocarbonylmethylphenyl)ethyl]phenyl}acetamide,
{4-[2-(1H-imidazol-2-yl)ethyl]phenyl}acetohydrazide,
{4-[2-(3H-imidazol-4-yl)ethyl]phenyl}acetohydrazide,
N-{5-[2-(4-hydrazinocarbonylmethylphenyl)ethyl]pyridin-2-yl}acetamide,
{4-[2-(6-morpholin-4-ylpyridin-3-yl)ethyl]phenyl}acetohydrazide,
2-{4-[2-(4-hydrazinocarbonylmethylphenyl)ethynyl]phenoxy}acetamide,
[4-(1H-imidazol-2-ylethynyl)phenyl]acetohydrazide,
[4-(6-morpholin-4-ylpyridin-3-ylethynyl)phenyl]acetohydrazide,
N-[5-(4-hydrazinocarbonylmethylphenylethynyl)pyrazin-2-yl]acetamide,
N-[2-acetylamino-4-(4-hydrazinocarbonylmethylphenylethynyl)phenyl]acetamide,
N-[3-acetylamino-5-(4-hydrazinocarbonylmethylphenylethynyl)pyridin-2-yl]acetamide,
5-[2-(4-hydrazinocarbonylmethylphenyl)ethyl]pyrazine-2-carboxamide,
2-{4-[2-(2-piperidin-4-yl-1,3-thiazol-4-yl)ethyl]phenyl}acetohydrazide,
2-acetylamino-4-[2-(4-hydrazinocarbonylmethylphenyl)ethyl]phenyl acetate,
{4-[2-(1-methyl-1H-imidazol-2-yl)ethyl]phenyl}acetohydrazide, N-[4-(4-hydrazinocarbonylmethylphenylethynyl)phenyl]acetamide,
N-[3-(4-hydrazinocarbonylmethylphenylethynyl)phenyl]acetamide,
[4-(1-methyl-1H-imidazol-2-ylethynyl)phenyl]acetohydrazide,
2-{4-[(2-piperidin-4-yl-1,3-thiazol-4-yl)ethynyl]phenyl}acetohydrazide,
N-[5-(4-hydrazinocarbonylmethylphenylethynyl)pyridin-2-yl]acetamide,
N-[6-(4-hydrazinocarbonylmethylphenylethynyl)pyridin-2-yl]acetamide,
2-(4-{2-[4-(dimethylamino)phenyl]ethyl}phenyl)acetohydrazide,
2-(4-{2-[4-(diethylamino)phenyl]ethyl}phenyl)acetohydrazide,
2-{4-[2-(4-pyrrolidin-1-ylphenyl)ethyl]phenyl}acetohydrazide,
2-{4-[2-(4-piperidin-1-ylphenyl)ethyl]phenyl}acetohydrazide,
2-{4-[2-(4-piperazin-1-ylphenyl)ethyl]phenyl}acetohydrazide,
2-(4-{2-[4-(4-acetylpiperazin-1-yl)phenyl]ethyl}phenyl)acetohydrazide,
2-(4-{2-[4-(4-methylpiperazin-1-yl)phenyl]ethyl}phenyl)acetohydrazide,
2-{4-[2-(4-morpholin-4-ylphenyl)ethyl]phenyl}acetohydrazide,
2-(4-{2-[3-(dimethylamino)phenyl]ethyl}phenyl)acetohydrazide,
2-{4-[2-(3-pyrrolidin-1-ylphenyl)ethyl]phenyl}acetohydrazide,
2-{4-[2-(4-piperidin-1-ylphenyl)ethyl]phenyl}acetohydrazide,
2-{4-[2-(3-piperazin-1-ylphenyl)ethyl]phenyl}acetohydrazide,
2-(4-{2-[3-(4-acetylpiperazin-1-yl)phenyl]ethyl}phenyl)acetohydrazide,
2-{4-[2-(3-morpholin-4-ylphenyl)ethyl]phenyl}acetohydrazide,
2-(4-{2-[6-(dimethylamino)pyridin-3-yl]ethyl}phenyl)acetohydrazide,
2-{4-[2-(6-pyrrolidin-1-ylpyridin-3-yl)ethyl]phenyl}acetohydrazide,
2-{4-[2-(6-piperidin-1-ylpyridin-3-yl)ethyl]phenyl}acetohydrazide,
2-{4-[2-(6-piperazin-1-ylpyridin-3-yl)ethyl]phenyl}acetohydrazide,
2-(4-{2-[6-(4-acetylpiperazin-1-yl)pyridin-3-yl]ethyl}phenyl)acetohydrazide,
2-(4-{2-[6-(4-methylpiperazin-1-yl)pyridin-3-yl]ethyl}phenyl)acetohydrazide,
2-{4-[2-(6-pyrrolidin-1-ylpyridin-2-yl)ethyl]phenyl}acetohydrazide,
2-{4-[2-(6-piperidin-1-ylpyridin-2-yl)ethyl]phenyl}acetohydrazide,
2-{4-[2-(6-piperazin-1-ylpyridin-2-yl)ethyl]phenyl}acetohydrazide,
2-(4-{2-[6-(4-acetylpiperazin-1-yl)pyridin-2-yl]ethyl}phenyl)acetohydrazide,
2-{4-[2-(6-morpholin-4-ylpyridin-2-yl)ethyl]phenyl}acetohydrazide,
2-{4-[2-(2-pyrrolidin-1-ylpyrimidin-5-yl)ethyl]phenyl}acetohydrazide,
2-{4-[2-(2-piperidin-1-ylpyrimidin-5-yl)ethyl]phenyl}acetohydrazide,
2-{4-[2-(2-piperazin-1-ylpyrimidin-5-yl)ethyl]phenyl}acetohydrazide,
2-(4-{2-[2-(4-acetylpiperazin-1-yl)pyrimidin-5-yl]ethyl}phenyl)acetohydrazide,
2-{4-[2-(2-morpholin-4-ylpyrimidin-5-yl)ethyl]phenyl}acetohydrazide,
2-(4-{2-[4-piperazin-1-yl-2-(trifluoromethyl)phenyl]ethyl}phenyl)acetohydrazide,
2-(4-{2-[4-(4-acetylpiperazin-1-yl)-2-(trifluoromethyl)phenyl]ethyl}phenyl)acetohydrazide,
N-[4-{2-[4-(hydrazinocarbonylmethyl)phenyl]ethyl}-2-(trifluoromethyl)phenyl]acetamide,
N-[3-{2-[4-(hydrazinocarbonylmethyl)phenyl]ethyl}-2-(trifluoromethyl)phenyl]acetamide,
2-{4-[2-(3-oxo-3,4-dihydro-2H-1,4-benzooxazin-6-yl)ethyl]phenyl}acetohydrazide,
2-{4-[2-(4-methyl-3,4-dihydro-2H-1,4-benzooxazin-7-yl)ethyl]phenyl}acetohydrazide,
2-(4-{2-[4-(2,5-diazabicyclo[2.2.1]hept-2-yl)phenyl]ethyl}phenyl)acetohydrazide,
2-(4-{2-[4-(5-acetyl-2,5-diazabicyclo[2.2.1]hept-2-yl)phenyl]ethyl}phenyl)acetohydrazide,
2-(4-{2-[6-(1H-pyrazol-1-yl)pyridin-2-yl]ethyl}phenyl)acetohydrazide,
2-(4-{2-[4-(piperazin-1-ylmethyl)phenyl]ethyl}phenyl)acetohydrazide,
2-(4-{2-[3-(piperazin-1-ylmethyl)phenyl]ethyl}phenyl)acetohydrazide,
2-(4-{2-[4-(morpholin-4-ylmethyl)phenyl]ethyl}phenyl)acetohydrazide,
2-(4-{2-[3-(morpholin-4-ylmethyl)phenyl]ethyl}phenyl)acetohydrazide,
2-(4-{2-[2-(1-acetylpiperidin-4-yl)-1,3-thiazol-4-yl]ethyl}phenyl)acetohydrazide,
N-{5-[2-(4-hydrazinocarbonylmethylphenyl)ethyl]-2-thienyl}acetamide,
2-{4-[2-(5-piperazin-1-ylthiophen-2-yl)ethyl]phenyl}acetohydrazide,
2-(4-{2-[5-(4-acetylpiperazin-1-yl)thiophen-2-yl]ethyl}phenyl)acetohydrazide,
2-{4-[2-(5-morpholin-4-ylthiophen-2-yl)ethyl]phenyl}acetohydrazide,
N-{4-[2-(4-hydrazinocarbonylmethylphenyl)ethyl]-1,3-thiazol-2-yl}ethanesulfonylamide,
N-{4-[2-(4-hydrazinocarbonylmethylphenyl)ethyl]-1,3-thiazol-2-yl}methanesulfonylamide,
2-[4-(2-{4-[ethyl(methyl)amino]phenyl}ethyl)phenyl]acetohydrazide,
2-[4-(2-{4-[methyl(propyl)amino]phenyl}ethyl)phenyl]acetohydrazide,
2-[4-(2-{4-[ethyl(propyl)amino]phenyl}ethyl)phenyl]acetohydrazide,
2-(4-{2-[4-(dipropylamino)phenyl]ethyl}phenyl)acetohydrazide,
2-[4-(2-{4-[(2-aminoethyl)(ethyl)amino]phenyl}ethyl)phenyl]acetohydrazide,
N-[2-(ethyl{4-[2-(4-hydrazinocarbonylmethylphenyl)ethyl]phenyl}amino)ethyl]-acetamide,
2-(4-{2-[6-(diethylamino)pyridin-3-yl]ethyl}phenyl)acetohydrazide,
2-{4-[2-(5-piperazin-1-ylpyridin-2-yl)ethyl]phenyl}acetohydrazide,
2-(4-{2-[5-(4-acetylpiperazin-1-yl)pyridin-2-yl]ethyl}phenyl)acetohydrazide,
2-(4-{2-[5-(diethylamino)pyridin-2-yl]ethyl}phenyl)acetohydrazide, 2-[4-(2-{6-[ethyl(methyl)amino]pyridin-3-yl}ethyl)phenyl]
acetohydrazide,
2-[4-(2-{6-[methyl(propyl)amino]pyridin-3-yl}ethyl)phe-
nyl]acetohydrazide,
2-[4-(2-{6-[ethyl(propyl)amino]pyridin-3-yl}ethyl)phenyl]
acetohydrazide,
2-(4-{2-[6-(dipropylamino)pyridin-3-yl]ethyl}phenyl)ac-
etohydrazide,
2-(4-{2-[6-(diethylamino)pyridin-2-yl]ethyl}phenyl)aceto-
hydrazide,
2-(4-{2-[2-(4-acetylpiperazin-1-yl)-1,3-thiazol-4-yl]
ethyl}phenyl)acetohydrazide,
2-{4-[2-(2-piperazin-1-yl-1,3-thiazol-4-yl)ethyl]
phenyl}acetohydrazide,
2-(4-{2-[6-(4-acetylpiperazin-1-yl)-3-(trifluoromethyl)pyri-
din-2-yl]ethyl}phenyl)acetohydrazide,
2-(4-{2-[6-piperazin-1-yl-3-(trifluoromethyl)pyridin-2-yl]
ethyl}phenyl)acetohydrazide,
2-{4-[2-(6-piperazin-1-ylpyridazin-3-yl)ethyl]
phenyl}acetohydrazide,
2-(4-{2-[6-(4-acetylpiperazin-1-yl)pyridazin-3-yl]
ethyl}phenyl)acetohydrazide,
2-{4-[2-(5-piperazin-1-ylpyrazin-2-yl)ethyl]
phenyl}acetohydrazide,
2-(4-{2-[5-(4-acetylpiperazin-1-yl)pyrazin-2-yl]
ethyl}phenyl)acetohydrazide,
2-{4-[2-(5-piperazin-1-ylpyridin-3-yl)ethyl]
phenyl}acetohydrazide,
2-{4-[2-(6-piperazin-1-ylpyrazin-2-yl)ethyl]
phenyl}acetohydrazide,
2-{4-[2-(4-piperazin-1-ylpyridin-2-yl)ethyl]
phenyl}acetohydrazide,
2-{4-[2-(2-piperazin-1-ylpyridin-4-yl)ethyl]
phenyl}acetohydrazide,
2-{4-[2-(6-piperazin-1-ylpyrimidin-4-yl)ethyl]
phenyl}acetohydrazide,
2-{4-[2-(4-piperazin-1-ylpyrimidin-2-yl)ethyl]
phenyl}acetohydrazide,
4-{2-[5-(4-acetylpiperazin-1-yl)pyridin-2-yl]ethyl}benzyl
hydrazinecarboxylate,
N-(4-{2-[5-(4-acetylpiperazin-1-yl)pyridin-2-yl]
ethyl}benzyl)hydrazinecarboxamide,
4-{2-[5-(4-acetylpiperazin-1-yl)pyridin-2-yl]ethyl}phenyl
hydrazinecarboxylate,
3-{2-[5-(4-acetylpiperazin-1-yl)pyridin-2-yl]ethyl}benzyl
hydrazinecarboxylate,
N-(3-{2-[5-(4-acetylpiperazin-1-yl)pyridin-2-yl]
ethyl}benzyl)hydrazinecarboxamide,
4-{2-[5-(4-acetylpiperazin-1-yl)pyridin-2-yl]ethyl}-3-fluo-
robenzyl hydrazinecarboxylate,
N-(4-{2-[5-(4-acetylpiperazin-1-yl)pyridin-2-yl]ethyl}-3-
fluorobenzyl)hydrazinecarboxamide,
2-(5-{2-[5-(4-acetylpiperazin-1-yl)pyridin-2-yl]
ethyl}thiophen-2-yl)ethyl hydrazinecarboxylate,
5-{2-[5-(4-acetylpiperazin-1-yl)pyridin-2-yl]
ethyl}thiophene-2-carbohydrazide,
N-[2-(5-{2-[5-(4-acetylpiperazin-1-yl)pyridin-2-yl]
ethyl}thiophen-2-yl)ethyl]hydrazinecarboxamide,
2-(3-{2-[5-(4-acetylpiperazin-1-yl)pyridin-2-yl]
ethyl}phenyl)acetohydrazide,
3-(4-{2-[5-(4-acetylpiperazin-1-yl)pyridin-2-yl]
ethyl}phenyl)propanehydrazide,
2-(5-{2-[5-(4-acetylpiperazin-1-yl)pyridin-2-yl]
ethyl}thiophen-2-yl)acetohydrazide,
3-(4-{2-[5-(4-acetylpiperazin-1-yl)pyridin-2-yl]
ethyl}thiophen-2-yl)propanehydrazide,
2-(4-{2-[5-(4-acetylpiperazin-1-yl)pyridin-2-yl]
ethyl}phenyl)ethyl hydrazinedicarboxylate,
N-[2-(4-{2-[5-(4-acetylpiperazin-1-yl)pyridin-2-yl]
ethyl}phenyl)ethyl]hydrazinecarboxamide,
3-(4-{2-[5-(4-acetylpiperazin-1-yl)pyridin-2-yl]
ethyl}thiophen-2-yl)propylhydrazinecarboxylate,
N-[3-(4-{2-[5-(4-acetylpiperazin-1-yl)pyridin-2-yl]
ethyl}thiophen-2-yl)propyl]hydrazinecarboxamide and
the like.

When compound (I) has an asymmetric carbon atom in the structure, the present invention encompasses all enantiomers and diastereomers.

Compound (I) can also be converted to a pharmaceutically acceptable salt. The pharmaceutically acceptable salt in the present invention is not particularly limited as long as it is a nontoxic pharmaceutically acceptable general salt, and a salt with an inorganic or organic base, acid addition salt and the like can be mentioned. Examples of the salt with an inorganic or organic base include alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like) and the like. Examples of the acid addition salt include salts derived from mineral acid (e.g., hydrochloric acid, hydrobromic acid, hydroiodic acid, phosphoric acid, metaphosphoric acid, nitric acid and sulfuric acid), and salts derived from organic acid (e.g., tartaric acid, acetic acid, citric acid, malic acid, lactic acid, fumaric acid, maleic acid, benzoic acid, glycol acid, gluconic acid, succinic acid and arylsulfonic acid (e.g., p-toluenesulfonic acid)) and the like.

The compound of the present invention can be used as a prodrug for the below-mentioned pharmaceutical agent and the like. The term "prodrug" means any compound that can be converted to a VAP-1 inhibitor in the body after administration. The prodrug may be any pharmaceutically acceptable prodrug of the compound of the present invention.

The compound of the present invention can be used as an active ingredient of a pharmaceutical agent such as a VAP-1 inhibitor, a pharmaceutical agent for the prophylaxis or treatment of a VAP-1 associated disease and the like.

The "vascular adhesion protein-1 (VAP-1) associated disease" is not particularly limited as long as it is a disease wherein VAP-1 is related to the expression and/or progress of the disease, and includes a disease selected from the group consisting of vascular hyperpermeable disease [e.g., macular edema (e.g., diabetic and nondiabetic macular edema), aged macular degeneration, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease caused by bacterial or viral infection, and by ophthalmic operation, ocular inflammatory disease caused by physical injury to the eye, symptom caused by ocular inflammatory disease including itching, flare, edema and ulcer, erythema, erythema exsudativum multiforme, erythema nodosum, erythema annulare, scleredema, dermatitis (e.g., psoriasis, allergic lesion, lichen planus, pityriasis rosea, contact dermatitis, atopic dermatitis, pityriasis rubra pilaris), angioneurotic edema, laryngeal edema, glottic edema, subglottic laryngitis, bronchitis, rhinitis, pharyngitis, sinusitis and laryngitis or otitis media], cirrhosis, essential stabilized hypertension, diabetes, arteriosclerosis, endothelial injury (in, for example, diabetes, arteriosclerosis and hypertension), cardiovascular disease relating to diabetes or uremia, pain relating to gout and arthritis, inflammatory disease or symptom of binding tissue (e.g., rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases and juvenile rheumatoid arthritis), inflammatory disease or symptom of gastrointestinal tract [e.g., Crohn's disease, ulcerative colitis, irritable bowel syndrome (e.g., spastic colon), fibrosis of the liver, inflammation of the oral mucous membrane (e.g., stomatitis and recurrent aphthous stomatitis)], inflammatory disease or symptom of central nervous system (e.g., multiple sclerosis, Alzheimer's disease, and ischemia-reperfusion injury relating to ischemic stroke), pulmonary inflammatory disease or symptom (e.g., asthma, adult respiratory distress syndrome, chronic obliterative pulmonary diseases), disease relating to carbohydrate metabolism (e.g., diabetes and complications derived from diabetes) including disease of microvessel and large vessel (e.g., arteriosclerosis, retinopathy, nephropathy, nephrotic syndrome and neuropathy (e.g., multiple neuropathy, mononeuropathy and autonomic neuropathy), foot ulcer, particular problem and increase in infection risk), disease relating to abnormality in the differentiation or function of adipocyte or function of smooth muscle cell (e.g., arteriosclerosis and obesity), vascular disease [e.g., artheromatous atherosclerosis, nonartheromatous atherosclerotic disease, ischemic cardiac diseases including myocardial infarction and peripheral arterial obstruction, Raynaud's disease and Raynaud's phenomenon, thromboangiitis obliterans (Buerger's disease)], chronic arthritis, inflammatory bowel disease, SSAO-mediated complications [e.g., diabetes (e.g., insulin-dependent diabetes (IDDM) and noninsulin-dependent diabetes (NIDDM)) and vascular complications (e.g., heart attack, angina pectoris, apoplexy, amputation, blindness and renal failure)], ophthalmic disease associated with hypoxia or ischemia [e.g., retinopathy of prematurity, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency], angiogenesis and cataract, and the like.

The "prophylaxis or treatment of a vascular adhesion protein-1 (VAP-1) associated disease" means administration of the compound of the present invention having a VAP-1 inhibitory action (i.e., VAP-1 inhibitor) to a subject of administration for the purpose of the treatment (including prophylaxis, amelioration of symptom, reduction of symptom, prevention of progress and cure) of the above-mentioned VAP-1 associated disease.

The subjects of the administration of the pharmaceutical agent, pharmaceutical composition, VAP-1 inhibitor, pharmaceutical agent for the prophylaxis or treatment of a VAP-1 associated disease in the present invention (hereinafter these are also collectively referred to as the pharmaceutical agent of the present invention) are various animals (e.g., mammals such as human, mouse, rat, swine, dog, cat, horse, bovine and the like, particularly human) and the like.

The pharmaceutical agent of the present invention can be administered by any route. The administration route in the present invention includes systemic administration (e.g., oral administration or injection administration), topical administration, periocular administration (e.g., sub-Tenon's capsule administration), conjunctiva administration, intraocular administration, subretinal administration, suprachoroidal administration and retrobulbar administration and the like. The administration mode of the pharmaceutical agent of the present invention can be appropriately determined according to whether the application to a VAP-1 associated disease is prophylactic or therapeutic and the like.

The pharmaceutical agent of the present invention is preferably administered rapidly after a subject of administration such as a mammal, particularly human, is diagnosed to have a risk of a VAP-1 associated disease (prophylactic treatment), or administered rapidly after the subject of administration shows the onset of a VAP-1 associated disease (therapeutic treatment). The treatment plan can be appropriately determined according to the kind of the active ingredient to be used, dose, administration route, cause and, where necessary, level of awareness of the VAP-1 associated disease and the like.

As an administration method of the pharmaceutical agent of the present invention, a method known per se for general pharmaceutical agents can be used. The administration route may be an appropriately effective one and one or more routes can be used. Accordingly, the above-mentioned administration routes are mere exemplifications free of any limitation.

The dose of the pharmaceutical agent of the present invention for a subject of administration such as animal including human, particularly human, is an amount sufficient to provide a desired response in the subject of administration for a reasonable period of time. The dose is appropriately determined according to various factors including the strength of the active ingredient to be used, age, kind, symptom, disease state, body weight and severity of disease of the subject of administration, the route, timing and frequency of the administration and the like. The dose can also be appropriately controlled according to the route, timing and frequency of the administration and the like. Depending on the symptom or disease state, a long-term treatment involving plural times of administration may be necessary.

The dose and administration schedule can be determined by a technique within the range known to those of ordinary skill in the art. In general, the prophylaxis or treatment is started from a dose lower than the optimal dose of the compound. Thereafter, the dose is gradually increased until the optimal effect is obtained under the circumstances. The pharmaceutical agent of the present invention (VAP-1 inhibitor and the like) can be administered generally at a dose of about 0.03 ng/kg body weight/day—about 300 mg/kg body weight/day, preferably about 0.003 µg/kg body weight/day—about 10 mg/kg body weight/day, by a single administration or 2-4 portions a day or in a sustained manner.

The pharmaceutical composition of the present invention preferably contains a "pharmaceutically acceptable carrier" and, as an active ingredient, the compound of the present invention (VAP-1 inhibitor) in an amount sufficient for the prophylactic or therapeutic treatment of a VAP-1 associated disease. The carrier may be any which is generally used as a pharmaceutical agent and is not particularly limited except when limited by physicochemical items for consideration (e.g., solubility, and lack of reactivity with the compound) and administration route.

While the amount of the compound of the present invention in the pharmaceutical agent of the present invention varies depending on the formulation of the composition, it is generally 0.00001-10.0 wt %, preferably 0.001-5 wt %, more preferably 0.001-1 wt %.

The administration form of the pharmaceutical agent of the present invention is not particularly limited, and can be administered in various forms to achieve the desired VAP-1 inhibitory action. The pharmaceutical agent of the present invention is formulated using the compound of the present invention alone or in a combination with a pharmaceutically acceptable carrier or an additive such as diluent and the like, and orally or parenterally administered. The characteristics and property of the preparation are determined by the solubility and chemical property of the active ingredient to be used, selected administration route and standard pharmaceutical practice. The preparation to be used for oral administration may be a solid dosage forms (e.g., capsule, tablet, powder) or a liquid form (e.g., solution or suspension) and the like. The preparation to be used for parenteral administration may be an injection, drip infusion, and the like, which are in the form of an aseptic solution or suspension. The solid oral preparation can contain a general excipient and the like. The liquid oral preparation can contain various aromatic, colorant, preservative, stabilizer, solubilizer, suspending agent and the like. The parenteral preparation is, for example, an aseptic aqueous or nonaqueous solution or suspension, and can contain particular various preservatives, stabilizer, buffer agent, solubilizer, suspending agent and the like. Where necessary, various isotonicity agents may be added.

The pharmaceutical agent of the present invention may contain other pharmaceutically active compound as long as it does not inhibit the effect of the invention.

The pharmaceutical agent of the present invention can be simultaneously administered with other pharmaceutically active compound as long as it does not inhibit the effect of the invention. The "simultaneous administration" means administration of other pharmaceutically active compound before or simultaneous (e.g., in the same or different preparation) or after administration of the pharmaceutical agent of the present invention. For example, corticosteroid, prednisone, methyl prednisone, dexamethasone or triamcinolone acetonide or noncorticosteroid anti-inflammatory compound (e.g., ibuprofen or flurbiprofen) can be simultaneously administered. Similarly, vitamin and mineral (e.g., zinc, antioxidant (e.g., carotenoid (e.g., xanthophyll carotenoid-like zeaxanthine or lutein))) and micronutrient and the like can be simultaneously administered.

The compound of the present invention is useful for the production of a pharmaceutical agent such as a VAP-1 inhibitor and a pharmaceutical agent for the prophylaxis or treatment of a VAP-1 associated disease.

Now the production methods of the compound of the present invention are explained.

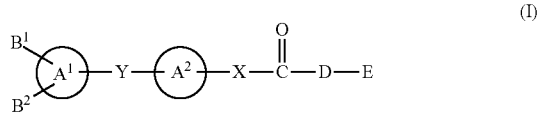

(I)

wherein each symbol is as defined above.

The above-mentioned formula (I) can be re-described as the following formula (I').

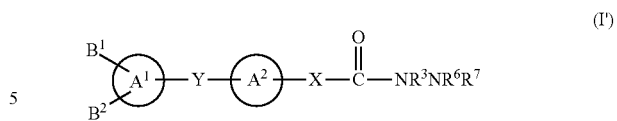

(I')

wherein each symbol is as defined above.

A compound represented by the formula (I') (hereinafter also referred to as compound (I')) can be produced by to chemically bonding 3 compounds (1), (2) and (3) as partial structures, as shown in the following scheme 1.

Compounds (1), (2) and (3) may be in the form of salts thereof. As to the order of bonding, a method including bonding compound (1) and compound (2), and then bonding compound (3), and a method including first bonding compound (2) and compound (3), and finally bonding compound (1) can be employed, and both orders result in the production of compound (I'). Functional group transformation of the side chain and the like after bonding, where necessary, may result in the conversion to the target molecule structure. In addition, deprotection of compound (I') or conversion to a pharmaceutically acceptable salt as necessary may be performed.

The production method of compound (I') is not limited to the above, and the artisan can appropriately modify the steps according to a general method known per se.

Scheme 1

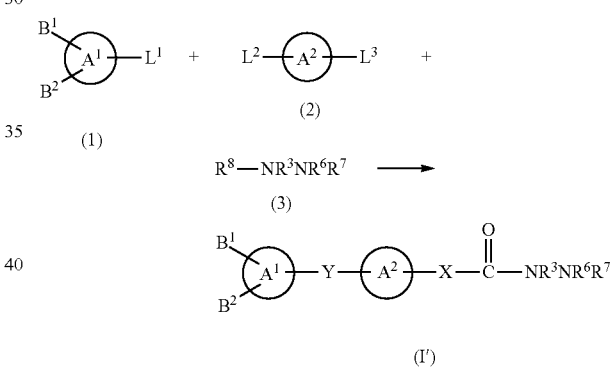

wherein $A^1$, $A^2$, $B^1$, $B^2$, X, $R^3$, $R^6$ and $R^7$ are as defined above, $R^8$ is hydrogen, 1H-imidazol-1-ylcarbonyl etc., $L^1$ is a reactive functional group which forms a chemical bond with $L^2$ of compound (2) to form Y, $L^2$ is a reactive functional group which forms a chemical bond with $L^1$ of compound (1) to form Y, and $L^3$ is a functional group that reacts with compound (3) to construct an acylhydrazine structure at the molecular terminal of compound (I') and constructs a —X—CO— structure.

$L^1$ of compound (1) is a reactive functional group necessary for forming a chemical bond with $L^2$ of compound (2) to form Y. Examples thereof include, but are not limited to, —$(CH_2)_u$—CH=$CH_2$, —$(CH_2)_u$—C≡CH, —$(CH_2)_u$—CHO, —$(CH_2)_u$-halogen, —$(CH_2)_u$—OH, —$(CH_2)_u$—COOH, —$(CH_2)_u$—CO-halogen, —$(CH_2)_u$—$NH_2$, —$(CH_2)_u$—$SO_3H$, —$(CH_2)_u$—$SO_2$-halogen, —$(CH_2)_u$—O-acyl derived from —$(CH_2)_u$—OH (e.g., —$(CH_2)_u$—O-acetyl and the like), —$(CH_2)_u$-sulfonic acid ester (e.g., —$(CH_2)_u$—$OSO_2CH_3$ and the like), Wittig reagent derived from —$(CH_2)_u$-halogen and the like, and the like (wherein u is an integer of 0-6 and halogen is chlorine, bromine or iodine).

Compound (1) or a salt thereof may be a commercially available compound, or can be produced from a commercially available compound by one or several steps of general organic reactions as shown in the following Production Examples, or according to a method known per se.

$L^2$ of compound (2) is a reactive functional group necessary for forming a chemical bond with $L^1$ of compound (1) to form Y. Examples thereof include, but are not limited to, —$(CH_2)_v$—CH═$CH_2$, —$(CH_2)_v$—C≡CH, —$(CH_2)_v$—CHO, —$(CH_2)_v$-halogen, —$(CH_2)_v$—OH, —$(CH_2)_v$—COOH, —$(CH_2)_v$—CO-halogen, —$(CH_2)_v$—$NH_2$, —$(CH_2)_v$—$SO_3H$, —$(CH_2)_v$—$SO_2$-halogen, —$(CH_2)_v$—O-acyl derived from —$(CH_2)_v$—OH (e.g., —$(CH_2)_v$—O-acetyl and the like), —$(CH_2)_v$-sulfonic acid ester (e.g., —$(CH_2)_v$—$OSO_2CH_3$ and the like), Wittig reagent derived from —$(CH_2)_v$- halogen and the like, and the like (wherein v is an integer of 0-6 and halogen is chlorine, bromine or iodine).

$L^3$ of compound (2) is a functional group necessary for reacting with compound (3) and constructing a —X—CO— structure to construct an acylhydrazine structure at the molecular terminal of compound (I'). It is, for example, —$(CH_2)_m$—COOH, —$(CH_2)_m$—CO-halogen, —$(CH_2)_m$—OH, —$(CH_2)_m$—$NH_2$, —$(CH_2)_m$—SH and the like (wherein m is as defined above and halogen is chlorine, bromine or iodine), or a functional group capable of developing these functional groups by a reaction such as deprotection, hydrolysis, oxidation reduction and the like. Examples thereof include, but are not particularly limited to, —$(CH_2)_m$—OSi(t-$C_4H_9$)($CH_3$)$_2$, —$(CH_2)_m$—OTHP wherein THP is tetrahydropyran), —$(CH_2)_m$—COOMe, —$(CH_2)_m$—CHO, —$(CH_2)_m$—$NHCOCH_3$, —$(CH_2)_m$—NHCOO(t-$C_4H_9$) and the like (wherein m is as defined above).

Compound (2) or a salt thereof may be a commercially available compound, or can be produced from a commercially available compound by one or several steps of general organic reactions as shown in the following Production Examples, or according to a method known per se described in WO2004/067521, 2006/28269 and the like.

Compound (3) is a hydrazine equivalent or hydrazinocarbonyl equivalent to construct an acylhydrazine structure at the molecular terminal of compound (I'). It may be commercially available or can also be produced according to a method known per se. In addition, $R^3$, $R^6$ and $R^7$ may be protecting groups, in which case they are finally substituted to hydrogen atoms. The protecting groups for $R^3$, $R^6$ and $R^7$ are introduced to avoid an unnecessary reaction and are functional groups to be removed by the final step. Examples thereof include —OCO—C($CH_3$)$_3$ shown in the following Production Examples and the like.

$R^8$ is hydrogen, 1H-imidazol-1-ylcarbonyl and the like, and a suitable reactive functional group is used according to the molecular terminal structure.

First, a reaction example to construct Y in compound (I') is explained.

When compound (I') wherein Y is a carbon chain is produced, compound (1) or a salt thereof is chemically bonded to compound (2) or a salt thereof (or a compound obtained by condensation of compound (2) and compound (3) in advance) utilizing Sonogashira-Hagiwara acetylene coupling, Sonogashira-Castero-Stephens acetylene coupling, Mizorogi-Heck reaction, Wittig reaction, Horner-Emmons reaction, aldol condensation reaction, Claisen condensation, or a similar carbon-carbon bond formation reaction to construct Y containing lower alkenylene or lower alkynylene. Appropriate salts of compound (1) and (2) may be the same as those exemplified with regard to compound (I). While various carbon-carbon bond forming reactions are utilizable, as preferable examples, when an acetylene coupling reaction is utilized, it is desirable that $L^1$ is —$(CH_2)_u$-halogen and $L^2$ is —$(CH_2)_v$—C≡CH, or $L^1$ is —$(CH_2)_u$—C≡CH and $L^2$ is —$(CH_2)_v$-halogen (wherein u and v are as defined above and halogen is chlorine, bromine or iodine). The reaction is generally performed in a general solvent such as N,N-dimethylformamide, dimethyl sulfoxide, acetonitrile and tetrahydrofuran, or other organic solvent that does not adversely influence the reaction, or a mixture thereof using a transition metal catalyst such as palladium (II) acetate, bis(acetonitrile) dichloropalladium (II) and the like, and a compound to be a ligand of the transition metal catalyst such as triphenylphosphine, 4,5-bis(diphenylphosphino)-9,9-dimethylxanthene, 2-dicyclohexylphosphino-2',4',6'-triisopropylbiphenyl and the like, and generally a base such as cesium carbonate, diisopropylamine and the like is added. The reaction temperature is not particularly important, and the reaction is performed at room temperature, under cooling or under heating.

When a Wittig reaction or a similar reaction is utilized as the carbon-carbon bond formation reaction, desirable examples include —$(CH_2)_u$—CHO for $L^1$ and a phosphonium salt (Wittig reagent) derived from —$(CH_2)_v$-halogen etc. for $L^2$, or a phosphonium salt (Wittig reagent) derived from —$(CH_2)_u$-halogen etc. for $L^1$ and —$(CH_2)_v$—CHO for $L^2$ (wherein u and v are as defined above, and halogen is chlorine, bromine or iodine). The reaction is generally performed in a general solvent such as N,N-dimethylformamide, dimethyl sulfoxide, tetrahydrofuran and dichloromethane, or other organic solvent that does not adversely influence the reaction, or a mixture thereof, in the presence of a general base such as sodium ethoxide, potassium tert-butoxide, butyllithium, sodium hydride, sodium hydroxide and the like. The reaction temperature is not particularly important, and the reaction is performed at room temperature, under cooling or under heating.

Even when any carbon-carbon bond formation reaction is used, the resultant product is isolated or purified by a known separation or purification means such as concentration, concentration under reduced pressure, solvent extraction, crystallization, recrystallization, phase transfer, chromatography and the like, or can also be converted to a salt similar to those exemplified for compound (I).

Where necessary, lower alkenylene or lower alkynylene produced in the above-mentioned carbon-carbon bond formation reaction can be hydrogenated to convert to lower alkylene. When Y including lower alkenylene or lower alkynylene is to be converted to an alkylene bond, a hydrogenation reaction is performed according to a general method in the presence of various homogeneous catalysts or heterogeneous catalysts. Particularly, catalytic hydrogenation using a heterogeneous catalyst is preferable, which is performed in the presence of a catalyst such as palladium carbon. While the reaction is performed in a reaction container such as a flask and the like or an autoclave, it can also be performed using a continuous hydrogenation reactor using a cartridge type reaction catalyst (trade name: H-CUBE, manufactured by ThalesNano) and the like.

When Y is to be converted to lower alkenylene, an alkenylene structure obtained by Wittig reaction of compound (1) and compound (2) and the like may be directly utilized, alkynylene obtained by Sonogashira-Castero-Stephens acetylene coupling and the like is partially reduced (triple bond to double bond) using Lindlar catalyst and the like.

When Y is to be converted to lower alkynylene, an alkynylene structure obtained by Wittig reaction of compound (1) and compound (2) and the like may be directly used. However, it can also be constructed by subjecting alkenylene obtained by Wittig reaction and the like to halogenation (for example, bromination), then dehydrohalogenation (for example, dehydrobromination) using a base and the like, according to a general method.

When compound (I') wherein Y is ester, amide or sulfonamide is produced, compound (1) or a salt thereof is condensed with compound (2) or a salt thereof (or a compound obtained by condensation of compound (2) and compound (3) in advance) to construct ester or amide bond. In this case, $L^1$ is —$(CH_2)_u$—OH, —$(CH_2)_u$—$NH_2$, —$(CH_2)_u$-halogen and the like and $L^2$ is —$(CH_2)_v$—COOH, —$(CH_2)_v$—CO-halogen, —$(CH_2)_v$—$SO_3H$, —$(CH_2)_v$—$SO_2$-halogen and the like, or $L^1$ is —$(CH_2)_u$—COOH, —$(CH_2)_u$—CO-halogen, —$(CH_2)_u$—$SO_3H$, —$(CH_2)_u$—$SO_2$-halogen and the like and $L^2$ is —$(CH_2)_v$—OH, —$(CH_2)_v$—$NH_2$, —$(CH_2)_v$-halogen and the like, and Y can be constructed based on a general organic synthesis method (wherein u and v are as defined above, and halogen is chlorine, bromine or iodine). The reaction is generally performed in a general solvent such as dichloromethane, acetonitrile, tetrahydrofuran, diethyl ether and N,N-dimethylformamide, and any other organic solvent that does not adversely influence the reaction, or a mixture thereof. Where necessary, a condensation agent such as 1-ethyl-3-(3-dimethylaminopropyl)carbodiimide hydrochloride, N,N'-dicyclohexylcarbodiimide, 1,1'-carbonyldiimidazole and the like is used. The reaction may be performed in the presence of an additive such as N,N-dimethyl-4-aminopyridine, 1-hydroxybenzotriazole, 1-hydroxysuccinimide and 3,4-dihydro-3-hydroxy-4-oxo-1,2,3-benzotriazine. The reaction temperature is not particularly important, and the reaction is performed at room temperature, under cooling or under heating.

When compound (I') wherein Y is amine is produced, $L^1$ is —$(CH_2)_u$—$NH_2$, or a salt thereof and the like and $L^2$ is —$(CH_2)_v$—CHO, —$(CH_2)_v$-halogen and the like, or $L^1$ is —$(CH_2)_u$—CHO, —$(CH_2)_u$-halogen and the like and $L^2$ is —$(CH_2)_v$—$NH_2$, or a salt thereof and the like, and Y can be constructed based on a general organic synthesis method (wherein u and v are as defined above, and halogen is chlorine, bromine or iodine). Generally, according to conventional method, amine and aldehyde is condensed to give a Schiff base, which is reduced by sodium borohydride, sodium cyanoborohydride and the like in a general solvent such as tetrahydrofuran, diethyl ether, alcohol and the like, or any other organic solvent that does not adversely influence the reaction, or a mixture thereof as a reaction solvent, whereby a secondary amine structure is constructed. The same structure is also constructed by condensation reaction of amine and a halogen compound. When a halogen compound is utilized, a base such as N,N-diisopropylamine, triethylamine, potassium carbonate and the like is used as a reaction agent, a general solvent such as tetrahydrofuran, acetonitrile and N,N-dimethylformamide, or other organic solvent that does not adversely influence the reaction, or a mixture thereof is used as a reaction solvent. The reaction temperature is not particularly important, and the reaction is performed at room temperature, under cooling or under heating. The resultant product can also be converted to a salt similar to those exemplified for compound (I).

When compound (I') wherein Y is an ether bond is produced, $L^1$ is —$(CH_2)_u$—OH and the like and $L^2$ is —$(CH_2)_v$—OH, —$(CH_2)_v$-halogen, —$(CH_2)_v$-sulfonic acid ester and the like, or $L^1$ is —$(CH_2)_u$—OH, —$(CH_2)_u$-halogen, —$(CH_2)_u$-sulfonic acid ester and the like and $L^2$ is —$(CH_2)_v$—OH and the like, and Y can be constructed based on a general organic synthesis method (wherein u and v are as defined above, and halogen is chlorine, bromine or iodine). An ether bond can be formed by Williamson method, ether synthesis method from aromatic halide using a copper catalyst and the like, Mitsunobu reaction, other production method known per se. These reactions are generally performed in a general solvent such as acetonitrile, dichloromethane, acetone, tetrahydrofuran and N,N-dimethylformamide, or any other organic solvent that does not adversely influence the reaction, or a mixture thereof. The reaction temperature is not particularly important, and the reaction is performed at room temperature, under cooling or under heating. The resultant product can also be converted to a salt similar to those exemplified for compound (I).

Now a reaction example for introducing a hydrazinocarbonyl group into the molecular terminal of compound (I') is explained.

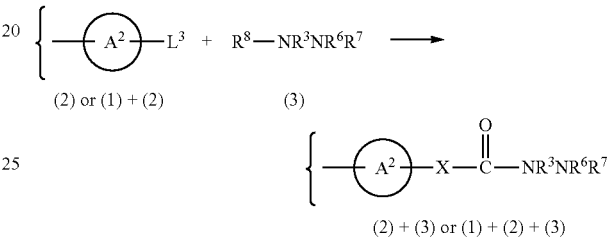

Scheme 2

When X is a carbon chain or a single bond, i.e., —$(CH_2)_m$—, $R^8$ is generally hydrogen, and $L^3$ is —$(CH_2)_m$—COOH, —$(CH_2)_m$—CO-halogen and the like (wherein m is as defined above and halogen is chlorine, bromine or iodine), when $L^3$ is —$(CH_2)_m$—COOH, a hydrazinocarbonyl group can be introduced into the molecular terminal by condensation with compound (3) using a condensation agent such as 1,1'-carbonyldiimidazole, N,N'-dialkylcarbodiimide and the like. When $L^3$ is —$(CH_2)_m$—CO-halogen, it is not particularly necessary to use a condensation agent, and a hydrazinocarbonyl group can be introduced by direct condensation in the presence of a base such as tertiary amine and the like. When compound (3) has high nucleophilic reactivity, a hydrazinocarbonyl group can also be introduced by a direct reaction with $L^3$ which is carboxylate such as —$(CH_2)_m$—$COOCH_3$ and the like. The reaction is generally performed in a general solvent such as dichloromethane, acetonitrile, tetrahydrofuran and N,N-dimethylformamide, or any other organic solvent that does not adversely influence the reaction, or a mixture thereof. The reaction temperature is not particularly important, and the reaction is performed at room temperature, under cooling or under heating. The above shows examples and the synthesis method is not limited thereto. Various organic reactions for forming hydrazide and amide bond can be utilized.

In addition, $L^3$: —$(CH_2)_m$—COOH can be constructed by hydrolysis of carboxylate such as —$(CH_2)_m$—$COOCH_3$ and the like, oxidation reaction of —$(CH_2)_m$—CHO, —$(CH_2)_m$—$CH_2OH$ and the like, as a part of the synthesis step. In addition, $L^3$: —$(CH_2)_m$—CO-halogen can be obtained by treating —$(CH_2)_m$—COOH with a halogenating agent such as thionyl chloride, oxalyl chloride and the like.

When compound (I') wherein X is —$(CH_2)_m$—NH— is to be produced, a structure of —$(CH_2)_m$—$NH_2$ (wherein m is as defined above) is necessary as $L^3$. It may be incorporated into compound (2) in advance from the stage of starting materials as an amino group or protected amino group, or may be constructed, as a part of the synthesis step, by reduction of the nitro group and the like. The target structure can be constructed by treating amino group with, for example, tert-butyl 2-(1H-imidazol-1-ylcarbonyl)hydrazinecarboxylate [compound (3): $R^6$=CO—C—$(CH_3)_3$, $R^3$=$R^7$=hydrogen, $R^8$=1H-imidazol-1-ylcarbonyl] prepared from 1,1'-carbonyldiimidazole and tert-butoxy carbazate and the like. The reaction is generally performed in a general solvent such as dichloromethane, acetonitrile, tetrahydrofuran and N,N-dimethylformamide, or any other organic solvent that does not adversely influence the reaction, or a mixture thereof. The reaction temperature is not particularly important, and the reaction is performed at room temperature, under cooling or under heating.

When compound (I') wherein X is —$(CH_2)_m$—O— is to be produced, a structure of —$(CH_2)_m$—OH (wherein m is as defined above) is necessary as $L^3$. It may be incorporated into compound (2) in advance from the stage of starting materials as a hydroxyl group or protected hydroxyl group, or may be constructed, as a part of the synthesis step, by reduction of the corresponding aldehyde or carboxylic acid, or carboxylate. The target structure can be constructed by treating a hydroxyl group with, for example, 1,1'-carbonyldiimidazole to give 1H-imidazole-1-carboxylate, which is then treated with tert-butoxy carbazate or hydrazine, or treating a hydroxyl group with tert-butyl 2-(1H-imidazol-1-ylcarbonyl)hydrazinecarboxylate [compound (3): $R^6$=CO—C—$(CH_3)_3$, $R^3$=$R^7$=hydrogen, $R^8$=1H-imidazol-1-ylcarbonyl] prepared froth 1,1'-carbonyldiimidazole and tert-butoxy carbazate and the like. The reaction is generally performed in a general solvent such as dichloromethane, acetonitrile, tetrahydrofuran and N,N-dimethylformamide, or any other organic solvent that does not adversely influence the reaction, or a mixture thereof. The reaction temperature is not particularly important, and the reaction is performed at room temperature, under cooling or under heating.

When compound (I') wherein X is —$(CH_2)_m$—S— is to be produced, a structure of —$(CH_2)_m$—SH (wherein m is as defined above) is necessary as $L^3$. It may be incorporated into compound (2) in advance from the stage of starting materials as a sulfanyl group or protected sulfanyl group, or may be constructed, as a part of the synthesis step, from the corresponding halide and the like by general organic synthesis method. For example, the target structure can be constructed by treating the sulfanyl group with 1,1'-carbonyldiimidazole to give 1H-imidazole-1-carbothioate, and then treating with tert-butoxy carbazate or hydrazine. The reaction is generally performed in a general solvent such as dichloromethane, acetonitrile, tetrahydrofuran and N,N-dimethylformamide, or any other organic solvent that does not adversely influence the reaction, or a mixture thereof. The reaction temperature is not particularly important, and the reaction is performed at room temperature, under cooling or under heating.

It is desirable to incorporate $B^1$ and $B^2$ (substituent of $A^1$) of compound (I') in advance into compound (1), which is a starting material, or incorporate a synthetic equivalent, and perform necessary transformation of functional group in the synthesis process.

The thus-produced compound (I') can be isolated or purified by a known separation or purification means such as crystallization, recrystallization, phase transfer, chromatography and the like. In addition, it can be converted to a pharmaceutically acceptable salt.

EXAMPLE

The present invention is explained in more detail in the following by referring to Examples (Production Examples and Experimental Examples), which are not to be construed as limitative. The structural formulas, property data and chemical structure data of Production Example compound are collectively shown in Table 1.

While the "room temperature" in the following Production Examples generally means about 10° C.—about 30° C., it is not particularly limited strictly. The mixing ratio of liquid is in a volume ratio. Unless otherwise specified, "%" means weight percent. For silica gel column chromatography, chromatography silica gel (Art. 7734 etc.) manufactured by Merck & Co. Inc. or chromatography silica gel (BW-300SP, FL-60D, DM-2035 etc.) manufactured by FUJI SILYSIA CHEMICAL LTD. was used; however, silica gel is not particularly limited and products of other manufacturers can be used. For mass spectrum (MS) was measured by atmospheric pressure chemical ionization (APCI) method or electrospray ionization (ESI) method. $^1$H-NMR spectrum was measured with tetramethylsilane (0 ppm) or $d_6$-dimethyl sulfoxide (2.49 ppm) as an internal standard, and all δ values are shown in ppm. The following abbreviations are used for indication of the measurement results. s: singlet, d: doublet, dd: doublet-doublet, dt: doublet-triplet, t: triplet, tt: triplet-triplet, q: quartet, tq: triplet-quartet, m: multiplet, brs: broad singlet, brt: broad triplet, J: coupling constant, Hz: Hertz.

In addition, the abbreviations in the Production Examples mean the following.

Boc: tert-butoxycarbonyl

EDC: 1-ethyl-3-(3-dimethylaminopropyl)carbodiimide hydrochloride

HOBt: 1-hydroxybenzotriazole monohydrate

TMS: trimethylsilyl

DMF: N,N-dimethylformamide

TBAF: tetra-n-butylammonium fluoride

THF: tetrahydrofuran

Xantphos: 4,5-bis(diphenylphosphino)-9,9-dimethyl-xanthene $Pd_2bda_3$: tris(dibenzylideneacetone)dipalladium (0)-chloroform adduct Ac: acetyl BINOL: 1,1'-bi-2-naphthol TFA: trifluoroacetic acid NBS: N-bromosuccinimide The starting material compounds used in the following Production Examples can be obtained as commercially available products or can be produced from commercially available compounds by one or several steps of general organic reactions as shown in the following Production Examples, or according to a method known per se described in WO2004/067521 and the like.

Production Example 1

N-{4-[2-(4-hydrazinocarbonylmethylphenyl)ethyl]phenyl}acetamide hydrochloride

Step 1

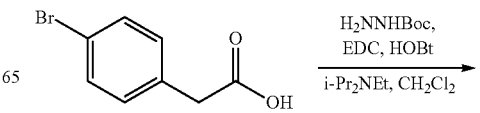

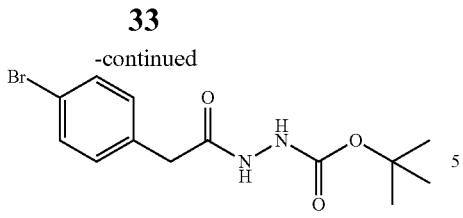

2-(4-Bromophenyl)acetic acid (20 g, 93 mmol), tert-butyl carbazate (14.7 g, 111 mmol), 1-ethyl-3-(3-dimethylaminopropyl)carbodiimide hydrochloride (21.4 g, 112 mmol) and 1-hydroxybenzotriazole monohydrate (17.1 g, 112 mmol) were dissolved in dichloromethane (400 ml), and N,N-diisopropylethylamine (80 ml) was added. After stirring at room temperature for 16 hrs, the reaction mixture was washed with 1M hydrochloric acid and saturated aqueous sodium hydrogen carbonate solution, dried over anhydrous magnesium sulfate and concentrated under reduced pressure. The concentration residue was purified by silica gel column chromatography (dichloromethane:methanol=99:1→90:10) to give tert-butyl 2-[(4-bromophenyl)acetyl]hydrazinecarboxylate (27 g, yield 88%) as a white solid.

$^1$H-NMR (DMSO-d$_6$) δ(ppm): 9.79 (brs, 1H), 8.75 (brs, 1H), 7.50 (d, J=8.4 Hz, 2H), 7.24 (d, J=8.4 Hz, 2H), 3.40 (s, 2H), 1.45-1.20 (brs, 9H).

Step 2

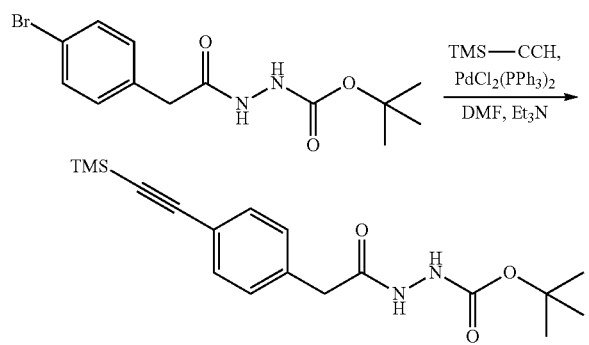

To a solution of tert-butyl 2-[(4-bromophenyl)acetyl]hydrazinecarboxylate (10 g, 30.4 mmol), copper (I) iodide (579 mg, 3.04 mmol), dichlorobis(triphenylphosphine)palladium (II) (2.13 g, 3.03 mmol) and triethylamine (8.5 ml, 61.0 mmol) in anhydrous N,N-dimethylformamide (50 ml) was added ethynyltrimethylsilane (6.3 ml, 45.5 mmol). After stirring overnight at 50° C., water was added to the reaction mixture, and the mixture was extracted with ethyl acetate and concentrated under reduced pressure. The concentrated residue was purified by silica gel column chromatography (ethyl acetate:hexane=30:70→35:65) to give tert-butyl 2-({4-[(trimethylsilyl)ethynyl]phenyl}acetyl)hydrazinecarboxylate (7.1 g, yield 68%) as a greeny brown solid.

Step 3

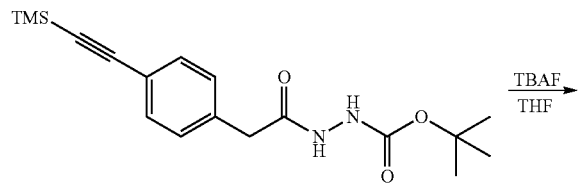

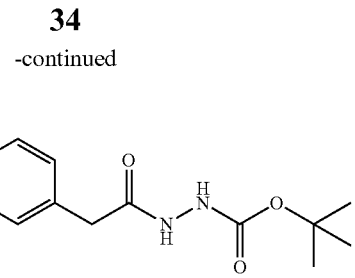

To a solution of tert-butyl 2-({4-[(trimethylsilyl)ethynyl]phenyl}acetyl)hydrazinecarboxylate (10.1 g, 29.4 mmol) in anhydrous tetrahydrofuran (150 ml) was added at 0° C. tetra-n-butylammonium fluoride (1M tetrahydrofuran solution, 29.4 ml, 29.4 mmol). After stirring at 0° C. for 45 mins, the mixture was concentrated under reduced pressure. Water was added to the residue and the mixture was extracted with ethyl acetate, and the extract was concentrated under reduced pressure. The concentrated residue was purified by silica gel column chromatography (ethyl acetate:hexane=1:1) to give tert-butyl 2-[(4-ethynylphenyl)acetyl]hydrazinecarboxylate (7.7 g, yield 96%) as a yellow solid.

$^1$H-NMR (DMSO-d$_6$) δ(ppm): 9.80(brs, 1H), 8.75(brs, 1H), 7.42(d, J=8.2 Hz, 2H), 7.29(d, J=8.2 Hz, 2H), 4.13(s, 1H), 3.44(s, 2H), 1.45-1.20(brs, 9H).

Step 4

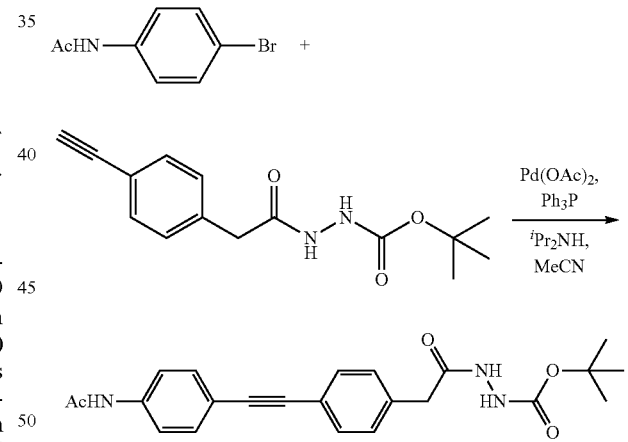

Palladium (II) acetate (2.5 mg, 0.011 mmol) and triphenylphosphine (11 mg, 0.044 mmol) were added to diisopropylamine (4 ml), and the mixture was stirred at room temperature for 20 mins. N-(4-Bromophenyl)acetamide (78 mg, 0.365 mmol) and tert-butyl 2-[(4-ethynylphenyl)acetyl]hydrazinecarboxylate (100 mg, 0.365 mmol) were added, and the mixture was stirred at 70° C. for 2 hrs. Anhydrous acetonitrile (2 ml) was added, and the mixture was further stirred at 70° C. for 1 hr. The reaction mixture was cooled and concentrated. The residue was purified by silica gel column chromatography (dichloromethane:methanol=97:3) to give tert-butyl 2-({4-[(4-acetamidophenyl)ethynyl]phenyl}acetyl)hydrazinecarboxylate (30 mg, yield 20%).

Step 5

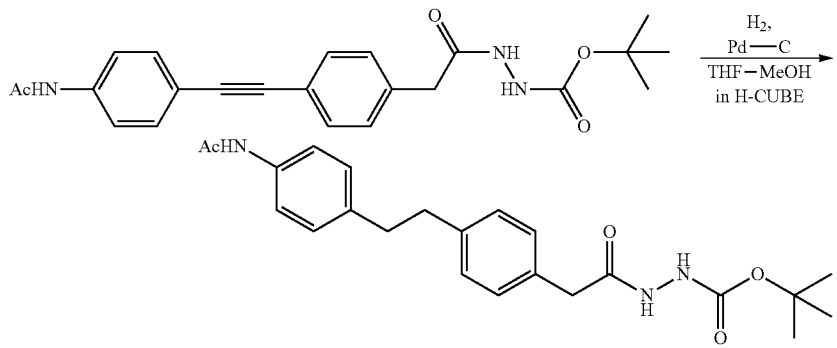

tert-Butyl 2-({4-[(4-acetamidophenyl)ethynyl]phenyl}acetyl)hydrazinecarboxylate (29 mg, 0.071 mmol) was dissolved in a mixture of tetrahydrofuran-methanol (1:1) and hydrogenated using a continuous hydrogenation reactor (trade name: H-CUBE, manufactured by ThalesNano) equipped with a 10%-palladium carbon cartridge. The reaction mixture was concentrated, and the residue was purified by silica gel column chromatography (dichloromethane:methanol=97:3) to give tert-butyl 2-({4-[(4-acetamidophenyl)ethyl]phenyl}acetyl)hydrazinecarboxylate (24 mg, yield 82%).

Step 6

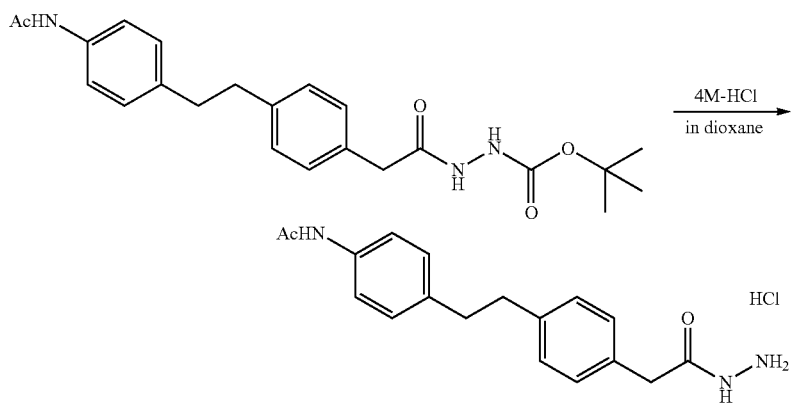

4M-Hydrogen chloride dioxane solution (1 ml, 4 mmol) was added to tert-butyl 2-({4-[(4-acetamidophenyl)ethyl]phenyl}acetyl)hydrazinecarboxylate (23 mg, 0.056 mmol), and the mixture was stirred at room temperature for 15 mins. The reaction mixture was concentrated under reduced pressure, dichloromethane was added, and the mixture was concentrated again, and hydrogen chloride gas was removed. The precipitate was collected by filtration, washed with diethyl ether and dried under reduced pressure to give the title compound (18 mg, yield 98%) as a slightly yellow solid.

Production Example 2

N-{3-[2-(4-hydrazinocarbonylmethylphenyl)ethyl]phenyl}acetamide hydrochloride

Using N-(3-bromophenyl)acetamide obtained by heating 3-bromophenylamine in acetic anhydride at 80° C. for 3 hrs as a starting material, the title compound was synthesized by a method similar to Production Example 1, steps 4-6.

Production Example 3

N-{2-acetylamino-5-[2-(4-hydrazinocarbonylmethylphenyl)ethyl]pyridin-3-yl}acetamide dihydrochloride Using N,N'-(5-bromopyridine-2,3-diyl)diacetamide as a starting material, the title compound was synthesized by a method similar to Production Example 1, steps 4-6.

Production Example 4

N-{6-[2-(4-hydrazinocarbonylmethylphenyl)ethyl]pyridin-2-yl}acetamide dihydrochloride Using N-(6-bromopyridin-2-yl)acetamide obtained by treating 6-bromopyridin-2-amine with acetic anhydride as a starting material, the title compound was synthesized by a method similar to Production Example 1, steps 4-6.

Production Example 5

N-{4-[2-(4-hydrazinocarbonylmethylphenyl)ethyl]-3-trifluoromethylphenyl}acetamide hydrochloride Using N-[4-bromo-3-(trifluoromethyl)phenyl]acetamide as a starting material, the title compound was synthesized by a method similar to Production Example 1, steps 4-6.

Production Example 6

2-{4-[2-(4-hydrazinocarbonylmethylphenyl)ethyl]phenoxy}acetamide hydrochloride

Step 1

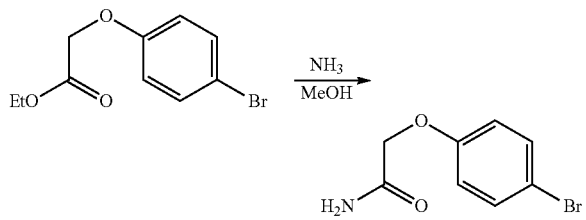

7M-Ammonia methanol solution (10 ml, 70 mmol) was added to ethyl 2-(4-bromophenoxy)acetate (1.0 g, 3.86 mmol), and the mixture was stirred at room temperature for 2.5 hrs. The reaction mixture was concentrated under reduced pressure to give 2-(4-bromophenoxy)acetamide (870 mg, yield 98%) as a white solid.

Step 2 and the Following

Using the above-mentioned 2-(4-bromophenoxy)acetamide as a starting material, the title compound was synthesized by a method similar to Production Example 1, steps 4-6.

Production Example 7

N-{5-[2-(hydrazinocarbonylmethylphenyl)ethyl]pyrazin-2-yl}acetamide dihydrochloride Using N-(5-bromopyrazin-2-yl)acetamide obtained by treating 5-bromopyrazine-2-amine with acetic anhydride as a starting material, the title compound was synthesized by a method similar to Production Example 1, steps 4-6.

Production Example 8

N-{2-acetylamino-5-[2-(4-hydrazinocarbonylmethylphenyl)ethyl]phenyl}acetamide hydrochloride Using N,N'-(4-bromo-1,2-phenylene)diacetamide obtained by treating 4-bromobenzene-1,2-diamine with acetic anhydride as a starting material, the title compound was synthesized by a method similar to Production Example 1, steps 4-6.

Production Example 9

{4-[2-(1H-imidazol-2-yl)ethyl]phenyl}acetohydrazide dihydrochloride

Using 2-iodo-1H-imidazole as a starting material, the title compound was synthesized by a method similar to Production Example 1, steps 4-6.

Production Example 10

{4-[2-(3H-imidazol-4-yl)ethyl]phenyl}acetohydrazide dihydrochloride

Using 4-iodo-3H-imidazole as a starting material, the title compound was synthesized by a method similar to Production Example 1, steps 4-6.

Production Example 11

N-{5-[2-(4-hydrazinocarbonylmethylphenyl)ethyl]pyridin-2-yl}acetamide dihydrochloride Using N-(5-bromopyridin-2-yl)acetamide obtained by treating 5-bromopyridin-2-amine with acetic anhydride as a starting material, the title compound was synthesized by a method similar to Production Example 1, steps 4-6.

Production Example 12

{4-[2-(6-morpholin-4-ylpyridin-3-yl)ethyl]phenyl}acetohydrazide dihydrochloride

Using 4-(5-bromopyridin-2-yl)morpholine as a starting material, the title compound was synthesized by a method similar to Production Example 1, steps 4-6.

Production Example 13

2-{4-[2-(4-hydrazinocarbonylmethylphenyl)ethynyl]phenoxy}acetamide hydrochloride Using 2-(4-bromophenoxy)acetamide synthesized according to Example 6 as a starting material, the title compound was synthesized by a method similar to Example 1, step 4 and step 6. (After step 4, step 6 was directly performed without performing step 5, which was a hydrogenation reaction of triple bond.)

Production Example 14

[4-(1H-imidazol-2-ylethynyl)phenyl]acetohydrazide dihydrochloride

Using 2-iodo-1H-imidazole as a starting material, the title compound was synthesized by a method similar to Production Example 1, steps 4 and step 6. (After step 4, step 6 was directly performed without performing step 5, which was a hydrogenation reaction of triple bond.)

Production Example 15

[4-(6-morpholin-4-ylpyridin-3-ylethynyl)phenyl]acetohydrazide dihydrochloride

Using 4-(5-bromopyridin-2-yl)morpholine as a starting material, the title compound was synthesized by a method similar to Production Example 1, steps 4 and step 6. (After step 4, step 6 was directly performed without performing step 5, which was a hydrogenation reaction of triple bond.)

Production Example 16

N-[5-(4-hydrazinocarbonylmethylphenylethynyl)pyrazin-2-yl]acetamide dihydrochloride Using N-(5-bromopyrazin-2-yl)acetamide obtained by treating 5-bromopyrazine-2-amine with acetic anhydride as a starting material, the title compound was synthesized by a method similar to Production Example 1, steps 4 and step 6. (After step 4, step 6 was directly performed without performing step 5, which was a hydrogenation reaction of triple bond.)

Production Example 17

N-[2-acetylamino-4-(4-hydrazinocarbonylmethylphenylethynyl)phenyl]acetamide hydrochloride Using N,N'-(4-bromo-1,2-phenylene)diacetamide obtained by treating 4-bromobenzene-1,2-diamine with acetic anhydride as a starting material, the title compound was synthesized by a method similar to Production Example 1, steps 4 and step 6. (After step 4, step 6 was directly performed without performing step 5, which was a hydrogenation reaction of triple bond.)

Production Example 18

N-[3-acetylamino-5-(4-hydrazinocarbonylmethylphenylethynyl)pyridin-2-yl]acetamide dihydrochloride Using N,N'-(5-bromopyridine-2,3-diyl)diacetamide as a starting material, the title compound was synthesized by a method similar to Production Example 1, steps 4 and step 6. (After step 4, step 6 was directly performed without performing step 5, which was a hydrogenation reaction of triple bond.)

Production Example 19

5-[2-(4-hydrazinocarbonylmethylphenyl)ethyl]pyrazine-2-carboxamide dihydrochloride Step 1

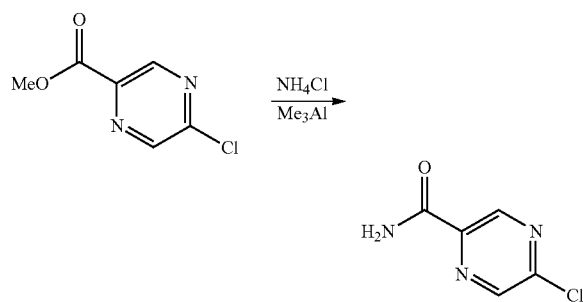

Ammonium chloride (558 mg, 10.4 mmol) was suspended in benzene (5 ml) and 2M-trimethylaluminum toluene solution (5.2 ml, 10.4 mmol) was added dropwise at 0° C. After stirring for 1 hr, a solution of methyl 5-chloropyrazine-2-carboxylate (600 mg, 3.48 mmol) in benzene (5 ml) was added. The reaction mixture was heated to 50° C., and stirred overnight. After cooling, the reaction mixture was poured into water, and neutralized with saturated aqueous sodium hydrogen carbonate solution. The mixture was extracted with ethyl acetate, and the organic layer was washed with water and saturated brine, dried over anhydrous sodium sulfate, and concentrated under reduced pressure. The residue was purified by silica gel column chromatography (dichloromethane:methanol=100:0→98:2) to give 5-chloropyrazine-2-carboxamide (236 mg, yield 43%) as a white solid.

Step 2 and the Following

Using the above-mentioned 5-chloropyrazine-2-carboxamide as a starting material, the title compound was synthesized by a method similar to Production Example 1, steps 4-6.

Production Example 20

2-{4-[2-(2-piperidin-4-yl-1,3-thiazol-4-yl)ethyl]phenyl}acetohydrazide dihydrochloride Step 1

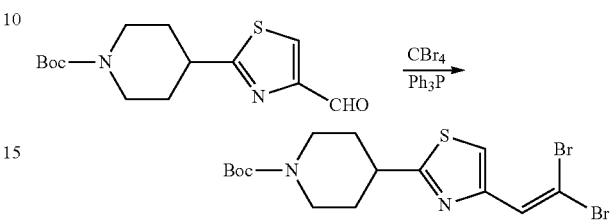

To a solution of triphenylphosphine (7.08 g, 27 mmol) in anhydrous dichloromethane (11 ml) was added dropwise a solution of carbon tetrabromide (4.3 g, 13 mmol) in anhydrous dichloromethane (5 ml) at 10° C., and the mixture was stirred at the same temperature for 15 mins. Stirring was stopped, the supernatant of the reaction mixture was collected, and a solution of tert-butyl 4-(4-formyl-1,3-thiazol-2-yl)piperidine-1-carboxylate (1.0 g, 3.4 mmol) in anhydrous dichloromethane (11 ml) was added dropwise at 10° C. After stirring at 5-10° C. for 40 mins, triethylamine (4 ml) and saturated aqueous sodium hydrogen carbonate solution (0.5 ml) were added. The mixture was filtered through a Celite pad, and the insoluble material was washed with dichloromethane. The filtrate and washing solution were combined and concentrated under reduced pressure. The residue was purified by silica gel column chromatography (ethyl acetate:hexane=1:4) to give tert-butyl 4-[4-(2,2-dibromovinyl)-1,3-thiazol-2-yl]piperidine-1-carboxylate (1.5 g, yield 97%) as a yellow oil.

Step 2

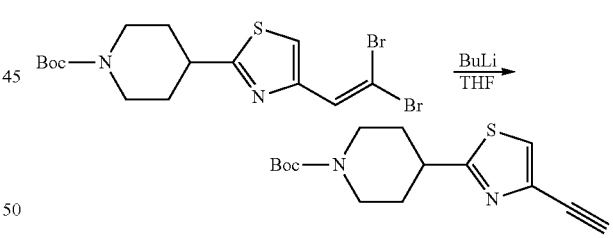

To a solution of tert-butyl 4-[4-(2,2-dibromovinyl)-1,3-thiazol-2-yl]piperidine-1-carboxylate (1.26 g, 2.79 mmol) in anhydrous tetrahydrofuran (25 ml) was added dropwise at −78° C. a mixture of 1.6M-n-butyllithium-hexane solution (5.2 ml, 8.4 mmol) and anhydrous tetrahydrofuran (10 ml). After stirring at −78° C. for 2 hrs, 1.25M hydrogen chloride-ethanol solution (6.7 ml, 8.4 mmol) was added dropwise to the reaction mixture. The mixture was warmed to room temperature, water was added, and the mixture was extracted with ethyl acetate. The extract was concentrated, and the concentrated residue was purified by silica gel column chromatography (ethyl acetate:hexane=1:9→1:4) to give tert-butyl 4-(4-ethynyl-1,3-thiazol-2-yl)piperidine-1-carboxylate (553 mg, yield 68%) as a yellow solid.

Step 3

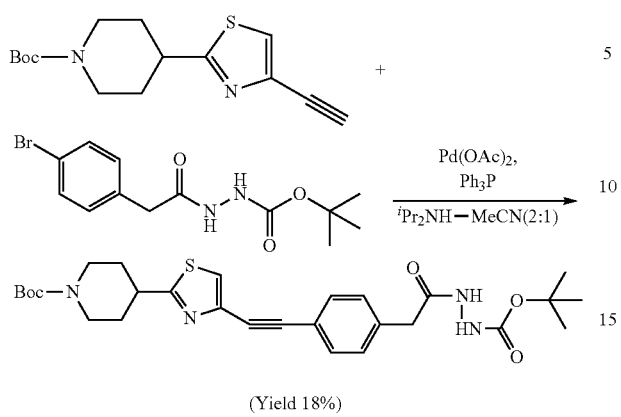

(Yield 18%)

Using tert-butyl 4-(4-ethynyl-1,3-thiazol-2-yl)piperidine-1-carboxylate and tert-butyl 2-[(4-bromophenyl)acetyl]hydrazinecarboxylate as starting materials, Sonogashira-Castero-Stephens acetylene coupling was performed under reaction conditions similar to those of Production Example 1, step 4 to give tert-butyl 4-[4-({4-[2-(tert-butoxycarbonyl)hydrazino]carbonylmethylphenyl}ethynyl)-1,3-thiazol-2-yl]piperidine-1-carboxylate (yield 18%).

Step 4 and the Following tert-Butyl 4-[4-({4-[2-(tert-butoxycarbonyl)hydrazino]carbonylmethylphenyl}ethynyl)-1,3-thiazol-2-yl]piperidine-1-carboxylate was treated by a method similar to Production Example 1, step 5-6, to synthesize the title compound.

Production Example 21

2-acetylamino-4-[2-(4-hydrazinocarbonylmethylphenyl)ethyl]phenyl acetate hydrochloride Step 1

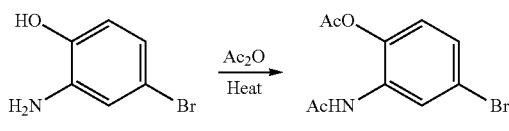 [SMILES: "Ac2O" ; Nc1cc(Br)ccc1O ; CC(=O)Nc1cc(Br)ccc1OC(C)=O]

Acetic anhydride (3.8 ml, 39.9 mmol) was added to 2-amino-4-bromophenol (1.5 g, 7.98 mmol), and the mixture was stirred at 80° C. for 3 hrs and at 100° C. for 2 hrs. After cooling to room temperature, the reaction mixture was poured into saturated aqueous sodium hydrogen carbonate solution, and the mixture was extracted with dichloromethane, dried over anhydrous sodium sulfate, and concentrated under reduced pressure. The residue was washed with diethyl ether and dried to give 2-acetylamino-4-bromophenyl acetate (760 mg, yield 35%) as a pale-white brown solid.

Step 2 and the Following

Using the above-mentioned 2-acetylamino-4-bromophenyl acetate as a starting material, the title compound was synthesized by a method similar to Production Example 1, steps 4-6.

Production Example 22

{4-[2-(1-methyl-1H-imidazol-2-yl)ethyl]phenyl}acetohydrazide dihydrochloride

Using 2-iodo-1-methyl-1H-imidazole as a starting material, the title compound was synthesized by a method similar to Production Example 1, steps 4-6.

Production Example 23

N-[4-(4-hydrazinocarbonylmethylphenylethynyl)phenyl]acetamide hydrochloride tert-Butyl 2-({4-[(4-acetamidophenyl)ethynyl]phenyl}acetyl)hydrazinecarboxylate synthesized by a method similar to Production Example 1, step 4, was deprotected by a method similar to Example 1, step 6, to synthesize the title compound.

Production Example 24

N-[3-(4-hydrazinocarbonylmethylphenylethynyl)phenyl]acetamide hydrochloride

Using N-(3-bromophenyl)acetamide as a starting material, the title compound was synthesized by a method similar to Production Example 1, steps 4 and step 6. (After step 4, step 6 was directly performed without performing step 5, which was a hydrogenation reaction of triple bond.)

Production Example 25

[4-(1-methyl-1H-imidazol-2-ylethynyl)phenyl]acetohydrazide dihydrochloride

Using 2-iodo-1-methyl-1H-imidazole as a starting material, the title compound was synthesized by a method similar to Production Example 1, steps 4 and step 6. (After step 4, step 6 was directly performed without performing step 5, which was a hydrogenation reaction of triple bond.)

Production Example 26

2-{4-[(2-piperidin-4-yl-1,3-thiazol-4-yl)ethynyl]phenyl}acetohydrazide dihydrochloride tert-butyl 4-[4-({4-[2-(tert-butoxycarbonyl)hydrazino]carbonylmethylphenyl}ethynyl)-1,3-thiazol-2-yl]piperidine-1-carboxylate synthesized by Production Example 20, step 3, was deprotected by a method similar to Example 1, step 6, to synthesize the title compound.

Production Example 27

N-[5-(4-hydrazinocarbonylmethylphenylethynyl)pyridin-2-yl]acetamide dihydrochloride Using N-(5-bromopyridin-2-yl)acetamide as a starting material, the title compound was synthesized by a method similar to Production Example 1, steps 4 and step 6. (After step 4, step 6 was directly performed without performing step 5, which was a hydrogenation reaction of triple bond.)

Production Example 28

N-[6-(4-hydrazinocarbonylmethylphenylethynyl)pyridin-2-yl]acetamide dihydrochloride Using N-(6-bromopyridin-2-yl)acetamide as a starting material, the title compound was synthesized by a method similar to Production Example 1, steps 4 and step 6. (After step 4, step 6 was directly performed without performing step 5, which was a hydrogenation reaction of triple bond.)

Production Example 29

2-(4-{2-[4-(dimethylamino)phenyl]ethyl}phenyl)acetohydrazide dihydrochloride

Step 1

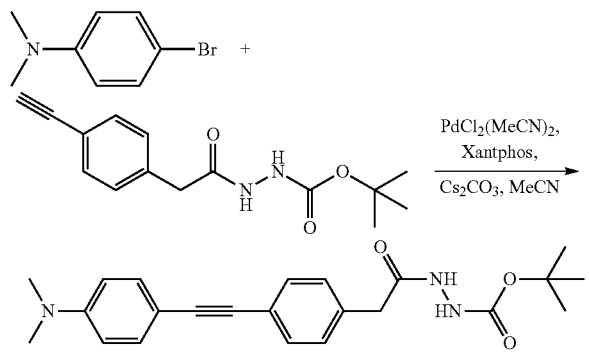

To a mixture of 4-bromo-N,N-dimethylaniline (175 mg, 0.88 mmol), cesium carbonate (476 mg, 1.46 mmol), 4,5-bis(diphenylphosphino)-9,9-dimethylxanthene (22 mg, 0.04 mmol) and bis(acetonitrile)dichloropalladium (II) (10 mg, 0.04 mmol) was added anhydrous acetonitrile (2 ml), and the mixture was stirred at room temperature for 15 mins. A solution of tert-butyl 2-[(4-ethynylphenyl)acetyl]hydrazinecarboxylate (200 mg, 0.73 mmol) in anhydrous acetonitrile (4 ml) was added, and the mixture was stirred at 80° C. for 5 hrs. After cooling, the reaction mixture was filtered, and the insoluble material was washed with ethyl acetate. The filtrate and washing solution were combined and concentrated under reduced pressure. The concentrated residue was purified by silica gel column chromatography (chloroform:methanol=97:3) to give tert-butyl 2-[(4-{[4-(dimethylamino)phenyl]ethynyl}phenyl)acetyl]hydrazinecarboxylate (110 mg, yield 38%) as a yellow solid.
Step 2 and the Following
tert-Butyl 2-[(4-{[4-(dimethylamino)phenyl]ethynyl}phenyl)acetyl]hydrazinecarboxylate was treated by a method similar to Production Example 1, step 5-step 6, to synthesize the title compound.

Production Example 30

2-(4-{2-[4-(diethylamino)phenyl]ethyl}phenyl)acetohydrazide dihydrochloride

Using 4-bromo-N,N-diethylaniline as a starting material, the title compound was synthesized by a method similar to Production Example 29, step 1 (coupling step), and then Production Example 1, step 5 (hydrogenation), step 6 (deprotection).

Production Example 31

2-{4-[2-(4-pyrrolidin-1-ylphenyl)ethyl]phenyl}acetohydrazide dihydrochloride

Using 1-(4-bromophenyl)pyrrolidine as a starting material, the title compound was synthesized by a method similar to Production Example 29, step 1, and then Production Example 1, steps 5-6.

Production Example 32

2-{4-[2-(4-piperidin-1-ylphenyl)ethyl]phenyl}acetohydrazide dihydrochloride

Using 1-(4-bromophenyl)piperidine as a starting material, the title compound was synthesized by a method similar to Production Example 29, step 1, and then Production Example 1, steps 5-6.

Production Example 33

2-{4-[2-(4-piperazin-1-ylphenyl)ethyl]phenyl}acetohydrazide trihydrochloride

Using tert-butyl 4-(4-iodophenyl)piperazine-1-carboxylate as a starting material, the title compound was synthesized by a method similar to Production Example 29, step 1, and then Production Example 1, steps 5-6.

Production Example 34

2-(4-{2-[4-(4-acetylpiperazin-1-yl)phenyl]ethyl}phenyl)acetohydrazide dihydrochloride Using 1-acetyl-4-(4-iodophenyl)piperazine obtained by treating (4-iodophenyl)piperazine with acetic anhydride as a starting material, the title compound was synthesized by a method similar to Production Example 1, steps 4-6.

Production Example 35

2-(4-{2-[4-(4-methylpiperazin-1-yl)phenyl]ethyl}phenyl)acetohydrazide trihydrochloride Using 1-(4-iodophenyl)-4-methylpiperazine as a starting material, the title compound was synthesized by a method similar to Production Example 29, step 1, and then Production Example 1, steps 5-6.

Production Example 36

2-{4-[2-(4-morpholin-4-ylphenyl)ethyl]phenyl}acetohydrazide dihydrochloride

Using 4-(4-iodophenyl)morpholine as a starting material, the title compound was synthesized by a method similar to Production Example 29, step 1, and then Production Example 1, steps 5-6.

Production Example 37

2-(4-{2-[3-(dimethylamino)phenyl]ethyl}phenyl)acetohydrazide dihydrochloride

Using 3-bromo-N,N-dimethylaniline as a starting material, the title compound was synthesized by a method similar to Production Example 1, steps 4-6.

Production Example 38

2-{4-[2-(3-pyrrolidin-1-ylphenyl)ethyl]phenyl}acetohydrazide dihydrochloride

Using 1-(3-bromophenyl)pyrrolidine as a starting material, the title compound was synthesized by a method similar to Production Example 1, steps 4-6.

Production Example 39

2-{4-[2-(4-piperidin-1-ylphenyl)ethyl]phenyl}acetohydrazide dihydrochloride

Using 1-(3-bromophenyl)piperidine as a starting material, the title compound was synthesized by a method similar to Production Example 1, steps 4-6.

Production Example 40

2-{4-[2-(3-piperazin-1-ylphenyl)ethyl]phenyl}acetohydrazide trihydrochloride

Using tert-butyl 4-(3-bromophenyl)piperazine-1-carboxylate as a starting material, the title compound was synthesized by a method similar to Production Example 1, steps 4-6.

Production Example 41

2-(4-{2-[3-(4-acetylpiperazin-1-yl)phenyl]ethyl}phenyl)acetohydrazide dihydrochloride Using 1-acetyl-4-(3-bromophenyl)piperazine obtained by treating (3-bromophenyl)piperazine with acetic anhydride as a starting material, the title compound was synthesized by a method similar to Production Example 1, steps 4-6.

Production Example 42

2-{4-[2-(3-morpholin-4-ylphenyl)ethyl]phenyl}acetohydrazide dihydrochloride

Using 4-(3-bromophenyl)morpholine as a starting material, the title compound was synthesized by a method similar to Production Example 1, steps 4-6.

Production Example 43

2-(4-{2-[6-(dimethylamino)pyridin-3-yl]ethyl}phenyl)acetohydrazide trihydrochloride Using 5-bromo-N,N-dimethylpyridin-2-amine as a starting material, the title compound was synthesized by a method similar to Production Example 1, steps 4-6.

Production Example 44

2-{4-[2-(6-pyrrolidin-1-ylpyridin-3-yl)ethyl]phenyl}acetohydrazide trihydrochloride Using 5-iodo-2-pyrrolidin-1-ylpyridine as a starting material, the title compound was synthesized by a method similar to Production Example 29, step 1, and then Production Example 1, steps 5-6.

Production Example 45

2-{4-[2-(6-piperidin-1-ylpyridin-3-yl)ethyl]phenyl}acetohydrazide trihydrochloride Using 5-iodo-2-piperidin-1-ylpyridine as a starting material, the title compound was synthesized by a method similar to Production Example 1, steps 4-6.

Production Example 46

2-{4-[2-(6-piperazin-1-ylpyridin-3-yl)ethyl]phenyl}acetohydrazide tetrahydrochloride Using tert-butyl 4-(5-iodopyridin-2-yl)piperazine-1-carboxylate as a starting material, the title compound was synthesized by a method similar to Production Example 1, steps 4-6.

Production Example 47

2-(4-{2-[6-(4-acetylpiperazin-1-yl)pyridin-3-yl]ethyl}phenyl)acetohydrazide trihydrochloride Using 1-acetyl-4-(5-bromopyridin-2-yl)piperazine obtained by treating 1-(5-bromopyridin-2-yl)piperazine with acetic anhydride as a starting material, the title compound was synthesized by a method similar to Production Example 1, steps 4-6.

Production Example 48

2-(4-{2-[6-(4-methylpiperazin-1-yl)pyridin-3-yl]ethyl}phenyl)acetohydrazide tetrahydrochloride Using 1-(5-bromopyridin-2-yl)-4-methylpiperazine as a starting material, the title compound was synthesized by a method similar to Production Example 1, steps 4-6.

Production Example 49

2-{4-[2-(6-pyrrolidin-1-ylpyridin-2-yl)ethyl]phenyl}acetohydrazide trihydrochloride Using 2-bromo-6-pyrrolidin-1-ylpyridine as a starting material, the title compound was synthesized by a method similar to Production Example 1, steps 4-6.

Production Example 50

2-{4-[2-(6-piperidin-1-ylpyridin-2-yl)ethyl]phenyl}acetohydrazide trihydrochloride Using 2-bromo-6-piperidin-1-ylpyridine as a starting material, the title compound was synthesized by a method similar to Production Example 1, steps 4-6.

Production Example 51

2-{4-[2-(6-piperazin-1-ylpyridin-2-yl)ethyl]phenyl}acetohydrazide tetrahydrochloride Using tert-butyl 4-(6-bromopyridin-2-yl)piperazine-1-carboxylate as a starting material, the title compound was synthesized by a method similar to Production Example 1, steps 4-6.

Production Example 52

2-(4-{2-[6-(4-acetylpiperazin-1-yl)pyridin-2-yl]ethyl}phenyl)acetohydrazide trihydrochloride Using 1-acetyl-4-(bromopyridin-2-yl)piperazine obtained by treating 1-(6-bromopyridin-2-yl)piperazine with acetic anhydride as a starting material, the title compound was synthesized by a method similar to Production Example 1, steps 4-6.

Production Example 53

2-{4-[2-(6-morpholin-4-ylpyridin-2-yl)ethyl]phenyl}acetohydrazide trihydrochloride Using 4-(6-bromopyridin-2-yl)morpholine as a starting material, the title compound was synthesized by a method similar to Production Example 1, steps 4-6.

Production Example 54

2-{4-[2-(2-pyrrolidin-1-ylpyrimidin-5-yl)ethyl]phenyl}acetohydrazide dihydrochloride Using 5-bromo-2-pyrrolidin-1-ylpyrimidine as a starting material, the title compound was synthesized by a method similar to Production Example 1, steps 4-6.

Production Example 55

2-{4-[2-(2-piperidin-1-ylpyrimidin-5-yl)ethyl]phenyl}acetohydrazide dihydrochloride Using 5-bromo-2-piperidin-1-ylpyrimidine as a starting material, the title compound was synthesized by a method similar to Production Example 1, steps 4-6.

Production Example 56

2-{4-[2-(2-piperazin-1-ylpyrimidin-5-yl)ethyl]phenyl}acetohydrazide trihydrochloride Using tert-butyl 4-(5-bromopyrimidin-2-yl)piperazine-1-carboxylate as a starting material, the title compound was synthesized by a method similar to Production Example 1, steps 4-6.

Production Example 57

2-(4-{2-[2-(4-acetylpiperazin-1-yl)pyrimidin-5-yl]ethyl}phenyl)acetohydrazide dihydrochloride Using 2-(4-acetylpiperazin-1-yl)-5-bromopyrimidine obtained by treating 5-bromo-2-piperazin-1-ylpyrimidine with acetic anhydride as a starting material, the title compound was synthesized by a method similar to Production Example 1, steps 4-6.

Production Example 58

2-{4-[2-(2-morpholin-4-ylpyrimidin-5-yl)ethyl]phenyl}acetohydrazide dihydrochloride Using 4-(5-bromopyrimidin-2-yl)morpholine as a starting material, the title compound was synthesized by a method similar to Production Example 1, steps 4-6.

Production Example 59

2-(4-{2-[4-piperazin-1-yl-2-(trifluoromethyl)phenyl]ethyl}phenyl)acetohydrazide trihydrochloride Step 1

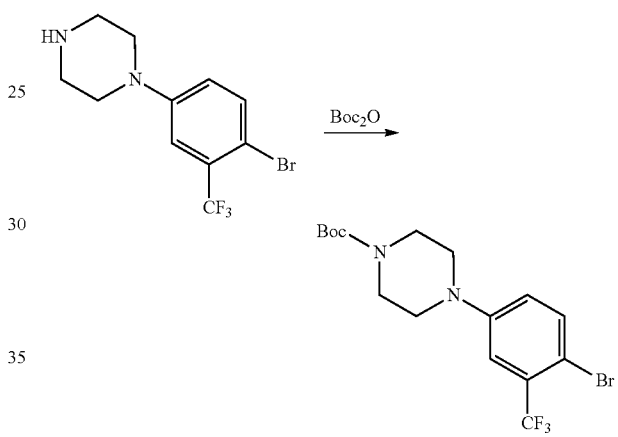

To a solution of 1-[4-bromo-3-(trifluoromethyl)phenyl]piperazine (1.56 g, 5.05 mmol) in anhydrous dichloromethane (17 ml) was added di-tert-butyl dicarbonate (1.2 g, 5.50 mmol), and the mixture was stirred at room temperature for 3 hrs. Dichloromethane was added to the reaction mixture, and the mixture was washed with water and saturated brine, dried over anhydrous sodium sulfate, and concentrated under reduced pressure to give tert-butyl 4-[4-bromo-3-(trifluoromethyl)phenyl]piperazine-1-carboxylate (2.1 g, yield 100%) as an oil.

Step 2 and the Following

Using the above-mentioned tert-butyl 4-[4-bromo-3-(trifluoromethyl)phenyl]piperazine-1-carboxylate as a starting material, the title compound was synthesized by a method similar to Production Example 1, steps 4-6.

Production Example 60

2-(4-{2-[4-(4-acetylpiperazin-1-yl)-2-(trifluoromethyl)phenyl]ethyl}phenyl)acetohydrazide dihydrochloride Using 1-acetyl-4-[4-bromo-3-(trifluoromethyl)phenyl]piperazine obtained by treating 1-[4-bromo-3-(trifluoromethyl)phenyl]piperazine with acetic anhydride as a starting material, the title compound was synthesized by a method similar to Production Example 1, steps 4-6.

Production Example 61

N-[4-{2-[4-(hydrazinocarbonylmethyl)phenyl]ethyl}-2-(trifluoromethyl)phenyl]acetamide hydrochloride Using N-[4-iodo-2-(trifluoromethyl)phenyl]acetamide as a starting material, the title compound was synthesized by a method similar to Production Example 1, steps 4-6.

Production Example 62

N-[3-{2-[4-(hydrazinocarbonylmethyl)phenyl]ethyl}-2-(trifluoromethyl)phenyl]acetamide hydrochloride Using N-[3-bromo-5-(trifluoromethyl)phenyl]acetamide obtained by treating 3-bromo-5-(trifluoromethyl)aniline with acetic anhydride as a starting material, the title compound was synthesized by a method similar to Production Example 1, steps 4-6.

Production Example 63

2-{4-[2-(3-oxo-3,4-dihydro-2H-1,4-benzooxazin-6-yl)ethyl]phenyl}acetohydrazide hydrochloride Using 6-bromo-2H-1,4-benzooxazin-3(4H)-one as a starting material, the title compound was synthesized by a method similar to Production Example 1, steps 4-6.

Production Example 64

2-{4-[2-(4-methyl-3,4-dihydro-2H-1,4-benzooxazin-7-yl)ethyl]phenyl}acetohydrazide dihydrochloride Using 7-bromo-4-methyl-3,4-dihydro-2H-1,4-benzooxazine as a stating material, the title compound was synthesized by a method similar to Production Example 29, step 1, and then Production Example 1, steps 5-6.

Production Example 65

2-(4-{2-[4-(2,5-diazabicyclo[2.2.1]hept-2-yl)phenyl]ethyl}phenyl)acetohydrazide trihydrochloride Step 1

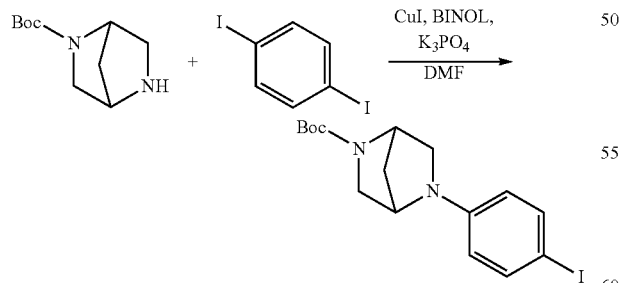

A mixture of 1,4-diiodobenzene (9.98 g, 30.3 mmol), tert-butyl 2,5-diazabicyclo[2.2.1]heptane-2-carboxylate (2.0 g, 10.1 mmol), copper (I) iodide (434 mg, 3.03 mmol), 1,1'-bi-2-naphthol (867 mg, 3.03 mmg), tripotassium phosphate (5.14 g, 24.2 mmol) and anhydrous N,N-dimethylformamide (50 ml) was stirred at 80° C. for 2 days. 1,4-Diiodobenzene (3.33 g, 10.1 mmol) was added, and the mixture was stirred at 90° C. overnight. After cooling to room temperature, the mixture was filtered through Celite, and the insoluble material was washed with ethyl acetate. The filtrate and washing solution were combined, and the mixture was washed with water and saturated brine, dried over anhydrous sodium sulfate and concentrated. The residue was purified by column chromatography (ethyl acetate:hexane=80:20) to, give tert-butyl 5-(4-iodophenyl)-2,5-diazabicyclo[2.2.1]heptane-2-carboxylate (1.34 g, yield 33%).

Step 2 and the Following

Using the above-mentioned tert-butyl 5-(4-iodophenyl)-2,5-diazabicyclo[2.2.1]heptane-2-carboxylate as a starting material, the title compound was synthesized by a method similar to Production Example 1, steps 4-6.

Production Example 66

2-(4-{2-[4-(5-acetyl-2,5-diazabicyclo[2.2.1]hept-2-yl)phenyl]ethyl}phenyl)acetohydrazide dihydrochloride Step 1

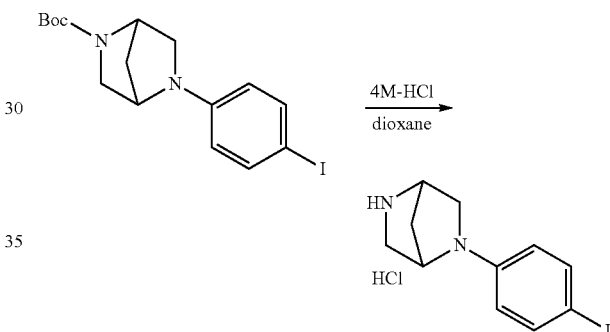

To a solution of tert-butyl 5-(4-iodophenyl)-2,5-diazabicyclo[2.2.1]heptane-2-carboxylate (335 mg, 0.84 mmol) in anhydrous dioxane (3 ml) was added 4M-hydrogen chloride dioxane solution (4 ml, 16 mmol). After stirring at room temperature for 2 hrs, the mixture was concentrated under reduced pressure, dichloromethane was added and the mixture was concentrated again. The residue was washed with diethyl ether and dichloromethane, and dried to give 5-(4-iodophenyl) -2,5-diazabicyclo[2.2.1]heptane hydrochloride (272 mg, 96%) as a pale-green solid.

Step 2

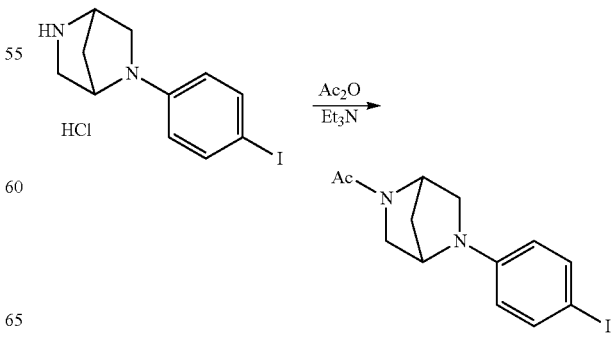

5-(4-Iodophenyl)-2,5-diazabicyclo[2.2.1]heptane hydrochloride (269 mg, 0.80 mmol) was suspended in dichloromethane (0.3 ml), and triethylamine (0.2 ml) and acetic anhydride (0.09 ml, 0.96 mmol) were added. After stirring at room temperature for 1 hr, dichloromethane was added, and the mixture was washed with saturated aqueous sodium hydrogen carbonate solution and saturated brine, dried over anhydrous sodium sulfate, and concentrated under reduced pressure to give 2-acetyl-5-(4-iodophenyl)-2,5-diazabicyclo[2.2.1]heptane (255 mg, yield 93%).

Step 3 and the Following

Using the above-mentioned 2-acetyl-5-(4-iodophenyl)-2,5-diazabicyclo[2.2.1]heptane as a starting material, the title compound was synthesized by a method similar to Production Example 29, step 1, and then Production Example 1, steps 5-6.

Production Example 67

2-(4-{2-[6-(1H-pyrazol-1-yl)pyridin-2-yl]ethyl}phenyl)acetohydrazide trihydrochloride Using 2-bromo-6-(1H-pyrazol-1-yl)pyridine as a starting material, the title compound was synthesized by a method similar to Production Example 1, steps 4-6.

Production Example 68

2-(4-{2-[4-(piperazin-1-ylmethyl)phenyl]ethyl}phenyl)acetohydrazide trihydrochloride Using tert-butyl 4-(4-bromobenzyl)piperazine-1-carboxylate as a starting material, the title compound was synthesized by a method similar to Production Example 1, steps 4-6.

Production Example 69

2-(4-{2-[3-(piperazin-1-ylmethyl)phenyl]ethyl}phenyl)acetohydrazide trihydrochloride Using tert-butyl 4-(3-iodobenzyl)piperazine-1-carboxylate as a starting material, the title compound was synthesized by a method similar to Production Example 1, steps 4-6.

Production Example 70

2-(4-{2-[4-(morpholin-4-ylmethyl)phenyl]ethyl}phenyl)acetohydrazide dihydrochloride Using 4-(4-iodobenzyl)morpholine as a starting material, the title compound was synthesized by a method similar to Production Example 1, steps 4-6.

Production Example 71

2-(4-{2-[3-(morpholin-4-ylmethyl)phenyl]ethyl}phenyl)acetohydrazide dihydrochloride Using 4-(3-iodobenzyl)morpholine as a starting material, the title compound was synthesized by a method similar to Production Example 1, steps 4-6.

Production Example 72

2-(4-{2-[2-(1-acetylpiperidin-4-yl)-1,3-thiazol-4-yl]ethyl}phenyl)acetohydrazide hydrochloride Step 1

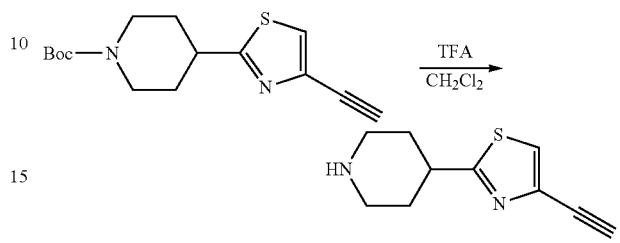

To a solution of tert-butyl 4-(4-ethynyl-1,3-thiazol-2-yl)piperidine-1-carboxylate (1.87 g, 6.40 mmol) in anhydrous dichloromethane (16 ml) was added at 0° C. trifluoroacetic acid (16 ml). After stirring at 0° C. for 30 mins, the mixture was concentrated under reduced pressure. Saturated aqueous sodium hydrogen carbonate solution was added to the residue, and the mixture was concentrated to dryness. The residue was washed with dichloromethane (extracted from solid phase) and the washing solution was concentrated to give 4-(4-ethynyl-1,3-thiazol-2-yl)piperidine (1.176 g, yield 98%) as a white solid.

Step 2 and the Following

Using 1-acetyl-4-(4-ethynyl-1,3-thiazol-2-yl)piperidine obtained by treating the above-mentioned 4-(4-ethynyl-1,3-thiazol-2-yl)piperidine with acetic anhydride as a starting material, the title compound was synthesized by a method similar to Production Example 1, steps 4-6.

Production Example 73

N-{5-[2-(4-hydrazinocarbonylmethylphenyl)ethyl]-2-thienyl}acetamide hydrochloride Step 1

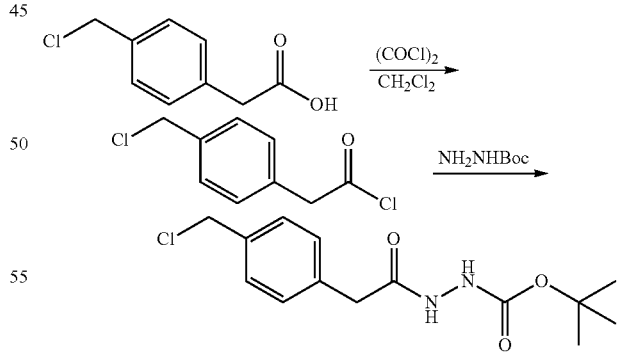

4-(Chloromethyl)phenylacetic acid (5.0 g, 27.1 mmol) was suspended in dichloromethane (50 ml), and oxalyl chloride (9.2 ml, 0.11 mol) and N,N-dimethylformamide (2 drops) were added. After stirring at room temperature for 1 hr, and the mixture was concentrated under reduced pressure. Dichloromethane (50 ml) and tert-butyl carbazate (4.29 g, 32.5 mmol) were added to the residue, and the mixture was cooled to 0° C. N,N-diisopropylethylamine (14 ml, 81.3 mmol) was added dropwise, and the mixture was stirred at room temperature overnight. The reaction mixture was diluted with dichloromethane, washed with saturated aqueous sodium hydrogen carbonate solution, water and saturated brine, dried over anhydrous sodium sulfate, and concentrated under reduced pressure. Diethyl ether was added to the residue and the resulting precipitate was collected by filtration. The filtrate was concentrated and added with diethyl ether to recover the secondary crystals. They were dried to give tert-butyl 2-{[4-(chloromethyl)phenyl]acetyl} hydrazinecarboxylate (5.9 g, primary and secondary crystals, total yield 73%) as a pale-yellow solid.
Step 2

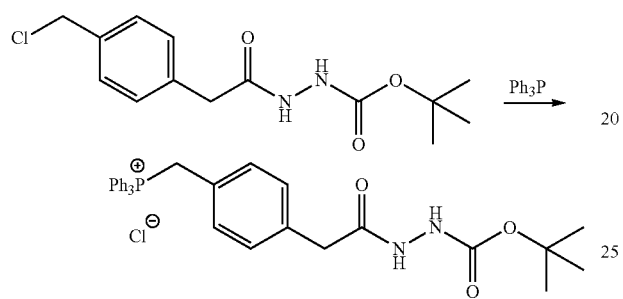

A mixture of tert-butyl 2-{[4-(chloromethyl)phenyl] acetyl}hydrazinecarboxylate (5.9 g, 19.7 mmol), triphenylphosphine (5.18 g, 19.7 mmol) and benzene (15 ml) was heated under reflux for 21 hrs. After cooling to room temperature, the precipitate was collected by filtration, washed 3 times with benzene, and dried under reduced pressure to give {4-[2-(tert-butoxycarbonyl)hydrazinocarbonylmethyl]benzyl}(triphenyl)phosphonium chloride (8.68 g, yield 78%) as a white solid.

$^1$H-NMR(DMSO-$d_6$) δ(ppm): 9.78 (brs, 1H), 8.74 (brs, 1H), 7.91 (m, 3H), 7.80-7.55 (m, 12H), 7.13 (d, J=7.9 Hz, 2H), 6.90 (d, J=7.9 Hz, 2H), 5.13 (d, J=15.6 Hz, 2H), 3.37 (s, 2H), 1.45-1.15 (brs, 9H).
Step 3

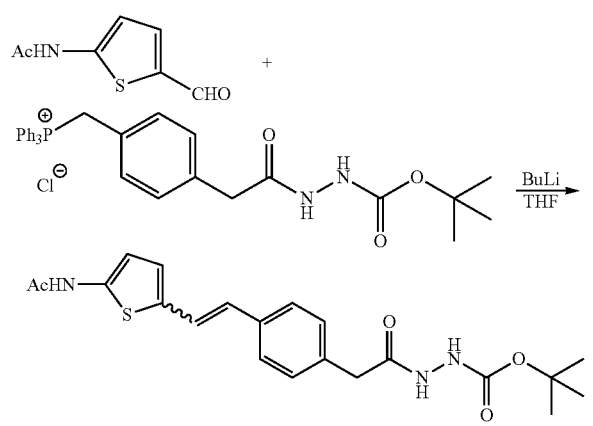

{4-[2-(tert-Butoxycarbonyl)hydrazinocarbonylmethyl] benzyl}(triphenyl)phosphonium chloride (2.97 g, 5.29 mmol) was suspended in anhydrous tetrahydrofuran (8 ml), and cooled to −78° C. n-Butyllithium (1.6M-hexane solution, 3.3 ml, 5.3 mmol) was added dropwise, and the mixture was stirred at −78° C. for 15 mins and at 0° C. for 2 hrs. A solution of N-(5-formylthiophen-2-yl)acetamide (280 mg, 1.65 mmol) in anhydrous tetrahydrofuran (2 ml) was added dropwise, and the mixture was warmed to room temperature. After stirring at room temperature overnight, saturated aqueous ammonium chloride solution was added. The mixture was extracted with dichloromethane and the combined organic layer was washed with water and saturated brine, dried over anhydrous sodium sulfate and concentrated. The residue was purified by silica gel column chromatography (dichloromethane:methanol=97:3→80:20) to give tert-butyl 2-({4-[2-(5-acetylaminothiophen-2-yl)vinyl]phenyl}acetyl)hydrazinecarboxylate (192 mg, yield 28%, E/Z mixture) as a yellow solid.
Step 4 and the Following The above-mentioned tert-butyl 2-({4-[2-(5-acetylaminothiophen-2-yl)vinyl]phenyl}acetyl)hydrazinecarboxylate was treated by a method similar to Production Example 1, step 5 (hydrogenation) and step 6 (deprotection) to synthesize the title compound.

Production Example 74

2-{4-[2-(5-piperazin-1-ylthiophen-2-yl)ethyl] phenyl}acetohydrazide trihydrochloride Step 1

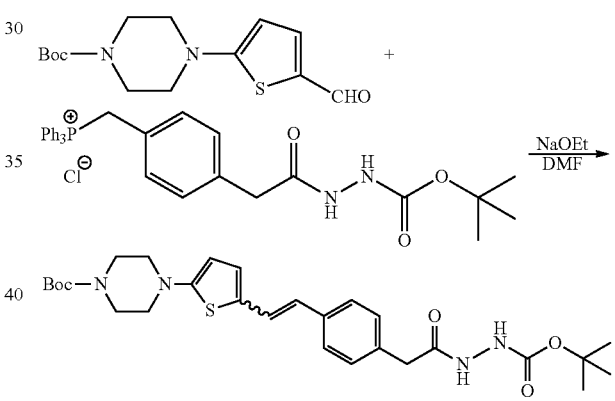

{4-[2-(tert-Butoxycarbonyl)hydrazinocarbonylmethyl] benzyl}(triphenyl)-phosphonium chloride (379 mg, 0.67 mmol) and tert-butyl 4-(5-formylthiphen-2-yl)piperidine-1-carboxylate (100 mg, 0.34 mmol) were suspended in anhydrous N,N-dimethylformamide (2 ml) and the suspension was cooled to 0° C. Sodium ethoxide (21% wt ethanol solution, 0.25 ml, 0.67 mmol) was diluted with anhydrous N,N-dimethylformamide (0.5 ml) and added dropwise thereto. The reaction mixture was warmed to room temperature, and stirred overnight. Saturated aqueous ammonium chloride solution was added and the mixture was extracted with ethyl acetate. The combined organic layer was washed with water and saturated brine, dried over anhydrous sodium sulfate, and concentrated. The residue was purified by silica gel column chromatography (ethyl acetate:hexane=1:1) to give tert-butyl 4-[5-(2-{4-[2-(tert-butoxycarbonylhydrazino)carbonylmethyl]phenyl}vinyl)-2-thienyl]piperazine-1-carboxylate (76 mg, yield 42%, E/Z mixture).
Step 2 and the Following The above-mentioned tert-butyl 4-[5-(2-{4-[2-(tert-butoxycarbonylhydrazino)carbonylmethyl]phenyl}vinyl)-2-thienyl]piperazine-1-carboxylate was treated by a method similar to Production Example 1, step 5 (hydrogenation) and step 6 (deprotection) to synthesize the title compound.

Production Example 75

2-(4-{2-[5-(4-acetylpiperazin-1-yl)thiophen-2-yl]ethyl}phenyl)acetohydrazide dihydrochloride Step 1

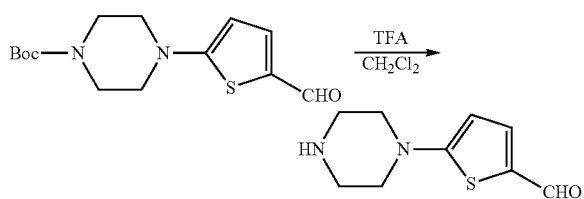

By a method similar to Production Example 72, step 1, tert-butyl 4-(5-formylthiophen-2-yl)piperidine-1-carboxylate (1.0 g, 3.37 mmol) was deprotected to give 5-piperazin-1-ylthiophene-2-carbaldehyde (320 mg, yield 48%).
Step 2 and the Following
5-(4-Acetylpiperazin-1-yl)thiophene-2-carbaldehyde obtained by treating the above-mentioned 5-piperazin-1-ylthiophene-2-carbaldehyde with acetic anhydride as a starting material was treated by a method similar to Production Example 74, step 1 (Wittig reaction) and Production Example 1, step 5 (hydrogenation), step 6 (deprotection) to synthesize the title compound.

Production Example 76

2-{4-[2-(5-morpholin-4-ylthiophen-2-yl)ethyl]phenyl}acetohydrazide dihydrochloride Using 5-morpholin-4-ylthiophene-2-carbaldehyde as a starting material, the title compound was synthesized by a method similar to Production Example 74, step 1 (Wittig reaction) and Production Example 1, step 5 (hydrogenation), step 6 (deprotection).

Production Example 77

N-{4-[2-(4-hydrazinocarbonylmethylphenyl)ethyl]-1,3-thiazol-2-yl}ethanesulfonylamide hydrochloride Step 1

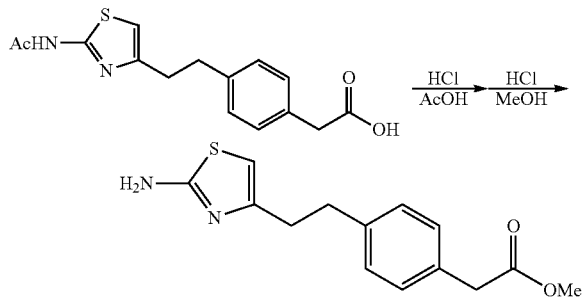

To {4-[2-(2-acetylamino-1,3-thiazol-4-yl)ethyl]phenyl}acetic acid (6.00 g, 19.7 mmol) that was synthesized from N-(4-formyl-1,3-thiazol-2-yl)acetamide by Wittig reaction and hydrogenation reaction based on the method described in WO2006/28269 were added acetic acid (18 ml) and concentrated hydrochloric acid (24 ml), and the mixture was heated at 105-110° C. for 5 hrs. After cooling, the reaction mixture was concentrated to dryness. 5% Hydrogen chloride methanol solution (30 ml) was added to the residue, and the mixture was stirred at 40° C. for 1.5 hrs and at room temperature for 12 hrs. The reaction mixture was concentrated, saturated aqueous sodium hydrogen carbonate solution was added, and the mixture was extracted with ethyl acetate. The combined organic layer was washed with saturated brine, dried over anhydrous magnesium sulfate, and concentrated under reduced pressure. Diisopropyl ether was added to the residue, and the precipitate was collected by filtration, washed with diisopropyl ether and dried under reduced pressure to give methyl{4-[2-(2-amino-1,3-thiazol-4-yl)ethyl]phenyl}acetate (5.36 g, yield 98%) as a white solid.
Step 2

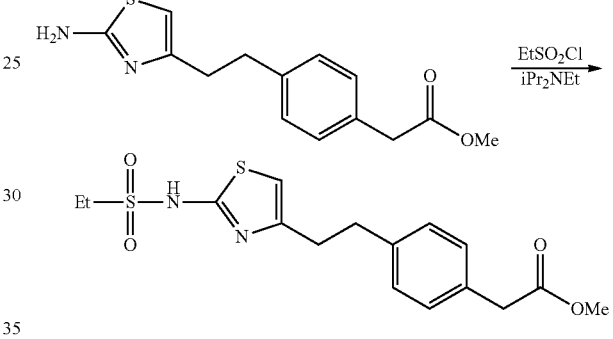

To a solution of methyl {4-[2-(2-amino-1,3-thiazol-4-yl)ethyl]phenyl}acetate (2.00 g, 7.24 mmol) in chloroform (20 ml) was added N,N-diisopropylethylamine (6.3 ml, 36.2 mmol), and the mixture was cooled to 0° C. Ethanesulfonyl chloride (0.82 ml, 8.7 mmol) was added dropwise, and the mixture was stirred at 0° C. overnight. Iced water (40 ml) was added to the reaction mixture, and the mixture was stirred for 10 mins. The mixture was extracted with ethyl acetate, and the combined organic layer was washed with 1M hydrochloric acid, saturated aqueous sodium hydrogen carbonate solution and saturated brine, dried over anhydrous magnesium sulfate, and concentrated. The residue was purified by silica gel column chromatography (ethyl acetate:hexane=2:1→1:0) to give methyl [4-(2-{2-[(ethylsulfonyl)amino]-1,3-thiazol-4-yl}ethyl)phenyl]acetate (1.76 g, yield 66%) as a white solid.
Step 3

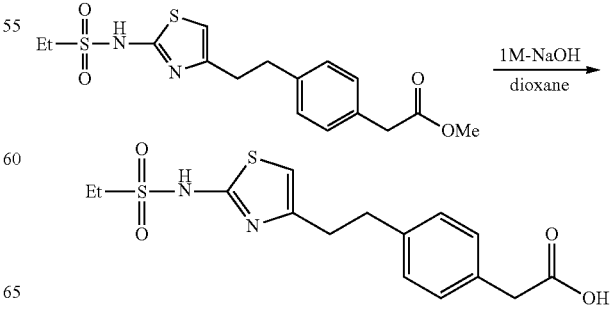

To a solution of methyl [4-(2-{2-[(ethylsulfonyl)amino]-1,3-thiazol-4-yl}ethyl)phenyl]acetate (1.74 g, 4.72 mmol) in dioxane (17.4 ml) was added at 0° C. 1M aqueous sodium hydroxide solution (11.8 ml, 11.8 mmol), and the mixture was stirred at room temperature for 2 hrs. The reaction mixture was concentrated under reduced pressure, and water (20 ml) was added. After cooling to 0° C., 1M hydrochloric acid (16 ml) was added dropwise with stirring. After stirring at 0° C. for 30 mins, the precipitate was collected by filtration, washed with water and dried under reduced pressure to give [4-(2-{2-[(ethylsulfonyl)amino]-1,3-thiazol-4-yl}ethyl)phenyl]acetic acid (1.66 g, yield 99%).

Step 4

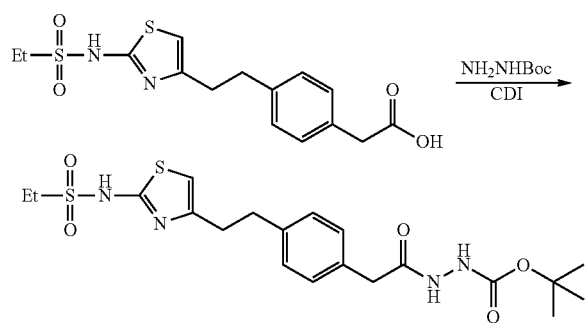

To a suspension of [4-(2-{2-[(ethylsulfonyl)amino]-1,3-thiazol-4-yl}ethyl)phenyl]acetic acid (700 mg, 1.98 mmol) in anhydrous tetrahydrofuran (5 ml) was added 1,1'-carbonyldiimidazole (480 mg, 2.96 mmol), and the mixture was stirred at 40-45° C. for 1 hr. After cooling to 0° C., tert-butyl carbazate (914 mg, 6.91 mmol) was added, and the mixture was stirred at room temperature for 4 hrs. Water was added to the reaction mixture and the mixture was extracted with ethyl acetate. The combined organic layer was washed with 1M hydrochloric acid, saturated aqueous sodium hydrogen carbonate solution and saturated brine, dried over anhydrous magnesium sulfate and concentrated. The residue was purified by silica gel column chromatography (ethyl acetate) to give tert-butyl 2-{[4-(2-{2-[(ethylsulfonyl)amino]-1,3-thiazol-4-yl}ethyl)phenyl]acetyl}hydrazinecarboxylate (989 mg, quantitatively) as a white solid.

Step 5

The above-mentioned tert-butyl 2-{[4-(2-{2-[(ethylsulfonyl)amino]-1,3-thiazol-4-yl}ethyl)phenyl] acetyl}hydrazinecarboxylate was treated by a method similar to Production Example 1, step 6 (deprotection) to synthesize the title compound.

Production Example 78

N-{4-[2-(4-hydrazinocarbonylmethylphenyl)ethyl]-1,3-thiazol-2-yl}methanesulfonylamide hydrochloride Using methanesulfonyl chloride instead of ethanesulfonyl chloride of Production Example 77, step 2, methyl [4-(2-{2-[(methylsulfonyl)amino]-1,3-thiazol-4-yl}methyl)phenyl] acetate was synthesized, and the title compound was synthesized by a method similar to Example 77, steps 3-5.

Production Example 79

2-[4-(2-{4-[ethyl(methyl)amino]phenyl}ethyl)phenyl]acetohydrazide dihydrochloride Step 1

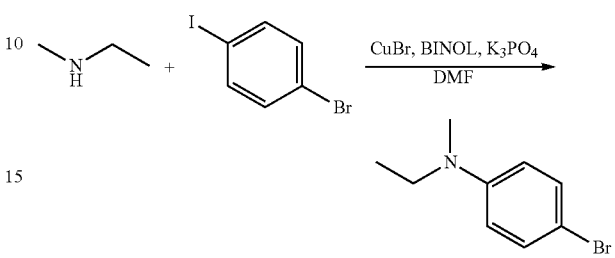

A mixture of 1-bromo-4-iodobenzene (2.0 g, 7.07 mmol), N-methylethylamine (3.0 ml, 35.3 mmol), copper(I) bromide (203 mg, 1.41 mmol), 1,1'-bi-2-naphthol (405 mg, 1.41 mmol), tripotassium phosphate (3.0 g, 14.1 mmol) and anhydrous N,N-dimethylformamide (20 ml) was stirred at 70° C. for 2 days. After cooling to room temperature, the mixture was filtered through a Celite pad, and the insoluble material was washed with ethyl acetate. The filtrate and washing solution were combined and washed with water, dried over anhydrous sodium sulfate, and concentrated under reduced pressure. The residue was purified by silica gel column chromatography (ethyl acetate:hexane=0:100→2:98) to give N-ethyl-4-bromo-N-methylaniline (1.04 g, yield 69%) as a yellow oil.

Step 2 and the Following

Using the above-mentioned N-ethyl-4-bromo-N-methylaniline as a starting material, the title compound was synthesized by a method similar to Production Example 29, steps 1 (coupling step), and then Production Example 1, step 5 (hydrogenation), step 6 (deprotection).

Production Example 80

2-[4-(2-{4-[methyl(propyl)amino]phenyl}ethyl)phenyl]acetohydrazide dihydrochloride Using 4-bromo-N-methyl-N-propylaniline synthesized from 1-bromo-4-iodobenzene and N-methylpropan-1-amine by a method similar to Production Example 79, step 1, as a starting material, the title compound was synthesized by a method similar to Production Example 29, steps 1 (coupling step), and then Production Example 1, step 5 (hydrogenation), step 6 (deprotection).

Production Example 81

2-[4-(2-{4-[ethyl(propyl)amino]phenyl}ethyl)phenyl]acetohydrazide dihydrochloride Using 4-bromo-N-ethyl-N-propylaniline synthesized from 1-bromo-4-iodobenzene and N-ethylpropan-1-amine by a method similar to Production Example 79, step 1, as a starting material, the title compound was synthesized by a method similar to Production Example 29, steps 1 (coupling step), and then Production Example 1, step 5 (hydrogenation), step 6 (deprotection).

Production Example 82

2-(4-{2-[4-(dipropylamino)phenyl]ethyl}phenyl)acetohydrazide dihydrochloride Using 4-bromo-N,N-dipropylaniline synthesized from 1-bromo-4-iodobenzene and N-propylpropan-1-amine by a method similar to Production Example 79, step 1, as a starting material, the title compound was synthesized by a method similar to Production Example 29, steps 1 (coupling step), and then Production Example 1, step 5 (hydrogenation), step 6 (deprotection).

Production Example 83

2-[4-(2-{4-[(2-aminoethyl)(ethyl)amino]phenyl}ethyl)phenyl]acetohydrazide trihydrochloride Step 1

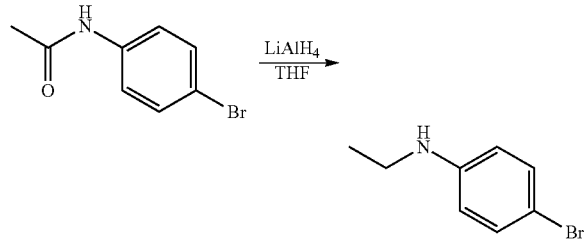

To a suspension of lithium aluminum hydride (1.1 g, 29 mmol) in anhydrous tetrahydrofuran (70 ml) was added dropwise at 0° C. a solution of N-(4-bromophenyl)acetamide (2.5 g, 12 mmol) in anhydrous tetrahydrofuran (30 ml). The reaction mixture was warmed to room temperature, and stirred for 15 mins. After further stirring at 60° C. for 2 hrs, the mixture was cooled to 0° C. Water (1.8 ml) was added dropwise by small portions, and 2M aqueous sodium hydroxide solution (1.55 ml) was added dropwise. After stirring for 15 mins, sodium sulfate was added, and the mixture was further stirred for 15 mins. The mixture was filtered through a Celite pad, and the insoluble material was washed with dichloromethane. The filtrate and washing solution were combined and concentrated under reduced pressure to give 4-bromo-N-ethylaniline (2.28 g, yield 95%) as a yellow oil.

Step 2

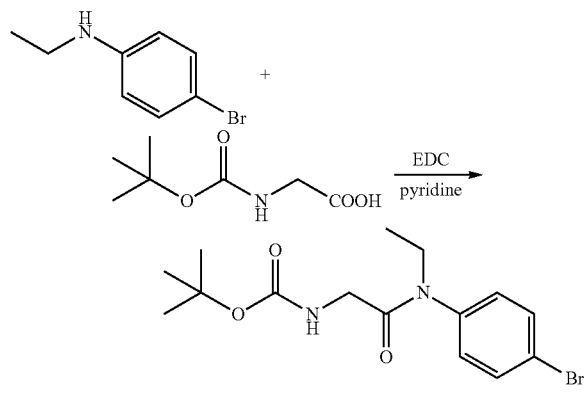

To a solution of 4-bromo-N-ethylaniline (1.28 g, 6.4 mmol), N-Boc-glycine (1.57 g, 9.0 mmol) in pyridine (10 ml) was added 1-ethyl-3-(3-dimethylaminopropyl)carbodiimide hydrochloride (1.47 g, 7.7 mmol) at 0° C. The reaction mixture was stirred at room temperature for 4 hrs. The reaction mixture was poured into a mixture of diluted aqueous sodium hydrogen carbonate solution and ethyl acetate. The mixture was stirred, stood still and partitioned. The aqueous layer was extracted with ethyl acetate. The combined organic layer was washed with water and saturated brine, dried over anhydrous sodium sulfate, and concentrated under reduced pressure to give tert-butyl [(4-bromophenyl)(ethyl)aminocarbonylmethyl]carbamate (2.255 g, yield 99%) as a yellow solid.

Step 3

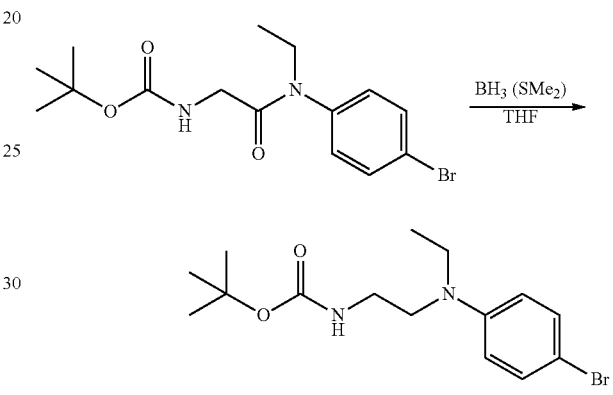

To a solution of tert-butyl [(4-bromophenyl)(ethyl)aminocarbonylmethyl]carbamate (1.82 g, 5.10 mmol) in anhydrous tetrahydrofuran (25 ml) was added dropwise borane•dimethylsulfide complex (2.4 ml, 25.5 mmol) at room temperature. Since heat generation was observed, the mixture was stirred in an ice bath for 10 mins, warmed to room temperature and stirred for 1.25 hrs. The reaction mixture was added dropwise to ice-cooled methanol (30 ml), and the mixture was warmed to room temperature, and stirred for 45 mins. This was poured into a mixture of diluted aqueous sodium hydrogen carbonate solution and ethyl acetate. The mixture was stirred, stood still and partitioned. The aqueous layer was extracted with ethyl acetate. The combined organic layer was washed twice with saturated brine, and dried over anhydrous sodium sulfate and concentrated under reduced pressure to give a pale-yellow oil (1.86 g). 896 mg therefrom was used for the synthesis of the starting material of Production Example 84. The remaining 964 mg was purified by silica gel column chromatography (ethyl acetate:hexane=1:4) to give tert-butyl{2-[(4-bromophenyl)(ethyl)amino]ethyl}carbamate (671 mg, yield 77%) as a white solid.

Step 4 and the Following

Using the above-mentioned tert-butyl{2-[(4-bromophenyl)(ethyl)amino]ethyl}carbamate as a starting material, the title compound was synthesized by a method similar to Production Example 29, steps 1 (coupling step), and then Production Example 1, step 5 (hydrogenation), step 6 (deprotection).

Production Example 84

N-[2-(ethyl{4-[2-(4-hydrazinocarbonylmethylphenyl)ethyl]phenyl}amino)ethyl]-acetamide dihydrochloride Step 1

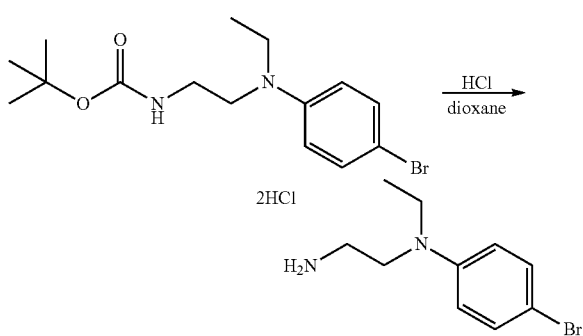

tert-Butyl{2-[(4-bromophenyl)(ethyl)amino]ethyl} carbamate (896 mg) synthesized in Production Example 83, step 3 was dissolved in dioxane (5 ml), and 4M-hydrogen chloride dioxane solution (5 ml, 20 mmol) was added dropwise at 0° C. After stirring at room temperature for 2 hrs, the mixture was concentrated under reduced pressure. Dichloromethane was added to the residue, and the mixture was concentrated under reduced pressure, which operation was performed 3 times to remove volatile components such as hydrogen chloride and the like. The residue was dried under reduced pressure to give N-(4-bromophenyl)-N-ethylethane-1,2-diamine dihydrochloride (1.044 g) as a yellow gum-like solid.

Step 2

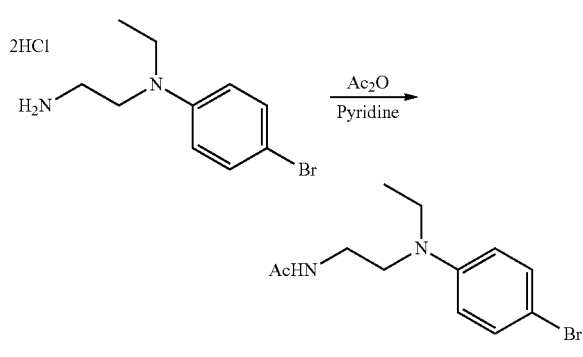

To a mixture of N-(4-bromophenyl)-N-ethylethane-1,2-diamine dihydrochloride (1.044 g, corresponding to 2.33 mmol), pyridine (4 ml) and anhydrous dichloromethane (8 ml) was added dropwise acetic anhydride (0.28 ml, 2.92 mmol) at 0° C. After stirring at room temperature for 70 mins, the reaction mixture was diluted with dichloromethane (50 ml), washed twice with diluted aqueous sodium hydrogen carbonate solution and with saturated brine, dried over anhydrous sodium sulfate, and concentrated under reduced pressure. The residue was purified by silica gel column chromatography (ethyl acetate:hexane=1:4→1:0) to give N-{2-[(4-bromophenyl)(ethyl)amino]ethyl}acetamide (460 mg, overall yield of 2 steps 92%) as a white solid.

Step 3 and the Following

Using the above-mentioned N-{2-[(4-bromophenyl)(ethyl)amino]ethyl}acetamide as a starting material, the title compound was synthesized by a method similar to Production Example 29, steps 1 (coupling step), and then Production Example 1, step 5 (hydrogenation), step 6 (deprotection).

Production Example 85

2-(4-{2-[6-(diethylamino)pyridin-3-yl]ethyl}phenyl)acetohydrazide trihydrochloride Step 1

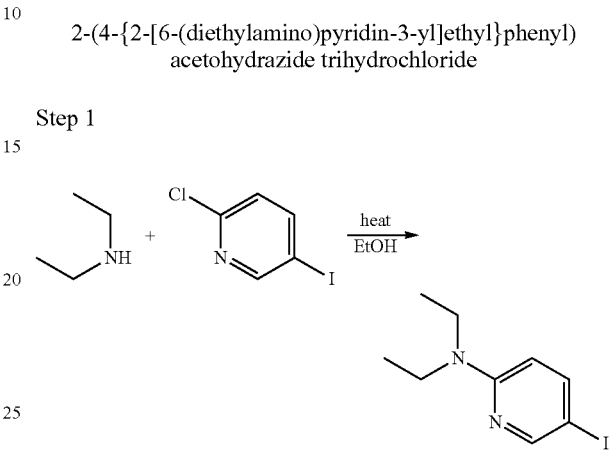

To a suspension of 2-chloro-5-iodopyridine (1.0 g, 4.18 mmol) in ethanol (8 ml) was added dropwise diethylamine (0.43 ml, 4.18 mmol). After stirring at 120° C. for 1 day, the mixture was stirred at 150° C. for 6.5 days (2 equivalents of diethylamine was added twice during the reaction). The reaction mixture was cooled to room temperature and concentrated under reduced pressure to give N,N-diethyl-5-iodopyridin-2-amine (460 mg, yield 40%).

Step 2 and the Following

Using the above-mentioned N,N-diethyl-5-iodopyridin-2-amine as a starting material, the title compound was synthesized by a method similar to Production Example 1, steps 4-6.

Production Example 86

2-{4-[2-(5-piperazin-1-ylpyridin-2-yl)ethyl]phenyl}acetohydrazide tetrahydrochloride Step 1

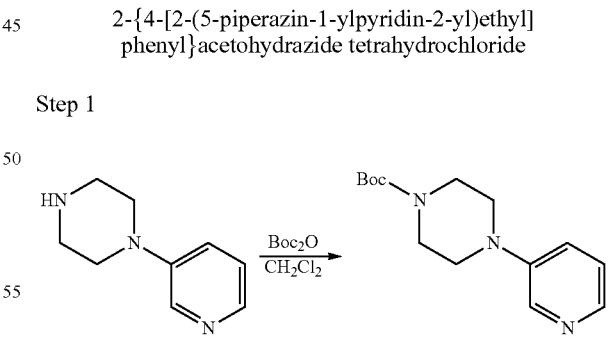

To a solution of 3-piperazin-4-ylpyridine (2.0 g, 12.25 mmol) in dichloromethane (20 ml) was added a solution of di-tert-butyl dicarbonate (3.21 g, 14.7 mmol) in dichloromethane (5 ml) at room temperature, and the mixture was stirred for 1 hr. The reaction mixture was diluted with dichloromethane, washed with saturated brine, dried over anhydrous sodium sulfate, and concentrated to give tert-butyl 4-pyridin-3-ylpiperazine-1-carboxylate (3.20 g, yield 99%) as a slightly yellow oil.

Step 2

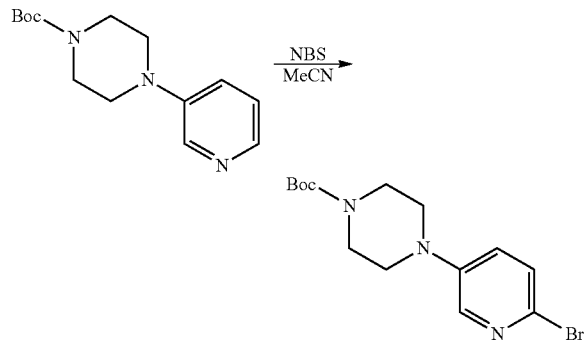

To a solution of tert-butyl 4-pyridin-3-ylpiperazine-1-carboxylate (1.0 g, 3.80 mmol) in acetonitrile (12 ml) was added N-bromosuccinimide (676 mg, 3.80 mmol) by small portions at room temperature. After stirring at room temperature for 1.5 hrs, the reaction mixture was poured into a mixture of 1M aqueous sodium hydroxide solution and ethyl acetate. The mixture was stirred, stood still and partitioned. The organic layer was washed with saturated brine, dried over anhydrous sodium sulfate, and concentrated under reduced pressure to give tert-butyl 4-(6-bromopyridin-3-yl)piperazine-1-carboxylate (1.26 g, yield 97%).

Step 3 and the Following

Using the above-mentioned tert-butyl 4-(6-bromopyridin-3-yl)piperazine-1-carboxylate as a starting material, the title compound was synthesized by a method similar to Production Example 1, steps 4-6.

Production Example 87

2-(4-{2-[5-(4-acetylpiperazin-1-yl)pyridin-2-yl]ethyl}phenyl)acetohydrazide trihydrochloride Step 1

1-Acetyl-4-pyridin-3-ylpiperazine was obtained by treating 3-piperazin-4-ylpyridine with acetic anhydride.

Step 2

1-Acetyl-4-(6-bromopyridin-3-yl)piperazine was synthesized from above-mentioned 1-acetyl-4-pyridin-3-ylpiperazine by brominating with N-bromosuccinimide by a method similar to Production Example 86, step 2, Step 3 and the Following The title compound was synthesized from above-mentioned 1-acetyl-4-(6-bromopyridin-3-yl)piperazine by a method similar to Production Example 1, steps 4-6.

Production Example 88

2-(4-{2-[5-(diethylamino)pyridin-2-yl]ethyl}phenyl)acetohydrazide trihydrochloride Step 1

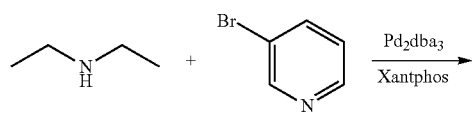

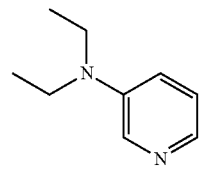

To a mixture of 4,5-bis(diphenylphosphino)-9,9'-dimethylxanthene (521 mg, 0.90 mmol), tris(dibenzylideneacetone)dipalladium (0)-chloroform adduct (311 mg, 0.30 mmol), sodium t-butoxide (2.16 g, 23 mmol) and anhydrous toluene (37 ml) were added 3-bromopyridine (1.5 ml, 15 mmol) and diethylamine (1.9 ml, 18.0 mmol). The mixture was heated to 70° C., and the mixture was stirred for 3 hrs and at room temperature overnight. Water and ethyl acetate were added to the reaction mixture. The mixture was stirred, stood still and partitioned. The aqueous layer was extracted with ethyl acetate, and the combined organic layer was washed with saturated brine, dried over anhydrous sodium sulfate, and concentrated. The residue was purified by silica gel column chromatography (ethyl acetate:hexane=1:1→2:1) to give N,N-diethylpyridin-3-amine (820 mg, yield 36%) as a brown oil.

Step 2 and the Following

Using 6-bromo-N,N-diethylpyridin-3-amine obtained by bromination of the above-mentioned N,N-diethylpyridin-3-amine by a method similar to Production Example 86, step 2 as a starting material, the title compound was synthesized by a method similar to Production Example 1, steps 4-6.

Production Example 89

2-[4-(2-{6-[ethyl(methyl)amino]pyridin-3-yl}ethyl)phenyl]acetohydrazide trihydrochloride Step 1

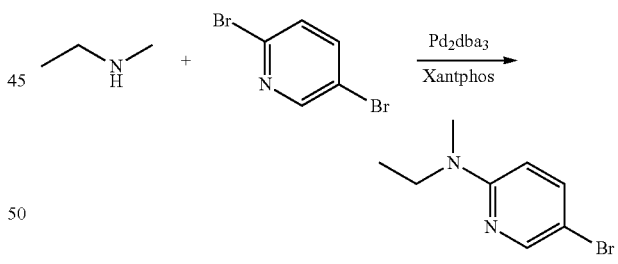

To a mixture of 4,5-bis(diphenylphosphino)-9,9'-dimethylxanthene (293 mg, 0.51 mmol), tris(dibenzylideneacetone)dipalladium (0)-chloroform adduct (174 mg, 0.17 mmol), sodium t-butoxide (974 mg, 10.0 mmol), 2,5-dibromopyridine (2.0 g, 8.44 mmol) and anhydrous toluene (30 ml) was added N-methylethylamine (1.09 ml, 12.7 mmol). The mixture was heated to 70° C., and the mixture was stirred for 3 hrs. The reaction mixture was cooled to room temperature, ethyl acetate was added, and the mixture was washed with water and saturated brine, dried over anhydrous sodium sulfate, and concentrated. The residue was purified by silica gel column chromatography (ethyl acetate:hexane=1:19) to give 5-bromo-N-ethyl-N-methylpyridin-2-amine (1.21 g, yield 66%) as a yellow oil.

Step 2 and the Following

Using the above-mentioned 5-bromo-N-ethyl-N-methylpyridin-2-amine as a starting material, the title compound was synthesized by a method similar to Production Example 1, steps 4-6.

Production Example 90

2-[4-(2-{6-[methyl(propyl)amino]pyridin-3-yl}ethyl)phenyl]acetohydrazide trihydrochloride Using 5-bromo-N-methyl-N-propylpyridin-2-amine synthesized from N-methylpropan-1-amine and 2,5-dibromopyridine by a method similar to Production Example 79, step 1, as a starting material, the title compound was synthesized by a method similar to Production Example 1, steps 4-6.

Production Example 91

2-[4-(2-{6-[ethyl(propyl)amino]pyridin-3-yl}ethyl)phenyl]acetohydrazide trihydrochloride Using 5-bromo-N-ethyl-N-propylpyridin-2-amine synthesized from N-ethylpropan-1-amine and 2,5-dibromopyridine by a method similar to Production Example 79, step 1, as a starting material, the title compound was synthesized by a method similar to Production Example 1, steps 4-6.

Production Example 92

2-(4-{2-[6-(dipropylamino)pyridin-3-yl]ethyl}phenyl)acetohydrazide trihydrochloride Using 5-bromo-N,N-dipropylpyridin-2-amine synthesized from N-propylpropan-1-amine and 2,5-dibromopyridine by a method similar to Production Example 79, step 1, as a starting material, the title compound was synthesized by a method similar to Production Example 1, steps 4-6.

Production Example 93

2-(4-{2-[6-(diethylamino)pyridin-2-yl]ethyl}phenyl)acetohydrazide trihydrochloride Using 6-bromo-N,N-diethylpyridin-2-amine synthesized from N-ethylethanamine and 2,6-dibromopyridine by a method similar to Production Example 79, step 1, as a starting material, the title compound was synthesized by a method similar to Production Example 1, steps 4-6.

Production Example 94

2-(4-{2-[2-(4-acetylpiperazin-1-yl)-1,3-thiazol-4-yl]ethyl}phenyl)acetohydrazide dihydrochloride Step 1

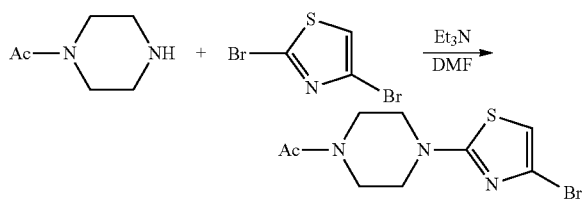

To a solution of 1-acetylpiperazine (316 mg, 4.78 mmol) and 2,4-dibromo-1,3-thiazole (900 mg, 3.71 mmol) in N,N-dimethylformamide (8 ml) was added triethylamine (0.78 ml, 5.56 mmol). The reaction mixture was stirred at 50° C. for 14 hrs and at 65° C. for 6 hrs. After cooling to room temperature, the reaction mixture was poured into water, and the mixture was extracted with ethyl acetate. The combined organic layer was washed with water and saturated brine, dried over anhydrous sodium sulfate, and concentrated. The residue was purified by silica gel column chromatography (dichloromethane:methanol=100:0→98:2) to give 1-acetyl-4-(4-bromo-1,3-thiazol-2-yl)piperazine (590 mg, yield 55%) as a pale-white brown solid.

Step 2 and the Following

Using the above-mentioned 1-acetyl-4-(4-bromo-1,3-thiazol-2-yl)piperazine as a starting material, the title compound was synthesized by a method similar to Production Example 1, steps 4-6.

Production Example 95

2-{4-[2-(2-piperazin-1-yl-1,3-thiazol-4-yl)ethyl]phenyl}acetohydrazide dihydrochloride Step 1

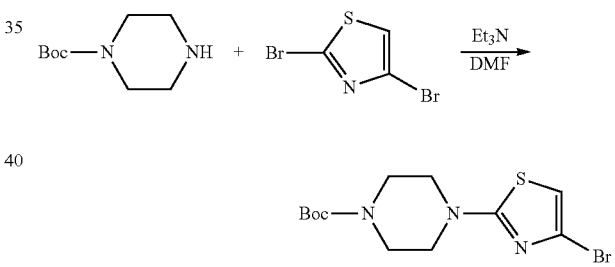

To a solution of tert-butyl piperazine-1-carboxylate (767 mg, 4.12 mmol), 2,4-dibromo-1,3-thiazole (1.0 g, 4.12 mmol) in N,N-dimethylformamide (9 ml) was added triethylamine (0.86 ml, 6.18 mmol). The reaction mixture was stirred at 50° C. for 6 hrs and at 60° C. for 39 hrs. After cooling to room temperature, the reaction mixture was poured into water, and the mixture was extracted with ethyl acetate. The combined organic layer was washed with water and saturated brine, dried over anhydrous sodium sulfate, and concentrated. The residue was purified by silica gel column chromatography (dichloromethane:methanol=100:0→98:2) to give tert-butyl 4-(4-bromo-1,3-thiazol-2-yl)piperazine-1-carboxylate (1.09 g, yield 76%) as a pale-white brown solid.

Step 2 and the Following

Using the above-mentioned tert-butyl 4-(4-bromo-1,3-thiazol-2-yl)piperazine-1-carboxylate as a starting material, the title compound was synthesized by a method similar to Production Example 1, steps 4-6.

Production Example 96

2-(4-{2-[6-(4-acetylpiperazin-1-yl)-3-(trifluoromethyl)pyridin-2-yl]ethyl}phenyl)acetohydrazide dihydrochloride Step 1

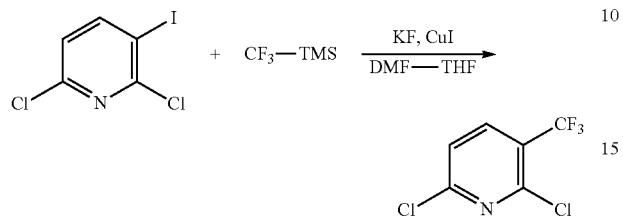

Potassium fluoride (2.24 g, 38.5 mmol) and copper (I) iodide (7.33 g, 38.5 mmol) were weighed in a flask, and the mixture was heated with a gas burner while gently shaking under high vacuum until the content becomes a pale-yellow green. After cooling to room temperature, anhydrous N,N-dimethylformamide (50 ml), anhydrous tetrahydrofuran (10 ml) and trimethyl(trifluoromethyl)silane (5.5 ml, 35 mmol) were added. The mixture was heated to 50° C., and stirred for 21 hrs. A mixed solution of 2,6-dichloro-3-iodopyridine (9.59 g, 35.0 mmol) in anhydrous N,N-dimethylformamide (10 ml)—anhydrous tetrahydrofuran (20 ml) was added dropwise to the above-mentioned reaction mixture at 50° C. After stirring at 50° C. for 21 hrs, trimethyl(trifluoromethyl)silane (0.55 ml, 3.5 mmol) was added, and the mixture was stirred for 24 hrs. The reaction mixture was cooled to room temperature, poured into 12% aqueous ammonia, and the mixture was extracted 3 times with diethyl ether. The combined organic layer was washed successively with 12% aqueous ammonia, 1M hydrochloric acid, saturated aqueous sodium hydrogen carbonate solution and saturated brine, dried over anhydrous sodium sulfate, and concentrated under reduced pressure. The residue was purified by silica gel column chromatography (dichloromethane:hexane=1:4) to give 2,6-dichloro-3-(trifluoromethyl)pyridine (7.32 g, yield 97.3%).

Step 2

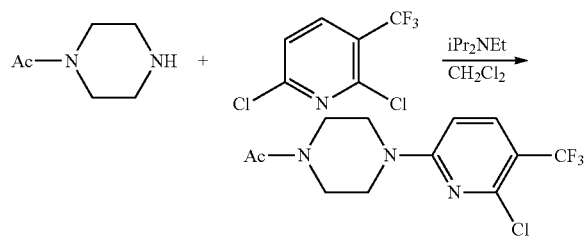

To a solution of 2,6-dichloro-3-(trifluoromethyl)pyridine (2.38 g, 11.0 mmol) in anhydrous dichloromethane (20 ml) was added dropwise N,N-diisopropylethylamine (3.7 ml, 225 mmol). A solution of 1-acetylpiperazine (1.69 g, 13.2 mmol) in anhydrous dichloromethane (10 ml) was added dropwise at 0° C., and the mixture was stirred at room temperature for 5 hrs. The mixture was warmed, heated under reflux for 2.5 hrs, and stirred at room temperature for 14 hrs. The reaction mixture was diluted with dichloromethane and washed with water. The aqueous layer was extracted twice with dichloromethane, and the combined organic layer was dried over anhydrous sodium sulfate, and concentrated under reduced pressure. The residue was purified by silica gel column chromatography (ethyl acetate:hexane=1:4→ethyl acetate→ethanol:ethyl acetate=1:20) to give 1-acetyl-4-[6-chloro-5-(trifluoromethyl)pyridin-2-yl]piperazine (451 mg, yield 13%) as a yellow solid.

Step 3 and the Following

Using the above-mentioned 1-acetyl-4-[6-chloro-5-(trifluoromethyl)pyridin-2-yl]piperazine as a starting material, the title compound was synthesized by a method similar to Production Example 29, steps 1 (coupling step), and then Production Example 1, step 5 (hydrogenation), step 6 (deprotection).

Production Example 97

2-(4-{2-[6-piperazin-1-yl-3-(trifluoromethyl)pyridin-2-yl]ethyl}phenyl)acetohydrazide trihydrochloride Step 1

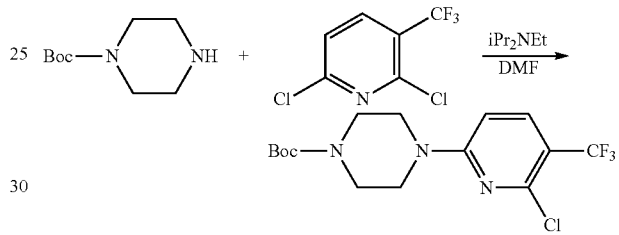

tert-Butyl 4-[6-chloro-5-(trifluoromethyl)pyridin-2-yl]piperazine-1-carboxylate (1.67 g, yield 65%, off-white solid) was synthesized from 2,6-dichloro-3-(trifluoromethyl)pyridine (1.51 g, 7.0 mmol) and tert-butyl piperazine-1-carboxylate (1.56 g, 8.38 mmol) by a method similar to Production Example 96, step 2.

Step 2 and the Following

Using the above-mentioned tert-butyl 4-[6-chloro-5-(trifluoromethyl)pyridin-2-yl]piperazine-1-carboxylate as a starting material, the title compound was synthesized by a method similar to Production Example 29, steps 1 (coupling step), and then Production Example 1, step 5 (hydrogenation), step 6 (deprotection).

Production Example 98

2-{4-[2-(6-piperazin-1-ylpyridazin-3-yl)ethyl]phenyl}acetohydrazide tetrahydrochloride Using tert-butyl 4-(6-chloropyridazin-3-yl)piperazine-1-carboxylate as a starting material, the title compound was synthesized by a method similar to Production Example 29, steps 1 (coupling step), and then Production Example 1, step 5 (hydrogenation), step 6 (deprotection).

Production Example 99

2-(4-{2-[6-(4-acetylpiperazin-1-yl)pyridazin-3-yl]ethyl}phenyl)acetohydrazide trihydrochloride Using 3-(4-acetylpiperazin-1-yl)-6-chloropyridazine obtained from 3,6-dichloropyridazine by a method similar to Production Example 94, step 1, as a starting material, the title compound was synthesized by a method similar to Produc-

Production Example 100

2-{4-[2-(5-piperazin-1-ylpyrazin-2-yl)ethyl]phenyl}acetohydrazide tetrahydrochloride Using, as a starting material, tert-butyl 4-(5-bromopyrazin-3-yl)piperazine-1-carboxylate obtained by treating 2-bromo-5-piperazin-1-ylpyrazine with di-tert-butyl dicarbonate in the similar manner as in Production Example 59, step 1, the title compound was synthesized by a method similar to Production Example 1, steps 4-6.

Production Example 101

2-(4-{2-[5-(4-acetylpiperazin-1-yl)pyrazin-2-yl]ethyl}phenyl)acetohydrazide trihydrochloride Using 2-(4-acetylpiperazin-1-yl)-5-bromopyrazine obtained by treating 2-bromo-5-piperazin-1-ylpyrazine with acetic anhydride, as a starting material, the title compound was synthesized by a method similar to Production Example 1, steps 4-6.

Production Example 102

2-{4-[2-(5-piperazin-1-ylpyridin-3-yl)ethyl]phenyl}acetohydrazide tetrahydrochloride Using tert-butyl 4-(6-bromopyridin-2-yl)piperazine-1-carboxylate synthesized from 3,5-dibromopyridine by a method similar to Production Example 88, step 1, as a starting material, the title compound was synthesized by a method similar to Production Example 1, steps 4-6.

Production Example 103

2-{4-[2-(6-piperazin-1-ylpyrazin-2-yl)ethyl]phenyl}acetohydrazide tetrahydrochloride Using tert-butyl 4-(6-chloropyrazin-2-yl)piperazine-1-carboxylate as a starting material, the title compound was synthesized by a method similar to Production Example 29, steps 1 (coupling step), and then Production Example 1, step 5 (hydrogenation), step 6 (deprotection).

Production Example 104

2-{4-[2-(4-piperazin-1-ylpyridin-2-yl)ethyl]phenyl}acetohydrazide tetrahydrochloride Using tert-butyl 4-(2-chloropyridin-4-yl)piperazine-1-carboxylate obtained by treating 1-(2-chloropyridin-4-yl)piperazine with di-tert-butyl dicarbonate in the similar manner as in Production Example 59, step 1, as a starting material, the title compound was synthesized by a method similar to Production Example 29, steps 1 (coupling step), and then Production Example 1, step 5 (hydrogenation), step 6 (deprotection).

Production Example 105

2-{4-[2-(2-piperazin-1-ylpyridin-4-yl)ethyl]phenyl}acetohydrazide tetrahydrochloride Using tert-butyl 4-(4-bromopyridin-2-yl)piperazine-1-carboxylate synthesized from 2,4-dibromopyridine by a method similar to Production Example 88, step 1, as a starting material, the title compound was synthesized by a method similar to Production Example 1, steps 4-6.

Production Example 106

2-{4-[2-(6-piperazin-1-ylpyrimidin-4-yl)ethyl]phenyl}acetohydrazide tetrahydrochloride Step 1

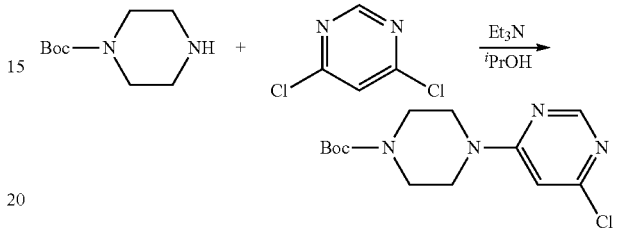

To a solution (60 ml) of 4,6-dichloropyrimidine (2.00 g, 13.4 mmol) and tert-butyl piperazine-1-carboxylate (3.00 g, 16.1 mmol) in 2-propanol was added triethylamine (4.7 ml, 33.6 mmol), and the mixture was heated under reflux for 2 hrs. The mixture was concentrated under reduced pressure, dichloromethane was added to the residue, and the mixture was washed with water. The aqueous layer was extracted with dichloromethane, and the combined organic layer was dried over anhydrous sodium sulfate, and concentrated under reduced pressure. The residue was purified by silica gel column chromatography (ethyl acetate:hexane=1:2) to give tert-butyl 4-(6-chloropyrimidin-2-yl)piperazine-1-carboxylate (3.80 g, yield 95%) as a white solid.

Step 2 and the Following

Using the above-mentioned tert-butyl 4-(6-chloropyrimidin-2-yl)piperazine-1-carboxylate as a starting material, the title compound was synthesized by a method similar to Production Example 29, steps 1 (coupling step), and then Production Example 1, step 5 (hydrogenation), step 6 (deprotection).

Production Example 107

2-{4-[2-(4-piperazin-1-ylpyrimidin-2-yl)ethyl]phenyl}acetohydrazide tetrahydrochloride Using tert-butyl 4-(2-chloropyrimidin-4-yl)piperazine-1-carboxylate as a starting material, the title compound was synthesized by a method similar to Production Example 29, steps 1 (coupling step), and then Production Example 1, step 5 (hydrogenation), step 6 (deprotection).

Production Example 108

4-{2-[5-(4-acetylpiperazin-1-yl)pyridin-2-yl]ethyl}benzyl hydrazinecarboxylate trihydrochloride Step 1

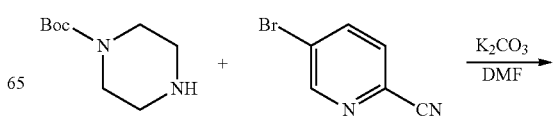

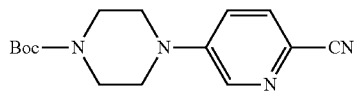

To a solution of 5-bromopyridine-2-carbonitrile (551.3 mg, 3.012 mmol) in anhydrous dimethylformamide (6.0 ml) were added tert-butyl piperazine-1-carboxylate (670.6 mg, 3.601 mmol) and potassium carbonate (829.0 mg, 5.998 mmol). The mixture was stirred at 120° C. for 63 hrs and cooled to room temperature. Ethyl acetate (30 ml) was added, and the precipitate was collected by filtration. Water (30 ml) was added to the filtrate, and the precipitated solid was collected by filtration and dried under reduced pressure to give tert-butyl 4-(6-cyanopyridin-3-yl)piperazine-1-carboxylate (642.9 mg, yield 74.0%) as a slightly yellow solid.

Step 2

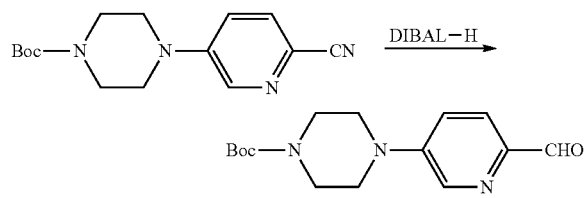

To a solution of tert-butyl 4-(6-cyanopyridin-3-yl)piperazine-1-carboxylate (144.2 mg, 0.500 mmol) in anhydrous dichloromethane (5 ml) was added dropwise at −78° C. 1.5M diisobutylaluminum hydride toluene solution (0.4 ml, 0.6 mmol) over 5 mins. After stirring at −78° C. for 1.5 hrs, 1M hydrochloric acid (1 ml) was added. The mixture was heated to room temperature and stirred for 1 hr. Saturated aqueous sodium carbonate solution was added, and the mixture was extracted with dichloromethane. The organic layer was dried over anhydrous magnesium sulfate, and concentrated under reduced pressure. The residue was purified by silica gel column chromatography (ethyl acetate:hexane=2:3) to give tert-butyl 4-(6-formylpyridin-3-yl)piperazine-1-carboxylate (73.4 mg, yield 50.4%) as a slightly yellow solid.

Step 3

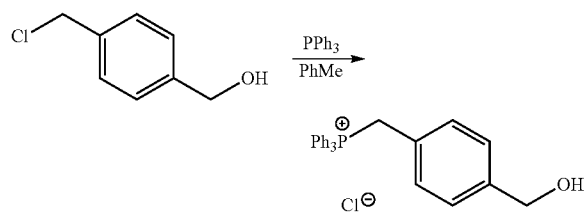

To a solution of [4-(chloromethyl)phenyl]methanol (4.691 g, 29.96 mmol) in toluene (30 ml) was added triphenylphosphine (9.444 g, 36.01 mmol). The mixture was heated under reflux for 20 hrs, and cooled to room temperature. The precipitate was collected by filtration, and dried under reduced pressure to give [4-(hydroxymethyl)benzyl](triphenyl)phosphonium chloride (11.47 g, yield 91.4%) as a white solid.

Step 4

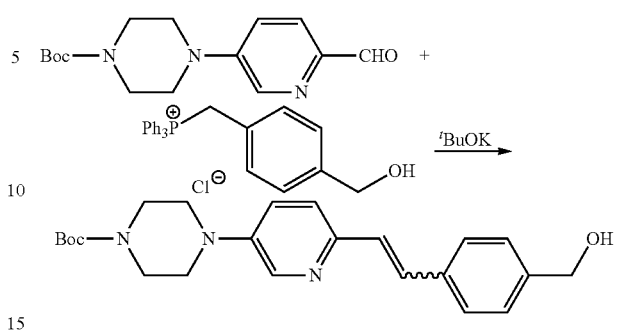

To a mixture of [4-(hydroxymethyl)benzyl](triphenyl)phosphonium chloride (1.283 g, 3.064 mmol), tert-butyl 4-(6-formylpyridin-3-yl)piperazine-1-carboxylate (876.3 mg, 3.008 mmol) and anhydrous tetrahydrofuran (10 ml) was added potassium tert-butoxide (383.9 mg, 3.421 mmol), and the mixture was stirred at room temperature for 1 hr. Water (20 ml) was added to the reaction mixture, and the mixture was extracted 3 times with ethyl acetate. The combined organic layer was dried over anhydrous magnesium sulfate, and concentrated under reduced pressure. The residue was purified by silica gel column chromatography (ethyl acetate: hexane=1:1). The fraction containing the target product was concentrated and the obtained solid was dissolved in ethyl acetate, and extracted twice with 0.2M hydrochloric acid. The aqueous layer was saturated with sodium carbonate, and the mixture was extracted with ethyl acetate. The organic layer was dried over anhydrous magnesium sulfate, and concentrated under reduced pressure to give tert-butyl 4-(6-{2-[4-(hydroxymethyl)phenyl]vinyl}pyridin-3-yl)piperazine-1-carboxylate (850.2 mg, yield 71.5%, E/Z mixture) as a pale-yellow solid.

Step 5

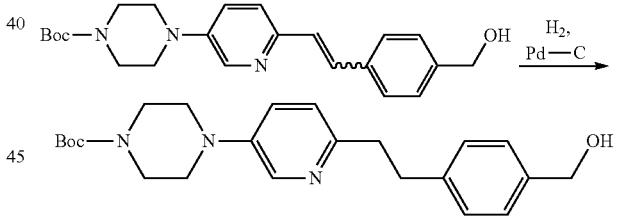

To a solution of tert-butyl 4-(6-{2-[4-(hydroxymethyl)phenyl]vinyl}pyridin-3-yl)piperazine-1-carboxylate (848.0 mg, 2.144 mmol) in ethyl acetate (45 ml) was added 5% palladium carbon (84.5 mg, 50% containing water), and the mixture was hydrogenated at room temperature, under atmospheric pressure for 11 hrs. The reaction mixture was filtered through Celite. The filtrate was concentrated under reduced pressure, and the residue was purified by silica gel column chromatography (ethyl acetate:hexane=6:4→7:3) to give tert-butyl 4-(6-{2-[4-(hydroxymethyl)phenyl]ethyl}pyridin-3-yl)piperazine-1-carboxylate (716.9 mg, yield 84.1%) as a white solid.

Step 6

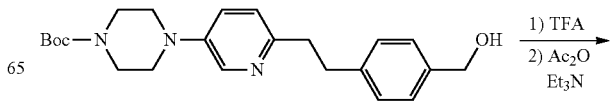

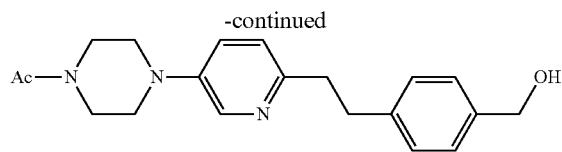

To a solution of tert-butyl 4-(6-{2-[4-(hydroxymethyl)phenyl]ethyl}pyridin-3-yl)piperazine-1-carboxylate (198.8 mg, 0.500 mmol) in dichloromethane (3 ml) was added trifluoroacetic acid (3 ml) at room temperature, and the mixture was stirred for 2.5 hrs. The reaction mixture was concentrated under reduced pressure, saturated aqueous sodium hydrogen carbonate solution was added to the residue, and the mixture was extracted twice with ethyl acetate. The combined organic layer was dried over anhydrous magnesium sulfate, and concentrated under reduced pressure. Anhydrous tetrahydrofuran (3 ml) was added to the residue, and acetic anhydride (0.047 ml, 0.50 mmol) and triethylamine (0.069 ml, 0.50 mmol) were added. After stirring at room temperature for 3 hrs, the mixture was concentrated under reduced pressure. The residue was purified by silica gel column chromatography (methanol:dichloromethane=1:20→4:10) to give (4-{2-[5-(4-acetylpiperazin-1-yl)pyridin-2-yl]ethyl}phenyl)methanol (113.4 mg, yield 66.8%) as a silghtly yellow solid.

Step 7

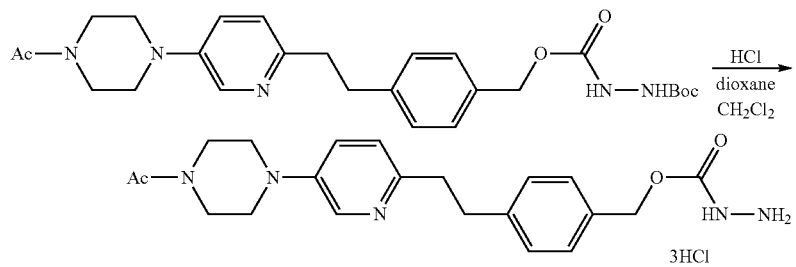

To a suspension of (4-{2-[5-(4-acetylpiperazin-1-yl)pyridin-2-yl]ethyl}phenyl)methanol (115.3 mg, 0.340 mmol) in anhydrous N,N-dimethylformamide (1.5 ml) was added 1,1'-carbonyldiimidazole (83.1 mg, 0.513 mmol), and the mixture was stirred at room temperature for 1.5 hrs. tert-Butyl carbazate (137.5 mg, 1.040 mmol) was added, and the mixture was stirred at room temperature 7 hrs. tert-Butyl carbazate (134.8 mg, 1.020 mmol) was added, and the mixture was stirred at room temperature for 16 hrs. tert-Butyl carbazate (135.7 mg, 1.027 mmol) was further added, and the mixture was stirred at 50° C. for 8 hrs. Water was added, and the mixture was extracted twice with ethyl acetate. The combined organic layer was washed with saturated brine, dried over anhydrous magnesium sulfate and concentrated under reduced pressure. The residue was suspended in dichloromethane (15 ml), collected by filtration, washed with dichloromethane and dried under reduced pressure. The residue was purified by silica gel column chromatography (methanol:dichloromethane=1:20). The fraction containing the target product was concentrated and the obtained solid was suspended in a mixture of ethyl acetate (1 ml) and diisopropyl ether (4 ml), collected by filtration and dried under reduced pressure to give 4-{2-[5-(4-acetylpiperazin-1-yl)pyridin-2-yl]ethyl}benzyl tert-butyl hydrazine-1,2-dicarboxylate (148.6 mg, yield 87.9%) as a white solid.

Step 8

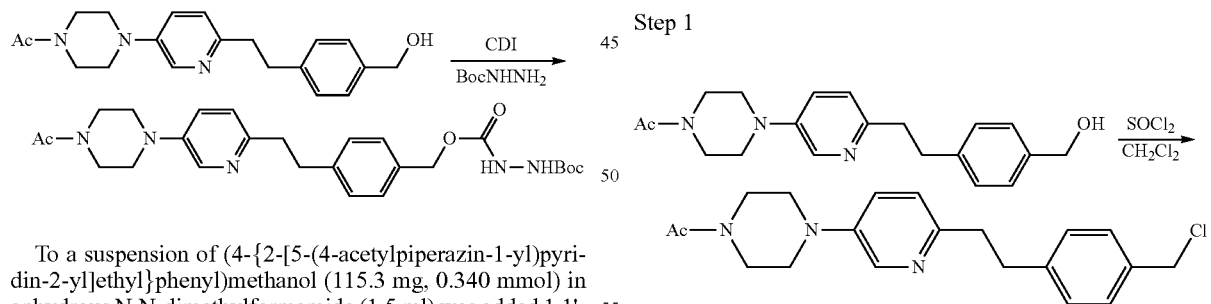

To a suspension of 4-{2-[5-(4-acetylpiperazin-1-yl)pyridin-2-yl]ethyl}benzyl tert-butyl hydrazine-1,2-dicarboxylate (139.2 mg, 0.2797 mmol) in anhydrous dichloromethane (1.4 ml) was added 4M hydrogen chloride dioxane solution (1.4 ml, 5.6 mmol). After stirring at room temperature for 8 hrs, the mixture was concentrated under reduced pressure. Ethyl acetate was added to the concentrated residue, and the mixture was concentrated again under reduced pressure. The operation was repeated twice to azeotropically remove hydrogen chloride gas. The residue was dissolved in ethanol (6 ml), and ethyl acetate (30 ml) was added. The precipitated solid was filtered and dried under reduced pressure to give the title compound (105.3 mg, yield 74.3%) as a slightly yellow solid.

Production Example 109

N-(4-{2-[5-(4-acetylpiperazin-1-yl)pyridin-2-yl]ethyl}benzyl)hydrazinecarboxamide trihydrochloride Step 1

To a solution of (4-{2-[5-(4-acetylpiperazin-1-yl)pyridin-2-yl]ethyl}phenyl)methanol (227.0 mg, 0.669 mmol) in dichloromethane (5 ml) was added thionyl chloride (0.096 ml, 1.331 mmol). After stirring at room temperature for 2 hrs, the reaction mixture was concentrated. To the residue was added aqueous sodium carbonate solution, and the mixture was extracted with ethyl acetate. The organic layer was dried over anhydrous magnesium sulfate and concentrated to dryness to give 1-acetyl-4-(6-{2-[4-(chloromethyl)phenyl]ethyl}pyridin-3-yl)piperazine (234.8 mg, yield 98.1%) as a slightly yellow solid.

Step 2

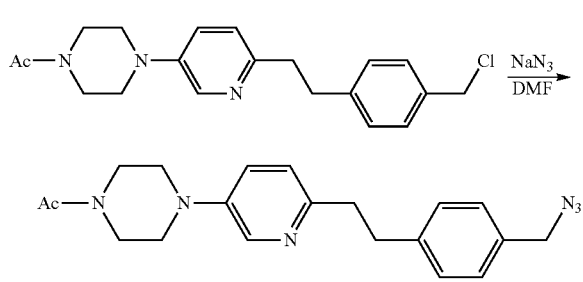

To a solution of 1-acetyl-4-(6-{2-[4-(chloromethyl)phenyl]ethyl}pyridin-3-yl)piperazine (234.8 mg, 0.656 mmol) in anhydrous N,N-dimethylformamide (5 ml) was added sodium azide (426.5 mg, 6.561 mmol), and the mixture was stirred at room temperature for 16 hrs. Aqueous sodium carbonate solution and ethyl acetate were added to the reaction mixture. The mixture was stirred, stood still and partitioned. The organic layer was dried over anhydrous magnesium sulfate, and concentrated to dryness to give 1-acetyl-4-(6-{2-[4-(azidomethyl)phenyl]ethyl}pyridin-3-yl)piperazine (226.8 mg, yield 94.9%) as a slightly yellow solid.

Step 3

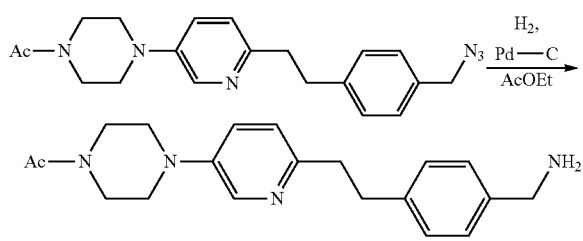

To a solution of 1-acetyl-4-(6-{2-[4-(azidomethyl)phenyl]ethyl}pyridin-3-yl)piperazine (226.8 mg, 0.622 mmol) in ethyl acetate (10 ml) was added 10% palladium carbon (45.1 mg, 50% containing water), and the mixture was hydrogenated at room temperature, under atmospheric pressure. Methanol (10 ml) was added to the reaction mixture, and the reaction mixture was filtered through Celite. The filtrate was concentrated under reduced pressure, and the residue was washed with a mixture of ethyl acetate/diisopropyl ether (1:1) and dried under reduced pressure to give 1-(4-{2-[5-(4-acetylpiperazin-1-yl)pyridin-2-yl]ethyl}phenyl)methanamine (144.0 mg, yield 68.2%) as a white solid.

Step 4

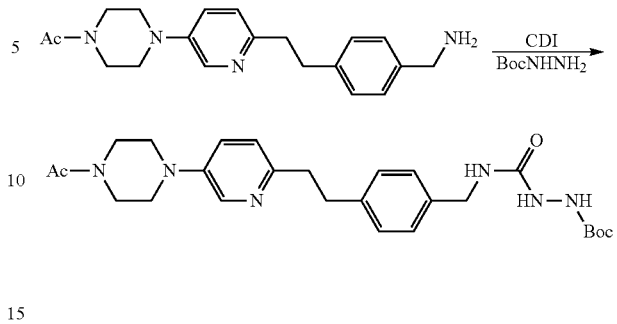

To a suspension of 1,1'-carbonyldiimidazole (125.2 mg, 0.792 mmol) in anhydrous tetrahydrofuran (1 ml) was added tert-butyl carbazate (102.1 mg, 0.792 mmol), and the mixture was stirred at room temperature for 1 hr. 1-(4-{2-[5-(4-Acetylpiperazin-1-yl)pyridin-2-yl]ethyl}phenyl)methanamine (130.7 mg, 0.386 mmol) was added, and the mixture was stirred at room temperature for 4 hrs. The reaction mixture was concentrated under reduced pressure, and ethyl acetate and aqueous sodium carbonate solution were added. The mixture was stirred, stood still and partitioned. The aqueous layer was extracted twice with ethyl acetate. The combined organic layer was dried over anhydrous magnesium sulfate and concentrated under reduced pressure, and the residue was purified by silica gel column chromatography (ethyl acetate→methanol:dichloromethane=1:20). The fraction containing the target product was concentrated and the obtained solid was suspended in a mixture of ethyl acetate (5 ml) and diisopropyl ether (10 ml), filtered and dried under reduced pressure to give tert-butyl 2-[(4-{2-[5-(4-acetylpiperazin-1-yl)pyridin-2-yl]ethyl}benzyl)carbamoyl]hydrazinecarboxylate (145.9 mg, yield 76.1%) as a white solid.

Step 5

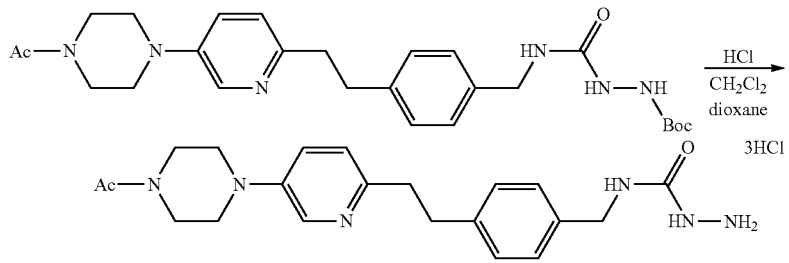

To a suspension of tert-butyl 2-[(4-{2-[5-(4-acetylpiperazin-1-yl)pyridin-2-yl]ethyl}benzyl)carbamoyl]hydrazinecarboxylate (121.0 mg, 0.243 mmol) in anhydrous dioxane (1.2 ml) was added 4M hydrogen chloride dioxane solution (1.2 ml). After stirring at room temperature for 5 hrs, the reaction mixture was concentrated under reduced pressure. Ethyl acetate (10 ml) was added to the residue, and the mixture was concentrated again under reduced pressure. This operation was performed 3 times to azeotropically remove hydrogen chloride gas. The residue was suspended in a mixture of ethanol (3 ml) and ethyl acetate (6 ml), filtered, washed with ethyl acetate and dried under reduced pressure to give the title compound (111.0 mg, yield 90.1%) as a slightly yellow solid.

Production Example 110

4-{2-[5-(4-acetylpiperazin-1-yl)pyridin-2-yl]ethyl}phenyl hydrazinecarboxylate trihydrochloride Step 1

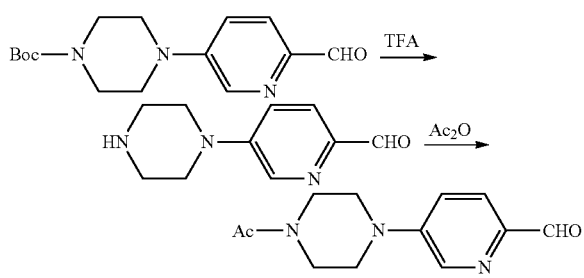

To a solution of tert-butyl 4-(6-formylpyridin-3-yl)piperazine-1-carboxylate (270.4 mg, 0.9281 mmol) in dichloromethane (2.5 ml) was added trifluoroacetic acid (2.5 ml) at 0° C. After stirring at 0° C. for 1 hr, the reaction mixture was concentrated under reduced pressure. Anhydrous dichloromethane (2.5 ml) was added to the residue, acetic anhydride (0.105 ml, 1.114 mmol) was added, and the mixture was stirred at room temperature for 1 hr. Saturated aqueous sodium hydrogen carbonate solution was added, and the mixture was extracted 5 times with ethyl acetate. The combined organic layer was dried over anhydrous magnesium sulfate, filtered, and the filtrate was concentrated under reduced pressure. The residue was purified by silica gel column chromatography (methanol:dichloromethane=1:30) to give 5-(4-acetylpiperazin-1-yl)pyridine-2-carbaldehyde (147.0 mg, yield 67.9%) as a slightly yellow solid.

Step 2

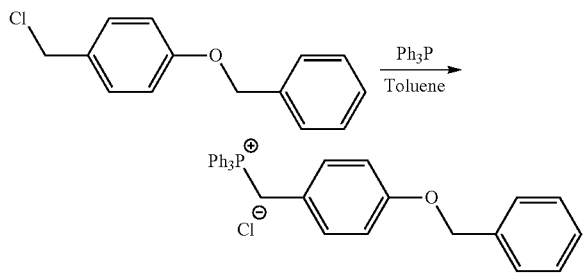

To a suspension of 1-(benzyloxy)-4-(chloromethyl)benzene (4.890 g, 21.01 mmol) in toluene (25 ml) was added triphenylphosphine (6.617 g, 25.23 mmol). The mixture was heated under reflux for 24 hrs, and cooled to room temperature. The precipitate was collected by filtration, and dried under reduced pressure to give [4-(benzyloxy)benzyl](triphenyl)phosphonium chloride (9.166 g, yield 88.1%) as a white solid.

Step 3

By a method similar to Production Example 108, step 4, [4-(benzyloxy)benzyl](triphenyl)phosphonium chloride (743.1 mg, 1.414 mmol) and 5-(4-acetylpyridin-1-yl)pyridine-2-carbaldehyde (329.8 mg, 1.414 mmol) were condensed to give 1-acetyl-4-(6-{2-[4-(benzyloxy)phenyl]vinyl}pyridin-3-yl)piperazine (386.3 mg; yield 66.1%, E/Z mixture) as a pale-yellow solid.

Step 4

By a method similar to Production Example 108, step 5, 1-acetyl-4-(6-{2-[4-(benzyloxy)phenyl]vinyl}pyridin-3-yl)piperazine (329.3 mg, 0.796 mmol) was hydrogenated to give 4-{2-[5-(4-acetylpiperazin-1-yl)pyridin-2-yl]ethyl}phenol (249.8 mg, yield 96.4%) as a slightly brown solid.

Step 5

By a method similar to Production Example 108, step 7, 4-{2-[5-(4-acetylpiperazin-1-yl)pyridin-2-yl]ethyl}phenyl tert-butyl hydrazine-1,2-dicarboxylate (139.2 mg, yield 42.4%) was obtained as a white solid from 4-{2-[5-(4-acetylpiperazin-1-yl)pyridin-2-yl]ethyl}phenol (221.1 mg, 0.680 mmol).

Step 6

By a method similar to Production Example 108, step 8, 4-{2-[5-(4-acetylpiperazin-1-yl)pyridin-2-yl]ethyl}phenyl tert-butyl hydrazine-1,2-dicarboxylate (182.0 mg, 0.376 mmol) was deprotected to give the title compound (130.7 mg, yield 70.5%) as a white solid.

Production Example 111

3-{2-[5-(4-acetylpiperazin-1-yl)pyridin-2-yl]ethyl}benzyl hydrazinecarboxylate trihydrochloride Step 1

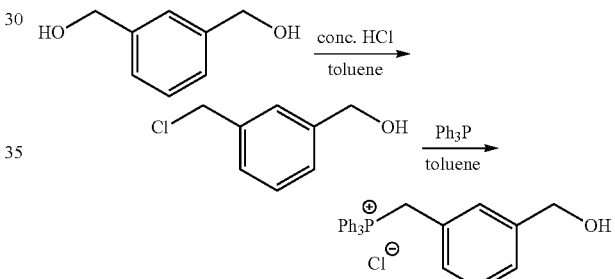

To a solution of m-xylyleneglycol (2.763 g, 20.00 mmol) in toluene (100 ml) was added concentrated hydrochloric acid (10 ml), and the mixture was stirred at room temperature for 8 hrs. Water (50 ml) was added and the mixture was stirred. Saturated aqueous sodium hydrogen carbonate (120 ml) was added, and the mixture was stood still and partitioned. The organic layer was washed with saturated brine, dried over anhydrous magnesium sulfate, and concentrated under reduced pressure. The residue was dissolved in toluene (10 ml), and triphenylphosphine (5.249 g, 20.00 mmol) was added. The mixture was heated under reflux for 14 hrs, and cooled to room temperature. The precipitated solid was collected by filtration, washed with a mixture of tert-butyl methyl ether, methanol (1 ml) and ethyl acetate (50 ml) and dried under reduced pressure to give [3-(hydroxymethyl)benzyl](triphenyl)chloride (3.898 g, yield 46.5%) as a white solid.

Step 2

By a method similar to Production Example 108, step 4, [3-(hydroxymethyl)benzyl](triphenyl)phosphonium chloride (1.675 g, 3.998 mmol) and tert-butyl 4-(6-formylpyridin-3-yl)piperazine-1-carboxylate (1.165 g, 4.000 mmol) were condensed to give tert-butyl 4-(6-{2-[3-(hydroxymethyl)phenyl]vinyl}pyridin-3-yl)piperazine-1-carboxylate (1.111 g, yield 70.2%, E/Z mixture) as a yellow solid.

Step 3

By a method similar to Production Example 108, step 5, 5 tert-butyl 4-(6-{2-[3-(hydroxymethyl)phenyl]vinyl}pyridin-3-yl)piperazine-1-carboxylate (1.109 g, 2.804 mmol) was hydrogenated to give tert-butyl 4-(6-{2-[3-(hydroxymethyl)phenyl]ethyl}pyridin-3-yl)piperazine-1-carboxylate (696.1 mg, yield 62.4%) as a white solid.

Step 4

By a method similar to Production Example 108, step 6, (3-{2-[5-(4-acetylpiperazin-1-yl)pyridin-2-yl]ethyl}phenyl)methanol (566.2 mg, yield 95.4%) was obtained as a white solid from tert-butyl 4-(6-{2-[3-(hydroxymethyl)phenyl]ethyl}pyridin-3-yl)piperazine-1-carboxylate (695.0 mg, 1.748 mmol).

Step 5

By a method similar to Production Example 108, step 7, 3-{2-[5-(4-acetylpiperazin-1-yl)pyridin-2-yl]ethyl}benzyl tert-butyl hydrazine-1,2-dicarboxylate (165.6 mg, yield 66.6%) was obtained as a white solid from (3-{2-[5-(4-acetylpiperazin-1-yl)pyridin-2-yl]ethyl}phenyl)methanol (170.3 mg, 0.502 mmol).

Step 6

By a method similar to Production Example 108, step 8, 3-{2-[5-(4-acetylpiperazin-1-yl)pyridin-2-yl]ethyl}benzyl tert-butyl hydrazine-1,2-dicarboxylate (153.5 mg, 0.328 mmol) was deprotected to give the title compound (130.5 mg, yield 78.4%) as a slightly yellow solid.

Production Example 112

N-(3-{2-[5-(4-acetylpiperazin-1-yl)pyridin-2-yl]ethyl}benzyl)hydrazinecarboxamide trihydrochloride Step 1

By a method similar to Production Example 109, step 1, (3-{2-[5-(4-acetylpiperazin-1-yl)pyridin-2-yl]ethyl}phenyl)methanol (340.3 mg, 1.003 mmol) was chlorinated to give 1-acetyl-4-(6-{2-[3-(chloromethyl)phenyl]ethyl}pyridin-3-yl)piperazine (276.8 mg, yield 77.1%) as a slightly yellow solid.

Step 2

By a method similar to Production Example 109, step 2, 1-acetyl-4-(6-{2-[4-(chloromethyl)phenyl]ethyl}pyridin-3-yl)piperazine (276.8 mg, 0.773 mmol) was azidated to give 1-acetyl-4-(6-{2-[4-(azidomethyl)phenyl]ethyl}pyridin-3-yl)piperazine (248.5 mg, yield 88.2%) as a slightly yellow solid.

Step 3

By a method similar to Production Example 109, step 3, 1-acetyl-4-(6-{2-[3-(azidomethyl)phenyl]ethyl}pyridin-3-yl)piperazine (243.5 mg, 0.668 mmol) was reduced to give 1-(3-{2-[5-(4-acetylpiperazin-1-yl)pyridin-2-yl]ethyl}phenyl)methanamine (187.2 mg, yield 82.8%) as a white solid.

Step 4

By a method similar to Production Example 109, step 4, tert-butyl 2-[(3-{2-[5-(4-acetylpiperazin-1-yl)pyridin-2-yl]ethyl}benzyl)carbamoyl]hydrazinecarboxylate (229.5 mg, yield 86.0%) was obtained as a white solid from 1-(3-{2-[5-(4-acetylpiperazin-1-yl)pyridin-2-yl]ethyl}phenyl)methanamine (182.5 mg, 0.538 mmol).

Step 5

By a method similar to Production Example 109, step 5, tert-butyl 2-[(3-{2-[5-(4-acetylpiperazin-1-yl)pyridin-2-yl]ethyl}benzyl)carbamoyl]hydrazinecarboxylate (223.6 mg, 0.450 mmol) was deprotected to give the title compound (207.8 mg, yield 91.2%) as a slightly yellow solid.

Production Example 113

4-{2-[5-(4-acetylpiperazin-1-yl)pyridin-2-yl]ethyl}-3-fluorobenzyl hydrazinecarboxylate trihydrochloride Step 1

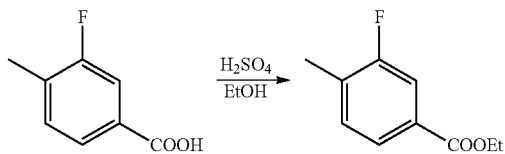

To a solution of 3-fluoro-4-methylbenzoic acid (7.707 g, 50.00 mmol) in ethanol (35 ml) was added concentrated sulfuric acid (1.5 ml), and the mixture was heated under reflux for 6 hrs. The reaction mixture was cooled to 0° C., iced water and saturated aqueous sodium hydrogen carbonate were added, and the mixture was extracted twice with diethyl ether. The combined organic layer was washed twice with saturated aqueous sodium hydrogen carbonate and once with saturated brine, dried over anhydrous magnesium sulfate, and concentrated under reduced pressure to give ethyl 3-fluoro-4-methylbenzoate (8.599 g, yield 94.4%) as a colorless oil.

Step 2

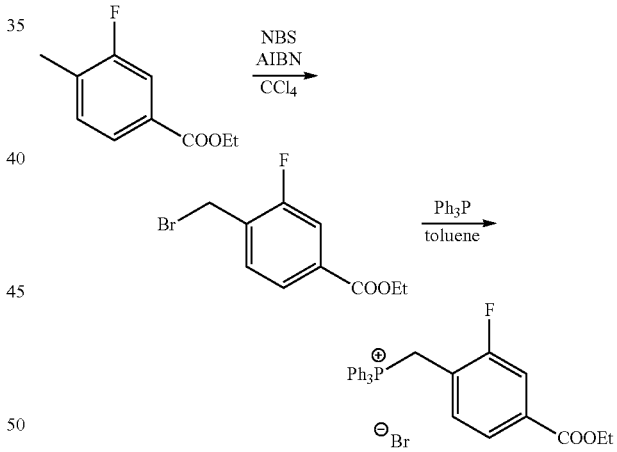

To a solution of ethyl 3-fluoro-4-methylbenzoate (8.586 g, 47.13 mmol) in carbon tetrachloride (70 ml) were added N-bromosuccinimide (8.388 g, 47.13 mmol) and 2,2'-azobisisobutyronitrile (309.6 mg, 1.885 mmol), and the mixture was stirred at 90° C. for 30 mins and at 100° C. for 16 hrs. The reaction mixture was cooled to 0° C., and the precipitated solid was filtered off and washed twice with hexane. The filtrate and washing solution were combined, and the mixture was washed twice with water and once with saturated brine, dried over anhydrous magnesium sulfate and concentrated under reduced pressure. The residue was dissolved in toluene (30 ml), and triphenylphosphine (9.891 g, 37.71 mmol) was added. The mixture was heated under reflux for 40 mins and cooled to room temperature. The precipitate was collected by filtration, and dried under reduced pressure to give [4-

(ethoxycarbonyl)-2-fluorobenzyl](triphenyl)phosphonium bromide (16.52 g, yield 67.0%) as a white solid.

Step 3

By a method similar to Production Example 108, step 4, [4-(ethoxycarbonyl)-2-fluorobenzyl](triphenyl)phosphonium bromide (2.513 g, 4.802 mmol) and tert-butyl 4-(6-formylpyridin-3-yl)piperazine-1-carboxylate (1.166 g, 4.002 mmol) were condensed to give tert-butyl 4-(6-{2-[4-(ethoxycarbonyl)-2-fluorophenyl]vinyl}pyridin-3-yl)piperazine-1-carboxylate (1.802 g, yield 98.9%, E/Z mixture) as a pale-brown solid.

Step 4

By a method similar to Production Example 108, step 5, tert-butyl 4-(6-{2-[4-(ethoxycarbonyl)-2-fluorophenyl]vinyl}pyridin-3-yl)piperazine-1-carboxylate (1.796 g, 3.942 mmol) was hydrogenated to give tert-butyl 4-(6-{2-[4-(ethoxycarbonyl)-2-fluorophenyl]ethyl}pyridin-3-yl)piperazine-1-carboxylate (1.727 g, yield 95.8%) as a slightly brown solid.

Step 5

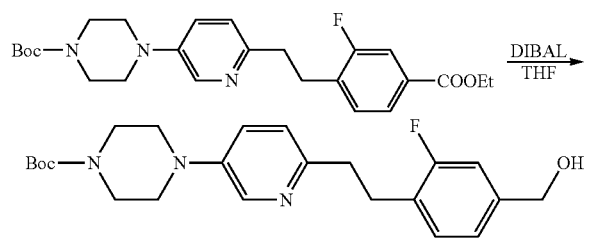

To a solution of tert-butyl 4-(6-{2-[4-(ethoxycarbonyl)-2-fluorophenyl]ethyl}pyridin-3-yl)piperazine-1-carboxylate (1.414 g, 3.091 mmol) in anhydrous tetrahydrofuran (15 ml) was added dropwise at −78° C. 1M diisobutylaluminum hydride tetrahydrofuran solution (12 ml, 12 mmol) over 10 mins. After stirring at −78° C. for 30 mins, the mixture was heated to room temperature and stirred for 1 hr 40 mins. After cooling to −78° C., 1M diisobutylaluminum hydride tetrahydrofuran solution (6 ml, 6 mmol) was added dropwise over 5 mins. The mixture was heated to room temperature and stirred for 40 mins. Saturated aqueous potassium sodium tartrate solution (150 ml) was added and the mixture was stirred and extracted 3 times with ethyl acetate. The combined organic layer was washed with saturated brine, dried over anhydrous magnesium sulfate, and concentrated under reduced pressure. The residue was purified by silica gel column chromatography (ethyl acetate:hexane=4:1→ethyl acetate) to give tert-butyl 4-(6-{2-[2-fluoro-4-(hydroxymethyl)phenyl]ethyl}pyridin-3-yl)piperazine-1-carboxylate (1.046 g, yield 81.4%) as a slightly yellow solid.

Step 6

By a method similar to Production Example 108, step 6, tert-butyl 4-(6-{2-[2-fluoro-4-(hydroxymethyl)phenyl]ethyl}pyridin-3-yl)piperazine-1-carboxylate (1.209 g, 2.910 mmol) was deprotected and acetylated to give (4-{2-[5-(4-acetylpiperazin-1-yl)pyridin-2-yl]ethyl}-3-fluorophenyl)methanol (838.9 mg, yield 80.3%) as a slightly yellow solid.

Step 7

By a method similar to Production Example 108, step 7, 4-{2-[5-(4-acetylpiperazin-1-yl)pyridin-2-yl]ethyl}-3-fluorobenzyl tert-butyl hydrazine-1,2-dicarboxylate (254.8 mg, yield 61.7%) was obtained as a white solid from (4-{2-[5-(4-acetylpiperazin-1-yl)pyridin-2-yl]ethyl}-3-fluorophenyl)methanol (286.4 mg, 0.801 mmol).

Step 8

By a method similar to Production Example 108, step 8, 4-{2-[5-(4-acetylpiperazin-1-yl)pyridin-2-yl]ethyl}-3-fluorobenzyl tert-butyl hydrazine-1,2-dicarboxylate (230.5 mg, 0.447 mmol) was deprotected to give the title compound (211.3 mg, yield 90.1%) as a slightly yellow solid.

Production Example 114

N-(4-{2-[5-(4-acetylpiperazin-1-yl)pyridin-2-yl]ethyl}-3-fluorobenzyl)hydrazinecarboxamide trihydrochloride Step 1

By a method similar to Production Example 109, step 1, (4-{2-[5-(4-acetylpiperazin-1-yl)pyridin-2-yl]ethyl}-3-fluorophenyl)methanol (357.4 mg, 1.000 mmol) was chlorinated to give 1-acetyl-4-(6-{2-[4-(chloromethyl)-2-fluorophenyl]ethyl}pyridin-3-yl)piperazine (375.0 mg, yield 99.8%) as a yellow solid.

Step 2

By a method similar to Production Example 109, step 2, 1-acetyl-4-(6-{2-[4-(chloromethyl)-2-fluorophenyl]ethyl}pyridin-3-yl)piperazine (373.3 mg, 0.993 mmol) was azidated to give 1-acetyl-4-(6-{2-[4-(azidomethyl)-2-fluorophenyl]ethyl}pyridin-3-yl)piperazine (356.7 mg, yield 93.9%) as a white solid.

Step 3

By a method similar to Production Example 109, step 3, 1-acetyl-4-(6-{2-[4-(azidomethyl)-2-fluorophenyl]ethyl}pyridin-3-yl)piperazine (352.1 mg, 0.921 mmol) was reduced to give 1-(4-{2-[5-(4-acetylpiperazin-1-yl)pyridin-2-yl]ethyl}-3-fluorophenyl)methanamine (265.9 mg, yield 81.0%) as a white solid.

Step 4

By a method similar to Production Example 109, step 4, tert-butyl 2-[(4-{2-[5-(4-acetylpiperazin-1-yl)pyridin-2-yl]ethyl}-3-fluorobenzyl)carbamoyl]hydrazinecarboxylate (314.4 mg, yield 90.2%) was obtained as a white solid from 1-(4-{2-[5-(4-acetylpiperazin-1-yl)pyridin-2-yl]ethyl}-3-fluorophenyl)methanamine (241.5 mg, 0.678 mmol).

Step 5

By a method similar to Production Example 109, step 5, tert-butyl 2-[(4-{2-[5-(4-acetylpiperazin-1-yl)pyridin-2-yl]ethyl}-3-fluorobenzyl)carbamoyl]hydrazinecarboxylate (298.9 mg, 0.581 mmol) was deprotected to give the title compound (279.6 mg, yield 91.9%) as a slightly yellow solid:

Production Example 115

2-(5-{2-[5-(4-acetylpiperazin-1-yl)pyridin-2-yl]ethyl}thiophen-2-yl)ethyl hydrazinecarboxylate Step 1

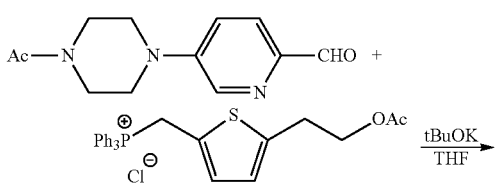

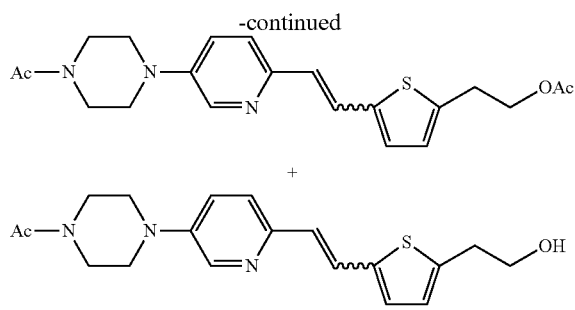

By a method similar to Production Example 108, step 4, ({5-[2-(acetyloxy)ethyl]thiophen-2-yl}methyl)(triphenyl)phosphonium chloride (2.320 g, 4.823 mmol) and 5-(4-acetylpyridin-1-yl)pyridine-2-carbaldehyde (1.000 g, 4.287 mmol) was condensed to give 2-(5-{2-[5-(4-acetylpiperazin-1-yl)pyridin-2-yl]vinyl}thiophen-2-yl)ethyl acetate (1.355 g, yield 79.1%, E/Z mixture) as a yellow oil and 2-(5-{2-[5-(4-acetylpiperazin-1-yl)pyridin-2-yl]vinyl}thiophen-2-yl)ethanol (307.0 mg, yield 20.0%, E/Z mixture) as a yellow oil.

Step 2

By a method similar to Production Example 108, step 5, 2-(5-{2-[5-(4-acetylpiperazin-1-yl)pyridin-2-yl]vinyl}thiophen-2-yl)ethyl acetate (1.100 g, 2.753 mmol) was hydrogenated to give 2-(5-{2-[5-(4-acetylpiperazin-1-yl)pyridin-2-yl]ethyl}thiophen-2-yl)ethyl acetate (956.5 mg, yield 86.5%) as a white solid.

Step 3

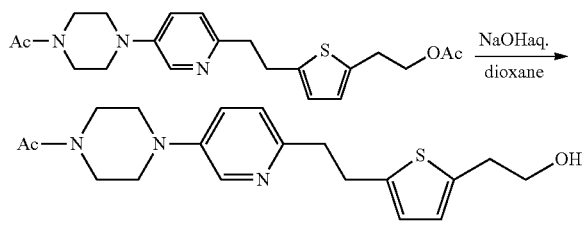

To a solution of 2-(5-{2-[5-(4-acetylpiperazin-1-yl)pyridin-2-yl]ethyl}thiophen-2-yl)ethyl acetate (719.0 mg, 1.791 mmol) in dioxane (6.3 ml) were added 1M aqueous sodium hydroxide solution (6.27 ml, 6.27 mmol) and water (6.3 ml) at 0° C. After stirring at room temperature for 1 hr, the mixture was cooled to 0° C., and 1M hydrochloric acid (8.0 ml, 8.0 mmol) was added. The mixture was concentrated under reduced pressure, saturated aqueous sodium hydrogen carbonate solution was added to the residue, and the mixture was extracted 3 times with ethyl acetate. The combined organic layer was washed with saturated brine, dried over anhydrous magnesium sulfate and concentrated under reduced pressure. The residue was purified by silica gel column chromatography (ethyl acetate:acetone=7:3→5:5) to give 2-(5-{2-[5-(4-acetylpiperazin-1-yl)pyridin-2-yl]ethyl}thiophen-2-yl)ethanol (608.7 mg, yield 94.5%) as a white solid.

Step 4

By a method similar to Production Example 108, step 7, 2-(5-{2-[5-(4-acetylpiperazin-1-yl)pyridin-2-yl]ethyl}thiophen-2-yl)ethyl tert-butyl hydrazine-1,2-dicarboxylate (544.7 mg) was obtained as a colorless oil from 2-(5-{2-[5-(4-acetylpiperazin-1-yl)pyridin-2-yl]ethyl}thiophen-2-yl)ethanol (350.0 mg, 0.974 mmol).

Step 5

By a method similar to Production Example 108, step 8, 2-(5-{2-[5-(4-acetylpiperazin-1-yl)pyridin-2-yl]ethyl}thiophen-2-yl)ethyl tert-butyl hydrazine-1,2-dicarboxylate (corresponding to 0.974 mmol) was treated with 4M hydrogen chloride dioxane solution. The obtained hydrochloride was dissolved in 2-propanol-ethanol (9:1) mixture, and filtered through aminopropylated silica gel. The aminopropylated silica gel was washed with 2-propanol-dichloromethane (1:9), the filtrate and the washing solution were combined and concentrated under reduced pressure to about 20 ml. Hexane (200 ml) was added, and the mixture was concentrated again under reduced pressure to about 40 ml. Hexane (200 ml) was added to the residue and the mixture was stirred. The resulting solid was collected by filtration, washed with hexane and dried under reduced pressure to give the title compound (350.1 mg, yield 86.1%) as a white solid.

Production Example 116

5-{2-[5-(4-acetylpiperazin-1-yl)pyridin-2-yl]ethyl}thiophene-2-carbohydrazide

Step 1

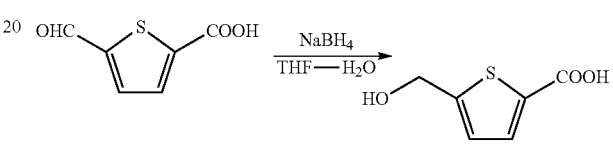

To a solution of 5-formylthiophene-2-carboxylic acid (2.000 g, 12.81 mmol) in tetrahydrofuran (25 ml) was added water (2.5 ml). Sodium borohydride (1.453 g, 38.42 mmol) was added by small portions, and the mixture was stirred at room temperature for 1 hr. The reaction mixture was adjusted to pH about 8 by adding a small amount of 1M hydrochloric acid, and washed with ethyl acetate. The aqueous layer was adjusted to pH 2-2.5 by adding concentrated hydrochloric acid, and saturated with sodium chloride. The mixture was extracted 3 times with ethyl acetate. The combined organic layer was washed with saturated brine, dried over anhydrous magnesium sulfate, and concentrated to dryness to give 5-(hydroxymethyl)thiophene-2-carboxylic acid (1.430 g, yield 70.6%) as a yellow solid.

Step 2

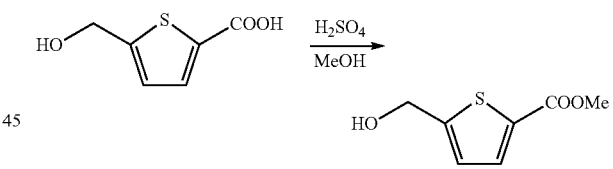

To a solution of 5-(hydroxymethyl)thiophene-2-carboxylic acid (1.430 g, 9.040 mmol) in anhydrous methanol (140 ml) concentrated sulfuric acid (88.7 mg, 0.904 mmol) was added, and the mixture was heated under reflux for 40 hrs. After cooling to 0° C., sodium carbonate (300 mg) was added, and the mixture was concentrated to about 50 ml under reduced pressure. Saturated brine was added, and the mixture was extracted 3 times with ethyl acetate. The combined organic layer was washed with saturated aqueous ammonium chloride solution and saturated brine, dried over anhydrous magnesium sulfate and concentrated under reduced pressure to give methyl 5-(hydroxymethyl)thiophene-2-carboxylate (1.444 g, yield 92.7%) as a yellow oil.

Step 3

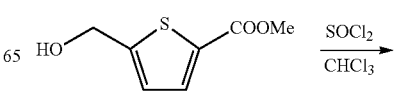

-continued

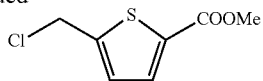

To a solution of methyl 5-(hydroxymethyl)thiophene-2-carboxylate (1.440 g, 8.362 mmol) in anhydrous chloroform (7.5 ml) was added dropwise thionyl chloride (3.62 ml, 50.17 mmol) at 0° C. After stirring at room temperature for 1.5 hrs, the mixture was concentrated under reduced pressure. The residue was dissolved in anhydrous chloroform (10 ml), and the mixture was concentrated again under reduced pressure. This operation was repeated 3 times to remove thionyl chloride azeotropically. The residue was dried under reduced pressure to give crude methyl 5-(chloromethyl)thiophene-2-carboxylate (1.782 g) as a brown oil.
Step 4

By a method similar to Production Example 108, step 3, {[5-(methoxycarbonyl)thiophen-2-yl]methyl}(thiophene) phosphonium chloride (2.759 g, yield 72.8%) was obtained as a pale-yellow ocher solid from crude methyl 5-(chloromethyl)thiophene-2-carboxylate (corresponding to 8.362 mmol).
Step 5

By a method similar to Production Example 108, step 4, {[5-(methoxycarbonyl)thiophen-2-yl]methyl}(thiophene) phosphonium chloride (1153.3 mg, 2.546 mmol) and 5-(4-acetylpyridin-1-yl)pyridine-2-carbaldehyde (540.0 mg, 2.315 mmol) were condensed to give methyl 5-{2-[5-(4-acetylpiperazin-1-yl)pyridin-2-yl]vinyl}thiophene-2-carboxylate (818.6 mg, yield 95.2%) as a yellow solid.
Step 6

By a method similar to Production Example 108, step 5, methyl 5-{2-[5-(4-acetylpiperazin-1-yl)pyridin-2-yl]vinyl}thiophene-2-carboxylate (730.0 mg, 1.965 mmol) was hydrogenated to obtain methyl 5-{2-[5-(4-acetylpiperazin-1-yl)pyridin-2-yl]ethyl}thiophene-2-carboxylate (657.9 mg, yield 89.6%) as a slightly yellow white solid.
Step 7

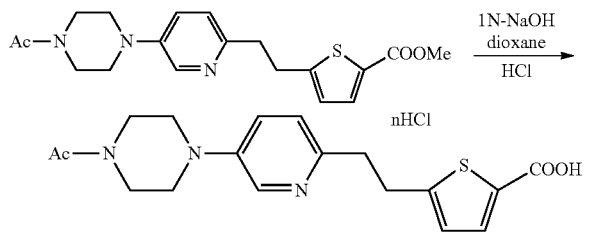

To a solution of methyl 5-{2-[5-(4-acetylpiperazin-1-yl)pyridin-2-yl]ethyl}thiophene-2-carboxylate (550.0 mg, 1.473 mmol) in dioxane (4.5 ml) were added 1M aqueous sodium hydroxide solution (5.15 ml, 5.15 mmol) and water (2.2 ml) at 0° C. After stirring at room temperature for 1 hr, the mixture was cooled to 0° C., and 1M hydrochloric acid (8.84 ml, 8.84 mmol) was added. The mixture was concentrated to dryness to give crude 5-{2-[5-(4-acetylpiperazin-1-yl)pyridin-2-yl]ethyl}thiophene-2-carboxylic acid hydrochloride as a pale-yellow solid.
Step 8

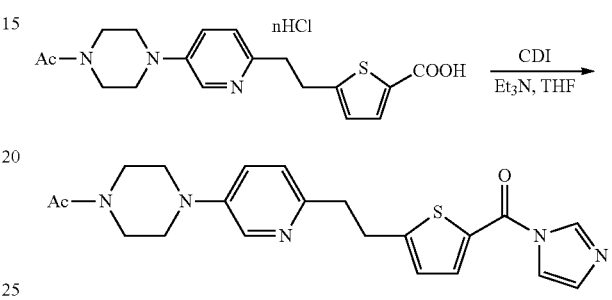

To crude 5-{2-[5-(4-acetylpiperazin-1-yl)pyridin-2-yl]ethyl}thiophene-2-carboxylic acid hydrochloride (corresponding to 1.473 mmol) were added anhydrous tetrahydrofuran (10 ml), triethylamine (10 ml) and 1,1'-carbonyldiimidazole (477.7 mg, 2.946 mmol), and the mixture was stirred at 45° C. for 2 hrs. After cooling to room temperature, tetrahydrofuran (20 ml) was added, and the insoluble material was filtered off. The filtrate was concentrated under reduced pressure, ethyl acetate (200 ml) and ice-cooled saturated aqueous sodium hydrogen carbonate solution (50 ml) were added to the residue. The mixture was stirred, stood still and partitioned. The aqueous layer was extracted twice with ethyl acetate. The combined organic layer was washed with saturated brine, dried over anhydrous magnesium sulfate and concentrated to about 20 ml under reduced pressure. Diisopropyl ether (100 ml) was added. The mixture was concentrated again to about 20 ml under reduced pressure, and diisopropyl ether (100 ml) was added. The precipitate was collected by filtration, washed with diisopropyl ether, and dried under reduced pressure to give crude 1-acetyl-4-(6-{2-[5-(1H-imidazol-1-ylcarbonyl)thiophen-2-yl]ethyl}pyridin-3-yl)piperazine (706.3 mg) as a slightly yellow white solid.
Step 9

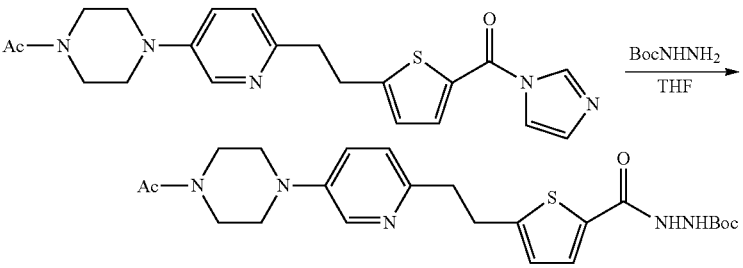

To a suspension of crude 1-acetyl-4-(6-{2-[5-(1H-imidazol-1-ylcarbonyl)thiophen-2-yl]ethyl}pyridin-3-yl)piperazine (481.8 mg, corresponding to 1.000 mmol) in anhydrous tetrahydrofuran (3 ml) was added tert-butyl carbazate (396.5 mg, 3.000 mmol), and the mixture was stirred at room temperature for 3 hrs. The reaction mixture was concentrated under reduced pressure, and the residue was purified by aminopropylated silica gel column chromatography (methanol: dichloromethane=2:98) to give a slightly yellow solid (448.2 mg). This was further purified by aminopropylated silica gel column chromatography (acetone:dichloromethane=1:10) to give a white solid (394.2 mg). This was dissolved in dichloromethane and diethyl ether was dropwise added thereto to allow recrystallization. The crystals were dried under reduced pressure to give tert-butyl 2-[(5-{2-[5-(4-acetylpiperazin-1-yl)pyridin-2-yl]ethyl}thiophen-2-yl)carbonyl]hydrazinecarboxylate (300.9 mg, yield 61.5%, overall 3 steps) as a white solid.

Step 10

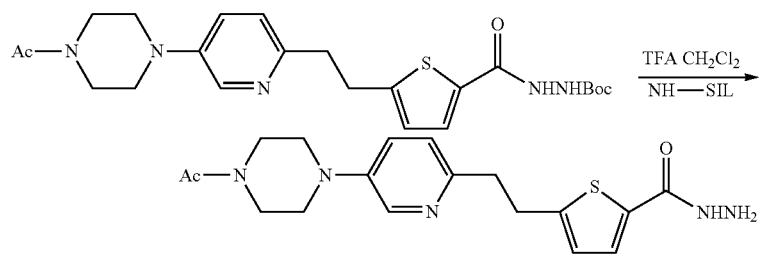

To a solution of tert-butyl 2-[(5-{2-[5-(4-acetylpiperazin-1-yl)pyridin-2-yl]ethyl}thiophen-2-yl)carbonyl]hydrazinecarboxylate (300.0 mg) in anhydrous dichloromethane (15 ml) was added trifluoroacetic acid (0.91 ml, 12.3 mmol) at 0° C. After stirring at room temperature for 1 hr, the mixture was cooled again to 0° C., and trifluoroacetic acid (0.91 ml, 12.3 mmol) was added. After stirring at room temperature for 12.5 hrs, the reaction mixture was concentrated under reduced pressure. Ethyl acetate (30 ml) was added to the residue, and the mixture was concentrated again under reduced pressure. This operation was repeated 3 times to remove trifluoroacetic acid azeotropically. The residue was purified by aminopropylated silica gel column chromatography (2-propanol: dichloromethane=1:9). The fraction containing the target product was concentrated to about 20 ml under reduced pressure, and hexane (50 ml) was added. This operation was repeated 3 times to crystallize the target product. Hexane (100 ml) was added to the mixture, and the precipitate was filtered, washed with a mixed solvent of diethyl ether-hexane (1:1), and dried under reduced pressure to give the title compound (173.2 mg, yield 75.7%) as a white solid.

Production Example 117

N-[2-(5-{2-[5-(4-acetylpiperazin-1-yl)pyridin-2-yl]ethyl}thiophen-2-yl)ethyl]hydrazinecarboxamide Step 1

By a method similar to Production Example 109, step 1, 2-(5-{2-[5-(4-acetylpiperazin-1-yl)pyridin-2-yl]ethyl}thiophen-2-yl)ethanol (300.0 mg, 1.113 mmol) was chlorinated to give crude 1-acetyl-4-(6-{2-[5-(2-chloroethyl)thiophen-2-yl]ethyl}pyridin-3-yl)piperazine (463.4 mg) as a brown oil.

Step 2

By a method similar to Production Example 109, step 2, crude 1-acetyl-4-(6-{2-[5-(2-chloroethyl)thiophen-2-yl]ethyl}pyridin-3-yl)piperazine (corresponding to 1.113 mmol) was azidated to give 1-acetyl-4-(6-{2-[5-(2-azidoethyl)thiophen-2-yl]ethyl}pyridin-3-yl)piperazine (376.6 mg, yield 88.0%, total of 2 steps) as a slightly yellow solid.

Step 3

By a method similar to Production Example 109, step 3, 1-acetyl-4-(6-{2-[5-(2-azidoethyl)thiophen-2-yl]ethyl}pyridin-3-yl)piperazine (375.0 mg, 0.975 mmol) was reduced to give 2-(5-{2-[5-(4-acetylpiperazin-1-yl)pyridin-2-yl]ethyl}thiophen-2-yl)ethanamine (360.4 mg, quantitatively) as a white solid.

Step 4

By a method similar to Production Example 109, step 4, tert-butyl 2-{[2-(5-{2-[5-(4-acetylpiperazin-1-yl)pyridin-2-yl]ethyl}thiophen-2-yl)ethyl]carbamoyl}hydrazinecarboxylate (499.4 mg, yield 99.1%) was obtained as a colorless oil from 2-(5-{2-[5-(4-acetylpiperazin-1-yl)pyridin-2-yl]ethyl}thiophen-2-yl)ethanamine (360.4 mg, 0.975 mmol).

Step 5

By a method similar to Production Example 115, step 5, tert-butyl 2-{[2-(5-{2-[5-(4-acetylpiperazin-1-yl)pyridin-2-yl]ethyl}thiophen-2-yl)ethyl]carbamoyl}hydrazinecarboxylate (498.0 mg, 0.964 mmol) was deprotected with 4M hydrogen chloride dioxane solution. The crude product was purified by aminopropylated silica gel and recrystallized from dichloromethane-methanol to give the title compound (170.8 mg, yield 42.5%) as a slightly yellow white solid.

Production Example 118

2-(3-{2-[5-(4-acetylpiperazin-1-yl)pyridin-2-yl]ethyl}phenyl)acetohydrazide trihydrochloride Step 1

By a method similar to Production Example 108, step 4, [3-(carboxymethyl)benzyl](triphenyl)phosphonium bromide (491.9 mg, 1.001 mmol) and 5-(4-acetylpyridin-1-yl)pyridine-2-carbaldehyde (257.9 mg, 1.106 mmol) were condensed to give (3-{2-[5-(4-acetylpiperazin-1-yl)pyridin-2-yl]vinyl}phenyl)acetic acid (296.3 mg, yield 81.0%, E/Z mixture) as a pale-brown solid.

Step 2

By a method similar to Production Example 108, step 5, (3-{2-[5-(4-acetylpiperazin-1-yl)pyridin-2-yl]vinyl}phenyl)acetic acid (294.0 mg, 0.805 mmol) was hydrogenated to give (3-{2-[5-(4-acetylpiperazin-1-yl)pyridin-2-yl]ethyl}phenyl)acetic acid (227.1 mg, 0.618 mmol, yield 76.8%) as a white solid.

89

Step 3

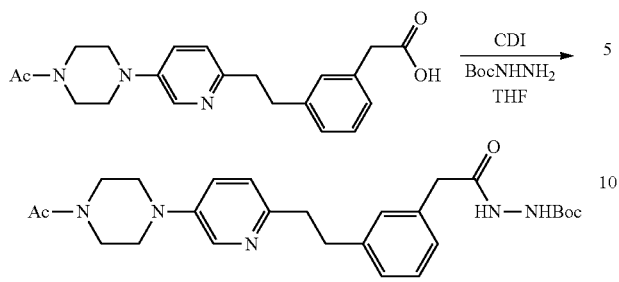

To a suspension of (3-{2-[5-(4-acetylpiperazin-1-yl)pyridin-2-yl]ethyl}phenyl)acetic acid (213.4 mg, 0.581 mmol) in anhydrous N,N-dimethylformamide (3 ml) was added 1,1'-carbonyldiimidazole (188.9 mg, 1.165 mmol), and the mixture was stirred at room temperature for 1.5 hrs. tert-Butyl carbazate (460.3 mg, 3.483 mmol) was added, and the mixture was stirred at room temperature for 14 hrs. Water and ethyl acetate were added to the reaction mixture, and the mixture was stirred, stood still and partitioned. The aqueous layer was extracted with ethyl acetate. The combined organic layer was dried over anhydrous magnesium sulfate and concentrated under reduced pressure. The residue was purified 3 times by silica gel column chromatography (ethyl acetate→methanol: dichloromethane=1:15, methanol:dichloromethane=1:20, methanol:dichloromethane=1:20) to give tert-butyl 2-[(3-{2-[5-(4-acetylpiperazin-1-yl)pyridin-2-yl]ethyl}phenyl)acetyl]hydrazinecarboxylate (219.4 mg, yield 78.4%) as a white solid.

Step 4

By a method similar to Production Example 1, step 6, tert-butyl 2-[(3-{2-[5-(4-acetylpiperazin-1-yl)pyridin-2-yl]ethyl}phenyl)acetyl]hydrazinecarboxylate (218.6 mg, 0.454 mmol) was deprotected to give the title compound (171.5 mg, yield 77.0%) as a yellow solid.

Production Example 119

3-(4-{2-[5-(4-acetylpiperazin-1-yl)pyridin-2-yl]ethyl}phenyl)propanehydrazide trihydrochloride Step 1

Production Example 108, step 4, {4-[(E)-2-carboxyvinyl]benzyl}(triphenyl)phosphonium bromide (503.9 mg, 1.001 mmol) and 5-(4-acetylpyridin-1-yl)pyridine-2-carbaldehyde (257.3 g, 1.103 mmol) were condensed to give (2E)-3-(4-{2-[5-(4-acetylpyridin-1-yl)pyridin-2-yl]vinyl}phenyl)prop-2-enoic acid (355.1 mg, yield 94.0%) as a pale-brown solid.

Step 2

By a method similar to Production Example 108, step 5, (2E)-3-(4-{2-[5-(4-acetylpyridin-1-yl)pyridin-2-yl]vinyl}phenyl)prop-2-enoic acid (346.9 mg, 0.919 mmol) was hydrogenated to give 3-(4-{2-[5-(4-acetylpyridin-1-yl)pyridin-2-yl]ethyl}phenyl)propionic acid (286.5 mg, yield 81.7%) as a white solid.

Step 3

By a method similar to Production Example 118, step 3, 3-(4-{2-[5-(4-acetylpyridin-1-yl)pyridin-2-yl]ethyl}phenyl)propionic acid (267.2 mg, 0.700 mmol) and tert-butyl carbazate (559.9 mg, 4.237 mmol) were condensed to give tert-butyl 2-[3-(4-{2-[5-(4-acetylpyridin-1-yl)pyridin-2-yl]ethyl}phenyl)propanoyl]hydrazinecarboxylate (292.0 mg, yield 84.1%) as a white solid.

90

Step 4

By a method similar to Production Example 1, step 6, tert-butyl 2-[3-(4-{2-[5-(4-acetylpyridin-1-yl)pyridin-2-yl]ethyl}phenyl)propanoyl]hydrazinecarboxylate (251.6 mg, 0.508 mmol) was deprotected to give the title compound (248.2 mg, yield 96.8%) as a white solid.

Production Example 120

2-(5-{2-[5-(4-acetylpiperazin-1-yl)pyridin-2-yl]ethyl}thiophen-2-yl)acetohydrazide Step 1

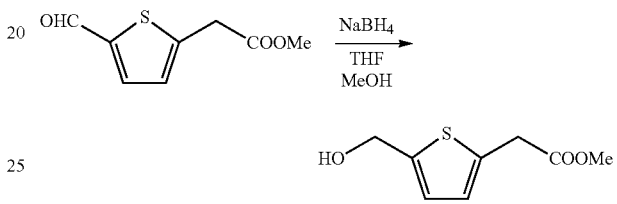

Methyl (5-formylthiophen-2-yl)acetate (2.700 g, 14.66 mmol) was dissolved in a mixed solvent of 20% methanol-tetrahydrofuran. The mixture was cooled to −10° C., and sodium borohydride (277.2 mg, 7.33 mmol) was added. After stirring at −10° C. to 0° C. for 1 hr, sodium borohydride (277.2 mg, 7.33 mmol) was added. After stirring at 0° C. for 2 hrs, acetic acid (0.84 ml, 14.7 mmol) was added, and the mixture was concentrated under reduced pressure. Water (50 ml) was added to the residue, and the mixture was extracted 3 times with ethyl acetate. The combined organic layer was washed with saturated brine, dried over anhydrous magnesium sulfate and concentrated under reduced pressure. The residue was purified by silica gel column chromatography (ethyl acetate:hexane=1:2) to give a slightly yellow oil (2.179 g). This was further purified by silica gel column chromatography (ethyl acetate:hexane=3:7) to give methyl (5-hydroxymethylthiophen-2-yl)acetate (1.987 g, yield 72.8%) as a slightly yellow oil.

Step 2

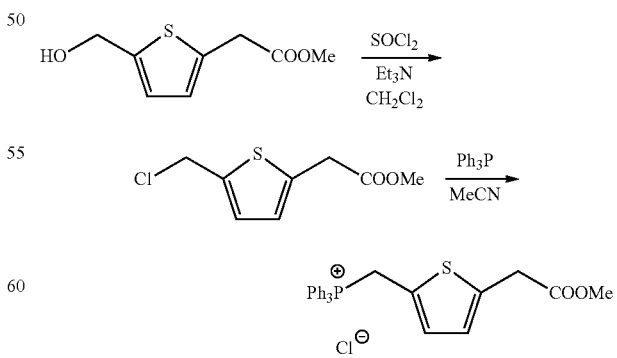

To a solution of methyl (5-hydroxymethylthiophen-2-yl)acetate (1.920 g, 10.31 mmol) in anhydrous dichloromethane (10 ml) was added triethylamine (1.349 g, 11.34 mmol), and the mixture was cooled to 0° C. Thionyl chloride (1.57 ml, 11.3 mmol) was added dropwise, and the mixture was stirred at 0° C. for 4 hrs. The reaction mixture was poured into iced water, and the mixture was extracted 3 times with diethyl ether. The combined organic layer was washed with saturated aqueous sodium hydrogen carbonate solution, saturated aqueous ammonium chloride solution and saturated brine, dried over anhydrous magnesium sulfate and concentrated under reduced pressure. The residue was dissolved in anhydrous acetonitrile (15 ml). Triphenylphosphine (3.515 g, 13.40 mmol) was added, and the mixture was stirred at 80° C. for 12 hrs. After cooling to room temperature, diisopropyl ether (30 ml) was added dropwise. The precipitate was collected by filtration and washed with diisopropyl ether, and dried under reduced pressure to give {[5-(2-methyloxycarbonylmethyl)thiophen-2-yl]methyl}(triphenyl)phosphonium chloride (4.011 g, yield 85.4%) as a yellow ocher solid.
Step 3

By a method similar to Production Example 108, step 4, {[5-(2-methyloxycarbonylmethyl)thiophen-2-yl]methyl} (triphenyl)phosphonium chloride (744.7 mg, 1.595 mmol) and 5-(4-acetylpyridin-1-yl)pyridine-2-carbaldehyde (310.0 mg; 1.329 mmol) were condensed to give methyl (5-{2-[5-(4-acetylpiperazin-1-yl)pyridin-2-yl]vinyl}thiophen-2-yl) acetate (490.2 mg, yield 95.7%, E/Z mixture) as a yellow oil.
Step 4

By a method similar to Production Example 108, step 5, methyl (5-{2-[5-(4-acetylpiperazin-1-yl)pyridin-2-yl] vinyl}thiophen-2-yl)acetate (490.0 mg, 1.271 mmol) was hydrogenated to give methyl (5-{2-[5-(4-acetylpiperazin-1-yl)pyridin-2-yl]ethyl}thiophen-2-yl)acetate (454.5 mg, yield 92.3%) as a colorless oil.
Step 5

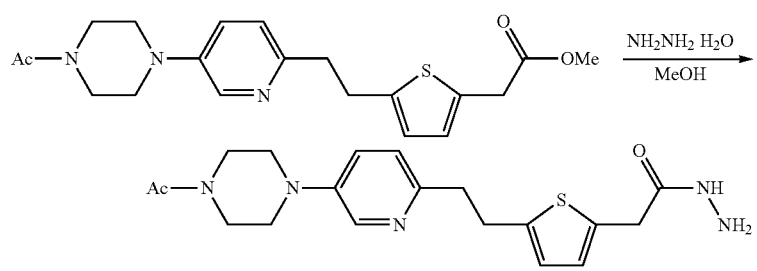

To a solution of methyl (5-{2-[5-(4-acetylpiperazin-1-yl) pyridin-2-yl]ethyl}thiophen-2-yl)acetate (390.0 mg, 1.006 mmol) in anhydrous methanol (15 ml) was added hydrazine monohydrate (503.8 mg, 10.06 mmol), and the mixture was stirred at 50° C. for 11 hrs and at room temperature for 12 hrs. The reaction mixture was concentrated under reduced pressure, and the residue was dissolved in 5% methanol-dichloromethane mixture, and filtered through aminopropylated silica gel. The filtrate was concentrated under reduced pressure, and the residue was purified by aminopropylated silica gel column chromatography (2% methanol-dichloromethane mixture) to give a white solid (381.2 mg). This was dissolved in dichloromethane (5 ml), and diethyl ether (50 ml) was added dropwise. The precipitate was collected by filtration, washed with diethyl ether and dried under reduced pressure to give the title compound (319.3 mg, yield 81.9%).

Production Example 121

3-(4-{2-[5-(4-acetylpiperazin-1-yl)pyridin-2-yl] ethyl}thiophen-2-yl)propanehydrazide trihydrochloride Step 1

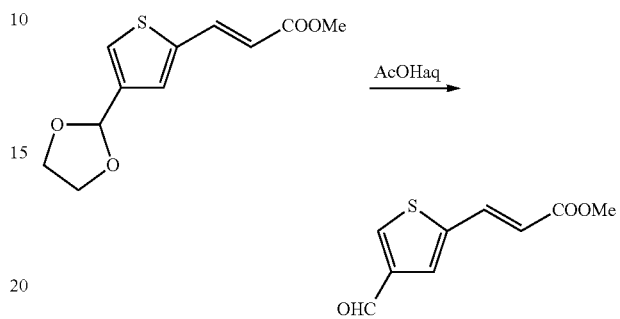

To methyl (2E)-3-[4-(1,3-dioxolan-2-yl)thiophen-2-yl] prop-2-enoate (2.200 g, 9.156 mmol) was added 50% acetic acid aqueous solution (22 ml), and the mixture was stirred at 35 to 40° C. for 2 hrs. The reaction mixture was concentrated under reduced pressure, and water (50 ml) was added. The mixture was concentrated again under reduced pressure, and water (100 ml) was added. The precipitate was collected by filtration, washed with water, and dried under reduced pressure to give methyl (2E)-3-(4-formylthiophen-2-yl)prop-2-enoate (1.701 g, yield 94.7%) as a white solid.
Step 2

By a method similar to Production Example 120, step 1, methyl (2E)-3-(4-formylthiophen-2-yl)prop-2-enoate (1.700 g, 8.664 mmol) was reduced with sodium borohydride to give methyl (2E)-3-[4-(hydroxymethyl)thiophen-2-yl]prop-2-enoate (1.591 g, yield 92.6%) as a white solid.
Step 3

By a method similar to Production Example 120, step 2, methyl (2E)-3-[4-(hydroxymethyl)thiophen-2-yl]prop-2-enoate (1.580 g, 7.970 mmol) was chlorinated, and then treated with triphenylphosphine to give ({5-[(1E)-3-methoxy-3-oxoprop-1-en-1-yl]thiophen-3-yl}methyl)(triphenyl) phosphonium chloride (2.952 g, yield 76.4%) as a white solid.
Step 4

By a method similar to Production Example 108, step 4, ({5-[(1E)-3-methoxy-3-oxoprop-1-en-1-yl]thiophen-3-yl}methyl)(triphenyl)phosphonium chloride (862.1 mg, 1.800 mmol) and 5-(4-acetylpyridin-1-yl)pyridine-2-carbaldehyde (350.0 mg, 1.500 mmol) were condensed to give methyl (2E)-3-(4-{2-[5-(4-acetylpiperazin-1-yl)pyridin-2-yl]vinyl}thiophen-2-yl)prop-2-enoate (578.8 mg, yield 97.1%) as a yellow oil.
Step 5

By a method similar to Production Example 108, step 5, methyl (2E)-3-(4-{2-[5-(4-acetylpiperazin-1-yl)pyridin-2-yl]vinyl}thiophen-2-yl)prop-2-enoate (570.0 mg, 1.434 mmol) was hydrogenated to give methyl 3-(4-{2-[5-(4-acetylpiperazin-1-yl)pyridin-2-yl]ethyl}thiophen-2-yl)propanoate (449.5 mg, yield 78.1%) as a slightly yellow solid.
Step 6

Step 2

By a method similar to Production Example 108, step 5, tert-butyl 4-(6-{2-[4-(2-hydroxyethyl)phenyl]vinyl}pyridin-3-yl)piperazine-1-carboxylate (2.312 g, 5.207 mmol) was hydrogenated to give tert-butyl 4-(6-{2-[4-(2-hydroxyethyl)phenyl]ethyl}pyridin-3-yl)piperazine-1-carboxylate (1.458 g, yield 68.0%) as a white solid.
Step 3

By a method similar to Production Example 108, step 6, tert-butyl 4-(6-{2-[4-(2-hydroxyethyl)phenyl]ethyl}pyridin-3-yl)piperazine-1-carboxylate (1.799 g, 4.371 mmol) was

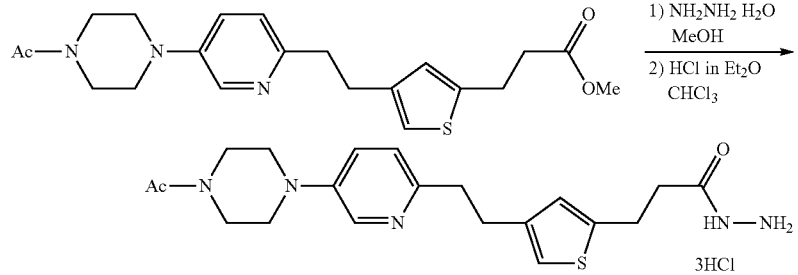

To a solution of methyl 3-(4-{2-[5-(4-acetylpiperazin-1-yl)pyridin-2-yl]ethyl}thiophen-2-yl)propanoate (360.0 mg, 0.897 mmol) in anhydrous methanol (14 ml) was added hydrazine monohydrate (449 mg, 8.97 mmol), and the mixture was stirred at 45 to 50° C. for 2 days. The reaction mixture was concentrated under reduced pressure, and the residue was dissolved in 10% methanol-dichloromethane mixture and filtered through aminopropylated silica gel. The filtrate was concentrated under reduced pressure, and the residue was purified by aminopropylated silica gel column chromatography (2% methanol-dichloromethane mixture) to give a colorless oil. This was dissolved in anhydrous chloroform (30 ml), and 1M hydrogen chloride diethyl ether solution (4.0 ml, 4.0 mmol) was added dropwise. After stirring for 15 min, the reaction mixture was concentrated under reduced pressure. Anhydrous chloroform (30 ml) was added to the residue, and the mixture was concentrated under reduced pressure. This operation was repeated 3 times to removed excess hydrogen chloride azeotropically. The residue was suspended in anhydrous chloroform (30 ml), filtered, washed with anhydrous chloroform, anhydrous diethyl ether and ethyl acetate, and dried under reduced pressure to give the title compound (347.5 mg, yield 75.8%) as a slightly yellow white solid.

Production Example 122

2-(4-{2-[5-(4-acetylpiperazin-1-yl)pyridin-2-yl]ethyl}phenyl)ethyl hydrazinecarboxylate trihydrochloride Step 1

By a method similar to Production Example 108, step 4, [4-(2-hydroxyethyl)benzyl](triphenyl)phosphonium bromide (2.866 g, 6.004 mmol) and tert-butyl 4-(6-formylpyridin-3-yl)piperazine-1-carboxylate (1.458 g, 5.003 mmol) were condensed to give tert-butyl 4-(6-{2-[4-(2-hydroxyethyl)phenyl]vinyl}pyridin-3-yl)piperazine-1-carboxylate (5.684 g, quantitatively) as a colorless oil.

deprotected and acetylated to give 2-(4-{2-[5-(4-acetylpiperazin-1-yl)pyridin-2-yl]ethyl}phenyl)ethanol (947.7 mg, yield 61.3%) as a white solid.
Step 4

By a method similar to Production Example 108, step 7, 2-(4-{2-[5-(4-acetylpiperazin-1-yl)pyridin-2-yl]ethyl}phenyl)ethyl tert-butyl hydrazine-1,2-dicarboxylate (394.2 mg, yield 96.2%) was obtained as a slightly yellow solid from 2-(4-{2-[5-(4-acetylpiperazin-1-yl)pyridin-2-yl]ethyl}phenyl)ethanol (283.0 mg, 0.801 mmol).
Step 5

By a method similar to Production Example 108, step 8, 2-(4-{2-[5-(4-acetylpiperazin-1-yl)pyridin-2-yl]ethyl}phenyl)ethyl tert-butyl hydrazine-1,2-dicarboxylate (341.2 mg, 0.667 mmol) was deprotected to give the title compound (262.5 mg, yield 75.6%) as a slightly yellow solid.

Production Example 123

N-[2-(4-{2-[5-(4-acetylpiperazin-1-yl)pyridin-2-yl]ethyl}phenyl)ethyl]hydrazinecarboxamide trihydrochloride Step 1

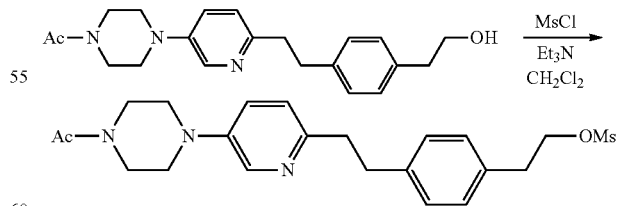

To a solution of 2-(4-{2-[5-(4-acetylpiperazin-1-yl)pyridin-2-yl]ethyl}phenyl)ethanol (354.1 mg, 1.002 mmol) in dichloromethane (14 ml) were added triethylamine (0.25 ml, 1.5 mmol) and methanesulfonyl chloride (0.116 ml, 1.67 mmol), and the mixture was stirred at room temperature for 45 mins. Water was added to the reaction mixture, and the mixture was extracted twice with dichloromethane. The combined organic layer was washed with saturated brine, dried over anhydrous magnesium sulfate, and concentrated to dryness to give 2-(4-{2-[5-(4-acetylpiperazin-1-yl)pyridin-2-yl]ethyl}phenyl)ethyl methanesulfonate (415.0 mg, yield 96.0%) as a slightly brown solid.
Step 2

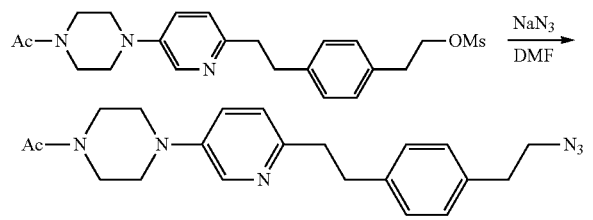

To a solution of 2-(4-{2-[5-(4-acetylpiperazin-1-yl)pyridin-2-yl]ethyl}phenyl)ethyl methanesulfonate (608.9 mg, 1.411 mmol) in anhydrous N,N-dimethylformamide (5 ml) was added sodium azide (918.0 mg, 14.12 mmol), and the mixture was stirred at room temperature for 24 hrs. Water was added to the reaction mixture, and the mixture was extracted twice with ethyl acetate. The organic layer was washed with saturated brine, dried over anhydrous magnesium sulfate and concentrated under reduced pressure. The residue was washed with tert-butyl methyl ether (10 ml) and dried under reduced pressure to give 1-acetyl-4-(6-{2-[4-(2-azidoethyl)phenyl]ethyl}pyridin-3-yl)piperazine (405.9 mg, yield 76.0%) as a white solid.
Step 3

By a method similar to Production Example 109, step 3, 1-acetyl-4-(6-{2-[4-(2-azidoethyl)phenyl]ethyl}pyridin-3-yl)piperazine (392.0 mg, 1.036 mmol) was reduced to give 2-(4-{2-[5-(4-acetylpiperazin-1-yl)pyridin-2-yl]ethyl}phenyl)ethanamine (278.0 mg, yield 76.1%) as a white solid.

Step 4

By a method similar to Production Example 109, step 4, tert-butyl 2-{[2-(4-{2-[5-(4-acetylpiperazin-1-yl)pyridin-2-yl]ethyl}phenyl)ethyl]carbamoyl}hydrazinecarboxylate (379.0 mg, yield 94.4%) was obtained as a white solid from 2-(4-{2-[5-(4-acetylpiperazin-1-yl)pyridin-2-yl]ethyl}phenyl)ethanamine (277.0 mg, 0.786 mmol).

Step 5

By a method similar to Production Example 109, step 5, tert-butyl 2-{[2-(4-{2-[5-(4-acetylpiperazin-1-yl)pyridin-2-yl]ethyl}phenyl)ethyl]carbamoyl}hydrazinecarboxylate (333.7 mg, 0.654 mmol) was deprotected to give the title compound (205.9 mg, yield 60.6%) as a slightly yellow solid.

Production Example 124

3-(4-{2-[5-(4-acetylpiperazin-1-yl)pyridin-2-yl]ethyl}thiophen-2-yl)propylhydrazinecarboxylate Step 1

By a method similar to Production Example 108, step 4, ({5-[(1E)-3-methoxy-3-oxoprop-1-en-1-yl]thiophen-3-yl}methyl)(triphenyl)phosphonium chloride (1.724 g, 3.600 mmol) and tert-butyl 4-(6-formylpyridin-3-yl)piperazine-1-carboxylate (874.1 mg, 3.000 mmol) were condensed to give tert-butyl 4-[6-(2-{5-[(1E)-3-methoxy-3-oxoprop-1-en-1-yl]thiophen-3-yl}vinyl)pyridin-3-yl]piperazine-1-carboxylate (1.295 g, yield 94.7%) as a yellow oil.

Step 2

By a method similar to Production Example 108, step 5, tert-butyl 4-[6-(2-{5-[(1E)-3-methoxy-3-oxoprop-1-en-1-yl]thiophen-3-yl}vinyl)pyridin-3-yl]piperazine-1-carboxylate (1.285 g, 2.821 mmol) was hydrogenated to give tert-butyl 4-(6-{2-[5-(3-methoxy-3-oxopropyl)thiophen-3-yl]ethyl}pyridin-3-yl)piperazine-1-carboxylate (850.1 mg, yield 65.6%) as a white solid.

Step 3

By a method similar to Production Example 113, step 5, tert-butyl 4-(6-{2-[5-(3-methoxy-3-oxopropyl)thiophen-3-yl]ethyl}pyridin-3-yl)piperazine-1-carboxylate (840.0 mg, 1.828 mg) was reduced with diisobutylaluminum hydride to give tert-butyl 4-(6-{2-[5-(3-hydroxypropyl)thiophen-3-yl]ethyl}pyridin-3-yl)piperazine-1-carboxylate (632.3 mg, yield 80.1%) as a white solid.

Step 4

By a method similar to Production Example 108, step 6, tert-butyl 4-(6-{2-[5-(3-hydroxypropyl)thiophen-3-yl]ethyl}pyridin-3-yl)piperazine-1-carboxylate (620.0 mg, 1.437 g) was deprotected and acetylated to give 3-(4-{2-[5-(4-acetylpiperazin-1-yl)pyridin-2-yl]ethyl}thiophen-2-yl)propan-1-ol (393.9 mg, yield 73.4%).

Step 5

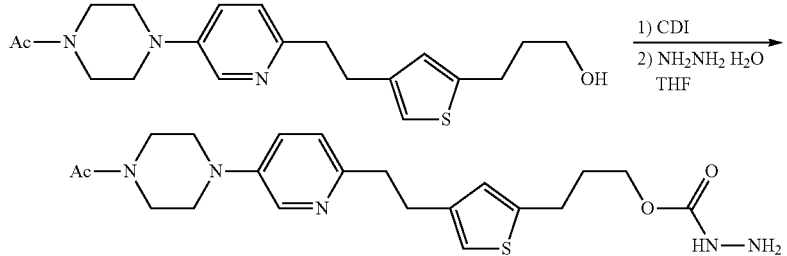

To a solution of 3-(4-{2-[5-(4-acetylpiperazin-1-yl)pyridin-2-yl]ethyl}thiophen-2-yl)propan-1-ol (150.0 mg, 0.402 mmol) in anhydrous tetrahydrofuran (3 ml) was added 1,1'-carbonyldiimidazole (84.7 mg, 0.522 mmol), and the mixture was stirred at room temperature for 2 hrs. 1M Hydrazine tetrahydrofuran solution (1.21 ml, 1.21 mmol) was added, and the mixture was stirred at room temperature for 2 hrs. Since the reaction did not proceed, hydrazine monohydrate (26.1 mg, 0.522 mmol) was added, and the mixture was stirred at room temperature for 1 hr. The reaction mixture was concentrated under reduced pressure, and the residue was purified by aminopropylated silica gel column chromatography (5%-2-propanol-dichloromethane mixture) and aminopropylated silica gel column chromatography (2%-methanoldichloromethane mixture) to give the title compound (148.8 mg, yield 85.9%) as a colorless syrup.

Production Example 125

N-[3-(4-{2-[5-(4-acetylpiperazin-1-yl)pyridin-2-yl]ethyl}thiophen-2-yl)propyl]hydrazinecarboxamide Step 1

By a method similar to Production Example 123, step 1, 3-(4-{2-[5-(4-acetylpiperazin-1-yl)pyridin-2-yl]ethyl}thiophen-2-yl)propan-1-ol (235.0 mg, 0.629 mmol) was mesylated to give crude 3-(4-{2-[5-(4-acetylpiperazin-1-yl)pyridin-2-yl]ethyl}thiophen-2-yl)propyl methanesulfonate (329.4 mg) as a pale-brown solid.

Step 2

By a method similar to Production Example 123, step 2, crude 3-(4-{2-[5-(4-acetylpiperazin-1-yl)pyridin-2-yl]ethyl}thiophen-2-yl)propyl methanesulfonate (329.4 mg, corresponding to 0.629 mmol) was azidated to give 1-acetyl-4-(6-{2-[5-(3-azidopropyl)thiophen-3-yl]ethyl}pyridin-3-yl)piperazine (236.4 mg, yield 94.3%, overall 2 steps) as a white solid.

Step 3

By a method similar to Production Example 109, step 3, 1-acetyl-4-(6-{2-[5-(3-azidopropyl)thiophen-3-yl]ethyl}pyridin-3-yl)piperazine (235.0mg, 0.590 mmol) was reduced to give 3-(4-{2-[5-(4-acetylpiperazin-1-yl)pyridin-2-yl]ethyl}thiophen-2-yl)propan-1-amine (181.3 mg, yield 82.5%) as a white soild.

Step 4

By a method similar to Production Example 109, step 5, tert-butyl 2-{[3-(4-{2-[5-(4-acetylpiperazin-1-yl)pyridin-2-yl]ethyl}thiophen-2-yl)propyl]carbamoyl}hydrazinecarboxylate (256.1 mg, yield 99.9%) was obtained as a coloress syrup from 3-(4-{2-[5-(4-acetylpiperazin-1-yl)pyridin-2-yl]ethyl}thiophen-2-yl)propan-1-amine (180.0 mg, 0.483 mmol).

Step 5

By a method similar to Production Example 116, step 10, tert-butyl 2-{[3-(4-{2-[5-(4-acetylpiperazin-1-yl)pyridin-2-yl]ethyl}thiophen-2-yl)propyl]carbamoyl}hydrazinecarboxylate (255.0 mg, 0.481 mmol) was deprotected with trifluoroacetic acid, and purified by aminopropylated silica gel column chromatography (2%-methanol-dichloromethane mixture) to give the title compound (48.3mg, yield 23.3%) as an off-white solid.

TABLE 1

| Compound | structural formula | starting material of ring A | synthesis method | properties | MS | ¹H-NMR |
|---|---|---|---|---|---|---|
| Production Example 1 | (4-bromophenethyl-phenyl)acetohydrazide·HCl | 4-Br-C₆H₄-NHCOCH₃ | method A | slightly yellow solid | 312 [M + H]⁺ (APCI) | (DMSO-d₆): 10.78 (brs, 1H), 9.83 (brs, 1H), 7.46 (d, J = 8.4 Hz, 2H), 7.19 (s, 4H), 7.16 (d, J = 8.4 Hz, 2H), 3.49 (s, 2H), 2.81 (s, 4H), 2.01 (s, 3H). |
| Production Example 2 | (3-bromophenethyl-phenyl)acetohydrazide·HCl | 3-Br-C₆H₄-NHCOCH₃ | method A | white solid | 312 [M + H]⁺ (APCI) | (DMSO-d₆): 10.74 (brs, 1H), 9.85 (brs, 1H), 7.49 (brs, 1H), 7.37 (d, J = 8.9 Hz, 1H), 7.20-7.10 (m, 5H), 6.90 (d, J = 7.4 Hz, 1H), 3.49 (s, 2H), 2.83 (s, 4H), 2.03 (s, 3H). |
| Production Example 3 | pyridine diacetamide derivative | 2,3-diacetamido-5-bromopyridine | method A | white solid | 370 [M + H]⁺ (APCI) | (DMSO-d₆): 11.23 (s, 1H), 10.52 (brs, 1H), 9.58 (brs, 1H), 8.23 (brs, 1H), 8.04 (d, J = 2.0 Hz, 1H), 7.14 (s, 4H), 3.54 (s, 2H), 2.89 (brs, 4H), 2.15 (s, 3H), 2.09 (s, 3H). |
| Production Example 4 | 6-bromopyridin-2-yl acetamide | 6-Br-pyridin-2-yl-NHCOCH₃ | method A | slightly yellow solid | 313 [M + H]⁺ (APCI) | (DMSO-d₆): 10.44 (brs, 1H), 7.88 (d, J = 8.0 Hz, 1H), 7.69 (t, J = 7.8 Hz, 1H), 7.19 (m, 4H), 6.96 (d, J = 7.4 Hz, 1H), 3.57 (s, 2H), 2.95 (s, 4H), 2.09 (s, 3H). |
| Production Example 5 | (4-bromo-3-trifluoromethylphenyl)acetamide | 4-Br-3-CF₃-C₆H₃-NHCOCH₃ | method A | slightly yellow-gray solid | 380 [M + H]⁺ (APCI) | (DMSO-d₆): 10.97 (brs, 1H), 10.22 (brs, 1H), 10.15-9.70 (brs, 2H), 8.00 (d, J = 2.0 Hz, 1H), 7.74 (dd, J = 8.4 Hz, 2.0 Hz, 1H), 7.45 (d, J = 8.5 Hz, 1H), 7.25-7.05 (m, 4H), 3.53 (s, 2H), 2.95 (m, 2H), 2.81 (m, 2H), 2.06 (s, 3H). |

TABLE 1-continued

| Compound | structural formula | starting material of ring A | synthesis method | properties | MS | ¹H-NMR |
|---|---|---|---|---|---|---|
| Production Example 6 | [structure with HCl] | [4-bromophenoxyacetamide structure] | method A | slightly yellow-gray solid | 328 [M + H]⁺ (APCI) | (DMSO-d₆): 11.08 (brs, 1H), 10.20-10.00 (brs, 2H), 7.48 (brs, 1H), 7.36 (brs, 1H), 7.25-7.10 (m, 6H), 6.85 (dd, J = 6.7 Hz, 2.0 Hz, 2H), 4.37 (s, 2H), 3.52 (s, 2H), 2.81 (m, 4H). |
| Production Example 7 | [structure with 2HCl] | [2-acetamido-5-bromopyrazine structure] | method A | pale-yellow white solid | 314 [M + H]⁺ (APCI) | (DMSO-d₆): 11.24 (brs, 1H), 10.65 (brs, 1H), 10.60-10.20 (brs, 2H), 9.22 (d, J = 1.3 Hz, 1H), 8.22 (d, J = 1.4 Hz, 1H), 7.18 (m, 4H), 3.54 (s, 2H), 2.99 (m, 4H), 2.11 (s, 3H). |
| Production Example 8 | [structure with HCl] | [2,4-diacetamido-bromobenzene structure] | method A | off-white solid | 369 [M + H]⁺ (APCI) | (DMSO-d₆): 11.01 (brs, 1H), 9.37 (brs, 1H), 9.35 (brs, 1H), 7.50-7.40 (m, 2H), 7.20 (m, 4H), 6.98 (d, J = 7.9 Hz, 1H), 3.52 (s, 2H), 2.83 (brs, 4H), 2.07 (s, 3H), 2.06 (s, 3H). |
| Production Example 9 | [structure with 2HCl] | [2-iodoimidazole structure] | method A | pale-yellow solid | 245 [M + H]⁺ (APCI) | (DMSO-d₆): 14.15 (brs, 1H), 11.06 (brs, 1H), 7.55 (s, 2H), 7.22 (d, J = 8.1 Hz, 2H), 7.14 (d, J = 8.2 Hz, 2H), 3.52 (s, 2H), 3.22 (m, 2H), 3.06 (m, 2H). |
| Production Example 10 | [structure with 2HCl] | [4-iodoimidazole structure] | method A | slightly yellow-gray solid | 245 [M + H]⁺ (APCI) | (DMSO-d₆): 8.99 (d, J = 1.2 Hz, 1H), 7.38 (d, J = 1.2 Hz, 1H), 7.20 (m, 4H), 3.52 (s, 2H), 2.94 (s, 4H). |

TABLE 1-continued

| Compound structural formula | starting material of ring A | synthesis method | properties | MS | 1H-NMR |
|---|---|---|---|---|---|
| Production Example 11 | | method A | pale-gray solid | 313 [M + H]+ (APCI) | (DMSO-d6): 11.29 (brs, 1H), 10.81 (brs, 1H), 8.13 (d, J = 1.9 Hz, 1H), 7.90 (d, J = 8.5 Hz, 1H), 7.76 (d, J = 8.6 Hz, 1H), 7.18 (m, 4H), 3.54 (s, 2H), 2.86 (s, 4H), 2.11 (s, 3H). |
| Production Example 12 | | method A | yellowish gray solid | 341 [M + H]+ (APCI) | (DMSO-d6): 11.25 (brs, 1H), 7.90-7.85 (m, 2H), 7.20 (m, 5H), 3.74 (m, 4H), 3.59 (m, 4H), 3.54 (s, 2H), 2.84 (s, 4H). |
| Production Example 13 | | method A (without hydrogenation step) | pale-brown solid | 324 [M + H]+ (APCI) | (DMSO-d6): 11.15 (brs, 1H), 10.40-9.70 (brs, 1H), 7.57 (brs, 1H), 7.51 (d, J = 7.4 Hz, 2H), 7.48 (d, J = 7.4 Hz, 2H), 7.40 (brs, 1H), 7.34 (d, J = 8.2 Hz, 2H), 6.99 (d, J = 8.8 Hz, 2H), 4.48 (s, 2H), 3.62 (s, 2H). |
| Production Example 14 | | method A (without hydrogenation step) | pale-brown solid | 241 [M + H]+ (APCI) | (DMSO-d6): 11.42 (brs, 1H), 7.70-7.60 (m, 4H), 7.46 (d, J = 8.2 Hz, 2H), 3.71 (s, 2H). |
| Production Example 15 | | method A (without hydrogenation step) | yellowish white solid | 337 [M + H]+ (APCI) | (DMSO-d6): 11.33 (brs, 1H), 10.80-10.10 (brs, 2H), 8.31 (d, J = 2.0 Hz, 1H), 7.71 (dd, J = 8.9 Hz, 2.4 Hz, 1H), 7.49 (d, J = 8.3 Hz, 2H), 7.34 (d, J = 9.0 Hz, 1H), 6.91 (d, J = 9.0 Hz, 1H), 3.69 (m, 4H), 3.64 (s, 2H), 3.54 (m, 4H). |
| Production Example 16 | | method A (without hydrogenation step) | yellow solid | 310 [M + H]+ (APCI) | (DMSO-d6): 11.29 (brs, 1H), 10.99 (brs, 1H), 9.34 (d, J = 1.5 Hz, 1H), 8.62 (d, J = 1.5 Hz, 1H), 7.60 (d, J = 8.2 Hz, 2H), 7.40 (d, J = 8.2 Hz, 2H), 3.67 (s, 2H), 2.16 (s, 3H). |

TABLE 1-continued

| Compound structural formula | starting material of ring A | synthesis method | properties | MS | ¹H-NMR |
|---|---|---|---|---|---|
| Production Example 17 | | method A (without hydrogenation step) | gray solid | 365 [M + H]⁺ (APCI) | (DMSO-d₆): 11.05 (brs, 1H), 9.57 (brs, 1H), 9.52 (brs, 1H), 7.76 (s, 1H), 7.70 (d, J = 8.4 Hz, 1H), 7.53 (d, J = 8.3 Hz, 2H), 7.35 (d, J = 8.3 Hz, 2H), 7.28 (dd, J = 8.3 Hz, 1.9 Hz, 1H), 3.62 (s, 2H), 2.11 (s, 3H), 2.10 (s, 3H). |
| Production Example 18 | | method A (without hydrogenation step) | off-white solid | 366 [M + H]⁺ (APCI) | (DMSO-d₆): 11.05 (brs, 1H), 9.57 (brs, 1H), 9.52 (brs, 1H), 7.76 (s, 1H), 7.70 (d, J = 8.4, 1H), 7.53 (d, J = 8.3, 2H), 7.35 (d, J = 8.3, 2H), 7.28 (dd, J = 8.3, 1.9, 1H), 3.62 (s, 2H), 2.11 (s, 3H), 2.10 (s, 3H). |
| Production Example 19 | | method A | yellowish gray solid | 300 [M + H]⁺ (APCI) | (DMSO-d₆): 11.03 (brs, 1H), 10.30-9.80 (brs, 2H), 9.09 (d, J = 1.2 Hz, 1H), 8.56 (d, J = 1.2 Hz, 1H), 8.16 (brs, 1H), 7.77 (brs, 1H), 7.19 (brs, 4H), 3.52 (s, 2H), 3.18 (m, 2H), 3.03 (m, 2H). |
| Production Example 20 | | method A | orange solid | 345 [M + H]⁺ (APCI) | (DMSO-d₆): 11.25 (brs, 1H), 9.15-8.70 (m, 3H), 7.19 (m, 5H), 3.47 (s, 2H), 3.32 (m, 3H), 3.04 (m, 2H), 2.95 (brs, 4H), 2.17 (m, 2H), 1.91 (m, 2H). |
| Production Example 21 | | method A | yellowish gray solid | 370 [M + H]⁺ (APCI) | (DMSO-d₆): 10.82 (brs, 1H), 9.34 (brs, 1H), 7.76 (brs, 1H), 7.21 (m, 4H), 7.01 (brs, 2H), 3.50 (s, 2H), 2.84 (s, 4H), 2.27 (s, 3H), 2.06 (s, 3H). |

TABLE 1-continued

| Compound | structural formula | starting material of ring A | synthesis method | properties | MS | ¹H-NMR |
|---|---|---|---|---|---|---|
| Production Example 22 | 4-(2-(1-methyl-1H-imidazol-2-yl)ethyl)phenylacetohydrazide · 2HCl | 2-iodo-1-methyl-1H-imidazole | method A | colorless oil | 259 [M + H]⁺ (APCI) | (DMSO-d₆): 11.10 (brs, 1H), 7.57 (s, 2H), 7.24 (d, J = 8.2 Hz, 2H), 7.18 (d, J = 8.2 Hz, 2H), 3.67 (s, 3H), 3.54 (s, 2H), 3.24 (m, 2H), 3.01 (m, 2H). |
| Production Example 23 | 4-((4-acetamidophenyl)ethynyl)phenylacetohydrazide · HCl | 4-bromoacetanilide | method A (without hydrogenation step) | yellowish gray solid | 308 [M + H]⁺ (APCI) | (DMSO-d₆): 11.27 (brs, 1H), 10.19 (s, 1H), 7.65 (d, J = 8.6 Hz, 2H), 7.50 (d, J = 8.4 Hz, 2H), 7.47 (d, J = 8.8 Hz, 2H), 7.34 (d, J = 8.2 Hz, 2H), 3.64 (s, 2H), 2.07 (s, 3H). |
| Production Example 24 | 4-((3-acetamidophenyl)ethynyl)phenylacetohydrazide · HCl | 3-bromoacetanilide | method A (without hydrogenation step) | pale-yellow solid | 308 [M + H]⁺ (APCI) | (DMSO-d₆): 10.95 (s, 1H), 10.07 (s, 1H), 7.90 (s, 1H), 7.60-7.50 (m, 3H), 7.40-7.30 (m, 3H), 7.20 (m, 1H), 3.62 (s, 2H), 2.06 (s, 3H). |
| Production Example 25 | 4-((1-methyl-1H-imidazol-2-yl)ethynyl)phenylacetohydrazide · 2HCl | 2-iodo-1-methyl-1H-imidazole | method A (without hydrogenation step) | yellow ocher solid | 255 [M + H]⁺ (APCI) | (DMSO-d₆): 11.38 (brs, 1H), 7.72 (d, J = 1.6 Hz, 1H), 7.69 (d, J = 8.3 Hz, 2H), 7.56 (d, J = 1.6 Hz, 1H), 7.46 (d, J = 8.3 Hz, 2H), 3.89 (s, 3H), 3.71 (s, 2H). |
| Production Example 26 | 4-((2-(piperidin-4-yl)thiazol-4-yl)ethynyl)phenylacetohydrazide · 2HCl | 4-(4-ethynylthiazol-2-yl)piperidine | method A (without hydrogenation step) | yellow solid | 341 [M + H]⁺ (APCI) | (DMSO-d₆): 9.20-8.70 (m, 3H), 8.01 (s, 1H), 7.54 (d, J = 8.2 Hz, 2H), 7.37 (d, J = 8.2 Hz, 2H), 3.62 (s, 2H), 3.03 (m, 4H), 2.20 (m, 2H), 2.05-1.85 (m, 2H). |
| Production Example 27 | 4-((6-acetamidopyridin-3-yl)ethynyl)phenylacetohydrazide · HCl | 2-acetamido-5-bromopyridine | method A (without hydrogenation step) | white solid | 309 [M + H]⁺ (APCI) | (DMSO-d₆): 11.04 (brs, 1H), 10.70 (s, 1H), 8.49 (dd, J = 2.3 Hz, 0.7 Hz, 1H), 8.13 (dd, J = 8.6 Hz, 0.7 Hz, 1H), 7.93 (dd, J = 8.6 Hz, 2.3 Hz, 1H), 7.54 (d, J = 8.3 Hz, 2H), 7.35 (d, J = 8.3 Hz, 2H), 3.63 (s, 2H), 2.12 (s, 3H). |

TABLE 1-continued

| Compound | structural formula | starting material of ring A | synthesis method | properties | MS | $^1$H-NMR |
|---|---|---|---|---|---|---|
| Production Example 28 | (structure with HCl, pyridine-acetylamino, alkyne linker, phenyl-acetamide-NH-NH$_2$) | (6-acetamido-2-bromopyridine) | method A (without hydrogenation step) | yellowish gray solid | 309 [M + H]$^+$ (APCI) | (DMSO-d$_6$): 11.17 (brs, 1H), 10.72 (s, 1H), 8.10 (d, J = 7.9 Hz, 1H), 7.82 (t, J = 7.9 Hz, 1H), 7.56 (d, J = 8.2 Hz, 2H), 7.38 (d, J = 8.2 Hz, 2H), 7.33 (dd, J = 7.5 Hz, 0.8 Hz, 1H), 3.65 (s, 2H), 2.09 (s, 3H). |
| Production Example 29 | (2HCl, 4-dimethylamino-phenyl ethylene phenyl-acetamide-NH-NH$_2$) | (4-bromo-N,N-dimethylaniline) | method B | white solid | 298 [M + H]$^+$ (APCI) | (DMSO-d$_6$): 11.34 (brs, 1H), 7.45 (brs, 2H), 7.34 (m, 2H), 7.21 (m, 4H), 3.55 (s, 2H), 3.04 (s, 6H), 2.86 (s, 4H). |
| Production Example 30 | (2HCl, 4-diethylamino-phenyl ethylene phenyl-acetamide-NH-NH$_2$) | (4-bromo-N,N-diethylaniline) | method B | white solid | 326 [M + H]$^+$ (APCI) | (DMSO-d$_6$): 11.24 (brs, 1H), 10.80-9.90 (brs, 2H), 7.60 (brs, 2H), 7.40 (m, 2H), 7.18 (m, 4H), 3.60-3.40 (m, 6H), 2.89 (s, 4H), 1.02 (t, J = 7.1, 6H). |
| Production Example 31 | (2HCl, 4-pyrrolidinyl-phenyl ethylene phenyl-acetamide-NH-NH$_2$) | (1-(4-bromophenyl)pyrrolidine) | method B | off-white solid | 324 [M + H]$^+$ (APCI) | (DMSO-d$_6$): 11.33 (brs, 1H), 11.00-10.10 (brs, 2H), 7.30-7.10 (m, 8H), 6.86 (brs, 2H), 3.55 (s, 2H), 3.32 (brs, 4H), 2.80 (brs, 4H), 2.00 (brs, 4H). |
| Production Example 32 | (2HCl, 4-piperidinyl-phenyl ethylene phenyl-acetamide-NH-NH$_2$) | (1-(4-bromophenyl)piperidine) | method B | white solid | 338 [M + H]$^+$ (APCI) | (DMSO-d$_6$): 11.32 (brs, 1H), 7.72 (d, J = 8.4 Hz, 2H), 7.40 (d, J = 8.4 Hz, 2H), 7.21 (m, 4H), 3.55 (s, 2H), 3.45 (t, J = 5.4 Hz, 4H), 2.88 (m, 4H), 1.97 (brs, 4H), 1.65 (brs, 2H). |

TABLE 1-continued

| Compound structural formula | starting material of ring A | synthesis method | properties | MS | ¹H-NMR |
|---|---|---|---|---|---|
| Production Example 33 · 3HCl | Boc-N(piperazine)-C₆H₄-I | method B | slightly green white solid | 339 [M + H]⁺ (APCI) | (DMSO-d₆): 11.18 (brs, 1H), 9.06 (brs, 2H), 7.19 (m, 4H), 7.13 (d, J = 8.6 Hz, 2H), 6.90 (d, J = 8.6 Hz, 2H), 3.53 (s, 2H), 2.50-2.15 (m, 9H), 2.79 (brs, 4H). |
| Production Example 34 · 2HCl | Ac-N(piperazine)-C₆H₄-I | method A | pale-brown solid | 381 [M + H]⁺ (APCI) | (DMSO-d₆): 11.18 (brs, 1H), 7.19 (m, 4H), 7.13 (d, J = 8.3, 2H), 6.97 (d, J = 8.3 Hz, 2H), 3.60 (brs, 4H), 3.54 (s, 2H), 3.15 (brs, 2H), 3.08 (brs, 2H), 2.80 (brs, 4H), 2.04 (s, 3H). |
| Production Example 35 · 3HCl | Me-N(piperazine)-C₆H₄-I | method B | off-white solid | 353 [M + H]⁺ (APCI) | (DMSO-d₆): 9.20 (brs, 1H), 7.14 (m, 4H), 7.07 (d, J = 8.5 Hz, 2H), 6.84 (d, J = 8.5 Hz, 2H), 3.30 (s, 2H), 3.09 (brs, 4H), 2.77 (brs, 4H), 2.51 (brs, 4H), 2.25 (s, 3H). |
| Production Example 36 · 2HCl | morpholine-C₆H₄-I | method B | yellowish white solid | 340 [M + H]⁺ (APCI) | (DMSO-d₆): 11.34 (brs, 1H), 7.20 (m, 8H), 3.85 (t, J = 4.3 Hz, 4H), 3.55 (s, 2H), 3.22 (brs, 4H), 2.82 (brs, 4H). |

TABLE 1-continued

| Compound structural formula | starting material of ring A | synthesis method | properties | MS | 1H-NMR |
|---|---|---|---|---|---|
| Production Example 37 | | method A | yellowish white solid | 298 [M + H]+ (APCI) | (DMSO-d6): 7.27 (m, 1H), 7.20 (m, 4H), 7.09 (m, 2H), 6.96 (m, 1H), 3.54 (s, 2H), 2.98 (s, 6H), 2.86 (s, 4H). |
| Production Example 38 | | method A | pale-brown solid | 324 [M + H]+ (APCI) | (DMSO-d6): 11.26 (brs, 1H), 7.21 (s, 4H), 7.09 (t, J = 7.7 Hz, 1H), 6.65-6.40 (m, 3H), 3.54 (s, 2H), 3.24 (m, 4H), 2.82 (m, 4H), 1.96 (t, J = 6.5 Hz, 4H). |
| Production Example 39 | | method A | yellowish white solid | 338 [M + H]+ (APCI) | (DMSO-d6): 11.33 (brs, 1H), 7.65 (brs, 1H), 7.60 (d, J = 7.4 Hz, 1H), 7.42 (t, J = 7.8 Hz, 1H), 7.30-7.20 (m, 1H), 7.20 (m, 4H), 3.55 (s, 2H), 3.40 (t, J = 6.9 Hz, 4H), 2.90 (m, 4H), 1.97 (brs, 4H), 1.66 (brs, 2H). |
| Production Example 40 | | method A | slightly yellow white solid | 339 [M + H]+ (APCI) | (DMSO-d6): 11.41 (brs, 1H), 11.00-10.20 (brs, 2H), 9.37 (brs, 2H), 7.25-7.10 (m, 5H), 6.85-6.70 (m, 3H), 3.56 (s, 2H), 3.35 (m, 4H), 3.19 (brs, 4H), 2.83 (m, 4H). |
| Production Example 41 | | method A | slightly yellow white solid | 381 [M + H]+ (APCI) | (DMSO-d6): 11.32 (brs, 1H), 7.20 (m, 5H), 7.10-6.95 (m, 2H), 6.84 (d, J = 7.2 Hz, 1H), 3.79 (m, 4H), 3.55 (s, 2H), 3.22 (m, 2H), 3.16 (m, 2H), 2.84 (brs, 4H), 2.06 (s, 3H). |
| Production Example 42 | | method A | white solid | 340 [M + H]+ (APCI) | (DMSO-d6): 11.36 (brs, 1H), 11.00-10.20 (brs, 2H), 7.20 (m, 5H), 7.15-7.00 (m, 2H), 6.89 (d, J = 7.2 Hz, 1H), 3.84 (m, 4H), 3.55 (s, 2H), 3.22 (brs, 4H), 2.85 (m, 4H). |

TABLE 1-continued

| Compound structural formula | starting material of ring A | synthesis method | properties | MS | ¹H-NMR |
|---|---|---|---|---|---|
| Production Example 43 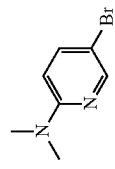 3HCl | 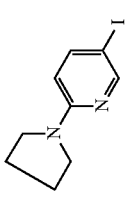 | method A | white solid | 299 [M + H]⁺ (APCI) | (DMSO-d₆): 11.36 (brs, 1H), 7.94 (dd, J = 9.4 Hz, 2.1, 1H), 7.77 (d, J = 1.7 Hz, 1H), 7.25-7.15 (m, 5H), 3.55 (s, 2H), 3.21 (s, 6H), 2.84 (s, 4H). |
| Production Example 44 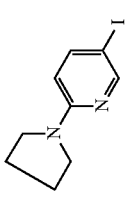 3HCl | 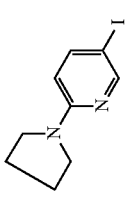 | method B | yellowish white solid | 325 [M + H]⁺ (APCI) | (DMSO-d₆): 11.29 (brs, 1H), 7.93 (dd, J = 9.3 Hz, 2.0 Hz, 1H), 7.73 (d, J = 1.7 Hz, 1H), 7.20 (m, 4H), 7.06 (d, J = 9.3 Hz, 1H), 3.70-3.40 (m, 6H), 2.84 (m, 4H), 2.01 (t, J = 6.5 Hz, 4H). |
| Production Example 45 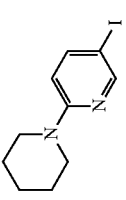 3HCl | 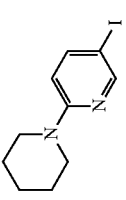 | method A | white solid | 339 [M + H]⁺ (APCI) | (DMSO-d₆): 11.35 (brs, 1H), 7.93 (dd, J = 9.4 Hz, 2.0 Hz, 1H), 7.78 (d, J = 2.0 Hz, 1H), 7.36 (d, J = 9.4, 1H), 7.21 (m, 4H), 3.68 (m, 4H), 3.55 (s, 2H), 2.83 (s, 4H), 1.63 (m, 6H). |
| Production Example 46 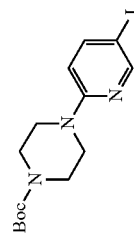 4HCl | 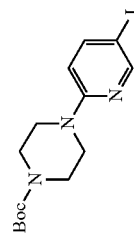 | method A | white solid | 340 [M + H]⁺ (APCI) | (DMSO-d₆): 11.36 (brs, 1H), 9.45 (brs, 2H), 7.95 (d, J = 1.9 Hz, 1H), 7.81 (d, J = 9.0 Hz, 1H), 7.30-7.10 (m, 5H), 3.85 (brs, 4H), 3.55 (s, 2H), 3.21 (brs, 4H), 2.83 (brs, 4H). |

TABLE 1-continued

| Compound | structural formula | starting material of ring A | synthesis method | properties | MS | ¹H-NMR |
|---|---|---|---|---|---|---|
| Production Example 47 | 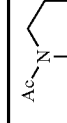 3HCl | 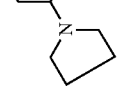 | method A | orange yellow solid | 382 [M + H]⁺ (APCI) | (DMSO-d₆): 11.33 (brs, 1H), 7.91 (d, J = 9.4 Hz, 1H), 7.87 (d, J = 1.9 Hz, 1H), 7.28 (d, J = 9.4 Hz, 1H), 7.21 (m, 4H), 3.73 (m, 2H), 3.62 (m, 6H), 3.55 (s, 2H), 2.84 (s, 4H), 2.05 (s, 3H). |
| Production Example 48 | 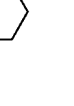 4HCl | 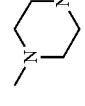 | method A | yellow solid | 354 [M + H]⁺ (APCI) | (DMSO-d₆): 11.32 (brs, 1H), 7.97 (d, J = 1.9 Hz, 1H), 7.74 (d, J = 7.9 Hz, 1H), 7.20 (m, 4H), 7.11 (d, J = 7.9 Hz, 1H), 4.37 (m, 2H), 3.55 (s, 2H), 3.55-3.30 (m, 4H), 3.09 (m, 2H), 2.82 (s, 4H), 2.80 (s, 3H). |
| Production Example 49 | 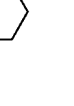 3HCl | 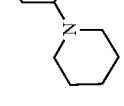 | method A | off-white solid | 325 [M + H]⁺ (APCI) | (DMSO-d₆): 11.36 (brs, 1H), 11.00-10.20 (brs, 2H), 7.84 (dd, J = 8.9 Hz, 7.2 Hz, 1H), 7.25 (m, 4H), 6.89 (d, J = 8.9 Hz, 1H), 6.71 (d, J = 7.2 Hz, 1H), 3.61 (brs, 4H), 3.56 (s, 2H), 3.20 (m, 2H), 3.00-2.90 (m, 2H), 2.02 (t, J = 6.4 Hz, 4H). |
| Production Example 50 | 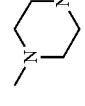 3HCl | 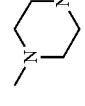 | method A | yellowish white solid | 339 [M + H]⁺ (APCI) | (DMSO-d₆): 11.44 (brs, 1H), 7.84 (t, J = 8.0 Hz, 1H), 7.24 (m, 4H), 7.15 (d, J = 9.0 Hz, 1H), 6.75 (d, J = 7.2 Hz, 1H), 3.71 (brs, 4H), 3.56 (s, 2H), 3.20 (m, 2H), 2.95 (m, 2H), 1.64 (brs, 6H). |
| Production Example 51 | 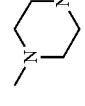 4HCl | 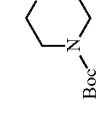 | method A | yellowish white solid | 340 [M + H]⁺ (APCI) | (DMSO-d₆): 11.42 (brs, 1H), 9.54 (brs, 2H), 7.72 (m, 1H), 7.21 (s, 4H), 6.95 (m, 1H), 6.76 (d, J = 6.8 Hz, 1H), 3.86 (brs, 4H), 3.56 (s, 2H), 3.19 (brs, 4H), 3.07 (m, 2H), 3.00-2.90 (m, 2H). |

TABLE 1-continued

| Compound | structural formula | starting material of ring A | synthesis method | properties | MS | 1H-NMR |
|---|---|---|---|---|---|---|
| Production Example 52 | | | method A | yellowish-green white solid | 382 [M + H]+ (APCI) | (DMSO-d6): 11.45 (brs, 1H), 7.84 (m, 1H), 7.24 (m, 4H), 7.07 (d, J = 8.0 Hz, 1H), 6.79 (d, J = 7.2 Hz, 1H), 3.90-3.60 (m, 8H), 3.52 (s, 2H), 3.09 (m, 2H), 2.94 (m, 2H), 2.05 (s, 3H). |
| Production Example 53 | | | method A | white solid | 341 [M + H]+ (APCI) | (DMSO-d6): 11.33 (brs, 1H), 7.75 (m, 1H), 7.22 (m, 4H), 6.98 (m, 1H), 6.75 (d, J = 7.0 Hz, 1H), 3.73 (m, 4H), 3.62 (m, 4H), 3.55 (s, 2H), 3.09 (m, 2H), 3.00-2.90 (m, 2H). |
| Production Example 54 | | | method A | white solid | 326 [M + H]+ (APCI) | (DMSO-d6): 11.45 (brs, 1H), 8.41 (s, 2H), 7.22 (d, J = 13.4 Hz, 2H), 7.19 (d, J = 13.4 Hz, 2H), 3.65-3.50 (m, 6H), 2.82 (brs, 4H), 1.97 (m, 4H). |
| Production Example 55 | | | method A | white solid | 340 [M + H]+ (APCI) | (DMSO-d6): 11.45 (brs, 1H), 8.36 (s, 2H), 7.21 (m, 4H), 3.77 (m, 4H), 3.57 (s, 2H), 2.80 (m, 4H), 1.62 (m, 2H), 1.56 (m, 4H). |
| Production Example 56 | | | method A | slightly yellow white solid | 341 [M + H]+ (APCI) | (DMSO-d6): 11.35 (brs, 1H), 10.90-10.20 (brs, 2H), 9.32 (brs, 2H), 8.28 (s, 2H), 7.21 (d, J = 14.2 Hz, 2H), 7.18 (d, J = 5.1 Hz, 4H), 3.91 (t, J = 5.1 Hz, 4H), 3.55 (s, 2H), 3.13 (brs, 4H), 2.90-2.70 (m, 4H). |

TABLE 1-continued

| Compound | structural formula | starting material of ring A | synthesis method | properties | MS | ¹H-NMR |
|---|---|---|---|---|---|---|
| Production Example 57 | [structure with Ac-N piperazine-pyrimidine-Br, phenyl-CH₂-C(O)-NH-NH₂, 2HCl] | [Ac-N piperazine-pyrimidine-Br] | method A | yellowish white solid | 383 [M + H]⁺ (APCI) | (DMSO-d₆): 11.33 (brs, 1H), 10.80-10.10 (brs, 2H), 8.25 (s, 2H), 7.21 (d, J = 13.4 Hz, 2H), 7.18 (d, J = 13.4 Hz, 2H), 3.73 (t, 2H), 3.66 (m, 2H), 3.55 (s, 2H), 3.50 (m, 4H), 2.81 (m, 2H), 2.74 (m, 2H), 2.04 (s, 3H). |
| Production Example 58 | [structure with morpholine-pyrimidine-Br, phenyl-CH₂-C(O)-NH-NH₂, 2HCl] | [morpholine-pyrimidine-Br] | method A | yellowish white solid | 342 [M + H]⁺ (APCI) | (DMSO-d₆): 11.35 (brs, 1H), 8.26 (s, 2H), 7.21 (d, J = 13.7 Hz, 2H), 7.18 (d, J = 13.7 Hz, 2H), 3.65 (brs, 8H), 3.55 (s, 2H), 2.81 (m, 2H), 2.75 (m, 2H). |
| Production Example 59 | [structure with HN piperazine-phenyl(CF₃)-Br, phenyl-CH₂-C(O)-NH-NH₂, 3HCl] | [Boc-N piperazine-phenyl(CF₃)-Br] | method A | pale-brown white solid | 407 [M + H]⁺ (APCI) | (DMSO-d₆): 11.35 (brs, 1H), 11.00-10.10 (brs, 2H), 9.29 (brs, 2H), 7.41 (d, J = 8.4 Hz, 1H), 7.30-7.15 (m, 6H), 3.56 (s, 2H), 3.43 (m, 4H), 3.21 (brs, 4H), 2.95-2.85 (m, 2H), 2.85-2.75 (m, 2H). |
| Production Example 60 | [structure with Ac-N piperazine-phenyl(CF₃)-Br, phenyl-CH₂-C(O)-NH-NH₂, 2HCl] | [Ac-N piperazine-phenyl(CF₃)-Br] | method A | pale-brown white solid | 449 [M + H]⁺ (APCI) | (DMSO-d₆): 11.31 (brs, 1H), 7.39 (d, J = 8.5 Hz, 1H), 7.30-7.15 (m, 6H), 3.75-3.50 (m, 6H), 3.22 (t, J = 4.9 Hz, 2H), 3.15 (t, J = 5.1 Hz, 2H), 2.95-2.85 (m, 2H), 2.85-2.75 (m, 2H), 2.04 (s, 3H). |

TABLE 1-continued

| Compound structural formula | starting material of ring A | synthesis method | properties | MS | ¹H-NMR |
|---|---|---|---|---|---|
| Production Example 61 | AcHN-(aryl with I, CF₃) | method A | white solid | 380 [M + H]⁺ (APCI) | (DMSO-d₆): 10.94 (brs, 1H), 10.20-9.60 (brs, 2H), 9.47 (brs, 1H), 7.58 (s, 1H), 7.52 (d, J = 8.3 Hz, 1H), 7.36 (d, J = 8.3 Hz, 1H), 7.21 (m, 4H), 3.51 (s, 2H), 2.91 (m, 4H), 2.03 (s, 3H). |
| Production Example 62 | CF₃-(aryl with Br, AcHN) | method A | white solid | 380 [M + H]⁺ (APCI) | (DMSO-d₆): 11.07 (brs, 1H), 10.27 (brs, 1H), 10.20-9.80 (brs, 2H), 7.89 (s, 1H), 7.67 (s, 1H), 7.26 (s, 1H), 7.21 (m, 4H), 3.53 (s, 2H), 2.89 (m, 4H), 2.07 (s, 3H). |
| Production Example 63 | (benzoxazinone with Br) | method A | pale-brown solid | 326 [M + H]⁺ (APCI) | (DMSO-d₆): 11.00-10.70 (brs, 1H), 10.63 (brs, 1H), 7.19 (m, 4H), 6.84 (d, J = 7.8 Hz, 1H), 6.80-6.70 (m, 2H), 4.52 (s, 2H), 3.57 (s, 2H), 2.79 (m, 4H). |
| Production Example 64 | (N-methyl benzoxazine with Br) | method B | brown solid | 326 [M + H]⁺ (APCI) | (DMSO-d₆): 11.37 (brs, 1H), 10.90-10.20 (brs, 2H), 7.19 (m, 4H), 6.75-6.65 (m, 2H), 6.61 (s, 1H), 4.24 (t, J = 4.4 Hz, 2H), 3.55 (s, 2H), 3.22 (t, J = 4.4 Hz, 2H), 2.83 (s, 3H), 2.80-2.65 (m, 4H). |
| Production Example 65 | Boc-N(bicyclic)-phenyl-I | method A | yellow-brown solid | 351 [M + H]⁺ (APCI) | (DMSO-d₆): 11.25 (brs, 1H), 10.80-9.80 (brs, 2H), 9.51 (brs, 1H), 8.84 (brs, 1H), 7.19 (m, 4H), 7.08 (d, J = 8.5 Hz, 2H), 6.57 (d, J = 8.5 Hz, 2H), 4.55 (s, 1H), 4.40 (s, 1H), 3.54 (s, 2H), 3.30-3.10 (m, 4H), 2.78 (m, 4H), 2.15-2.05 (m, 1H), 2.00-1.90 (m, 1H). |

TABLE 1-continued

| Compound | structural formula | starting material of ring A | synthesis method | properties | MS | ¹H-NMR |
|---|---|---|---|---|---|---|
| Production Example 66 | [structure with 2HCl] | [4-iodophenyl-N-Ac-diazabicycle] | method B | yellow-brown solid | 393 [M + H]⁺ (APCI) | (DMSO-d₆): 9.27 (brs, 1H), 7.24 (m, 4H), 7.13 (d, J = 8.5 Hz, 2H), 6.62 (dd, J = 8.5 Hz, 3.1, 2H), 4.85-4.50 (m, 2H), 4.29 (brs, 2H), 3.70-3.55 (m, 1H), 3.15-2.95 (m, 1H), 2.85 (m, 4H), 2.10-1.85 (m, 5H). |
| Production Example 67 | [structure with 3HCl] | [2-bromo-6-pyrazolyl-pyridine] | method A | white solid | 322 [M + H]⁺ (APCI) | (DMSO-d₆): 11.34 (brs, 1H), 10.90-10.10 (brs, 2H), 8.62 (d, J = 2.5, 1H), 7.90-7.80 (m, 2H), 7.72 (d, J = 8.0, 1H), 7.21 (m, 4H), 6.57 (dd, J = 2.5 Hz, 1.7 Hz, 1H), 3.54 (s, 2H), 3.07 (brs, 4H). |
| Production Example 68 | [structure with 3HCl] | [4-bromobenzyl-N-Boc-piperazine] | method A | white solid | 353 [M + H]⁺ (APCI) | (DMSO-d₆): 10.99 (brs, 1H), 7.43 (d, J = 7.8 Hz, 2H), 7.30 (d, J = 7.8 Hz, 2H), 7.21 (m, 4H), 4.07 (brs, 2H), 3.52 (s, 2H), 3.33 (brs, 4H), 3.07 (brs, 4H), 2.87 (brs, 4H). |
| Production Example 69 | [structure with 3HCl] | [3-iodobenzyl-N-Boc-piperazine] | method A | yellowish white solid | 353 [M + H]⁺ (APCI) | (DMSO-d₆): 11.29 (brs, 1H), 10.80-9.70 (brs, 2H), 7.50-7.40 (m, 2H), 7.40-7.25 (m, 2H), 7.21 (d, J = 10.9 Hz, 2H), 7.18 (d, J = 10.9 Hz, 2H), 4.27 (brs, 2H), 3.55 (s, 2H), 3.50-3.15 (m, 8H), 2.89 (brs, 4H). |
| Production Example 70 | [structure with 2HCl] | [4-iodobenzyl-morpholine] | method A | white solid | 354 [M + H]⁺ (APCI) | (DMSO-d₆): 11.21 (brs, 1H), 7.52 (d, J = 8.1 Hz, 2H), 7.32 (d, J = 8.1 Hz, 2H), 7.20 (m, 4H), 4.27 (s, 2H), 3.87 (brs, 4H), 3.54 (s, 2H), 3.12 (brs, 4H), 2.88 (brs, 4H). |

TABLE 1-continued

| Compound structural formula | starting material of ring A | synthesis method | properties | MS | $^1$H-NMR |
|---|---|---|---|---|---|
| Production Example 71 | | method A | off-white solid | 354 [M+H]$^+$ (APCI) | (DMSO-d$_6$): 11.32 (brs, 1H), 10.80-10.20 (brs, 2H), 7.51 (s, 1H), 7.44 (d, J = 7.3 Hz, 1H), 7.40-7.25 (m, 2H), 7.19 (m, 4H), 4.27 (s, 2H), 3.89 (brs, 4H), 3.54 (s, 2H), 3.25-3.00 (m, 4H), 2.90 (s, 4H). |
| Production Example 72 | | method B | off-white solid | 387 [M+H]$^+$ (APCI) | (DMSO-d$_6$): 11.33 (brs, 1H), 10.80-10.00 (brs, 2H), 7.25-7.10 (m, 5H), 4.41 (d, J = 13.5 Hz, 1H), 3.88 (d, J = 13.5 Hz, 1H), 3.55 (s, 2H), 3.35-3.10 (m, 2H), 2.95 (s, 4H), 2.70 (t, J = 11.6 Hz, 1H), 2.10-1.95 (m, 5H), 1.75-1.60 (m, 1H), 1.60-1.40 (m, 1H). |
| Production Example 73 | | method D | yellowish white solid | 318 [M+H]$^+$ (APCI) | (DMSO-d$_6$): 10.90 (s, 1H), 9.15 (brs, 1H), 7.15 (s, 4H), 6.51 (d, J = 3.7 Hz, 1H), 6.39 (d, J = 3.7 Hz, 1H), 4.18 (d, J = 3.0 Hz, 2H), 2.94 (m, 2H), 2.86 (m, 2H), 2.02 (s, 3H). |
| Production Example 74 | | method C | pale-brown solid | 345 [M+H]$^+$ (APCI) | (DMSO-d$_6$): 10.97 (brs, 1H), 9.01 (brs, 1H), 7.19 (m, 4H), 6.49 (d, J = 3.6 Hz, 1H), 6.06 (d, J = 3.6 Hz, 1H), 3.52 (s, 2H), 3.21 (s, 4H), 3.00-2.90 (m, 4H), 2.90-2.80 (m, 4H). |
| Production Example 75 | | method C | yellow solid | 387 [M+H]$^+$ (APCI) | (DMSO-d$_6$): 9.17 (brs, 1H), 7.15 (m, 4H), 6.46 (d, J = 3.6 Hz, 1H), 5.98 (d, J = 3.6 Hz, 1H), 3.55 (brs, 4H), 3.05-2.80 (m, 8H), 2.03 (s, 3H). |
| Production Example 76 | | method C | yellowish white solid | 346 [M+H]$^+$ (APCI) | (DMSO-d$_6$): 9.16 (brs, 1H), 7.15 (s, 4H), 6.46 (d, J = 3.7 Hz, 1H), 5.95 (d, J = 3.7 Hz, 1H), 4.18 (brs, 2H), 3.70 (m, 4H), 2.96 (t, J = 4.7 Hz, 4H), 2.91 (m, 2H), 2.83 (m, 2H). |

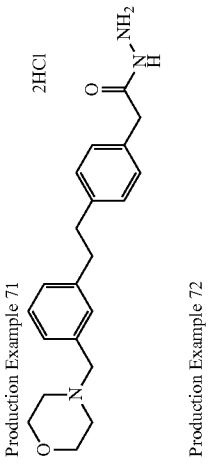

TABLE 1-continued

| Compound structural formula | starting material of ring A | synthesis method | properties | MS | ¹H-NMR |
|---|---|---|---|---|---|
| Production Example 77 | AcHN—[thiazole]—CHO; Et-S(O)(O)-NH- | method E | white solid | 369 [M + H]⁺ (ESI) | (DMSO-d₆): 12.58 (brs, 1H), 11.27 (brs, 1H), 10.35 (brs, 2H), 7.21 (d, J = 8.1 Hz, 2H), 7.16 (d, J = 8.1 Hz, 2H), 6.34 (s, 1H), 3.53 (s, 2H), 2.96 (q, J = 7.4 Hz, 2H), 2.89-2.82 (m, 2H), 2.73-2.68 (m, 2H), 1.173 (t, J = 7.4 Hz, 3H). |
| Production Example 78 | AcHN—[thiazole]—CHO; Me-S(O)(O)-NH- | method E | white solid | 355 [M + H]⁺ (ESI) | (DMSO-d₆): 12.55 (brs, 1H), 11.16 (brs, 1H), 10.23 (brs, 2H), 7.21 (d, J = 8.2 Hz, 2H), 7.16 (d, J = 8.2 Hz, 2H), 6.37 (s, 1H), 3.52 (s, 2H), 2.87 (s, 3H), 2.87-2.83 (m, 2H), 2.74-2.69 (m, 2H). |
| Production Example 79 | 4-Br-C₆H₄-N(Et)(Et) · 2HCl | method B | slightly yellow white solid | 321 [M + H]⁺ (APCI) | (DMSO-d₆ + D₂O): 11.30 (brs, 1H), 10.54 (brs, 2H), 7.53 (brs, 2H), 7.37 (d, J = 8.2 Hz, 2H), 7.26-7.14 (m, 4H), 3.54 (s, 2H), 3.47 (q, J = 7.1 Hz, 2H), 3.04 (s, 3H), 2.87 (s, 4H), 1.04 (t, J = 7.1 Hz, 3H). |
| Production Example 80 | 4-Br-C₆H₄-N(Me)(nPr) · 2HCl | method B | slightly yellow white solid | 326 [M + H]⁺ (APCI) | (DMSO-d₆ + D₂O): 7.45-7.32 (m, 4H), 7.23-7.12 (m, 4H), 3.51 (s, 2H), 3.42 (dd, J = 6.7 Hz, 2H), 3.07 (s, 3H), 2.85 (s, 4H), 1.46-1.32 (m, 2H), 0.82 (t, J = 7.4, 3H). |
| Production Example 81 | 4-Br-C₆H₄-N(Et)(nPr) · 2HCl | method B | white solid | 340 [M + H]⁺ (APCI) | (DMSO-d₆): 11.31-11.24 (m, 1H), 10.41 (brs, 2H), 7.58 (brs, 2H), 7.44-7.33 (m, 2H), 7.26-7.12 (m, 4H), 3.60-3.33 (m, 6H), 2.87 (s, 4H), 1.57-1.30 (m, 2H), 1.02 (t, J = 7.1 Hz, 3H), 0.82 (t, J = 7.4 Hz, 3H). |

TABLE 1-continued

| Compound structural formula | starting material of ring A | synthesis method | properties | MS | ¹H-NMR |
|---|---|---|---|---|---|
| Production Example 82 (2HCl) | propyl,propyl-N-(4-bromophenyl) | method B | slightly orange white solid | 354 [M + H]⁺ (APCI) | (DMSO-$d_6$ + $D_2O$): 7.38 (brs, 4H), 7.16 (brs, 4H), 3.50 (s, 2H), 3.41 (dd, J = 8.0 Hz, 4H), 2.85 (s, 4H), 1.33 (brs, 4H), 0.80 (t, J = 7.4 Hz, 6H). |
| Production Example 83 (3HCl) | Boc-HN-CH2CH2-N(ethyl)-(4-bromophenyl) | method B | yellowish white solid | 341 [M + H]⁺ (APCI) | (DMSO-$d_6$ + $D_2O$): 7.18 (s, 4H), 7.12 (d, J = 8.6 Hz, 2H), 6.83 (d, J = 8.5 Hz, 2H), 3.57-3.43 (m, 4H), 3.36 (q, J = 7.0 Hz, 2H), 2.90 (t, J = 7.0 Hz, 2H), 2.84-2.70 (m, 4H), 1.01 (t, J = 7.0 Hz, 3H). |
| Production Example 84 (2HCl) | AcHN-CH2CH2-N(ethyl)-(4-bromophenyl) | method B | slightly yellow white solid | 383 [M + H]⁺ (APCI) | (DMSO-$d_6$ + $D_2O$): 7.32 (brs, 4H), 7.23-7.13 (m, 4H), 3.62-3.40 (m, 6H), 3.11 (dd, J = 6.7 Hz, 2H), 2.85 (s, 4H), 1.77 (s, 3H), 1.00 (t, J = 7.0 Hz, 3H). |
| Production Example 85 (2HCl) | diethyl-N-(5-iodopyridin-2-yl) | method A | slightly white yellow solid | 327 [M + H]⁺ (APCI) | (DMSO-$d_6$): 11.29 (brs, 1H), 10.85 (brs, 2H), 7.93 (dd, J = 8.4 Hz, 2.0, 1H), 7.76 (d, J = 1.8 Hz, 1H), 7.22 (s, 4H), 7.27-7.15 (m, 1H), 3.61 (q, J = 7.0 Hz, 4H), 3.68-3.55 (m, 2H), 2.82 (s, 4H), 1.16 (t, J = 7.0 Hz, 6H). |

TABLE 1-continued

| Compound structural formula | starting material of ring A | synthesis method | properties | MS | ¹H-NMR |
|---|---|---|---|---|---|
| Production Example 86<br><br>HN–[piperazine]–[pyridine]–CH₂CH₂–[phenyl]–CH₂–C(O)–NH–NH₂ · 4HCl | Boc–N[piperazine]–[pyridine]–Br | method A | slightly white yellow solid | 340 [M+H]⁺ (ESI) | (DMSO-$d_6$): 11.22 (brs, 1H), 9.31 (brs, 2H), 8.34 (d, J = 2.8 Hz, 1H), 8.03-7.93 (m, 1H), 7.68 (d, J = 2.7 Hz, 1H), 7.26-7.16 (m, 4H), 3.54 (s, 2H), 3.63-3.35 (m, 4H), 3.23 (brs, 4H), 3.27-3.13 (m, 2H), 3.03-2.94 (m, 2H). |
| Production Example 87<br><br>Ac–N[piperazine]–[pyridine]–CH₂CH₂–[phenyl]–CH₂–C(O)–NH–NH₂ · 3HCl | Ac–N[piperazine]–[pyridine]–Br | method A | yellow solid | 382 [M+H]⁺ (APCI) | (DMSO-$d_6$): 11.29 (brs, 1H), 8.26 (d, J = 2.5 Hz, 1H), 8.03 (dd, J = 9.0 Hz, 2.0 Hz, 1H), 7.72 (d, J=9.2Hz, 1H), 7.29-7.16 (m, 4H), 3.63-3.53 (m, 6H), 3.46-3.30 (m, 4H), 3.24-3.14 (m, 2H), 3.04-2.95 (m, 2H), 2.05 (s, 3H). |
| Production Example 88<br><br>Et₂N–[pyridine]–CH₂CH₂–[phenyl]–CH₂–C(O)–NH–NH₂ · 3HCl | Et₂N–[pyridine]–Br | method A | pale-yellow solid | 327 [M+H]⁺ (APCI) | (DMSO-$d_6$): 11.13 (brs, 1H), 7.94 (d, J = 2.8 Hz, 1H), 7.75 (dd, J = 9.2 Hz, 2.9 Hz, 1H), 7.24 (d, J = 8.7 Hz, 1H), 7.26-7.18 (m, 4H), 3.53 (s, 2H), 3.44 (q, J = 7.0 Hz, 4H), 3.18-3.09 (m, 2H), 2.96 (dd, J = 9.9 Hz, 5.6 Hz, 2H), 1.10 (t, J = 7.0 Hz, 3H). |
| Production Example 89<br><br>Et₂N–[pyridine]–CH₂CH₂–[phenyl]–CH₂–C(O)–NH–NH₂ · 3HCl | Et₂N–[pyridine]–Br | method A | pale-yellow solid | 313 [M+H]⁺ (APCI) | (DMSO-$d_6$): 11.30 (brs, 1H), 7.94 (dd, J = 9.4 Hz, 2.1, 1H), 7.76 (d, J = 2.1 Hz, 1H), 7.21 (s, 4H), 7.27-7.15 (m, 1H), 3.64 (q, J = 7.1, 2H), 3.55 (s, 2H), 3.16 (s, 3H), 2.83 (s, 4H), 1.14 (t, J = 7.1 Hz, 3H). |

TABLE 1-continued

| Compound structural formula | starting material of ring A | synthesis method | properties | MS | ¹H-NMR |
|---|---|---|---|---|---|
| Production Example 90 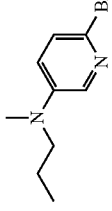 3HCl | 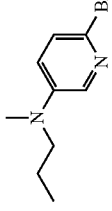 | method A | yellowish white solid | 327 [M + H]⁺ (APCI) | (DMSO-d₆): 11.29 (brs, 1H), 10.93 (brs, 2H), 7.93 (dd, J = 9.4 Hz, 2.1 Hz, 1H), 7.76 (d, J = 1.9 Hz, 1H), 7.21 (s, 4H), 7.28-7.15 (m, 1H), 3.63-3.38 (m, 2H), 3.54 (s, 2H), 3.17 (s, 3H), 2.83 (s, 4H), 1.58 (tq, J = 7.5 Hz, 7.3 Hz, 2H), 0.90 (t, J = 7.3 Hz, 3H). |
| Production Example 91 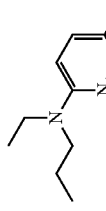 3HCl | 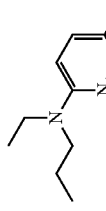 | method A | pale-yellow solid | 341 [M + H]⁺ (ESI) | (DMSO-d₆): 11.16 (brs, 1H), 7.95-7.87 (m, 1H), 7.75 (d, J = 1.9 Hz, 1H), 7.21 (s, 4H), 7.26-7.15 (m, 1H), 3.66-3.27 (m, 6H), 2.82 (s, 4H), 1.58 (dt, J = 7.1 Hz, 7.0 Hz, 2H), 1.17 (t, J = 7.0 Hz, 3H), 0.92 (t, J = 7.3 Hz, 3H). |
| Production Example 92 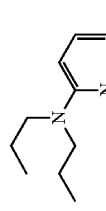 3HCl | 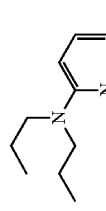 | method A | slightly yellow white solid | 355 [M + H]⁺ (APCI) | (DMSO-d₆): 11.28 (brs, 1H), 10.49 (brs, 2H), 7.91 (dd, J = 8.5 Hz, 2.1 Hz, 1H), 7.75 (d, J = 2.0 Hz, 1H), 7.22 (s, 4H), 7.28-7.16 (m, 1H), 3.62-3.40 (m, 6H), 2.83 (s, 4H), 1.58 (tq, J = 7.5 Hz, 7.5 Hz, 4H), 0.91 (t, J = 7.3 Hz, 6H). |
| Production Example 93 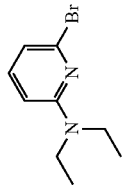 3HCl | 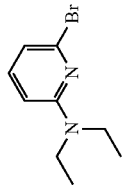 | method A | slightly yellow white solid | 327 [M + H]⁺ (APCI) | (DMSO-d₆): 11.36 (brs, 1H), 10.43 (brs, 2H), 7.79 (brs, 1H), 7.23 (s, 4H), 6.98 (brs, 1H), 6.69 (brs, 1H), 3.76-3.60 (m, 4H), 3.57 (s, 2H), 3.18 (brs, 2H), 2.99-2.90 (m, 2H), 1.16 (t, J = 7.0 Hz, 6H). |
| Production Example 94 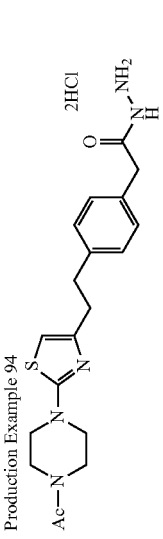 2HCl | 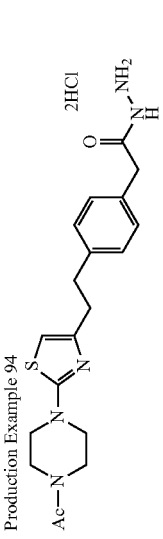 | method A | slightly yellow white solid | 388 [M + H]⁺ (APCI) | (DMSO-d₆): 7.26 (s, 4H), 6.50 (s, 1H), 3.66-3.35 (m, 10H), 2.93-2.84 (m, 2H), 2.82-2.71 (m, 2H), 2.05 (s, 3H). |

TABLE 1-continued

| Compound structural formula | starting material of ring A | synthesis method | properties | MS | ¹H-NMR |
|---|---|---|---|---|---|
| Production Example 95 | Boc-N(piperazine)-imidazole-Br | method A | slightly yellow white solid | 346 [M + H]⁺ (APCI) | (DMSO-d₆): 11.26 (s, 1H), 10.38 (brs, 2H), 9.23 (brs, 2H), 7.23-7.12 (m, 4H), 6.55 (s, 1H), 3.68-3.58 (m, 4H), 3.54 (s, 2H), 3.22 (brs, 4H), 2.93-2.84 (m, 2H), 2.82-2.71 (m, 2H). |
| Production Example 96 | Ac-N(piperazine)-pyridine(CF₃)(Cl) | method B | slightly yellow white solid | 450 [M + H]⁺ (APCI) | (DMSO-d₆): 11.32 (brs, 1H), 10.49 (brs, 2H), 7.74 (d, J = 8.9 Hz, 1H), 7.28-7.13 (m, 4H), 6.76 (d, J = 8.9 Hz, 1H), 3.75-3.48 (m, 10H), 2.99 (brs, 4H), 2.05 (s, 3H). |
| Production Example 97 | Boc-N(piperazine)-pyridine(CF₃)(Cl) | method B | slightly yellow white solid | 408 [M + H]⁺ (APCI) | (DMSO-d₆): 11.28 (brs, 1H), 10.41 (brs, 2H), 9.27 (brs, 2H), 7.79 (d, J = 9.0 Hz, 1H), 7.20 (d, J = 8.2 Hz, 2H), 7.16 (d, J = 8.2 Hz, 2H), 6.83 (d, J = 9.0 Hz, 1H), 3.53 (s, 2H), 3.16-3.14 (m, 4H), 3.02-2.94 (m, 4H). |
| Production Example 98 | Boc-N(piperazine)-pyridazine-Cl | method B | yellowish white solid | 341 [M + H]⁺ (ESI) | (DMSO-d₆): 11.34 (brs, 1H), 9.47 (brs, 2H), 7.94-7.82 (m, 2H), 7.26-7.15 (m, 4H), 3.88 (dd, J = 5.0 Hz, 5.0 Hz, 4H), 3.55 (s, 2H), 3.27-3.14 (m, 6H), 2.99 (dd, J = 8.5 Hz, 7.0 Hz, 2H). |
| Production Example 99 | Ac-N(piperazine)-pyridazine-Cl | method B | yellowish white solid | 383 [M + H]⁺ (ESI) | (DMSO-d₆): 11.39, (brs, 1H), 10.58 (brs, 2H), 8.04 (s, 2H), 7.27-7.16 (m, 4H), 3.78-3.57 (m, 8H), 3.56 (s, 4H), 3.25-3.15 (m, 2H), 3.00 (dd, J = 8.4 Hz, 6.9 Hz, 2H), 2.06 (s, 3H). |

| Compound structural formula | starting material of ring A | synthesis method | properties | MS | ¹H-NMR |
|---|---|---|---|---|---|
| Production Example 100 | Boc-N piperazine-pyrazine-Cl | method A | pale-yellow solid | 341 [M + H]⁺ (ESI) | (DMSO-d₆): 11.33 (brs, 1H), 10.47 (brs, 2H), 9.29 (brs, 2H), 8.34 (d, J = 1.3 Hz, 1H), 8.01 (d, J = 1.2 Hz, 1H), 7.18 (dd, J = 8.3 Hz, 4.2 Hz, 4H), 3.78-3.69 (m, 4H), 3.54 (s, 2H), 3.18 (brs, 4H), 2.92 (s, 4H). |
| Production Example 101 | Ac-N piperazine-pyrazine-Br | method A | deep-yellow solid | 383 [M + H]⁺ (ESI) | (DMSO-d₆): 11.30 (brs, 1H), 10.49 (brs, 2H), 8.29 (d, J = 1.3 Hz, 1H), 7.99 (s, 1H), 7.18 (dd, J = 8.5 Hz, 3.3 Hz, 4H), 3.60-3.45 (m, 10H), 2.91 (s, 4H), 2.04 (s, 3H). |
| Production Example 102 | Boc-N piperazine-pyridine-Br | method A | yellowish white solid | 340 [M + H]⁺ (ESI) | (DMSO-d₆): 11.27 (brs, 1H), 9.48 (brs, 2H), 8.37 (d, J = 2.5 Hz, 1H), 8.17 (s, 1H), 7.91 (s, 1H), 7.21 (dd, J = 8.6 Hz, 2.7 Hz, 4H), 3.66-3.57 (m, 4H), 3.55 (s, 2H), 3.27-3.17 (m, 4H), 3.04-2.88 (m, 4H). |
| Production Example 103 | Boc-N piperazine-pyrimidine-Br | method B | yellow solid | 341 [M + H]⁺ (ESI) | (DMSO-d₆): 11.32 (brs, 1H), 10.46 (brs, 2H), 9.29 (brs, 2H), 8.20 (s, 1H), 7.81 (s, 1H), 7.18 (dd, J = 8.6 Hz, 2.4 Hz, 4H), 3.83-3.75 (m, 4H), 3.54 (s, 2H), 3.18 (brs, 4H), 3.00-2.87 (m, 4H). |
| Production Example 104 | Boc-N piperazine-pyridine-Br | method B | yellowish white solid | 340 [M + H]⁺ (ESI) | (DMSO-d₆): 11.24 (brs, 1H), 9.92 (brs, 4H), 8.27 (d, J = 7.2 Hz, 1H), 7.23 (s, 4H), 7.28-7.09 (m, 2H), 3.91 (brs, 4H), 3.55 (s, 2H), 3.27-3.19 (m, 4H), 3.11-2.95 (m, 4H). |

TABLE 1-continued

| Compound structural formula | starting material of ring A | synthesis method | properties | MS | ¹H-NMR |
|---|---|---|---|---|---|
| Production Example 105 | | method A | white solid | 340 [M + H]⁺ (ESI) | (DMSO-d₆): 11.43 (brs, 1H), 9.63 (brs, 2H), 8.01 (d, J = 6.1 Hz, 1H), 7.27-7.12 (m, 5H), 6.92 (d, J = 5.8 Hz, 1H), 3.92 (brs, 4H), 3.56 (s, 2H), 3.23 (brs, 4H), 2.92 (s, 4H). |
| Production Example 106 | | method B | white solid | 341 [M + H]⁺ (ESI) | (DMSO-d₆): 11.30 (brs, 1H), 9.60 (brs, 2H), 8.84 (s, 1H), 7.24 (s, 4H), 7.29-7.15 (m, 1H), 4.07 (brs, 4H), 3.56 (s, 2H), 3.24 (brs, 4H), 2.99 (s, 4H). |
| Production Example 107 | | method B | white solid | 341 [M + H]⁺ (ESI) | (DMSO-d₆): 11.29 (brs, 1H), 8.39 (d, J = 7.4 Hz, 1H), 7.22 (s, 4H), 7.14 (d, J = 7.4 Hz, 1H), 4.08 (brs, 4H), 3.55 (s, 2H), 3.23 (brs, 4H), 3.18-3.09 (m, 2H), 3.09-3.02 (m, 2H). |
| Production Example 108 | | (see Production Example) | slightly yellow solid | 398 [M + H]⁺ (ESI) | (DMSO-d₆): 10.39 (3H, brs), 8.25 (d, J = 3.0 Hz, 1H), 8.06 (dd, J = 9.2 Hz, 2.9 Hz, 1H), 7.75 (d, J = 9.2 Hz, 1H), 7.35-7.27 (m, 4H), 5.14 (s, 4H), 3.68-3.52 (m, 4H), 3.46-3.32 (m, 4H), 3.24 (t, J = 7.9 Hz, 2H), 3.03 (t, J = 8.0 Hz, 2H), 2.05 (s, 3H). |
| Production Example 109 | | (see Production Example) | slightly yellow solid | 397 [M + H]⁺ (ESI) | (DMSO-d₆): 9.98 (brs, 3H), 8.96 (brs, 1H), 8.24 (d, J = 2.3 Hz, 1H), 8.04 (dd, J = 9.0 Hz, 2.4 Hz, 1H), 7.72 (d, J = 9.2 Hz, 1H), 7.55 (t, J = 6.0 Hz, 1H), 7.23-7.16 (m, 4H), 4.22 (d, J = 5.9 Hz, 2H), 3.63-3.52 (m, 4H), 3.46-3.28 (m, 4H), 3.21 (t, J = 7.9 Hz, 2H), 2.99 (t, J = 7.7 Hz, 2H), 2.04 (s, 3H). |

TABLE 1-continued

| Compound structural formula | starting material of ring A | synthesis method | properties | MS | $^1$H-NMR |
|---|---|---|---|---|---|
| Production Example 110 (structure with Ac-N piperazine-pyridine-CH2CH2-phenyl-O-C(O)-NH-NH2, 3HCl) | Ac-piperazine-pyridine-CHO | (see Production Example) | slightly yellow solid | 384 [M + H]$^+$ (ESI) | (DMSO-d$_6$): 10.79 (brs, 3H), 8.25 (d, J = 2.4 Hz, 1H), 8.04 (dd, J = 9.0 Hz, 2.4 Hz, 1H), 7.74 (d, J = 9.1 Hz, 1H), 7.32 (d, J = 8.4 Hz, 2H), 7.09 (d, J = 8.0 Hz, 2H), 3.63-3.51 (m, 4H), 3.45-3.28 (m, 4H), 3.23 (t, J = 7.7 Hz, 2H), 3.02 (t, J = 7.8 Hz, 2H), 2.04 (s, 3H). |
| Production Example 111 (structure with Boc-N piperazine-pyridine-CH2CH2-phenyl-CH2-O-C(O)-NH-NH2, 3HCl) | Boc-piperazine-pyridine-CHO | (see Production Example) | slightly yellow solid | 398 [M + H]$^+$ (ESI) | (DMSO-d$_6$): 10.40 (brs, 1H), 8.05 (dd, J = 9.0 Hz, 2.3 Hz, 1H), 8.04 (d, J = 2.4 Hz, 1H), 7.32-7.23 (m, 4H), 5.13 (s, 2H), 3.63-3.49 (m, 4H), 3.49-3.29 (m, 4H), 3.24 (t, J = 7.9 Hz, 2H), 3.02 (t, J = 7.8 Hz, 2H), 2.03 (s, 3H). |
| Production Example 112 (structure with Boc-N piperazine-pyridine-CH2CH2-phenyl-CH2-NH-C(O)-NH-NH2, 3HCl) | Boc-piperazine-pyridine-CHO | (see Production Example) | slightly yellow solid | 397 [M + H]$^+$ (ESI) | (DMSO-d$_6$): 10.09 (brs, 3H), 9.02 (1H, brs), 8.24 (1H, d, J = 2.4 Hz), 8.04 (1H, dd, J = 9.0, 2.4 Hz), 7.73 (1H, d, J = 9.0 Hz), 7.59 (1H, t, J = 5.9 Hz), 7.27-7.07 (4H, m), 4.23 (2H, d, J = 5.9 Hz), 3.65-3.49 (4H, m), 3.42-3.25 (4H, m), 3.23 (2H, t, J = 7.8 Hz), 2.99 (2H, t, J = 7.8 Hz), 2.04 (3H, s). |
| Production Example 113 (structure with Ac-N piperazine-pyridine-CH2CH2-phenyl(F)-CH2-O-C(O)-NH-NH2, 3HCl) | Ac-piperazine-pyridine-CHO | (see Production Example) | slightly yellow solid | 416 [M + H]$^+$ (ESI) | (DMSO-d$_6$): 10.61 (brs, 3H), 8.25 (d, J = 2.7 Hz, 1H), 8.04 (dd, J = 9.2 Hz, 2.7 Hz, 1H), 7.70 (d, J = 9.0 Hz, 1H), 7.36 (t, J = 8.0 Hz, 1H), 7.21-7.12 (m, 2H), 5.14 (s, 2H), 3.63-3.50 (m, 4H), 3.48-3.27 (m, 4H), 3.23 (t, J = 7.6 Hz, 2H), 3.06 (t, J = 7.6 Hz, 2H), 2.03 (s, 3H). |

| Compound structural formula | starting material of ring A | synthesis method | properties | MS | ¹H-NMR |
|---|---|---|---|---|---|
| Production Example 114 | Boc-N(piperazine)-pyridine-CHO | (see Production Example) | slightly yellow solid | 415 [M + H]⁺ (ESI) | (DMSO-d₆): 10.01 (brs, 3H), 9.07 (brs, 1H), 8.24 (d, J = 2.8 Hz, 1H), 8.01 (dd, J = 9.1 Hz, 2.7 Hz, 1H), 7.67 (d, J = 9.2 Hz, 1H), 7.64 (t, J = 6.1 Hz, 1H), 7.28 (t, J = 7.9 Hz, 1H), 7.02 (d, J = 9.4 Hz, 2H), 4.29 (d, J = 6.1 Hz, 2H), 3.65-3.49 (m, 4H), 3.43-3.29 (m, 4H), 3.20 (t, J = 7.6 Hz, 2H), 3.02 (t, J = 7.6 Hz, 2H), 2.03 (s, 3H). |
| Production Example 115 | Ac-N(piperazine)-pyridine-CHO | (see Production Example) | white solid | 418 [M + H]⁺ (ESI) | (CDCl₃): 8.25 (d, J = 3.0 Hz, 1H), 7.14 (dd, J = 3.0 Hz, 8.4 Hz, 1H), 7.02 (d, J = 8.4 Hz, 1H), 6.62 (d, J = 3.4 Hz, 1H), 6.59 (d, J = 3.4 Hz, 1H), 6.01 (brs, 1H), 4.29 (t, J = 6.7 Hz, 2H), 3.79 (t, J = 5.2 Hz, 2H), 3.74 (brs, 2H), 3.64 (t, J = 5.2 Hz, 2H), 3.20-3.12 (m, 6H), 3.08-3.02 (m, 4H), 2.15 (s, 3H). |
| Production Example 116 | Ac-N(piperazine)-pyridine-CHO | (see Production Example) | white solid | 374 [M + H]⁺ (ESI) | (CDCl₃): 8.25 (d, J = 2.9 Hz, 1H), 7.33 (d, J = 3.7 Hz, 1H), 7.25 (brs, 1H), 7.12 (dd, J = 2.9 Hz, 8.4 Hz, 1H), 7.00 (d, J = 8.4 Hz, 1H), 6.74 (d, J = 3.7 Hz, 1H), 3.79 (t, J = 5.3 Hz, 2H), 3.64 (t, J = 5.2 Hz, 2H), 3.27 (t, J = 7.6 Hz, 2H), 3.19 (t, J = 5.2 Hz, 2H), 3.15 (t, J = 5.3 Hz, 2H), 3.08 (t, J = 7.6 Hz, 2H), 2.15 (s, 3H). |
| Production Example 117 | Ac-N(piperazine)-pyridine-CHO | (see Production Example) | pale-yellow white solid | 417 [M + H]⁺ (ESI) | (CDCl₃): 8.24 (d, J = 2.8 Hz, 1H), 7.22 (dd, J = 2.8 Hz, 8.6 Hz, 1H), 7.09 (d, J = 8.6 Hz, 1H), 6.61 (d, J = 3.4 Hz, 1H), 6.57 (d, J = 3.4 Hz, 1H), 6.21 (brt, 1H), 5.99 (brs, 1H), 3.79 (t, J = 5.2 Hz, 2H), 3.65 (t, J = 5.0 Hz, 2H), 3.50-3.44 (m, 6H), 3.13-3.09 (m, 2H), 2.95 (t, J = 6.7 Hz, 2H), 2.15 (s, 3H). |
| Production Example 118 | Ac-N(piperazine)-pyridine-CHO | (see Production Example) | slightly yellow solid | 382 [M + H]⁺ (ESI) | (DMSO-d₆): 11.44 (brs, 1H), 8.25 (d, J = 2.8 Hz, 1H), 8.04 (dd, J = 9.1, 2.7 Hz, 1H), 7.73 (d, J = 9.0 Hz, 1H), 7.24 (t, J = 7.6 Hz, 1H), 7.21 (s, 1H), 7.14 (d, J = 7.7 Hz, 2H), 3.65-3.48 (m, 6H), 3.30 (m, 4H), 3.22 (t, J = 7.9 Hz, 2H), 2.99 (t, J = 7.8 Hz, 2H), 2.04 (3H, s). |

TABLE 1-continued

| Compound | structural formula | starting material of ring A | synthesis method | properties | MS | ¹H-NMR |
|---|---|---|---|---|---|---|
| Production Example 119 | Ac-N(piperazine)-pyridine-CH₂CH₂-phenyl-CH₂CH₂-C(O)-NH-NH₂ · 3HCl | Ac-N(piperazine)-pyridine-CHO | (see Production Example) | slightly yellow solid | 396 [M + H]⁺ (ESI) | (DMSO-d₆): 11.19 (brs, 3H), 8.25 (d, J = 2.7 Hz, 1H), 8.04 (dd, J = 9.1, 2.9 Hz, 1H), 7.72 (d, J = 9.1 Hz, 1H), 7.19-7.11 (m, 4H), 4.23 (d, J = 5.9 Hz, 2H), 3.65-3.51 (m, 4H), 3.42-3.30 (m, 4H), 3.20 (t, J = 7.9 Hz, 2H), 2.95 (t, J = 7.8 Hz, 2H), 2.82 (t, J = 7.7 Hz, 2H), 2.52 (t, J = 7.7 Hz, 2H), 2.04 (s, 3H). |
| Production Example 120 | Ac-N(piperazine)-pyridine-CH₂CH₂-thiophene-CH₂-C(O)-NH-NH₂ · 3HCl | Ac-N(piperazine)-pyridine-CHO | (see Production Example) | white solid | 388 [M + H]⁺ (ESI) | (CDCl₃): 8.26 (d, J = 2.9 Hz, 1H), 7.15 (dd, J = 2.9 Hz, 8.6 Hz, 1H), 7.04 (d, J = 8.6 Hz, 1H), 6.91 (brs, 1H), 6.71 (d, J = 3.4 Hz, 1H), 6.64 (d, J = 3.4 Hz, 1H), 3.86 (brs, 2H), 3.79 (t, J = 5.2 Hz, 2H), 3.70 (s, 2H), 3.65 (t, J = 5.2 Hz, 2H), 3.21-3.17 (m, 4H), 3.15 (t, J = 5.2 Hz, 2H), 3.08-3.03 (m, 2H), 2.16 (s, 3H). |
| Production Example 121 | Ac-N(piperazine)-pyridine-CH₂CH₂-thiophene-CH₂-C(O)-NH-NH₂ | Ac-N(piperazine)-pyridine-CHO | (see Production Example) | yellowish white solid | 402 [M + H]⁺ (ESI) | (DMSO-d₆): 11.10 (brs, 1H), 8.24 (d, J = 2.8 Hz, 1H), 8.01 (dd, J = 9.0 Hz, 2.8 Hz, 1H), 7.67 (d, J = 9.0 Hz, 1H), 6.95 (s, 1H), 6.79 (s, 1H), 3.59-3.56 (m, 4H), 3.89 (t, J = 4.9 Hz, 2H), 3.32 (t, J = 5.1 Hz, 2H), 3.18 (t, J = 7.7 Hz, 2H), 3.01 (t, J = 7.3 Hz, 2H), 2.92 (t, J = 7.7 Hz, 2H), 2.56 (t, J = 7.3 Hz, 2H), 2.04 (s, 3H). |
| Production Example 122 | Boc-N(piperazine)-pyridine-CH₂CH₂-phenyl-CH₂CH₂-O-C(O)-NH-NH₂ | Boc-N(piperazine)-pyridine-CHO | (see Production Example) | slightly yellow solid | 412 [M + H]⁺ (ESI) | (DMSO-d₆): 10.17 (brs, 1H), 8.25 (d, J = 2.9 Hz, 1H), 8.02 (dd, J = 9.0 Hz, 2.7 Hz, 1H), 7.22-7.16 (m, 4H), 4.29 (t, J = 6.7 Hz, 2H), 3.65-3.51 (m, 4H), 3.43-3.27 (m, 4H), 3.16 (t, J = 7.8 Hz, 2H), 2.97 (t, J = 7.9 Hz, 2H), 2.87 (t, J = 6.8 Hz, 2H), 2.04 (s, 3H). |
| Production Example 123 | Boc-N(piperazine)-pyridine-CH₂CH₂-phenyl-CH₂CH₂-NH-C(O)-NH-NH₂ · 3HCl | Boc-N(piperazine)-pyridine-CHO | (see Production Example) | slightly yellow solid | 411 [M + H]⁺ (ESI) | (DMSO-d₆): 9.83 (brs, 3H), 8.67 (brs, 1H), 8.25 (d, J = 2.7 Hz, 1H), 8.01-7.91 (m, 1H), 7.66 (d, J = 8.6 Hz, 1H), 7.17 (d, J = 8.3 Hz, 2H), 7.13 (d, J = 8.4 Hz, 2H), 3.63-3.53 (m, 4H), 3.42-3.22 (m, 6H), 3.14 (t, J = 7.8 Hz, 2H), 2.95 (t, J = 7.9 Hz, 2H), 2.68 (t, J = 7.4 Hz, 2H), 2.04 (3H, s). |

TABLE 1-continued

| Compound structural formula | starting material of ring A | synthesis method | properties | MS | ¹H-NMR |
|---|---|---|---|---|---|
| Production Example 124 [structure: Ac-N-piperazine-pyridine-CH₂CH₂-thiophene-(CH₂)₃-O-C(O)-NH-NH₂; ring A starting material: Boc-N-piperazine-pyridine-CHO] | | (see Production Example) | colorless syrup | 432 [M + H]⁺ (ESI) | (CDCl₃): 8.24 (d, J = 2.8 Hz, 1H), 7.14 (dd, J = 8.4 Hz, 2.8 Hz, 1H), 7.00 (d, J = 8.4 Hz, 1H), 6.71 (s, 1H), 6.62 (s, 1H), 6.06 (brs, 1H), 4.15 (t, J = 6.4 Hz, 2H), 3.79 (t, J = 5.2 Hz, 2H), 3.74 (brs, 2H), 3.64 (t, J = 5.2 Hz, 2H), 3.18 (t, J = 5.2 Hz, 2H), 3.14 (t, J = 7.4 Hz, 2H), 3.03-2.91 (m, 4H), 2.80 (t, J = 7.4 Hz, 2H), 2.15 (s, 3H), 1.98 (tt, J = 7.4 Hz, 6.4 Hz, 2H). |
| Production Example 125 [structure: Ac-N-piperazine-pyridine-CH₂CH₂-thiophene-(CH₂)₃-NH-C(O)-NH-NH₂; ring A starting material: Boc-N-piperazine-pyridine-CHO] | | (see Production Example) | off-white solid | 431 [M + H]⁺ (ESI) | (CDCl₃): 8.24 (d, J = 2.9 Hz, 1H), 7.14 (dd, J = 8.4 Hz, 2.9 Hz, 1H), 7.00 (d, J = 8.4 Hz, 1H), 6.70 (d, J = 1.1 Hz, 1H), 6.67 (d, J = 1.1 Hz, 1H), 6.07 (brt, 1H), 5.98 (brs, 1H), 3.78 (t, J = 5.2 Hz, 2H), 3.18 (t, J = 5.2 Hz, 2H), 3.69 (q, J = 6.6 Hz, 2H), 3.18 (t, J = 5.2 Hz, 2H), 3.13 (t, J = 5.2 Hz, 2H), 3.03-2.91 (m, 2H), 2.82 (t, J = 7.4 Hz, 2H), 2.15 (s, 3H), 1.88 (tt, J = 7.4 Hz, 6.6 Hz). |

In Table 1, the synthesis methods are as follows.

Method A: coupling by Sonogashira-Castero-Stephens reaction (palladium acetate, triphenylphosphine, diisopropylamine, acetonitrile)→hydrogenation using palladium carbon as a catalyst→deprotection, hydrochlorination with hydrogen chloride dioxane solution Method B: coupling by Sonogashira-Castero-Stephens reaction (bis(acetonitrile)dichloropalladium (II), Xantphos, cesium carbonate, acetonitrile)→hydrogenation using palladium carbon as a catalyst→deprotection, hydrochlorination with hydrogen chloride dioxane solution Method C: coupling by Wittig reaction (sodium ethoxide, DMF)→hydrogenation using palladium carbon as a catalyst→deprotection, hydrochlorination with hydrogen chloride dioxane solution Method D: coupling by Wittig reaction (butyllithium, THF)→hydrogenation using palladium carbon as a catalyst→deprotection, hydrochlorination with hydrogen chloride dioxane solution Method E: coupling by Wittig reaction (potassium tert-butoxide, DMF)→hydrogenation using palladium carbon as a catalyst→functional group conversion from acetyl group to sulfonyl group→hydrolysis→BocNHNH$_2$→condensation→deprotection, hydrochlorination with hydrogen chloride dioxane solution Experimental Example 1

Inhibitory Effect on Human and Rat VAP-1 Enzyme (SSAO)

The compounds of the present invention obtained in Production Examples were examined for the inhibitory effect on human and rat VAP-1 enzyme (SSAO) by the following method.

The VAP-1 enzyme (SSAO) activity in both human and rat was measured by a radiochemical-enzyme assay using $^{14}$C-benzylamine as an artificial substrate. Human or rat VAP-1 was cloned from the cDNA library and expressed in a cell. The cell extract was preincubated with a test compound solution (final concentration $1\times10^{-7}$-$1\times10^{-10}$ mol/L) at room temperature for 20 minutes. Then, $^{14}$C-benzylamine (final concentration $1\times10^{-5}$ mol/L) was added, and the mixture was incubated at a final volume of 200 μL at 37° C. for 2 hours. The enzyme reaction was stopped by addition of 2 mol/L (200 μL) citric acid. The oxidation product was extracted with 1 mL toluene/ethyl acetate (1:1), and the radioactivity thereof was measured by a liquid scintillation counter. The results are shown in Table 2.

As shown in Table 2, the compound of the present invention markedly inhibited the enzyme activity of human and rat SSAO.

TABLE 2

Inhibitory effect on human and rat VAP-1 enzyme (SSAQ)

| Production Example No. | Chemical structural formula | SSAO inhibitory activity (IC$_{50}$) nM | |
|---|---|---|---|
| | | human | rat |
| 12 | 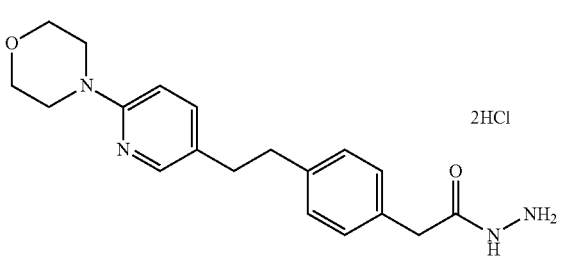 [SMILES: NNC(=O)Cc1ccc(CCc2ccc(N3CCOCC3)nc2)cc1] | 20.8 | 1.1 |
| 20 | 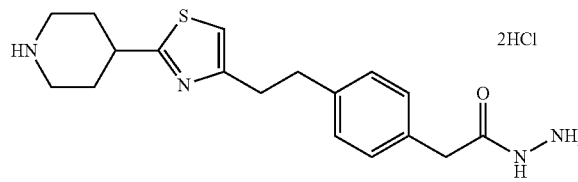 | 23.3 | 5.1 |
| 30 | 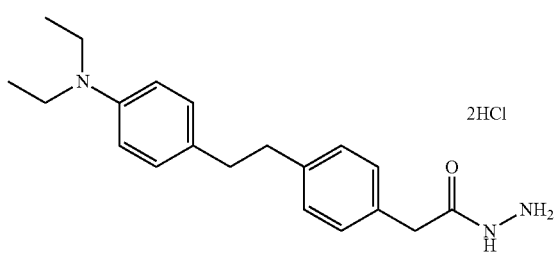 [SMILES: CCN(CC)c1ccc(CCc2ccc(CC(=O)NN)cc2)cc1] | 13.0 | 2.2 |

TABLE 2-continued
Inhibitory effect on human and rat VAP-1 enzyme (SSAQ)
| Production Example No. | Chemical structural formula | SSAO inhibitory activity (IC$_{50}$) nM | |
|---|---|---|---|
| | | human | rat |
| 44 | 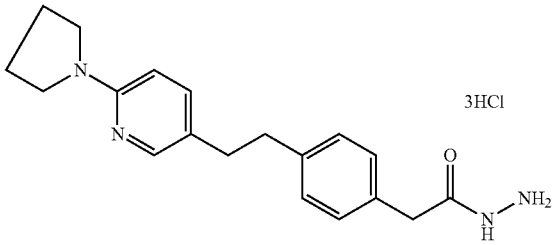 [SMILES: NNC(=O)Cc1ccc(CCc2ccc(N3CCCC3)nc2)cc1] 3HCl | 18.3 | 5.4 |
| 45 | 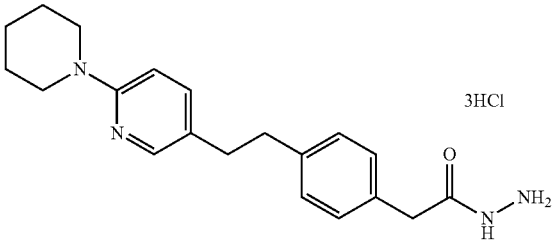 [SMILES: NNC(=O)Cc1ccc(CCc2ccc(N3CCCCC3)nc2)cc1] 3HCl | 17.2 | 1.2 |
| 47 | 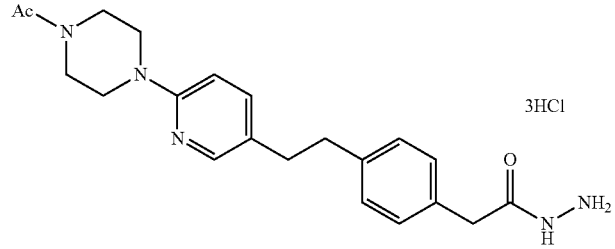 [SMILES: CC(=O)N1CCN(c2ccc(CCc3ccc(CC(=O)NN)cc3)cn2)CC1] 3HCl | 16.1 | 3.6 |
| 51 | 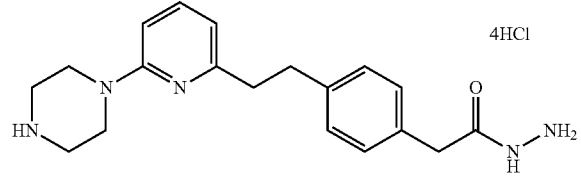 [SMILES: NNC(=O)Cc1ccc(CCc2cccc(N3CCNCC3)n2)cc1] 4HCl | 9.8 | 29.4 |
| 59 | 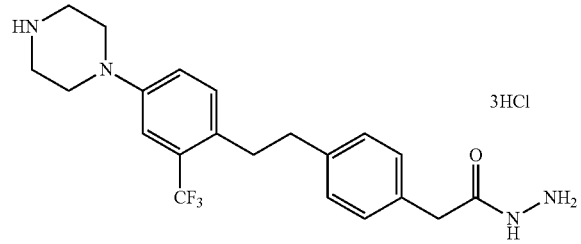 [SMILES: NNC(=O)Cc1ccc(CCc2ccc(N3CCNCC3)cc2C(F)(F)F)cc1] 3HCl | 11.3 | 6.1 |
| 70 | 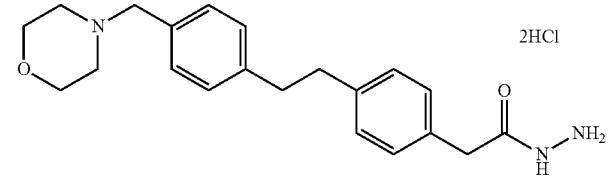 [SMILES: NNC(=O)Cc1ccc(CCc2ccc(CN3CCOCC3)cc2)cc1] 2HCl | 17.6 | 1.3 |

TABLE 2-continued

Inhibitory effect on human and rat VAP-1 enzyme (SSAQ)

| Production Example No. | Chemical structural formula | SSAO inhibitory activity (IC$_{50}$) nM | |
|---|---|---|---|
| | | human | rat |
| 74 | [piperazinyl-thiophene-ethyl-phenyl-CH$_2$-C(O)NH-NH$_2$] · 3HCl | 12.2 | 4.1 |
| 83 | [H$_2$N-CH$_2$CH$_2$-N(Et)-phenyl-CH$_2$-phenyl-CH$_2$-C(O)NH-NH$_2$] · 3HCl | 20.4 | 5.8 |
| 85 | [diethylamino-pyridyl-ethyl-phenyl-CH$_2$-C(O)NH-NH$_2$] · 3HCl | 15.7 | 1.9 |
| 86 | [piperazinyl-pyridyl-ethyl-phenyl-CH$_2$-C(O)NH-NH$_2$] · 4HCl | 9.8 | 1.0 |
| 87 | [Ac-piperazinyl-pyridyl-ethyl-phenyl-CH$_2$-C(O)NH-NH$_2$] · 3HCl | 3.2 | 1.4 |
| 88 | [diethylamino-pyridyl-ethyl-phenyl-CH$_2$-C(O)NH-NH$_2$] · 3HCl | 10.2 | 0.9 |

TABLE 2-continued

Inhibitory effect on human and rat VAP-1 enzyme (SSAQ)

| Production Example No. | Chemical structural formula | SSAO inhibitory activity (IC$_{50}$) nM | |
|---|---|---|---|
| | | human | rat |
| 89 | [structure: 6-(N-ethyl-N-methylamino)pyridin-3-yl ethylene phenyl acetohydrazide] 3HCl | 15.4 | 0.9 |
| 90 | [structure: 6-(N-methyl-N-propylamino)pyridin-3-yl ethylene phenyl acetohydrazide] 3HCl | 22.1 | 1.4 |
| 92 | [structure: 6-(N,N-dipropylamino)pyridin-3-yl ethylene phenyl acetohydrazide] 3HCl | 20.5 | 0.8 |
| 95 | [structure: 2-(piperazin-1-yl)thiazol-4-yl ethylene phenyl acetohydrazide] 3HCl | 6.3 | 3.5 |
| 99 | [structure: 6-(4-acetylpiperazin-1-yl)pyridazin-3-yl ethylene phenyl acetohydrazide] 3HCl | 13.5 | 2.5 |
| 101 | [structure: 5-(4-acetylpiperazin-1-yl)pyrazin-2-yl ethylene phenyl acetohydrazide] 3HCl | 3.4 | 2.1 |

TABLE 2-continued

Inhibitory effect on human and rat VAP-1 enzyme (SSAQ)

| Production Example No. | Chemical structural formula | SSAO inhibitory activity (IC$_{50}$) nM | |
|---|---|---|---|
| | | human | rat |
| 102 | (structure) 4HCl | 19.4 | 9.4 |
| 105 | (structure) 4HCl | 7.3 | 7.2 |
| 106 | (structure) 4HCl | 19.0 | 7.5 |
| 108 | (structure) 3HCl | 0.9 | 0.8 |
| 109 | (structure) 3HCl | 3.7 | 1.4 |
| 110 | (structure) 3HCl | 3.5 | 1.6 |
| 111 | (structure) 3HCl | 0.5 | 0.4 |

TABLE 2-continued
Inhibitory effect on human and rat VAP-1 enzyme (SSAQ)
| Production Example No. | Chemical structural formula | SSAO inhibitory activity (IC$_{50}$) nM | |
|---|---|---|---|
| | | human | rat |
| 112 | 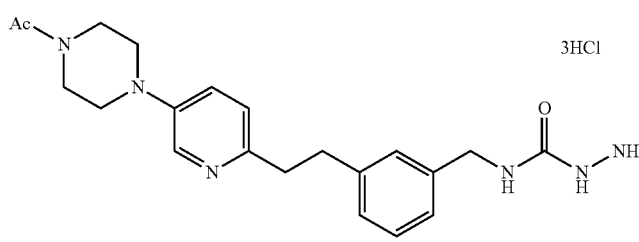 [SMILES: CC(=O)N1CCN(c2ccc(CCc3cccc(CNC(=O)NN)c3)nc2)CC1] 3HCl | 0.7 | 0.7 |
| 113 | 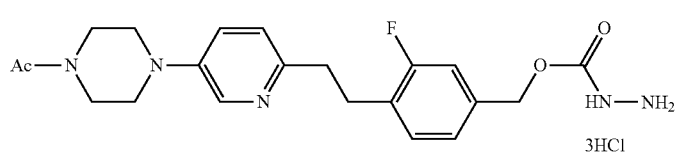 [SMILES: CC(=O)N1CCN(c2ccc(CCc3ccc(COC(=O)NN)cc3F)nc2)CC1] 3HCl | 0.9 | 0.7 |
| 114 | 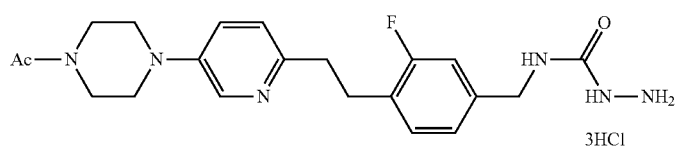 [SMILES: CC(=O)N1CCN(c2ccc(CCc3ccc(CNC(=O)NN)cc3F)nc2)CC1] 3HCl | 2.0 | 1.2 |
| 115 | 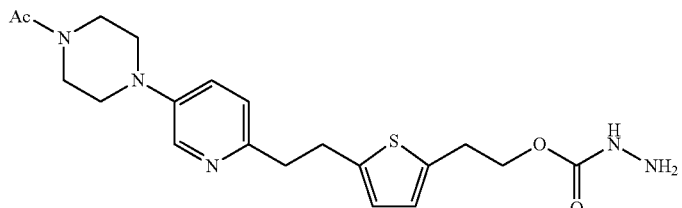 | 4.0 | 10.1 |
| 116 | 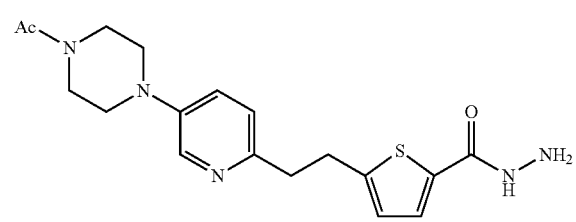 [SMILES: CC(=O)N1CCN(c2ccc(CCc3ccc(C(=O)NN)s3)nc2)CC1] | 9.5 | 9.8 |
| 117 | 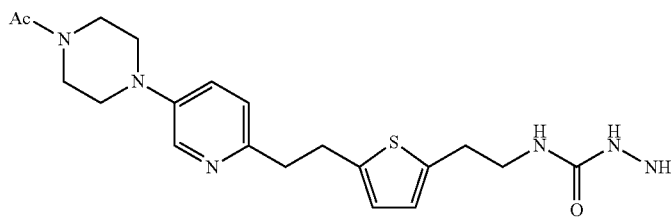 | 18.7 | 2.7 |
| 119 | 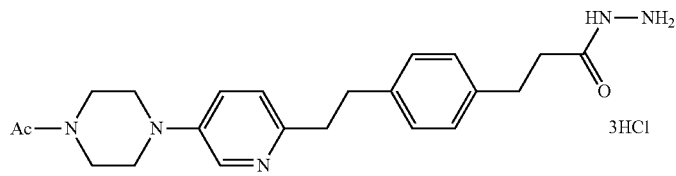 3HCl | 4.7 | 8.7 |

TABLE 2-continued

Inhibitory effect on human and rat VAP-1 enzyme (SSAO)

| Production Example No. | Chemical structural formula | SSAO inhibitory activity (IC$_{50}$) nM | |
|---|---|---|---|
| | | human | rat |
| 120 | 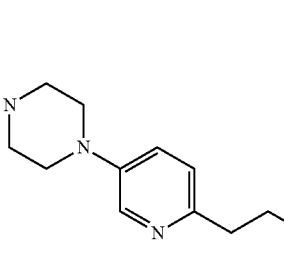 | 3.7 | 0.6 |
| 121 | 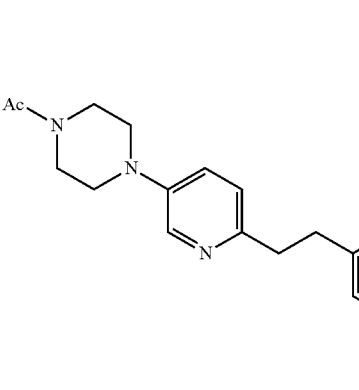 | 2.2 | 1.6 |
| 122 | 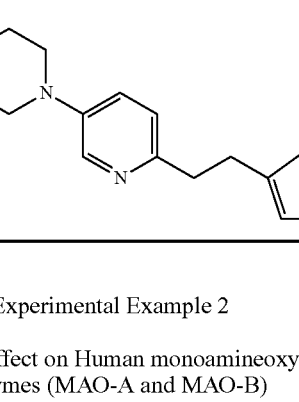 | 6.6 | 8.0 |
| 124 | 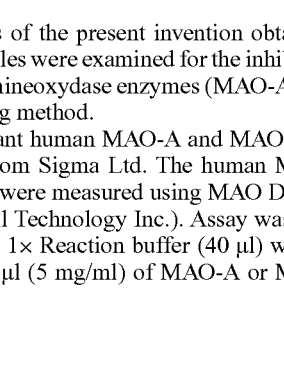 | 4.7 | 5.5 |

Experimental Example 2

Inhibitory Effect on Human monoamineoxydase Enzymes (MAO-A and MAO-B)

The compounds of the present invention obtained in the Production Examples were examined for the inhibitory effect on human monoamineoxydase enzymes (MAO-A and MAO-B) by the following method.

Gene recombinant human MAO-A and MAO-B enzymes were purchased from Sigma Ltd. The human MAO-A and MAO-B activities were measured using MAO Detection Kit (Fluoro MAO, Cell Technology Inc.). Assay was performed in a 96-well plate. 1× Reaction buffer (40 μl) was added to each well, and 50 μl (5 mg/ml) of MAO-A or MAO-B was added. Then, test compound solutions (final concentration $1\times10^{-4}$-$1\times10^{-10}$ mol/l) (10 μl) were added and the mixtures were incubated at 37° C. for 20 mins. Reaction cocktail (100 μl) was added, and the mixtures (final volume 200 μl) were incubated at 37° C. for 2 hrs. Thereafter, the fluorescence at 590 nm was detected with an excitation wavelength of 570 nm using a multispectro microplate reader (Varioskan, Thermo Fisher Scientific K.K.). The results are shown in Table 3.

As shown in Table 3, the compounds of the present invention did not show a remarkable inhibitory action on human MAO-A and MAO-B. Since they do not substantially show an inhibitory action on other monoamineoxydases, it is clear that the compounds of the present invention show selective and specific inhibitory action on SSAO.

TABLE 3

Inhibitory effect on human monoamineoxydase (MAO-A and MAO-B)

| Production Example No. | Chemical structural formula | MAO-A inhibition IC$_{50}$ (µM) | MAO-B inhibition IC$_{50}$ (µM) |
|---|---|---|---|
| 35 | 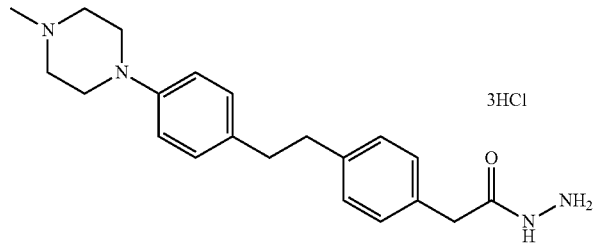 [SMILES: CN1CCN(c2ccc(CCc3ccc(CC(=O)NN)cc3)cc2)CC1] 3HCl | >100 | >100 |
| 51 | 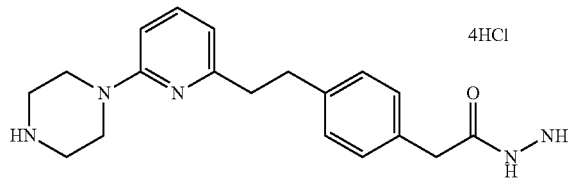 4HCl | >100 | >100 |
| 87 | 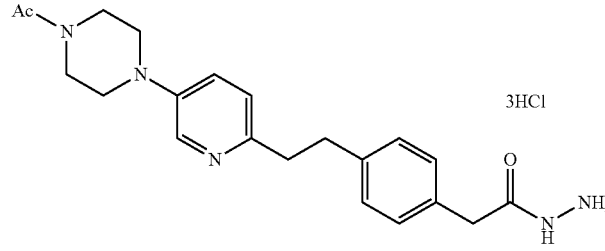 [SMILES: CC(=O)N1CCN(c2ccc(CCc3ccc(CC(=O)NN)cc3)nc2)CC1] 3HCl | >100 | >100 |
| 105 | 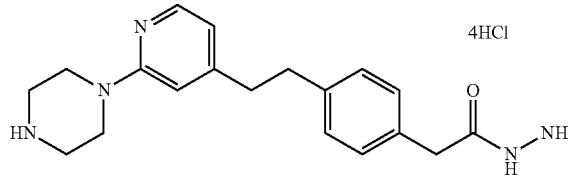 4HCl | >100 | >100 |
| Clorgyline | 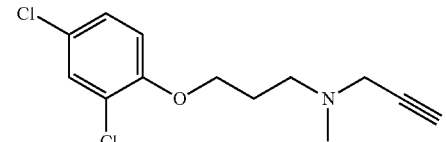 | 0.0005 | No data |
| Pargyline | 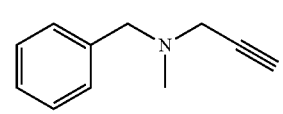 | No data | 0.095 |

INDUSTRIAL APPLICABILITY

Since the compound of the present invention is superior in VAP-1 inhibitory activity and has superior enzyme selectivity, it can eliminate side effects and the like unpreferable for a pharmaceutical product. Hence, the compound is useful as a VAP-1 inhibitor, a medicament for the prophylaxis or treatment of VAP-1 associated diseases and the like.

This application is based on a patent application No. 2008-143197 filed in Japan, the contents of which are incorporated in full herein by this reference.

The invention claimed is:

1. A compound which is 2-(4-{2-[5-(4-acetylpiperazin-1-yl)pyridine-2-yl]ethyl}phenyl)acetohyrazide, or a pharmaceutically acceptable salt thereof.

2. A pharmaceutical composition comprising (a) the compound of claim 1 or a pharmaceutically acceptable salt thereof and (b) a pharmaceutically acceptable carrier.

3. A method of inhibiting VAP-1 in a subject, which comprises administering an effective amount of the compound of claim 1 or a pharmaceutically acceptable salt thereof to a subject, thereby inhibiting VAP-1 in the subject.

4. A method of inhibiting VAP-1 in a subject that has a VAP-1 associated disease, which comprises administering an effective amount of the compound of claim 1 or a pharmaceutically acceptable salt thereof to the subject, thereby inhibiting VAP-1 in the subject.

5. A method for the treatment of a VAP-1 associated disease in a subject, which method comprises administering an effective amount of the compound of claim 1 or a pharmaceutically acceptable salt thereof to a subject that has a VAP-1 associated disease, thereby treating the VAP-1 associated disease in the subject,
wherein the VAP-1 associated disease is macular edema, aged macular degeneration, aged disciform macular degeneration, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, ocular inflammatory disease or a symptom thereof, erythema, erythema exsudativum multiforme, erythema nodosum, erythema annulare, scleredema, dermatitis angioneurotic edema, laryngeal edema, glottic edema, subglottic laryngitis, bronchitis, rhinitis, pharyngitis, sinusitis otitis media, cirrhosis, essential stabilized hypertension, diabetes, arteriosclerosis, endothelial injury relating to diabetes, arteriosclerosis and hypertension, cardiovascular disease relating to diabetes or uremia, pain relating to gout and arthritis, inflammatory disease of connective tissue or symptom thereof of binding tissue, inflammatory disease of gastrointestinal tract or a symptom thereof, inflammatory disease of central nervous system or a symptom thereof, pulmonary inflammatory disease or symptom thereof, disease relating to carbohydrate metabolism, disease relating to abnormality in the differentiation or function of adipocyte or function of smooth muscle cell, vascular disease, chronic arthritis, inflammatory bowel disease, SSAO-mediated complications, ophthalmic disease associated with hypoxia or ischemia, angiogenesis or cataract.

6. The method of claim 5, wherein the VAP-1 associated disease is macular edema, and the macular edema is diabetic macular edema, nondiabetic macular edema, or cystoid macular edema.

7. The method of claim 5, wherein the VAP-1 associated disease is ocular inflammatory disease or a symptom thereof, wherein the ocular inflammatory disease is caused by physical injury to the eye, bacterial infection, viral infection, or ophthalmic operation, and wherein the symptom of the ocular inflammatory disease is itching, flare, edema, or ulcer.

8. The method of claim 5, wherein the VAP-1 associated disease is dermatitis, and the dermatitis is psoriasis, allergic lesion, lichen planus, pityriasis rosea, contact dermatitis, atopic dermatitis, or pityriasis rubra pilaris.

9. The method of claim 5, wherein the VAP-1 associated disease is dermatitis, and the dermatitis is psoriasis or atopic dermatitis.

10. The method of claim 5, wherein the VAP-1 associated disease is inflammatory disease of connective tissue or a symptom thereof, and the inflammatory disease of connective tissue or symptom thereof is rheumatoid arthritis, ankylosing spondylitis, psoriatic arthritis, osteoarthritis, degenerative joint disease, Reiter's syndrome, Sjogren's syndrome, Behcet's syndrome, relapsing polychondritis, systemic lupus erythematosus, discoid lupus erythematodes, systemic sclerosis, eosinophilic fasciitis, polymyositis, dermatomyositis, polymyalgia rheumatica, vasculitis, temporal arthritis, polyarteritis nodosa, Wegener's granulomatosis, mixed connective tissue diseases, or juvenile rheumatoid arthritis.

11. The method of claim 5, wherein the VAP-1 associated disease is inflammatory disease of gastrointestinal tract or a symptom thereof, and the inflammatory disease of gastrointestinal tract or symptom thereof is Crohn's disease, ulcerative colitis, irritable bowel syndrome, spastic colon, inflammatory bowel disease, fibrosis of the liver, inflammation of the oral mucous membrane, stomatitis, or recurrent aphthous stomatitis.

12. The method of claim 5, wherein the VAP-1 associated disease is inflammatory disease of gastrointestinal tract or a symptom thereof, and the inflammatory disease of gastrointestinal tract or symptom thereof is ulcerative colitis.

13. The method of claim 5, wherein the VAP-1 associated disease is inflammatory disease of central nervous system or a symptom thereof, and the inflammatory disease of central nervous system or symptom thereof is multiple sclerosis, Alzheimer's disease, or ischemia-reperfusion injury relating to ischemic stroke.

14. The method of claim 5, wherein the VAP-1 associated disease is pulmonary inflammatory disease or a symptom thereof, and the pulmonary inflammatory disease or symptom thereof is asthma, adult respiratory distress syndrome, or chronic obliterative pulmonary disease.

15. The method of claim 5, wherein the VAP-1 associated disease is disease relating to carbohydrate metabolism, and the disease relating to carbohydrate metabolism is diabetes, complications derived from diabetes, diabetic neuropathy, diabetic nephropathy, disease of microvessel and large vessel, arteriosclerosis, retinopathy, nephropathy, nephrotic syndrome, neuropathy, multiple neuropathy, mononeuropathy, autonomic neuropathy, foot ulcer, articular problem, or increase in infection risk.

16. The method of claim 5, wherein the VAP-1 associated disease is disease relating to carbohydrate metabolism, and the disease relating to carbohydrate metabolism is diabetic neuropathy.

17. The method of claim 5, wherein the VAP-1 associated disease is disease relating to abnormality in the differentiation or function of adipocyte or function of smooth muscle cell, and the disease relating to abnormality in the differentiation or function of adipocyte or function of smooth muscle cell is arteriosclerosis or obesity.

18. The method of claim 5, wherein the VAP-1 associated disease is vascular disease, and the vascular disease is artheromatous atherosclerosis, nonartheromatous atherosclerotic disease, ischemic cardiac diseases, myocardial infarction, peripheral arterial obstruction, Raynaud's disease, Raynaud's phenomenon, or thromboangiitis obliterans.

19. The method of claim 5, wherein the VAP-1 associated disease is SSAO-mediated complications, and the SSAO-mediated complications are diabetes, insulin-dependent diabetes, noninsulin-dependent diabetes, vascular complications, heart attack, angina pectoris, apoplexy, amputation, blindness, or renal failure.

20. The method of claim 5, wherein the VAP-1 associated disease is ophthalmic disease associated with hypoxia or ischemia, and the ophthalmic disease associated with hypoxia or ischemia is retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease, Eales disease, antiphospholipid antibody syndrome, leukemic retinopathy, blood hyperviscosity syndrome, macroglobulinemia, interferon-associated retinopathy, hypertensive retinopathy, radiation retinopathy, or corneal epithelial stem cell deficiency.

21. The method of claim 5, wherein the VAP-1 associated disease is angiogenesis.

\* \* \* \* \*

UNITED STATES PATENT AND TRADEMARK OFFICE
CERTIFICATE OF CORRECTION

PATENT NO. : 8,999,989 B2
APPLICATION NO. : 12/991035
DATED : April 7, 2015
INVENTOR(S) : Matsukawa et al.

It is certified that error appears in the above-identified patent and that said Letters Patent is hereby corrected as shown below:

IN THE CLAIMS:

Claim 1 at column 166, lines 58-59, "2-(4-{2-[5-(4-acetylpiperazin-1-yl)pyridine-2-yl]ethyl}phenyl)acetohyrazide" should read "2-(4-{2-[5-(4-acetylpiperazin-1-yl)pyridin-2-yl]ethyl}phenyl)acetohydrazide"

Signed and Sealed this
Twenty-sixth Day of July, 2016

Michelle K. Lee
*Director of the United States Patent and Trademark Office*